US009421250B2

(12) United States Patent
McMullan et al.

(10) Patent No.: US 9,421,250 B2
(45) Date of Patent: Aug. 23, 2016

(54) PATHOGENIC PHLEBOVIRUS ISOLATES AND COMPOSITIONS AND METHODS OF USE

(71) Applicant: The United States of America as represented by the Secretary of the Department of Health and Human Services, Washington, DC (US)

(72) Inventors: Laura K. McMullan, Decatur, GA (US); Cynthia Goldsmith, Lilburn, GA (US); Aubree Kelly, Atlanta, GA (US); William L. Nicholson, Atlanta, GA (US); Stuart T. Nichol, Atlanta, GA (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 14/386,923

(22) PCT Filed: Mar. 22, 2013

(86) PCT No.: PCT/US2013/033541
§ 371 (c)(1),
(2) Date: Sep. 22, 2014

(87) PCT Pub. No.: WO2013/142808
PCT Pub. Date: Sep. 26, 2013

(65) Prior Publication Data
US 2015/0086577 A1 Mar. 26, 2015

Related U.S. Application Data

(60) Provisional application No. 61/614,926, filed on Mar. 23, 2012.

(51) Int. Cl.
| | | |
|---|---|---|
| *A61K 39/12* | (2006.01) | |
| *C12N 7/04* | (2006.01) | |
| *C12N 7/00* | (2006.01) | |
| *C12Q 1/70* | (2006.01) | |
| *C07K 14/175* | (2006.01) | |
| *C07K 16/10* | (2006.01) | |
| *C07K 14/08* | (2006.01) | |
| *C07H 21/04* | (2006.01) | |
| *G01N 33/569* | (2006.01) | |

(52) U.S. Cl.
CPC ............... *A61K 39/12* (2013.01); *C07H 21/04* (2013.01); *C07K 14/08* (2013.01); *C07K 14/175* (2013.01); *C07K 16/10* (2013.01); *C12N 7/00* (2013.01); *C12N 7/04* (2013.01); *C12Q 1/701* (2013.01); *G01N 33/56983* (2013.01); *C12N 2760/12221* (2013.01); *C12N 2760/12222* (2013.01); *C12N 2760/12234* (2013.01); *C12N 2760/12251* (2013.01); *C12Q 2600/158* (2013.01); *G01N 2333/175* (2013.01)

(58) Field of Classification Search
None
See application file for complete search history.

(56) References Cited

U.S. PATENT DOCUMENTS

| | | | |
|---|---|---|---|
| 7,312,035 B2 * | 12/2007 | Makeev | ......... 435/6.11 |
| 8,084,248 B2 | 12/2011 | Makino et al. | |
| 2005/0048531 A1 | 3/2005 | Mittman et al. | |

FOREIGN PATENT DOCUMENTS

| | | |
|---|---|---|
| WO | WO 02/20548 | 3/2002 |
| WO | WO 2007/110869 | 10/2007 |
| WO | WO 2009/061752 | 5/2009 |

OTHER PUBLICATIONS

McMullan et al., "A New Phlebovirus Associated with Severe Febrile Illness in Missouri," *N. Engl. J. Med.*, vol. 367:834-841, 2012.
Palacios et al., "Characterization of the Candiru Antigenic Complex (Bunyaviridae: Phlebovirus), a Highly Diverse and Reassorting Group of Viruses Affecting Humans in Tropical America," *J. Virol.*, vol. 85:3811-3820, 2011.
Xu et al., "Metagenomic Analysis of Fever, Thrombocytopenia and Leukopenia Syndrome (FTLS) in Henan Province, China: Discovery of a New Bunyavirus," *PLoS Patho*, Vo. 7:e1002369, 2011.
Yu et al., "Fever with Thrombocytopenia Associated with a Novel Bunyavirus in China," *N. Engl. J. Med.*, vol. 364:1523-1532, 2011.

* cited by examiner

*Primary Examiner* — Nicole Kinsey White
(74) *Attorney, Agent, or Firm* — Klarquist Sparkman, LLP

(57) ABSTRACT

Described herein are the clinical and laboratory characteristics of two patients bitten by ticks and infected with a unique member of the genus *Phlebovirus* (family Bunyaviridae) with a proposed name of Heartland virus (HRTLV). Provided herein are nucleotide and amino acid sequences of the *Phlebovirus* isolates, primers and probes that specifically hybridize with the *Phlebovirus* isolates, and antibodies specific for the *Phlebovirus* proteins. Also provided are detection assays using the *Phlebovirus* nucleic acid molecules, proteins, probes, primers and antibodies. Further provided are recombinant *Phleboviruses* and their use for eliciting an immune response in a subject.

23 Claims, 8 Drawing Sheets

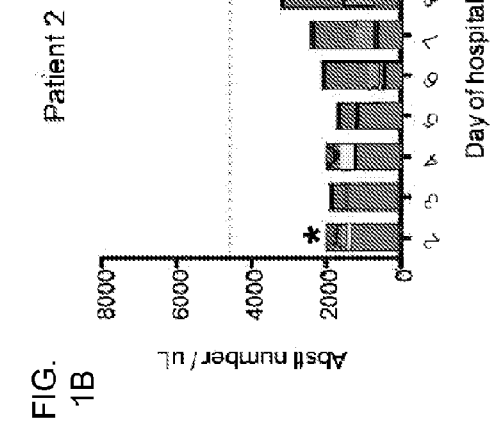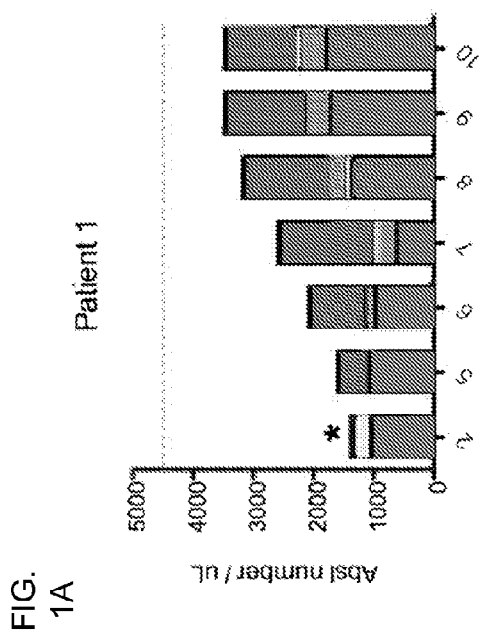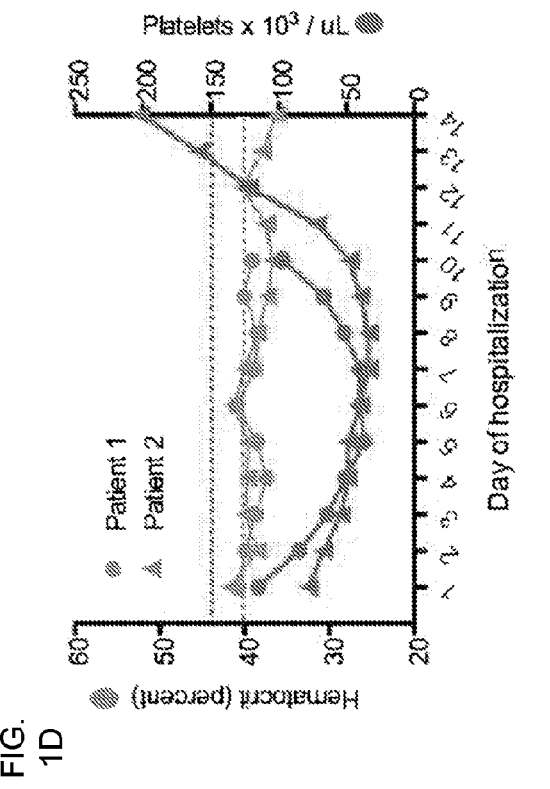
FIG. 1A
FIG. 1B
FIG. 1C
FIG. 1D

FIG. 3A Nucleoprotein

FIG. 3B Nonstructural S

FIG. 3D
Polymerase

- Gouleako
- SFTSV
- Patient 1
- Patient 2 (100)
- Uukuniemi
- Massilia
- Toscana AR France
- Toscana Italy (100)
- Candiru
- Sandfly Sicilian
- Rift Valley ZH584
- Rift Valley ZH501 (100, 54)

0.2

FIG. 3C
Glycoprotein

- Uukuniemi
- SFTSV
- Patient 1
- Patient 2 (100)
- Massilia
- Toscana (100)
- Sandfly Sicilian
- Rift Valley ZH501 (72)
- Candiru
- Punta Toro Adams
- Punta Toro M11156 (100)

| Patient 1 | Normal Range | 6/18/2009 | 6/19/2009 | 6/20/2009 | 6/21/2009 | 6/22/2009 | 6/23/2009 | 6/24/2009 | 6/25/2009 | 6/26/2009 | 6/27/2009 |
|---|---|---|---|---|---|---|---|---|---|---|---|
| Day of hospitalization | | 1 | 2 | 3 | 4 | 5 | 6 | 7 | 8 | 9 | 10 |
| White cell count (×10³/mL) | 4.5-11 | 2.9 | 2.4 | 1.2 | 1.5 | 1.6 | 2.1 | 2.6 | 3.2 | 3.5 | 3.5 |
| Differential Absolute Number | | | | | | | | | | | |
| Neutrophils | 3000-5800 | | 2078 | | | 1104 | 1008 | 650 | 1376 | 1750 | 1820 |
| Band forms | 150-400 | | 252 | | | | | | 96 | | |
| Lymphocytes | 1500-3000 | | 28 | | | 432 | 882 | 1534 | 1440 | 1330 | 1390 |
| Monocytes | 285-500 | | 42 | | | 64 | 126 | 286 | 288 | 385 | 320 |
| Eosinophils | 50-250 | | | | | 0 | 0 | 0 | 0 | 35 | 70 |
| Basophils | 15-50 | | | | | 16 | 21 | 130 | 0 | 0 | 0 |
| Hematocrit (%) | 40-51 (males) | 40.8 | 39.9 | 38.7 | 37.2 | 38.6 | 41 | 38.8 | 38.5 | 40.2 | 39.3 |
| Hemoglobin (g/dL) | 13.5-17.5 (males) | 14.7 | 14.2 | 13.7 | 13.3 | 13.9 | 14.4 | 14.4 | 13.3 | 13.5 | 13.5 |
| Platelet count (×10³ cells/mL) | 150-450 | 115 | 85 | 64 | 52 | 37 | 40 | 40 | 52 | 67 | 97 |
| Erythrocyte count (×10⁶ cells/mL) | 4.3-5.7 (males) | 4.62 | 4.54 | 4.4 | 4.27 | 4.42 | 4.66 | 4.35 | 4.28 | 4.46 | 4.38 |
| Mean corpuscular volume (fL) | 80-100 | 88 | 88 | 88 | 89 | 87 | 88 | 89 | 90 | 90 | 90 |
| Mean corpuscular hemoglobin (pg/cell) | 26-34 | 31.8 | 31.3 | 31.1 | 31.1 | 31.4 | 30.9 | 30.8 | 31.1 | 30.3 | 30.8 |
| Mean corpuscular hemoglobin concentration (%Hb/cell) | 32-37 | 36 | 35.6 | 35.4 | 35.6 | 36 | 35.1 | 34.5 | 34.5 | 33.6 | 34.4 |
| Red blood cell distribution width (%) | 11-14 | 12.9 | 12.9 | 12.9 | 12.9 | 13.1 | 13.3 | 13.4 | 13.6 | 13.4 | 13.3 |
| Prothrombin time seconds | 9-13 | | | | | 10 | | | | | |
| International normalized ratio | 0.9-1.2 | | | | | 0.92 | | | | | |
| Activated partial thromboplastin time (sec) | 25-35 | | | | | 29.9 | | | | | |
| Fibrinogen (mg/L) | 200-400 | | | | | | | | | | |
| D-Dimer (mg/L) | 0-3.0 | | | | | | | | | | |
| Total protein (g/dL) | 6.4-8.3 | | 6.7 | 6.1 | 5.8 | 5.9 | 6.3 | 6.1 | 6.3 | 6.5 | 6.6 |
| Albumin (g/dL) | 3.4-4.8 | | 3.4 | 3 | 2.9 | 2.9 | 3.1 | 2.9 | 2.8 | 2.9 | 2.9 |
| Calcium (mg/dL) | 8.6-10 | 8 | 7.7 | 7.4 | 7.2 | 7.4 | | | | | |
| Bilirubin Total (mg/dL) | 0.3-1.2 | | 0.3 | 0.3 | 0.4 | 0.5 | 0.9 | 1 | 0.8 | 0.7 | 0.7 |
| Alkaline Phosphatase (U/L) | 25-100 | | 71 | 71 | 65 | 70 | 72 | 88 | 98 | 101 | 99 |
| Sodium (mEq/L) | 136-146 | 132 | 131 | 132 | 128 | 131 | | | | | |
| Potassium (mEq/L) | 3.5-5.1 | 5.5 | 3.6 | 3.5 | 3.2 | 4.2 | | | | | |
| Chloride (mEq/L) | 98-106 | 100 | 99 | 100 | 100 | 101 | | | | | |
| Total CO₂ (mEq/L) | 23-29 | 23 | 22 | 24 | 22 | 23 | | | | | |
| Creatinine | 0.7-1.3 (males) | 1.8 | 1.4 | 1.3 | 1.2 | 1.1 | | | | | |
| ALT (U/L) | 10-40 (males) | | 57 | 50 | 68 | 107 | 163 | 209 | 315 | 261 | 202 |
| AST (U/L) | 10-30 | | 44 | 41 | 85 | 155 | 253 | 331 | 431 | 223 | 115 |
| Glucose tvl (mg/dL) | 80-115 | 88 | 101 | 99 | 135 | 122 | | | | | |
| BUN (mg/dL) | 6-20 | 17 | 17 | 18 | 14 | 12 | | | | | |
| Bilirubin Conjugated (Direct) (mg/dL) | 0-0.2 | | | | | 0.1 | 0.4 | 0.7 | 0.4 | 0.2 | 0.2 |
| Magnesium (mEq/L) | 1.3-2.1 | | | 1.7 | 1.5 | | | | | | |

FIG. 4B  Patient 2

| | 6/4/2009 | 6/5/2009 | 6/5/2009 | 6/6/2009 | 6/7/2009 | 6/8/2009 | 6/9/2009 | 6/10/2009 | 6/11/2009 | 6/12/2009 | 6/13/2009 | 6/14/2009 | 6/15/2009 |
|---|---|---|---|---|---|---|---|---|---|---|---|---|---|
| | 1 | 1.5 | 2 | 2.5 | 3 | 4 | 5 | 6 | 7 | 8 | 9 | 10 | 11 | 12 |
| | 2.2 | 1.7 | 1.6 | 2 | 1.9 | 2 | 1.7 | 2.1 | 2.4 | 3.2 | 3.8 | 6.5 | 6.2 | 7.5 |
| | | | 1280 | 1320 | 1444 | 1280 | 1241 | 504 | 672 | 736 | 1254 | 2640 | 3108 | 4350 |
| | | | 64 | 160 | 0 | 380 | 85 | 84 | 48 | 0 | 0 | 0 | 0 | 0 |
| | | | 240 | 420 | 262 | 340 | 374 | 1176 | 1352 | 1600 | 1558 | 2330 | 2736 | 1950 |
| | | | 16 | 180 | 95 | 0 | 0 | 336 | 528 | 800 | 912 | 1518 | 1240 | 1200 |
| | | | 0 | 0 | 0 | 0 | 0 | 0 | 0 | 0 | 0 | 0 | 0 | 0 |
| | | | 0 | 0 | 19 | 0 | 0 | 0 | 0 | 64 | 38 | 66 | 62 | 0 |
| | 41.7 | 38.5 | 39.9 | 39.7 | 39.6 | 41.3 | 40 | 38.5 | 37.3 | 36.7 | 37.6 | 40.3 | 37.9 | 36.3 |
| | 14.4 | 13.4 | 14.3 | 14 | 14.2 | 14.8 | 14.4 | 13.8 | 13.7 | 13.7 | 13.8 | 15 | 14.1 | 13.3 |
| | 78 | 67 | 54 | 49 | 49 | 40 | 34 | 34 | 40 | 48 | 72 | 122 | 159 | 102 |
| | | 4.35 | 4.6 | 4.5 | 4.59 | 4.75 | 4.64 | 4.48 | 4.43 | 4.39 | 4.55 | 4.87 | 4.52 | 4.27 |
| | | 89 | 87 | 88 | 86 | 87 | 86 | 86 | 84 | 84 | 83 | 83 | 84 | 85 |
| | | 30.8 | 32.1 | 31.1 | 30.7 | 31.2 | 31 | 30.8 | 30.9 | 31.2 | 30.3 | 30.8 | 31.2 | 31.2 |
| | | 34.8 | 35.8 | 35.3 | 35.6 | 35.8 | 36 | 35.8 | 36.7 | 37.3 | 36.7 | 37.2 | 37.2 | 36.6 |
| | | 13.4 | 13.3 | 13.2 | 13.2 | 13.2 | 13.3 | 13.2 | 13 | 12.8 | 12.8 | 12.7 | 12.9 | 13 |
| | | | 18.7 | | | | | | | | | | | |
| | | | 8.99 | | | | | | | | | | | |
| | | | 27.9 | | | | | | | | | | | |
| | | | 229.6 | | | | | | | | | | | |
| | | | 4.08 | | | | | | | | | | | |
| | | 7.8 | | | 6.1 | 6.1 | 5.5 | 5.4 | 5.7 | 6 | | 6.8 | 6.4 | 6.3 |
| | | | | | 3.3 | 3.1 | 2.8 | 2.6 | 2.8 | 2.9 | | 3.2 | 3 | 2.9 |
| | | | | | 7.3 | 7.3 | 7.6 | 7.7 | 7.6 | 8.1 | | 8.8 | 8.7 | 8.6 |
| | | | | | 0.5 | 0.5 | 0.5 | 0.8 | 1.1 | 1.2 | | 0.9 | 0.7 | 0.6 |
| | | 138 | | | 68 | 60 | 52 | 55 | 58 | 70 | 133 | 107 | 96 | 98 |
| | | 4.8 | | | 125 | 127 | 129 | 127 | 131 | 131 | 3.9 | 122 | 133 | 134 |
| | | 97 | | | 3.6 | 3.8 | 4.1 | 3.9 | 3.7 | 3.5 | 97 | 3.6 | 3.8 | 3.9 |
| | | 30 | | | 92 | 92 | 96 | 96 | 97 | 98 | 25 | 97 | 98 | 100 |
| | | | | | 25 | 29 | 27 | 26 | 25 | 23 | 0.8 | 24 | 26 | 27 |
| | | | | | 1.1 | 1.2 | 1.1 | 2 | 0.9 | 0.8 | | 0.8 | 0.8 | 0.8 |
| | | 130 | | | 63 | 81 | 81 | 76 | 148 | 263 | 144 | 302 | 268 | 234 |
| | | 12 | | | 92 | 166 | 175 | 259 | 253 | 355 | 15 | 294 | 140 | 102 |
| | | | | | 258 | 174 | 151 | 155 | 181 | 175 | | 156 | 133 | 109 |
| | | | | | 26 | 16 | 18 | 26 | 22 | 20 | | 22 | 23 | 21 |
| | 1.3 | | | | | | 0.3 | 0.5 | 0.4 | 0.4 | | | 0.2 | |
| | 5.4 | | | 1.3 | | | | | | | 0.8 | | | |

FIG. 5A

```
SFSV_J04418                      MD...EYQKI AVEFGEQAID ETVIQDWLQA FAYQGFDART IIENLVQ...
RFV_ZH501_DQ380149               MD...NYQEL AIQFAACAVD RNEIEQWVRE FAYQGFDARR VIELLKQ...
SALV_BeAn_578142_EF201815        MA...DYARI AVEFSGEAIN LAEIQGWVTD FAYQGFDARR IVELVQQ...
SALV_BeAn416992_EF201816         MA...DYARI AVEFSGEAIN LAEIQGWVTD FAYQGFDARR IVELVQQ...
BeAr371637_EF201820              MT...DYART AVAFAGEPVN NAEVMGWVNE FAYEGFSAQR TTQTVQE...
VP161A_EF201819                  MT...DYADI AIAFAGEPIN NAEVMGWVNE FAYEGFNAQR IIQLVQE...
Sabin_EF201829                   MS..EENYREI ALAFLDEAAD SGTITAWVNE FAYQGFDPKR IVQLVKE...
Massila_W_EU725773               MS.EDNYRTI ALAFLDESAD STTINAWVNE FAYQGFDPKR IVQLVKE...
Toscana_H_IMISSA_FJ153286        MS.DENYRDI ALAFLDESAD SCTINAWVNE FAYQGFDPKR IVQLVKE...
UUK_S23_M33551                   MAMPENWVRF ATETSDAQWE EEEIREFINL FQYQGFDAAV VLSRIFELAK
SSFTSV_HB29_HM745932             MS...EWSRI AVEFGEQQLN LTELEDFARE LAYEGLDPAL IIKKLKE...
Mo7                              MT...DWSAI AVEIGNEPLD VPALVEFAKE IAYEGLDPAV IFGLLRE...
Mo4                              MT...DWSAI AVEIGNEPLD VPALVEFAKE IAYEGLDPAV ILGLLRE...
Gabek_Forest_Virus_NP_partial    .......... .......... .......... .....FDPRI VVKLVSE...
PTV_Adames_EF201835              MS....YEEI AVQFASESID EQAVAGWVTD FAYQGFDAKR VIALVKE...
RFV_Entebbe_DQ380156             MD...NYQEL AIQFAACAVD RNEIEQWVRE FAYQGFDAKR VIELLKQ...
Candiru_HM119409                 MS....YEKL AVDIAGHEID ADTIKAWVQA FAYQGFDAKR VMELLVE...
RioGrandeVirusNPpartial          .......... .......... .......... .AYQGFDANR VVELVQE...

SFSV_J04418                      LC...CKSWE EDAKKMITLS LTRGNKPKKM VERMSPEGAR EVKSLVAKYK
RFV_ZH501_DQ380149               YG...GADWR KDAKKMIVLA LTRGNKPRRM MMKMSKEGKA TVEALINKYK
SALV_BeAn_578142_EF201815        KG...GAGWK DDVKMMIVLC LTRGNKPTKM VEKMSPEGKV KVNRLISTYG
SALV_BeAn416992_EF201816         KG...GAGWK DDVKMMIVLC LTRGNKPTKM VEKMSPEGKV KVNRLISTYG
BeAr371637_EF201820              RG...PQTWQ TDVKMMIVLA LTRGNKPAKM IEKMSAEGKK KATRLITMYN
VP161A_EF201819                  KG...PQTWQ TDVKMMIVLA LTRGNKPSKM IEKMSAEGKK KASRLITIYG
Sabin_EF201829                   RGTAKGRDWK KDVKMMIVLN LVRGNKPEAM MKKMSEKGAG IVAQLTSVYQ
Massila_W_EU725773               RGTAKGRDWK KDVKMMIVLN LVRGNKPESM MKKMSEKGAA IVTQLISTYQ
Toscana_H_IMISSA_FJ153286        RGTAKGRDWK KDVKMMIVLN LVRGNKPEAM MKKMSEKGAS IVANLISVYQ
UUK_S23_M33551                   KADLSRDQML RDIRALITLH LTRGNKLSSI EKRLSEEGKK EFAILKARYQ
SSFTSV_HB29_HM745932             TG...GDDWV KDTKFTIVFA LTRGNKIVKA SCKMSNSGSK RLMALQEKYG
Mo7                              RG...GENWR NDVKYIIVFA LTRGNKIVKA CGKMSKKGAE RMTNLARVYE
Mo4                              RG...GENWR NDVKYIIVFA LTRGNKIVKA CGKMSKKGAE RMTNLARVYE
Gabek_Forest_Virus_NP_partial    VE...G..WQ TDVKKMIILA LTRGNKPEKM VTKMSAKGRE EVAKLVKKYK
PTV_Adames_EF201835              RG...GEDWK QDVKKMIVLS LTRGNKPENM VLKMSDKGKA MVNELVLKYK
RFV_Entebbe_DQ380156             YG...GADWR KDAKKMIVLA LTRGNKPRRM MMKMSKEGKA TVEALINKYK
Candiru_HM119409                 RG...GDDWV EDAKQMIILC LTRGNKPSKM MVKMSEKGKK IVQALVKRYS
RioGrandeVirusNPpartial          RA..KGRKWQ EDVKRMIILA LTRGNKPDKM RKKMSPEGIA VLDDLVKTYQ SFSV_J04418                      IVEGRPGRNG ITLSRVLQPW LGGQSKLWKW LKTSYQSQGA QWTALCGQTY
RFV_ZH501_DQ380149               LKEGNPSRDE LTLSRVAAAL AGWTCQALVV LSEWLPVTGI TMDGLSP.AY
SALV_BeAn_578142_EF201815        LKSCNPCRDD ITLSRVAAAF ACWTCQALNV LHPYLPVSCT TMDAISP.NY
SALV_BeAn416992_EF201816         LKSGNPGRDD ITLSRVAAAF AGWTCQALNV LHPYLPVSGI TMDAISP.NY
BeAr371637_EF201820              LKSGNPGRDD LTLSRVASAF AGWTCQALAV LHPYLPVTGA SMDSISP.GY
VP161A_EF201819                  LKSGNPGRDD LTLSRIAAAF AGWTCQALAT LHPYLPVTGA AMDAISP.GY
Sabin_EF201829                   LKEGNPSRDT ITLSRVSAAF VPWTIQALRV LSDSLPVTGI TMDAIAGVTY
Massila_W_EU725773               LKEGNPSRDT ITLSRVSAAF VPWIVQALKT LSESLPVTGI TMDSIAGTTY
Toscana_H_IMISSA_FJ153286        LKEGNPSRDT ITLSRVSAAF VPWIVQALRV LSESLPVSGI TMDAIAGVTY
UUK_S23_M33551                   LVDKAKEAAD LTLSRIAIAN AGLICRILPQ VVAHTAVTRS RMESLSA.DY
SSFTSV_HB29_HM745932             LVERAETRLS ITPVRVAQSL PTWICAAAAA LKEYLPVGPA VMNLKVE.NY
Mo7                              LKENAVDRMA VTPVRVAQCL PTWICAAAAA IKEYLPVGPA IMENKIQ.GY
Mo4                              LKENAVDRMA VTPVRVAQCL PTWICAAAAA IKEYLPVGPA IMENKIQ.GY
Gabek_Forest_Virus_NP_partial    LKSGNPGRND LTLSRVAAAF ASWTCNAIYH VQYYLPVTGN HMDAISK...
PTV_Adames_EF201835              LKSGNPSRDD LTLSRITAAF AGWTCQAADY VQEYLPVTGR AMDTISS.GY
RFV_Entebbe_DQ380156             LKEGNPSRDE LTLSRVAAAL AGWTCQALVV LSEWLPVTGI TMDGLSP.AY
Candiru_HM119409                 LKEGNPSRDD LTLSRVTAAL AGYTCQATEY VEEFLPVTGK NMDDLSK.NY
RioGrandeVirusNPpartial          LKSSSPGRDD LTLARIAAAF APWTCQATEA VENYMPVNGA ..........
```

FIG. 5B

```
SFSV_J04418                      PRQMMHPSFA GLI.DPSLDQ EDFNAVLDAH KLFLFMFSKT INVSLRGAQK
RFV_ZH501_DQ380149               PRHMMHPSFA CMV.DPSLPC DYLRAILDAH SLYLQFSRV INPNLRGRTK
SALV_BeAn_578142_EF201815        PRAMMHPCFA GLV.DQTIPT EYCQTIVDAM SVFLIQFSRT TNKNLRGCPK
SALV_BeAn416992_EF201816         PRAMMHPCFA GLV.DQTIPT EYCQTIVDAM SVFLIQFSRT INKNLRGCPK
BeAr371637_EF201820              PRAMMHPSFA GLI.DNSIPE AFLQTVVDAH ALYLLQFSRV INKNMRGCPK
VP161A_EF201819                  PRAMMHPSFA GLI.DNSIPE AYLQVVVDAH ALYLLQFSRV INRNMRGCPK
Sabin_EF201829                   PRAMMHPSFA GTI.DLDLPN RAGFATADAH GLFMLEFSKT TNPSLRTKQP
Massila_W_EU725773               PRCMMHPSFA GII.DLELPN NTGAMLADAH GLFMLEFSKT INPSLRTKQP
Toscana_H_IMTSSA_FJ153286        PRAMMHPSFA GLI.DLDLPN GAGATTADAH GLFMIEFSKT INPSLRTKQA
UUK_S23_M33551                   PVCMMINAFA GLI.DETLPE DSIKALVDAH RLYLLEFSRT INVKIIRGMEA
SSFTSV_HB29_HM745932             PPEMMCMAFG SLIPTAGVSE ATTKTLMEAY SLWQDAFTKT INVKMRGASK
Mo7                              PLEMMCMAFG SLIPQADVSI EVIKDFMDAY SLWQDTFART INVDQRKMTK
Mo4                              PLEMMCMAFG SLIPQADVSI EVIKDFMDAY SLWQDTFART INVDQRKMTK
Gabek_Forest_Virus_NP_partial    .......... .......... .......... .......... ..........
PTV_Adames_EF201835              PRAMMHPSFA GLI.DQELPA DVLSEITQAH CLFMIQFSKT INPSLRGLSK
RFV_Entebbe_DQ380156             PRHMMHPSFA GMV.DPSLPE DYLRAILDAH SLYLQFSRV INPNLRGKTK
Candiru_HM119409                 PRAMMHPSFA GLI.DPKLPP DVLSTICDAF SLFMVQFSRT INDRNRGLSV
RioGrandeVirusNPpartial          .......... .......... .......... .......... ..........

SFSV_J04418                      RDIEESFSQP MLAAINSSFI DNTQRRAFLT KFGILTSGAR ATAVVKKIAE
RFV_ZH501_DQ380149               EEVAATFTQP MNAAVNSNFI SHEKRREFLK AFGLVDSNGK PSAAVMAAAQ
SALV_BeAn_578142_EF201815        EVVIESFIQP MQAAMSSSFI APAERRKLMI ALGIVDANGK PSANVAAAAA
SALV_BeAn416992_EF201816         EVVIESFIQP MQAAMSSSFI APAERRKLMI ALGIVDANGK PSANVAAAAA
BeAr371637_EF201820              SVVVSSFLQP MNAAIVSGFI SIIDKRRKMLM AFGIVDQNGK PTQAVETAAK
VP161A_EF201819                  SVVVSSFLQP MNAAIVSGFI SNDRRRKMLM AFGIVDQNGK PTAAVESAAK
Sabin_EF201829                   NEIAATFEKP NMAAMSGFFI TREDKKKLLM AVGILNEDLV LTPAIVKCAE
Massila_W_EU725773               NEIAATFEKP NMAAMTGRFF TRDDKKKLLI AIGVLDEDLV PNPAIEKCAE
Toscana_H_IMTSSA_FJ153286        NLVAATFEKP NMAAMSGRFF TREDKKKLLI AVGIIDEDLV LASAVVRSAE
UUK_S23_M33551                   KEILDANDSA LQAGLASSFL TPSQKRAYLL SFKLVDGNGK VNKAVQQAAT
SSFTSV_HB29_HM745932             TEVYNSFRDP LHAAVNSVFF PNDVRVKWLK AKGILGPDGV PSRAAEVAAA
Mo7                              AEVYAKFRDP LHAAVNSLFF PNATRISWLQ AKGLLTATKE ASGSVKAAAA
Mo4                              AEVYAKFRDP LHAAVNSLFF PNATRISWLQ AKGLLTATKE ASGSVKAAAA
Gabek_Forest_Virus_NP_partial    .......... .......... .......... .......... ..........
PTV_Adames_EF201835              DEIVSSFERP MQAAISSTFL TSANRRAMLK TLGIINDNLK PSSSTVSAAK
RFV_Entebbe_DQ380156             EEVAATFTQP MNAAVNSSFI SHEKRREFLR AFGLVDSNGK PSAAVMAAAQ
Candiru_HM119409                 SEVASTFDRP INAAMNSSFI SGEQRKSFLR NLGILDENMQ PSNPVKAAAK
RioGrandeVirusNPpartial          .......... .......... .......... .......... ..........

SFSV_J04418                      VYRKLE...    (SEQ ID NO: 24)
RFV_ZH501_DQ380149               AYKTAA...    (SEQ ID NO: 25)
SALV_BeAn_578142_EF201815        VFPRLL...    (SEQ ID NO: 26)
SALV_BeAn416992_EF201816         VFPRLL...    (SEQ ID NO: 27)
BeAr371637_EF201820              AFMTIN...    (SEQ ID NO: 28)
VP161A_EF201819                  AFMTAV...    (SEQ ID NO: 29)
Sabin_EF201829                   KYCSKVGK.    (SEQ ID NO: 30)
Massila_W_EU725773               KYKAKVGKV    (SEQ ID NO: 31)
Toscana_H_IMTSSA_FJ153286        KYRAKVGK.    (SEQ ID NO: 32)
UUK_S23_M33551                   VLRSLI...    (SEQ ID NO: 33)
SSFTSV_HB29_HM745932             AYRNL....    (SEQ ID NO: 34)
Mo7                              AYRNM....    (SEQ ID NO: 11)
Mo4                              AYRNM....    (SEQ ID NO: 4)
Gabek_Forest_Virus_NP_partial    .........    (SEQ ID NO: 35)
PTV_Adames_EF201835              VFRSL....    (SEQ ID NO: 36)
RFV_Entebbe_DQ380156             AYKTAA...    (SEQ ID NO: 37)
Candiru_HM119409                 VFRGLK...    (SEQ ID NO: 38)
RioGrandeVirusNPpartial          .........    (SEQ ID NO: 39)
```

PATHOGENIC PHLEBOVIRUS ISOLATES AND COMPOSITIONS AND METHODS OF USE

CROSS REFERENCE TO RELATED APPLICATIONS

This is the U.S. National Stage of International Application No. PCT/US2013/033541, filed Mar. 22, 2013, published in English under PCT Article 21(2), which claims the benefit of U.S. Provisional Application Ser. No. 61/614,926, filed Mar. 23, 2012, which is incorporated by reference herein in its entirety.

FIELD

This disclosure concerns the isolation, identification and sequencing of a unique *Phlebovirus*, and the use of the *Phlebovirus* nucleic acid molecules and proteins as detection and diagnostic reagents, as well as in reverse genetics and mini-genome reporter systems.

BACKGROUND

The genus *Phlebovirus* is one of five genera of the Bunyaviridae family. *Phleboviruses* are enveloped spherical viruses with icosahedral symmetry. The genome of *Phleboviruses* consists of three single-stranded RNA genome segments—small (S), medium (M) and large (L). The M and L segments use a negative sense coding strategy, while the S segment encodes two proteins using an ambisense strategy. The S segment encodes the non-structural protein NSs in the positive sense orientation and the nucleoprotein (NP) in the negative sense orientation; each protein is translated from a subgenomic virus mRNA. The M segment encodes the glycoprotein precursor that is cleaved by host proteases into two structural domains—Gn and Gc. The L segment encodes the L protein, which functions as the RNA dependent RNA polymerase in primary and secondary transcription to generate mRNA and replicative intermediates, respectively.

There are approximately 70 named viruses in the *Phlebovirus* genus. These viruses are classified based on their serological relationships into two antigenic groups, the phlebotomus or sandfly fever group and the Uukuniemi group (Nichol et al., *Virus Taxonomy: Classification and Nomenclature of Viruses. Eighth Report of the International Committee of the Taxonomy of Viruses*. Elsevier Academic Press, Genus *Phlebovirus*, pp. 706-716, 2005). *Phleboviruses* have a worldwide distribution and are transmitted by a wide variety of arthropods, including sandflies, mosquitoes and ticks. Several *Phleboviruses* have been linked to human disease, in some cases causing febrile illness, fever, hepatitis, meningitis, encephalitis or hemorrhagic syndrome.

Ticks (Acari: *Ixodidae*) transmit bacterial and viral pathogens to humans in the United States and elsewhere. Lyme disease, rickettsioses, ehrlichioses, tularemia, babesiosis, and Powassan virus infections of humans have all increased over the last decade. Reasons for these increases are multifactorial and include improved diagnosis, climate effects, and changes in land use (Roche et al., First culture isolations of *Ehrlichia chaffeensis* from a Missouri patient. In: 22nd Annual Meeting of the Society for Vector Ecology. Ft. Collins, Colo., 2008). An important species of tick that can transmit numerous pathogens is the lone star tick, *Amblyomma americanum*. In many parts of the country, humans are regularly exposed to this species and the pathogens it may carry (Goddard and Varela-Stokes, *Vet Parasitol* 160:1-12, 2009; Paddock and Yabsley, *Curr Top Microbiol Immunol* 315:289-324, 2007).

SUMMARY

Disclosed herein is the isolation and identification of a previously unidentified *Phlebovirus*. In particular, disclosed are two *Phlebovirus* isolates from patients who had recently been bitten by ticks. The sequences of all three genome segments of each isolate, as well as the amino acid sequences of the proteins encoded by the virus isolates, are further disclosed.

Provided herein is an isolated *Phlebovirus* comprising an S segment, an M segment and an L segment, wherein the nucleotide sequences of the S, M and L segments are at least 80% identical to the nucleotide sequences of the *Phlebovirus* isolates disclosed herein.

Further provided are isolated nucleic acid molecules of the *Phlebovirus* isolates and polypeptides encoded by the *Phlebovirus* isolates. Oligonucleotides, such as primers and probes, specific for a nucleic acid molecule of the *Phlebovirus* isolates are also provided by the present disclosure.

Also provided are isolated antibodies, or antigen-binding fragments thereof, that specifically bind the *Phlebovirus* isolates disclosed herein, or a polypeptide encoded by the *Phlebovirus* isolates.

Methods for detecting a *Phlebovirus*, *Phlebovirus* polypeptide, *Phlebovirus* nucleic acid molecule or *Phlebovirus*-specific antibody in a biological sample are also provided. The present disclosure further provides a method for identifying a subject infected with *Phlebovirus*.

Also provided are recombinant *Phleboviruses*, such as *Phleboviruses* encoding a reporter molecule and/or *Phleboviruses* comprising an attenuating mutation.

Immunogenic compositions comprising a recombinant Phlebovirus or *Phlebovirus* polypeptide and methods of eliciting an immune response against *Phlebovirus* using the immunogenic compositions are also provided by the present disclosure.

Also provided are *Phlebovirus* reverse genetics and mini-genome reporter systems. Further provided is a method of producing *Phlebovirus* pseudo-virus using the mini-genome reporter system.

The foregoing and other objects, features, and advantages of the invention will become more apparent from the following detailed description, which proceeds with reference to the accompanying figures.

BRIEF DESCRIPTION OF THE DRAWINGS

FIG. 1A is a graph showing absolute values of white blood cell count and differential for Patient 1 during hospitalization. The normal limit is indicated with a dotted line. An asterisk denotes when virus was isolated from patient blood.

FIG. 1B is a graph showing absolute values of white blood cell count and differential for Patient 2 during hospitalization. The normal limit is indicated with a dotted line. An asterisk denotes when virus was isolated from patient blood.

FIG. 1C is a graph showing aspartate aminotransferase (AST) and alanine aminotransferase (ALT) levels for Patient 1 and Patient 2 during hospitalization. AST values are the dotted line and ALT values are the solid line. Normal values are indicated with the solid line (ALT) and the dashed line (AST) at the bottom of the graph.

FIG. 1D is a graph showing hematocrit values and platelet counts during hospitalization. Hematocrit values are on the left y-axis and indicated by the two lower lines. Platelet counts are on the right y-axis and indicated by the two upper lines. Patient 1 is indicated with a circle and Patient 2 is indicated with a square. Normal values are indicated by dotted lines at the center of the graph.

FIGS. 3A-3D show phylogenetic analyses of nucleoprotein (FIG. 3A), NSs (FIG. 3B), glycoprotein (FIG. 3C) and polymerase (FIG. 3D) amino acid sequences of representative members of the *Phlebovirus* genus. GenBank™ accession numbers are as follows. Nucleoprotein: Gouleako HQ541736, Uukuniemi M33551, Catch Me Cave EU274384, SFTSV HM745932, Sandfly Sicilian J04418, Massilia EU725773, Sandfly Naples Sabin EF201829, Toscana FJ153286, Punta Toro EF201835, Chandiru HM119409, RFV ZHS501 DQ380149, RFV Entebbe DQ380156, Salobo 578142 EF201815, Salobo 416992 EF201816, Joa EF201819, Frijoles EF201820. Nonstructural NSs: Uukuniemi M33551, SFTSV HM745932, Massilia EU725773, Sandfly Naples Sabin EF201829, Toscana FJ153286, Punta Toro EF201835, Chandiru HM119409, Sandfly Sicilian J04418, RFV ZHS501 DQ380149, RFV Entebbe DQ380156, Salobo 578142 EF201815, Salobo 416992 EF201816, Joa EF201819, Frijoles EF201820. Glycoprotein: Uukuniemi M17417, Massilia EU725772, Toscana EU003180, RFV ZH501 DQ380200, SFTSV HM745931, Punta Toro Adames DQ363407, Chandiru HM119408, Sandfly Sicilian U30500, Punta Toro M11156. Polymerase: RFV ZH501 DQ375406, RFV ZH548 DQ375403, Toscana AR France EF656363, Sandfly Sicilian GQ847513, Uukuniemi D10759, Chandiru HM119407, Massilia EU725771, SFTSV HM745930, Gouleako HQ541738.

FIGS. 4A-4B are tables showing laboratory results of Patient 1 (FIG. 4A) and Patient 2 (FIG. 4B) during hospitalization.

FIGS. 5A-5B are an amino acid alignment of NP from *Phlebovirus* isolate #1 (Mo4), *Phlebovirus* isolate #2 (Mo7) and several different *Phlebovirus* species.

SEQUENCE LISTING

Figure 2:
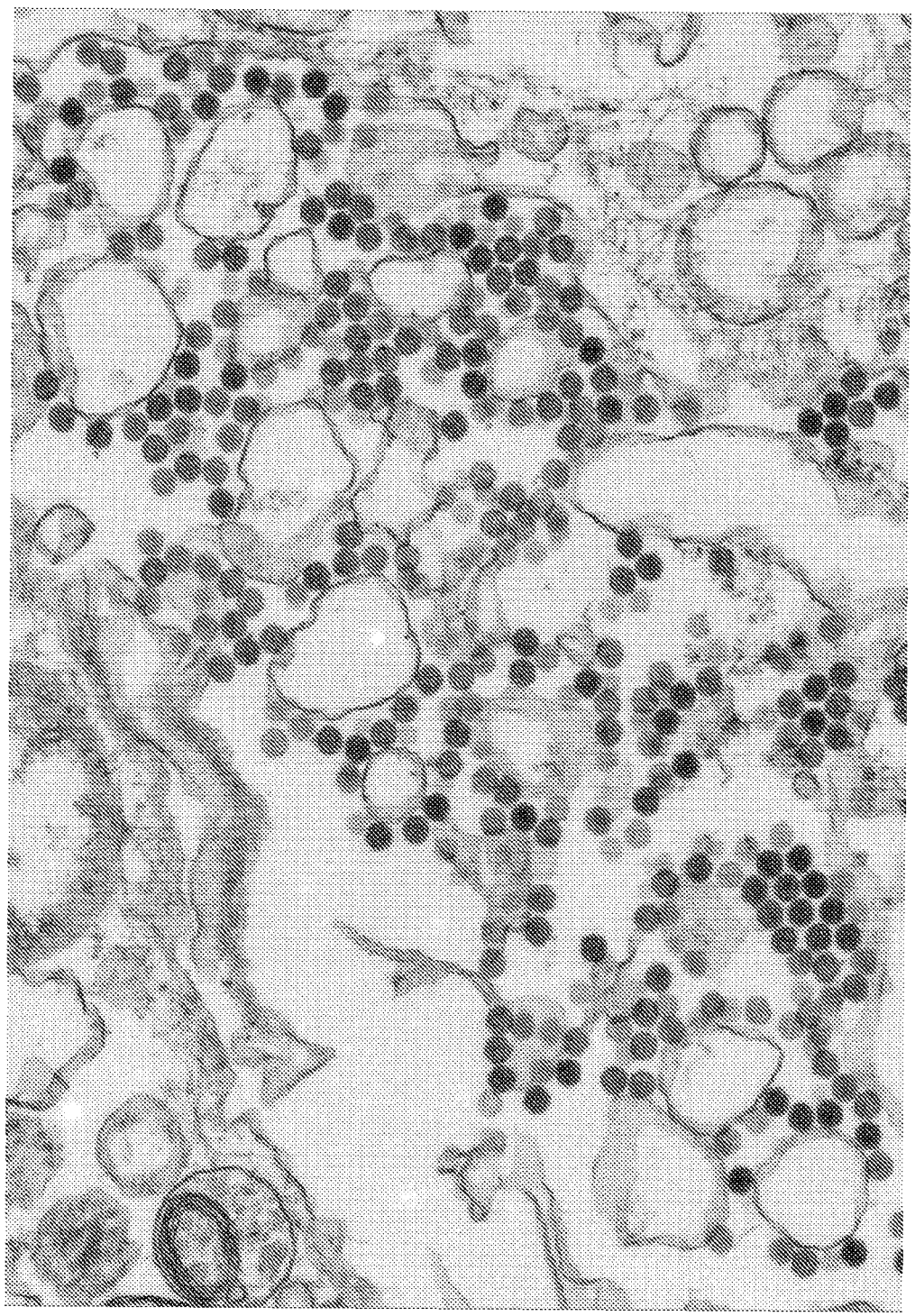
FIG. 2 is a thin section electron microscopy image of infected VeroE6 cells, revealing spherical virion particles averaging 86 nm in diameter.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Sep. 15, 2014, 226 KB, which is incorporated by reference herein. In the accompanying sequence listing:

SEQ ID NO: 1 is the nucleotide sequence of the S segment of *Phlebovirus* isolate #1.

SEQ ID NO: 2 is the nucleotide sequence of the M segment of *Phlebovirus* isolate #1.

SEQ ID NO: 3 is the nucleotide sequence of the L segment of *Phlebovirus* isolate #1.

SEQ ID NO: 4 is the amino acid sequence of the nucleoprotein (NP) of *Phlebovirus* isolate #1.

SEQ ID NO: 5 is the amino acid sequence of the NSs protein of *Phlebovirus* isolate #1.

SEQ ID NO: 6 is the amino acid sequence of the glycoprotein (GP) polyprotein of *Phlebovirus* isolate #1.

SEQ ID NO: 7 is the amino acid sequence of the polymerase protein of *Phlebovirus* isolate #1.

SEQ ID NO: 8 is the nucleotide sequence of the S segment of *Phlebovirus* isolate #2.

SEQ ID NO: 9 is the nucleotide sequence of the M segment of *Phlebovirus* isolate #2.

SEQ ID NO: 10 is the nucleotide sequence of the L segment of *Phlebovirus* isolate #2.

SEQ ID NO: 11 is the amino acid sequence of the nucleoprotein (NP) of *Phlebovirus* isolate #2.

SEQ ID NO: 12 is the amino acid sequence of the NSs protein of *Phlebovirus* isolate #2.

SEQ ID NO: 13 is the amino acid sequence of the glycoprotein (GP) polyprotein of *Phlebovirus* isolate #2.

SEQ ID NO: 14 is the amino acid sequence of the polymerase protein of *Phlebovirus* isolate #2.

SEQ ID NOs: 15-23 are nucleotide sequences of primers and probes used for qRT-PCR.

SEQ ID NO: 24 is the amino acid sequence of NP from Sandfly fever Sicilian virus (SFSV; GenBank™ Accession No. J04418).

SEQ ID NO: 25 is the amino acid sequence of NP from Rift Valley fever virus (RFV) strain ZH-501 (GenBank™ Accession No. DQ380149).

SEQ ID NO: 26 is the amino acid sequence of NP from *Phlebovirus* sp. Be An 578142 (GenBank™ Accession No. EF201815).

SEQ ID NO: 27 is the amino acid sequence of NP from *Phlebovirus* sp. Be An 416992 (GenBank™ Accession No. EF201816).

SEQ ID NO: 28 is the amino acid sequence of NP from *Phlebovirus* sp. Be Ar 371637 (GenBank™ Accession No. EF201820).

SEQ ID NO: 29 is the amino acid sequence of NP from *Phlebovirus* sp. VP161A (GenBank™ Accession No. EF201819).

SEQ ID NO: 30 is the amino acid sequence of NP from Sandfly fever Naples virus Sabin strain (GenBank™ Accession No. EF201829).

SEQ ID NO: 31 is the amino acid sequence of NP from Massilia virus strain W (GenBank™ Accession No. EU725773).

SEQ ID NO: 32 is the amino acid sequence of NP from Toscana virus isolate H/IMTSSA (GenBank™ Accession No. FJ153286).

SEQ ID NO: 33 is the amino acid sequence of NP from Uukuniemi (UUK) virus (GenBank™ Accession No. M33551).

SEQ ID NO: 34 is the amino acid sequence of NP from *Phlebovirus* HB29/China/2010 (GenBank™ Accession No. HM745932), which is also known as severe fever with thrombocytopenia syndrome virus (SFTSV).

SEQ ID NO: 35 is the amino acid sequence of NP (partial) from Gabek Forest virus (GenBank™ Accession No. FJ235927).

SEQ ID NO: 36 is the amino acid sequence of NP from Punta Toro virus (PTV) strain Adames (GenBank™ Accession No. EF201835).

SEQ ID NO: 37 is the amino acid sequence of NP from Rift Valley fever virus (RFV) strain Entebbe (GenBank™ Accession No. DQ380156).

SEQ ID NO: 38 is the amino acid sequence of NP from Chandiru virus (GenBank™ Accession No. HM119409).

SEQ ID NO: 39 is the amino acid sequence of NP (partial) from Rio Grande virus (GenBank™ Accession No. FJ235929).

SEQ ID NO: 40 is the nucleotide sequence of the pcMo4GnGc vector.

SEQ ID NO: 41 is the nucleotide sequence of the pcMo4L vector.

SEQ ID NO: 42 is the nucleotide sequence of the pcMo4NP vector.

SEQ ID NO: 43 is the nucleotide sequence of the pcMo4Morf vector.

SEQ ID NO: 44 is the nucleotide sequence of the pLCK-Mo4Lvc vector.

SEQ ID NO: 45 is the nucleotide sequence of the pLCK-Mo4Mvc vector.

SEQ ID NO: 46 is the nucleotide sequence of the pLCK-Mo4Svc vector.

SEQ ID NO: 47 is the nucleotide sequence of the pLCK-Mo4SvcDelNSs_GLuc vector.

SEQ ID NO: 48 is the nucleotide sequence of the pLCK-Mo4M_EGFPBlastNeg vector.

SEQ ID NO: 49 is the nucleotide sequence of the pLCK-Mo7Lvc vector.

SEQ ID NO: 50 is the nucleotide sequence of the pLCK-Mo7Mvc vector.

SEQ ID NO: 51 is the nucleotide sequence of the pLCK-Mo7Svc vector.

SEQ ID NOs: 52 and 53 are primer sequences.

DETAILED DESCRIPTION

I. Abbreviations
ALT alanine aminotransferase
AST aspartate aminotransferase
cDNA complementary DNA
GP glycoprotein
HRTLV Heartland virus
NGS next generation sequencing
NP nucleoprotein
NS non-structural
ORF open reading frame
qRT-PCR quantitative reverse transcriptase polymerase chain reaction
RVF Rift Valley fever
SFTSV severe fever with thrombocytopenia syndrome virus
UUK Uukuniemi virus II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adjuvant: A substance or vehicle that non-specifically enhances the immune response to an antigen. Adjuvants can include a suspension of minerals (alum, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207,646; 6,214,806; 6,218, 371; 6,239,116; 6,339,068; 6,406,705; and 6,429,199). Adjuvants also include biological molecules, such as costimulatory molecules. Exemplary biological adjuvants include IL-2, RANTES, GM-CSF, TNF-α, IFN-γ, G-CSF, LFA-3, CD72, B7-1, B7-2, OX-40L and 41 BBL.

Administer: To give, apply or bring the composition into contact with the subject. Administration can be accomplished by any of a number of routes, such as, for example, topical, oral, intranasal, subcutaneous, intramuscular, intraperitoneal, intravenous and intrathecal.

Ambisense: Refers to a genome or genomic segments having both positive sense and negative sense portions. For example, the S segment of a *Phlebovirus* is ambisense, encoding nucleoprotein (NP) in the negative sense and the non-structural protein (NSs) in the positive sense.

Antibody: A polypeptide ligand comprising at least a light chain or heavy chain immunoglobulin variable region which specifically recognizes and binds an epitope of an antigen. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Antibodies include intact immunoglobulins and the variants and portions of antibodies well known in the art, such as Fab fragments, Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook*, 1994-1995 (Pierce Chemical Co., Rockford, Ill.); Kuby, J., *Immunology*, 3$^{rd}$ Ed., W. H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Each heavy and light chain contains a constant region and a variable region (the regions are also known as "domains"). References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs (which generally confer antigen binding) from another species, such as a murine antibody.

A "humanized" immunoglobulin is an immunoglobulin including a human framework region and one or more complementarity determining regions (CDRs) from a non-human (for example a mouse, rat, or synthetic) immunoglobulin. The non-human immunoglobulin providing the CDRs is termed a "donor," and the human immunoglobulin providing the framework is termed an "acceptor." Generally, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. Humanized immunoglobulins can be constructed by means of genetic engineering (see for example, U.S. Pat. No. 5,585,089).

A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. All parts of a human immunoglobulin are substantially identical to corresponding parts of natural human immunoglobulin sequences.

Antigen: A compound, composition, or substance that can stimulate the production of antibodies or a T-cell response in an animal, including compositions that are injected or absorbed into an animal. An antigen reacts with the products of specific humoral or cellular immunity.

Anti-genomic: As used herein, "anti-genomic" refers to a genomic segment of a *Phlebovirus* in the orientation opposite to the viral genome. For example, *Phleboviruses* are negative-sense RNA viruses. Thus, "anti-genomic" refers to the positive-sense orientation (or virus complementary sense), while "genomic" refers to the negative-sense orientation of a gene segment.

Attenuated: In the context of a live virus, the virus is attenuated if its ability to infect a cell or subject and/or its ability to produce disease is reduced (for example, eliminated) compared to a wild-type virus. Typically, an attenuated virus retains at least some capacity to elicit an immune response following administration to an immunocompetent subject. In some cases, an attenuated virus is capable of eliciting a protective immune response without causing any signs or symptoms of infection. In some embodiments, the ability of an attenuated virus to cause disease in a subject is reduced at least about 10%, at least about 25%, at least about 50%, at least about 75% or at least about 90% relative to wild-type virus. Accordingly, an "attenuating mutation" is a mutation in the viral genome and/or an encoded polypeptide that results in an attenuated virus.

Biological sample: A sample obtained from a subject (such as a human or veterinary subject). Biological samples, include, for example, fluid, cell and/or tissue samples. In some embodiments herein, the biological sample is a fluid sample. Fluid samples include, but are not limited to, serum, blood, plasma, urine, feces, saliva, cerebral spinal fluid (CSF) or other bodily fluid. Biological samples can also refer to cells or tissue samples, such as biopsy samples, tissue sections or isolated leukocytes.

Contacting: Placement in direct physical association; includes both in solid and liquid form. "Contacting" is often used interchangeably with "exposed." In some cases, "contacting" includes transfecting, such as transfecting a nucleic acid molecule into a cell. In other examples, "contacting" refers to incubating a molecule (such as an antibody) with a biological sample.

Fluorophore: A chemical compound, which when excited by exposure to a particular wavelength of light, emits light (i.e., fluoresces), for example at a different wavelength. In some embodiments herein, a probe is labeled with a fluorophore, such as at the 5' end of the probe. Probes used for real-time PCR assays typically include a fluorophore and a quencher. Fluorophores suitable for use with real-time PCR assays, such as TaqMan™ PCR, include, but are not limited to, 6-carboxyfluorescein (FAM), tetrachlorofluorescein (TET), tetramethylrhodamine (TMR), hexachlorofluorescein (HEX), JOE, ROX, CAL Fluor™, Pulsar™, Quasar™, Texas Red™, Cy™3 and Cy™5.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are discussed by Sambrook et al. (ed.), *Molecular Cloning: A Laboratory Manual,* $2^{nd}$ ed., vol. 1-3, Cold Spring Harbor Laboratory Press, Cold Spring Harbor, N.Y., 1989, chapters 9 and 11; and Ausubel et al. *Short Protocols in Molecular Biology,* $4^{th}$ ed., John Wiley & Sons, Inc., 1999.

For purposes of the present disclosure, "stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize.

"Specific hybridization" refers to the binding, duplexing, or hybridizing of a molecule only or substantially only to a particular nucleotide sequence when that sequence is present in a complex mixture (for example, total cellular DNA or RNA). Specific hybridization may also occur under conditions of varying stringency.

Immune response: A response of a cell of the immune system, such as a B-cell, T-cell, macrophage or polymorphonucleocyte, to a stimulus such as an antigen. An immune response can include any cell of the body involved in a host defense response, including for example, an epithelial cell that secretes an interferon or a cytokine. An immune response includes, but is not limited to, an innate immune response or inflammation. As used herein, a protective immune response refers to an immune response that protects a subject from infection (prevents infection or prevents the development of disease associated with infection).

Immunogen: A compound, composition, or substance which is capable, under appropriate conditions, of stimulating an immune response, such as the production of antibodies or a T-cell response in an animal, including compositions that are injected or absorbed into an animal. As used herein, an "immunogenic composition" is a composition comprising an immunogen.

Immunize: To render a subject protected from an infectious disease, such as by vaccination.

Isolated: An "isolated" biological component (such as a nucleic acid, protein or virus) has been substantially separated or purified away from other biological components (such as cell debris, or other proteins or nucleic acids). Biological components that have been "isolated" include those components purified by standard purification methods. The term also embraces recombinant nucleic acids, proteins or viruses, as well as chemically synthesized nucleic acids or peptides.

Oligonucleotide: A short nucleic acid polymer. Oligonucleotides are generally less than 100 nucleotides in length. In some embodiments herein, the oligonucleotide is 8-100, 10-50, 12-40, 16-30 or 18-24 nucleotides in length. In particular examples, the oligonucleotide is 12, 13, 14, 15, 16, 17, 18, 19, 20, 21, 22, 23, 24, 25, 26, 27, 28, 29 or 30 nucleotides in length.

ORF (open reading frame): A series of nucleotide triplets (codons) coding for amino acids without any termination codons. These sequences are usually translatable into a peptide.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carrier: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds or molecules, such as one or more recombinant *Phleboviruses*, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

*Phlebovirus*: One of five genera of the Bunyaviridae family. *Phleboviruses* are enveloped spherical viruses with icosahedral symmetry. The genome of *Phleboviruses* consists of three single-stranded RNA genome segments—small (S), medium (M) and large (L). The M and L segments are negative sense RNA strands, while the S segment is ambisense RNA. The S segment encodes the non-structural protein NSs in the positive sense orientation and the nucleoprotein (NP) in the negative sense orientation. The M segment encodes the glycoprotein precursor that is cleaved by host proteases into two structural domains—Gn and Gc. The L segment encodes the L protein, which functions as the RNA dependent RNA polymerase in primary and secondary transcription to generate mRNA and replicative intermediates, respectively. *Phleboviruses* have a worldwide distribution and are transmitted by a wide variety of arthropods, including sandflies, mosquitoes and ticks. Several *Phleboviruses* have been linked to human disease, in some cases causing febrile illness, fever, hepatitis, meningitis, encephalitis or hemorrhagic syndrome.

Polypeptide: A polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced. The term "residue" or "amino acid residue" includes reference to an amino acid that is incorporated into a protein, polypeptide, or peptide.

Conservative amino acid substitutions are those substitutions that, when made, least interfere with the properties of the original protein, that is, the structure and especially the function of the protein is conserved and not significantly changed by such substitutions. Examples of conservative substitutions are shown below.

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |

-continued

| Original Residue | Conservative Substitutions |
|---|---|
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Probes and primers: A probe comprises an isolated nucleic acid molecule attached to a detectable label or other reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, for example, in Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989 and Ausubel et al. *Short Protocols in Molecular Biology*, $4^{th}$ ed., John Wiley & Sons, Inc., 1999.

Primers are short nucleic acid molecules, for instance DNA oligonucleotides 10 nucleotides or more in length, for example that hybridize to contiguous complementary nucleotides or a sequence to be amplified. Longer DNA oligonucleotides may be about 12, 15, 18, 20, 25, 30, or 50 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, for example, by the polymerase chain reaction (PCR) or other nucleic-acid amplification methods known in the art. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification; gap filling ligase chain reaction amplification, as disclosed in U.S. Pat. No. 5,427,930; and NASBA™ RNA transcription-free amplification, as disclosed in U.S. Pat. No. 6,025,134.

Methods for preparing and using nucleic acid probes and primers are described, for example, in Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989; Ausubel et al. *Short Protocols in Molecular Biology*, $4^{th}$ ed., John Wiley & Sons, Inc., 1999; and Innis et al. *PCR Protocols, A Guide to Methods and Applications*, Academic Press, Inc., San Diego, Calif., 1990. Amplification primer pairs can be derived from a known sequence, for example, by using computer programs intended for that purpose such as Primer (Version 0.5, © 1991, Whitehead Institute for Biomedical Research, Cambridge, Mass.).

Quencher: A substance that absorbs excitation energy from a fluorophore when in close proximity. Probes used for real-time PCR assays, such as TaqMan™ PCR, typically include a fluorophore and a quencher. Quenchers suitable for use with real-time PCR assays include, but are not limited to, ZEN™, Iowa Black™ FQ, tetramethylrhodamine (TAMRA), black hole quencher (BHQ)1, BHQ2, BHQ3 and 4-(4'-dimethylaminophenylazo)benzoic acid (DABCYL). In some examples, a probe contains two quenchers. In one non-limiting example, the probe contains both ZEN™ and Iowa Black™ FQ.

Recombinant: A recombinant nucleic acid, protein or virus is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, for example, by genetic engineering techniques. For example, a recombinant *Phlebovirus* can be generated using a reverse genetics system. In some examples, the recombinant *Phleboviruses* comprise one or more deletions in a viral virulence factor, such as NSs. In other examples, the recombinant RVF viruses comprise a heterologous gene, such as a reporter gene.

Reporter gene: A reporter gene is a gene operably linked to another gene or nucleic acid sequence of interest (such as a promoter sequence). Reporter genes are used to determine whether the gene or nucleic acid of interest is expressed in a cell or has been activated in a cell. Reporter genes typically have easily identifiable characteristics, such as fluorescence, or easily assayed products, such as an enzyme. Reporter genes can also confer antibiotic resistance to a host cell or tissue. Reporter genes include, for example, GFP (or eGFP) or other fluorescence genes, luciferase, β-galactosidase and alkaline phosphatase.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a given gene or protein will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237-244, 1988; Higgins and Sharp, *CABIOS* 5:151-153, 1989; Corpet et al., *Nucleic Acids Research* 16:10881-10890, 1988; and Pearson and Lipman, *Proc. Natl. Acad. Sci. U.S.A.* 85:2444, 1988. Altschul et al., *Nature Genet.* 6:119-129, 1994.

The NCBI Basic Local Alignment Search Tool (BLAST™) (Altschul et al., *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx.

In some embodiments herein, provided are nucleotide or amino acid sequences at least 80%, at least 85%, at least 90%, at least 95%, at least 96%, at least 97%, at least 98% or at least 99% identical to any one of SEQ ID NOs: 1-51.

Subject: Living multi-cellular vertebrate organisms, a category that includes both human and non-human mammals.

Therapeutically effective amount: A quantity of a specified agent sufficient to achieve a desired effect in a subject being treated with that agent. For example, this may be the amount of a recombinant *Phlebovirus* useful for eliciting an immune response in a subject and/or for preventing infection by *Phlebovirus*. Ideally, in the context of the present disclosure, a therapeutically effective amount of a recombinant *Phlebovirus* is an amount sufficient to increase resistance to, prevent, ameliorate, and/or treat infection caused by *Phlebovirus* in a subject without causing a substantial cytotoxic effect in the subject. The effective amount of a recombinant *Phlebovirus* useful for increasing resistance to, preventing, ameliorating, and/or treating infection in a subject will be dependent on, for example, the subject being treated, the manner of administration of the therapeutic composition and other factors.

Vaccine: A preparation of immunogenic material capable of stimulating an immune response, administered for the prevention, amelioration, or treatment of infectious or other types of disease. The immunogenic material may include attenuated or killed microorganisms (such as attenuated viruses), or antigenic proteins, peptides or DNA derived from them. Vaccines may elicit both prophylactic (preventative) and therapeutic responses. Methods of administration vary according to the vaccine, but may include inoculation, ingestion, inhalation or other forms of administration. Inoculations can be delivered by any of a number of routes, including parenteral, such as intravenous, subcutaneous or intramuscular. Vaccines may be administered with an adjuvant to boost the immune response.

Vector: A nucleic acid molecule as introduced into a host cell, thereby producing a transformed host cell. A vector may include nucleic acid sequences that permit it to replicate in a host cell, such as an origin of replication (DNA sequences that participate in initiating DNA synthesis). A vector may also include one or more selectable marker genes and other genetic elements known in the art.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. All GenBank™ Accession numbers are incorporated by reference herein as they appear in the database on Feb. 29, 2012. In case of conflict, the present specification, including explanations of terms, will control. In addition, the materials, methods, and examples are illustrative only and not intended to be limiting.

III. Overview of Several Embodiments

Disclosed herein is the discovery of a new member of the genus *Phlebovirus* (family Bunyaviridae) with a proposed name of Heartland virus (HRTLV). HRTLV is associated with severe febrile illness following tick bite. Described are the clinical and laboratory characteristics of two patients bitten by ticks and infected with HRTLV. In particular, provided herein are the complete nucleotide sequences of all three genome segments of two *Phlebovirus* isolates, as well as the amino acid sequences of the proteins encoded by each isolate, including the NP, GP, NSs and polymerase (L) proteins. Oligonucleotides, such as primers and probes, that specifically hybridize with the *Phlebovirus* isolates, and antibodies specific for the *Phlebovirus* proteins are further provided. Also provided are diagnostic and detection assays using the *Phlebovirus* nucleic acid molecules, proteins, probes, primers and antibodies. Further provided are recombinant *Phleboviruses*, such as recombinant *Phleboviruses* lencoding a reporter molecule and/or comprising an attenuating mutation, and their use for eliciting an immune response in a subject. Also provided are reverse genetics and mini-genome reporters systems using plasmids containing nucleic acid sequence derived from the *Phlebovirus* isolates.

In some embodiments, infection with a *Phlebovirus* disclosed herein is associated with recent tick bite and/or one or more of the following clinical features: thrombocytopenia, leukopenia, fever, and decreased calcium level. In some embodiments, the *Phlebovirus* disclosed herein has an average viral particle diameter of approximately 80-90 nm, such as about 86 nm.

A. *Phlebovirus* Isolates, Nucleic Acid Molecules and Polypeptides

Provided herein are isolated *Phleboviruses* comprising an S segment, an M segment and an L segment at least 80% identical to the *Phlebovirus* isolates disclosed herein. In some embodiments, the nucleotide sequence of the S segment is at least 80%, at least 85%, at least 90%, at least 95%, at least 96%, at least 97%, at least 98% or at least 99% identical to SEQ ID NO: 1 or SEQ ID NO: 8; the nucleotide sequence of the M segment is at least 80%, at least 85%, at least 90%, at least 95%, at least 96%, at least 97%, at least 98% or at least 99% identical to SEQ ID NO: 2 or SEQ ID NO: 9; the nucleotide sequence of the L segment is at least 80%, at least 85%, at least 90%, at least 95%, at least 96%, at least 97%, at least 98% or at least 99% identical to SEQ ID NO: 3 or SEQ ID NO: 10; or any combination thereof.

In some examples, the nucleotide sequence of the S segment comprises or consists of SEQ ID NO: 1 or SEQ ID NO: 8; the nucleotide sequence of the M segment comprises or consists of SEQ ID NO: 2 or SEQ ID NO: 9; the nucleotide sequence of the L segment comprises or consists of SEQ ID NO: 3 or SEQ ID NO: 10; or any combination thereof.

In particular non-limiting examples, the S segment comprises or consists of SEQ ID NO: 1, the M segment comprises or consists of SEQ ID NO: 2 and the L segment comprises or consists of SEQ ID NO: 3; or the S segment comprises or consists of SEQ ID NO: 8, the M segment comprises or consists of SEQ ID NO: 9 and the L segment comprises or consists of SEQ ID NO: 10.

Further provided are isolated polypeptides encoded by a *Phlebovirus* disclosed herein. In some embodiments, the amino acid sequence of the *Phlebovirus*-encoded polypeptide is at least 80%, at least 85%, at least 90%, at least 95%, at least 96%, at least 97%, at least 98% or at least 99% identical to SEQ ID NO: 4, 5, 6, 7, 11, 12, 13 or 14. In particular examples, the amino acid sequence of the *Phlebovirus* polypeptide comprises or consists of SEQ ID NO: 4, 5, 6, 7, 11, 12, 13 or 14.

Also provided are isolated polypeptides, wherein the amino acid sequence of the polypeptide is at least 80%, at least 85%, at least 90%, at least 95%, at least 96%, at least 97%, at least 98% or at least 99% identical to SEQ ID NO: 4, 5, 6, 7, 11, 12, 13 or 14. In some embodiments, the amino acid sequence of the polypeptide comprises or consists of SEQ ID NO: 4, 5, 6, 7, 11, 12, 13 or 14.

Further provided are isolated nucleic acid molecules. In some embodiments, the nucleotide sequence of the nucleic acid molecule is at least 80%, at least 85%, at least 90%, at least 95%, at least 96%, at least 97%, at least 98% or at least 99% identical to SEQ ID NO: 1, 2, 3, 8, 9, or 10. In some examples, the nucleotide sequence of the nucleic acid molecule comprises or consists of SEQ ID NO: 1, 2, 3, 8, 9, or 10.

Vectors comprising any of the nucleic acid molecules disclosed herein are further provided by the present disclosure. The vector can be any suitable vector, such as a plasmid vector or a viral vector. In some embodiments, the vector comprises a promoter, an origin of replication and/or a selectable marker. In some examples, the nucleic acid molecule of the vector is operably linked to a promoter. Also provided are host cells comprising such vectors.

Also provided are oligonucleotides that specifically hybridize with a *Phlebovirus* nucleic acid molecule. Oligonucleotides are generally less than 100 nucleotides in length. In some embodiments, the oligonucleotide is less than 80, less than 60, less than 40 or less than 30 nucleotides in length. In other embodiments, the oligonucleotide is 8-100, 10-50, 12-40, 16-30 or 18-24 nucleotides in length. In particular examples, the oligonucleotide is 12, 13, 14, 15, 16, 17, 18, 19, 20, 21, 22, 23, 24, 25, 26, 27, 28, 29 or 30 nucleotides in length. In one non-limiting example, the oligonucleotide is 12 to 40 nucleotides in length. In another non-limiting example, the oligonucleotide is 18 to 24 nucleotides in length.

In some embodiments, the oligonucleotide is at least 85%, at least 90%, at least 95%, at least 96%, at least 97%, at least 98% or at least 99% identical to SEQ ID NO: 15, 16, 17, 18, 19, 20, 21, 22 or 23. In some examples, the nucleotide sequence of the oligonucleotide comprises or consists of SEQ ID NO: 15, 16, 17, 18, 19, 20, 21, 22 or 23.

In some embodiments, the oligonucleotide comprises a fluorophore. Numerous fluorophores are known in the art and an appropriate fluorophore can be selected by a skilled artisan based on the intended use of the oligonucleotide. As one example, for real-time PCR assays, such as TaqMan™ PCR, exemplary fluorophores include, but are not limited to, FAM, TET, TMR, HEX, JOE, ROX, CAL Fluor™, Pulsar™, Quasar™, Texas Red™, Cy™ 3 and Cy™ 5.

In some embodiments, the oligonucleotide comprises a quencher. In some instances, the oligonucleotide comprises more than one quencher, such as two quenchers. A suitable quencher (or quenchers) can be selected by one of skill in the art depending on the intended purpose of the oligonucleotide. As one example, for real-time PCR assays, such as TaqMan™ PCR, exemplary quenchers include, but are not limited to, ZEN™, Iowa Black™ FQ, TAMRA, BHQ1, BHQ2, BHQ3 and DABCYL. In some examples, the oligonucleotide includes two quenchers, such as ZEN™ and Iowa Black™ FQ.

In one non-limiting example, the oligonucleotide, such as when the oligonucleotide will be used as a probe, comprises a fluorophore and a quencher. In another non-limiting example, the oligonucleotide comprises a fluorophore and two quenchers.

B. *Phlebovirus*-Specific Antibodies

Provided herein are isolated antibodies, or antigen-binding fragments thereof, that specifically bind to the *Phlebovirus* isolates and/or the *Phlebovirus* polypeptides disclosed herein. In some embodiments, the antibody is a polyclonal antibody. In other embodiments, the antibody is a monoclonal antibody.

In some embodiments, the antibody or antigen-binding fragment thereof specifically binds an epitope of a *Phlebovirus* virion, and can thus detect virus particles. In some embodiments, the antibody or antigen-binding fragment thereof specifically binds a linear epitope, or conformational epitope, or both, of a *Phlebovirus* polypeptide.

In some embodiments, the antibody or antigen-binding fragment thereof specifically binds to a NSs, NP, GP or L protein of *Phlebovirus*. In particular examples, the antibody or antigen-binding fragment thereof specifically binds a polypeptide that is at least 80%, at least 85%, at least 90%, at least 95%, at least 96%, at least 97%, at least 98% or at least 99% identical to SEQ ID NO: 4, 5, 6, 7, 11, 12, 13 or 14. In other particular examples, the antibody or antigen-binding fragment thereof specifically binds a polypeptide with an amino acid sequence comprising or consisting of SEQ ID NO: 4, 5, 6, 7, 11, 12, 13 or 14.

In some embodiments, the antigen-binding fragment is an Fab, Fab', F(ab')$_2$ scFv or dsFv. In some embodiments, the antibodies are mouse, rat or rabbit antibodies. In other embodiments, the antibodies are humanized antibodies or fully human antibodies. In other embodiments, the antibodies are chimeric antibodies.

Methods of generating monoclonal and polyclonal antibodies are well known in the art and are described in section IV below.

C. Methods for the Diagnosis and Detection of *Phlebovirus*

The isolation and sequencing of the *Phlebovirus* isolates disclosed herein has enabled the development of a series of assays that can be used for the detection of a *Phlebovirus* in a biological sample and/or the diagnosis of a *Phlebovirus* infection in a subject.

Provided herein is a method for detecting a *Phlebovirus* or *Phlebovirus* polypeptide in a biological sample using a Phlebovirus-specific antibody disclosed herein. In some embodiments, the method includes contacting the biological sample with a *Phlebovirus*-specific antibody, or antigen-binding fragment thereof; and detecting binding of the antibody or antigen-binding fragment to the biological sample. Binding of the antibody or antigen-binding fragment to the biological sample indicates the presence of the *Phlebovirus* or the *Phlebovirus* polypeptide in the biological sample.

In some embodiments of the detection method, the antibody or antigen-binding fragment thereof specifically binds to a NSs, NP, GP or L protein of *Phlebovirus*. In particular examples, the antibody or antigen-binding fragment thereof specifically binds a polypeptide that is at least 80%, at least 85%, at least 90%, at least 95%, at least 96%, at least 97%, at least 98% or at least 99% identical to SEQ ID NO: 4, 5, 6, 7, 11, 12, 13 or 14. In other particular examples, the antibody or antigen-binding fragment thereof specifically binds a polypeptide with an amino acid sequence comprising or consisting of SEQ ID NO: 4, 5, 6, 7, 11, 12, 13 or 14.

Also provided is a method for detecting *Phlebovirus*-specific antibodies in a biological sample using the *Phlebovirus* polypeptides disclosed herein. In some embodiments, the method includes contacting the biological sample with a

*Phlebovirus*-specific polypeptide; and detecting binding of the polypeptide to the biological sample. Binding of the polypeptide to the biological sample indicates the presence of the *Phlebovirus*-specific antibodies in a biological sample.

In some embodiments of the detection method, the *Phlebovirus* polypeptide is a NSs, NP, GP or L protein. In particular examples, the amino acid sequence of the *Phlebovirus* polypeptide is at least 80%, at least 85%, at least 90%, at least 95%, at least 96%, at least 97%, at least 98% or at least 99% identical to SEQ ID NO: 4, 5, 6, 7, 11, 12, 13 or 14. In other particular examples, the amino acid sequence of the *Phlebovirus* polypeptide comprises or consists of SEQ ID NO: 4, 5, 6, 7, 11, 12, 13 or 14.

Detection assays based on binding of a polypeptide to an antibody are well known in the art and include, for example, ELISA, Western blot, fluorescence activated cell sorting (FACS), radioimmunoassay and immunohistochemistry. As is well known to one of skill in the art, in some cases the detection assay further includes the step of contacting an antigen-antibody complex with a detection reagent, such as a labeled secondary antibody (e.g., an anti-isotype antibody, such as an anti-IgG antibody), or in the case of a sandwich ELISA, a second antibody that recognizes the same antigen as the first antibody and is labeled for detection. Secondary antibodies can also be conjugated to magnetic beads to allow for magnetic sorting. In other cases, the primary antibody is directly labeled. Directly labeled antibodies can be used for a variety of detection assays, such as FACS.

Further provided is a method for detecting a *Phlebovirus* nucleic acid molecule in a biological sample using an oligonucleotide probe specific for the *Phlebovirus* nucleic acid molecules disclosed herein. In some embodiments, the method includes contacting the biological sample with an oligonucleotide probe that specifically hybridizes with a *Phlebovirus* nucleic acid molecule; and detecting hybridization of the probe with the biological sample. Hybridization of the probe to the biological sample indicates the presence of the *Phlebovirus* nucleic acid molecule in the biological sample.

In some embodiments, the biological sample is a nucleic acid amplification product obtained by a method comprising isolating RNA from the biological sample; reverse transcribing the RNA to generate cDNA; and amplifying the cDNA using a pair of primers that specifically hybridize to a *Phlebovirus* nucleic acid molecule, thereby producing a nucleic acid amplification product.

Also provided is a method for identifying a subject infected with a *Phlebovirus* using a pair of primers that specifically hybridize with a *Phlebovirus* nucleic acid molecule disclosed herein. In some embodiments, the method includes isolating RNA from a biological sample obtained from the subject; reverse transcribing the RNA to generate cDNA; amplifying the cDNA using a pair of primers that specifically hybridize to a *Phlebovirus* nucleic acid molecule; and detecting an amplification product. Detection of the amplification product identifies the subject as infected with the *Phlebovirus*.

In some embodiments of the nucleic acid-based detection methods, the nucleotide sequence of the *Phlebovirus* nucleic acid molecule is at least 80%, at least 85%, at least 90%, at least 95%, at least 96%, at least 97%, at least 98% or at least 99% identical to SEQ ID NO: 1, 2, 3, 8, 9, or 10. In some examples, the nucleotide sequence of the *Phlebovirus* nucleic acid molecule comprises or consists of SEQ ID NO: 1, 2, 3, 8, 9, or 10.

In some embodiments of the nucleic acid-based detection methods, the pair of primers comprises: (i) a first primer having a nucleotide sequence at least 85%, at least 90% or at least 95% identical to SEQ ID NO: 16 and a second primer having a nucleotide sequence at least 85%, at least 90% or at least 95% identical to SEQ ID NO: 17; (ii) a first primer having a nucleotide sequence comprising or consisting of SEQ ID NO: 16 and a second primer having a nucleotide sequence comprising or consisting of SEQ ID NO: 17; (iii) a first primer having a nucleotide sequence at least 85%, at least 90% or at least 95% identical to SEQ ID NO: 19 and a second primer having a nucleotide sequence at least 85%, at least 90% or at least 95% identical to SEQ ID NO: 20; (iv) a first primer having a nucleotide sequence comprising or consisting of SEQ ID NO: 19 and a second primer having a nucleotide sequence comprising or consisting of SEQ ID NO: 20; (v) a first primer having a nucleotide sequence at least 85%, at least 90% or at least 95% identical to SEQ ID NO: 22 and a second primer having a nucleotide sequence at least 85%, at least 90% or at least 95% identical to SEQ ID NO: 23; or (iv) a first primer having a nucleotide sequence comprising or consisting of SEQ ID NO: 22 and a second primer having a nucleotide sequence comprising or consisting of SEQ ID NO: 23.

In some embodiments, detecting the amplification product comprises hybridizing the amplification product to a probe. In some examples, the probe comprises a nucleotide sequence at least 85%, at least 90% or at least 95% identical to SEQ ID NO: 15, SEQ ID NO: 18 or SEQ ID NO: 21. In particular non-limiting examples, the probe comprises a nucleotide sequence comprising or consisting of SEQ ID NO: 15, SEQ ID NO: 18 or SEQ ID NO: 21.

In some embodiments, the probe comprises a fluorophore, a quencher or both. In one non-limiting example, the probe comprises a fluorophore and two quenchers.

Methods of detecting specific nucleic acid molecules in a sample using polymerase chain reaction (PCR) are well known in the art. In some embodiments, the PCR detection method is a real-time PCR method, such as TaqMan™ PCR. TaqMan™ PCR assays typically use self-quenching probes, and in some cases, include a fluorophore and two quenchers. In some instances when a probe contains two quenchers, a first quencher is placed at the 3' end of the probe and a second quencher is inserted into the oligonucleotide, such as by using a linker. The fluorophore is typically placed at the 5' end of the oligonucleotide probe. During the annealing phase of each PCR cycle, the primers and double-quenched probe both bind complementary sections of the DNA. During the elongation phase, polymerization of the new DNA strand is initiated from the primers. Once the polymerase reaches the bound probe, its 5' to 3' exonuclease activity degrades the probe, thereby physically separating the quencher from the fluorophore. As a result, fluorescence can be measured and will increase in real-time with the exponential increase in PCR product.

In some embodiments of the detection and diagnosis assays, the method further includes the step of obtaining a biological sample from a subject. In some examples, the sample is obtained directly from the subject and used in one of the above-described assays. In other examples, the sample is obtained indirectly without directly removing the biological sample from the subject. In some cases where the sample is obtained indirectly, the sample is obtained from, for example, a clinician or laboratory personnel.

In some embodiments, the biological sample is a cell or tissue sample, such as a biopsy sample, bone marrow aspirate or isolated leukocytes. In other embodiments, the biological sample is a bodily fluid sample. In some examples, the bodily fluid sample comprises serum, blood, plasma, urine, feces, saliva or cerebral spinal fluid.

D. Recombinant *Phleboviruses*

Further provided herein are recombinant *Phleboviruses*. In some embodiments, the genome of the recombinant *Phlebovirus* comprises an S segment having a nucleotide sequence at least 85%, at least 90%, at least 95%, at least 96%, at least 97%, at least 98% or at least 99% identical to SEQ ID NO: 1 or SEQ ID NO: 8; an M segment having a nucleotide sequence at least 85%, at least 90%, at least 95%, at least 96%, at least 97%, at least 98% or at least 99% identical to SEQ ID NO: 2 or SEQ ID NO: 9; and an L segment having a nucleotide sequence at least 85%, at least 90%, at least 95%, at least 96%, at least 97%, at least 98% or at least 99% identical to SEQ ID NO: 3 or SEQ ID NO: 10.

In some examples, the recombinant *Phlebovirus* comprises a deletion, such as a deletion of the NSs open reading frame (ORF). In particular examples, the deleted ORF is replaced with a reporter gene, such as a gene encoding a fluorescent protein or an antibiotic resistance gene.

In some examples, the recombinant *Phlebovirus* comprises at least one attenuating mutation. The attenuating mutation can be any insertion, deletion or substitution that results in a decrease in virus infectivity or virus-induced disease. The attenuating mutation can be in any of the gene segments and/or viral proteins. In some examples, the attenuating mutation results in an alteration or deletion of a virulence protein, such as NSs.

Recombinant *Phleboviruses* can be generated, for example, using a reverse genetics system. Reverse genetics systems for *Phleboviruses* are known in the art and are described in PCT Publication No. WO 2009/082647 and U.S. Pat. No. 8,084,248. An exemplary reverse genetics system is also described below and in Example 3.

E. Reverse Genetics System

Provided herein is a reverse genetics system for producing recombinant *Phlebovirus*, comprising a first plasmid that contains an anti-genomic copy of an S segment, a second plasmid that contains an anti-genomic copy of an M segment and a third plasmid that contains an anti-genomic copy of an L segment, wherein each plasmid comprises a T7 promoter and a hepatitis delta virus ribozyme. In some embodiments, the nucleotide sequence of the first plasmid is at least 90%, at least 95%, at least 96%, at least 97%, at least 98% or at least 99% identical to SEQ ID NO: 46 (pLCK-Mo4Svc), SEQ ID NO: 47 (pLCK-Mo4SvcDelNSs_GLuc) or SEQ ID NO: 51 (pLCK-Mo7Svc); or comprises or consists of the nucleotide sequence of SEQ ID NO: 46, SEQ ID NO: 47 or SEQ ID NO: 51. In some embodiments, the nucleotide sequence of the second plasmid is at least 90%, at least 95%, at least 96%, at least 97%, at least 98% or at least 99% identical to SEQ ID NO: 45 (pLCK-Mo4Mvc), SEQ ID NO: 48 (pLCK-Mo4M_EGFPBlastNeg) or SEQ ID NO: 50 (pLCK-Mo7Mvc), or comprises or consists of the nucleotide sequence of SEQ ID NO: 45, SEQ ID NO: 48 or SEQ ID NO: 50. In some embodiments, the nucleotide sequence of the third plasmid is at least 90%, at least 95%, at least 96%, at least 97%, at least 98% or at least 99% identical to SEQ ID NO: 44 (pLCK-Mo4Lv) or SEQ ID NO: 49 (pLCK-Mo7Lvc), or comprises or consists of the nucleotide sequence of SEQ ID NO: 44 or SEQ ID NO: 49.

Also provided are nucleic acid molecules comprising an anti-genomic copy of the L, M or S segment of *Phlebovirus* isolate #1 (Mo4) or *Phlebovirus* isolate #2 (Mo7), or a modified version thereof. In some embodiments, the nucleic acid molecule comprises a nucleotide sequence that is at least 80%, at least 85%, at least 90%, at least 95%, at least 96%, at least 97%, at least 98% or at least 99% identical to (i) nucleotides 107-6474 of SEQ ID NO: 44 (Mo4 anti-genomic L segment); (ii) nucleotides 107-3533 of SEQ ID NO: 45 (Mo4 anti-genomic M segment); (iii) nucleotides 107-1878 of SEQ ID NO: 46 (Mo4 anti-genomic S segment); (iv) nucleotides 107-1536 of SEQ ID NO: 47 (Mo4 anti-genomic S segment in which the NSs ORF is replaced by luciferase); (v) nucleotides 107-6474 of SEQ ID NO: 49 (Mo7 anti-genomic L segment); nucleotides 107-3533 of SEQ ID NO: 50 (Mo7 anti-genomic M segment); or nucleotides 107-1878 of SEQ ID NO: 51 (Mo7 anti-genomic S segment). In some examples, the nucleic acid molecule comprises a vector.

F. Mini-Genome Reporter System

Also provided herein is a *Phlebovirus* mini-genome reporter system, which can be used, for example, to detect viral replication, package pseudo-virus and to screen for anti-viral compounds. In some embodiments, the mini-genome reporter system comprises three plasmids. The first plasmid comprises a reporter gene flanked by UTR sequences of a *Phlebovirus* S, M or L segment. The first plasmid need not contain the complete UTR sequences of the gene segment, but generally includes at least the first 15 nucleotides of 3' UTR and the last 15 nucleotides of 5' UTR sequence. The second plasmid encodes a *Phlebovirus* NP. For example, the second plasmid can contain an anti-genomic copy of the S segment, which encodes NP, or the second plasmid can be an expression vector encoding NP. The third plasmid encodes a *Phlebovirus* L protein. For example, the third plasmid can contain an anti-genomic copy of the L segment, which encodes the L protein, or the third plasmid can be an expression vector encoding the L protein.

In some examples, the first plasmid encodes an EGFP-blasticidin reporter flanked by M segment UTRs. In one non-limiting example, the first plasmid is at least 80%, at least 85%, at least 90%, at least 95%, at least 96%, at least 97%, at least 98% or at least 99% identical to SEQ ID NO: 48 (pLCK-Mo4M_EGFPBlastNeg); or comprises or consists of SEQ ID NO: 48.

In some examples, the second plasmid comprises a nucleotide sequence at least 80%, at least 85%, at least 90%, at least 95%, at least 96%, at least 97%, at least 98% or at least 99% identical to nucleotides 107-1878 of SEQ ID NO: 46 (Mo4 anti-genomic S segment); or comprises nucleotides 107-1878 of SEQ ID NO: 46. In other examples, the second plasmid comprises a nucleotide sequence at least 80%, at least 85%, at least 90%, at least 95%, at least 96%, at least 97%, at least 98% or at least 99% identical to nucleotides 107-1878 of SEQ ID NO: 51 (Mo7 anti-genomic S segment); or comprises nucleotides 107-1878 of SEQ ID NO: 51. In further examples, the second plasmid is at least 80%, at least 85%, at least 90%, at least 95%, at least 96%, at least 97%, at least 98% or at least 99% identical to SEQ ID NO: 46 or SEQ ID NO: 51; or comprises or consists of SEQ ID NO: 46 or SEQ ID NO: 51. In yet other examples, the second plasmid is at least 80%, at least 85%, at least 90%, at least 95%, at least 96%, at least 97%, at least 98% or at least 99% identical to SEQ ID NO: 42 (pcMo4NP); or comprises or consists of SEQ ID NO: 42.

In some examples, the third plasmid comprises a nucleotide sequence at least 80%, at least 85%, at least 90%, at least 95%, at least 96%, at least 97%, at least 98% or at least 99% identical to nucleotides 107-6474 of SEQ ID NO: 44 (Mo4 anti-genomic L segment); or comprises nucleotides 107-6474 of SEQ ID NO: 44. In other examples, the third plasmid comprises a nucleotide sequence at least 80%, at least 85%, at least 90%, at least 95%, at least 96%, at least 97%, at least 98% or at least 99% identical to nucleotides 107-6474 of SEQ ID NO: 49 (Mo7 anti-genomic L segment); or comprises nucleotides 107-6474 of SEQ ID NO: 49. In further examples, the second plasmid is at least 80%, at least 85%, at least 90%, at least 95%, at least 96%, at least 97%, at least 98% or at least 99% identical to SEQ ID NO: 44 or SEQ ID NO: 49; or comprises or consists of SEQ ID NO: 44 or SEQ ID NO: 49. In yet other examples, the third plasmid is at least 80%, at least 85%, at least 90%, at least 95%, at least 96%, at least 97%, at least 98% or at least 99% identical to SEQ ID NO: 41 (pcMo4L); or comprises or consists of SEQ ID NO: 41.

In some embodiments, the mini-genome reporter system further comprises a fourth plasmid encoding the *Phlebovirus* glycoproteins. In some examples, the fourth plasmid is an expression vector encoding GnGc. Thus, in particular examples, the fourth plasmid comprises a nucleotide sequence at least 80%, at least 85%, at least 90%, at least 95%, at least 96%, at least 97%, at least 98% or at least 99% identical to SEQ ID NO: 40; or comprises of consists of SEQ ID NO: 40. In other examples, the fourth plasmid is an expression vector encoding the complete M ORF. In particular examples, the fourth plasmid comprises a nucleotide sequence at least 80%, at least 85%, at least 90%, at least 95%, at least 96%, at least 97%, at least 98% or at least 99% identical to SEQ ID NO: 43; or comprises of consists of SEQ ID NO: 43.

Further provided is a method of producing *Phlebovirus* pseudo-virus, comprising transfecting the first, second, third and fourth plasmids into cells expressing T7 polymerase.

G. Immunogenic Compositions and Use Thereof

The *Phlebovirus* polypeptides and recombinant viruses described herein can be used in immunogenic compositions to elicit an immune response, such as to provide protection against infection by a *Phlebovirus*.

Provided herein are immunogenic compositions comprising a *Phlebovirus* polypeptide as described herein, or an immunogenic fragment thereof, and a pharmaceutically acceptable carrier. The immunogenic composition can further include an adjuvant. In some examples, the immunogenic composition comprises a *Phlebovirus* NSs, NP, GP or L protein. In particular examples, the amino acid sequence of the *Phlebovirus* polypeptide is at least 80%, at least 85%, at least 90%, at least 95%, at least 96%, at least 97%, at least 98% or at least 99% identical to SEQ ID NO: 4, 5, 6, 7, 11, 12, 13 or 14. In other particular examples, the amino acid sequence of the *Phlebovirus* polypeptide comprises or consists of SEQ ID NO: 4, 5, 6, 7, 11, 12, 13 or 14. In yet other examples, the polypeptide comprises an immunogenic fragment of SEQ ID NO: 4, 5, 6, 7, 11, 12, 13 or 14.

Also provided are immunogenic compositions comprising a recombinant *Phlebovirus* as described herein and a pharmaceutically acceptable carrier. The immunogenic composition optionally includes an adjuvant. In some embodiments, the recombinant *Phlebovirus* comprises an S segment having a nucleotide sequence at least 85%, at least 90%, at least 95%, at least 96%, at least 97%, at least 98% or at least 99% identical to SEQ ID NO: 1 or SEQ ID NO: 8; an M segment having a nucleotide sequence at least 85%, at least 90%, at least 95%, at least 96%, at least 97%, at least 98% or at least 99% identical to SEQ ID NO: 2 or SEQ ID NO: 9; and an L segment having a nucleotide sequence at least 85%, at least 90%, at least 95%, at least 96%, at least 97%, at least 98% or at least 99% identical to SEQ ID NO: 3 or SEQ ID NO: 10.

Further provided is a method of eliciting an immune response against *Phlebovirus* in a subject by administering to the subject a therapeutically effective amount of a recombinant *Phlebovirus*, a *Phlebovirus* polypeptide, or an immunogenic composition as disclosed herein. In some embodiments, the subject is administered the recombinant *Phlebovirus, Phlebovirus* polypeptide, or immunogenic composition prophylactically to prevent infection by a *Phlebovirus*. In other cases, the recombinant *Phlebovirus, Phlebovirus* polypeptide, or immunogenic composition is administered as a treatment for *Phlebovirus* infection.

Also provided is a method of immunizing a subject against *Phlebovirus* infection by administering to the subject a therapeutically effective amount of a recombinant *Phlebovirus*, a *Phlebovirus* polypeptide, or an immunogenic composition as disclosed herein.

IV. Methods of Producing *Phlebovirus*-Specific Antibodies

Provided by the present disclosure are antibodies or antibody fragments that specifically bind the *Phlebovirus* isolates and/or *Phlebovirus* polypeptides disclosed herein. The *Phlebovirus*-specific antibodies can be used, for example, in assays for the detection of a *Phlebovirus* or *Phlebovirus* polypeptide in a biological sample. Exemplary immunodetection assays include the enzyme-linked immunosorbent assay (ELISA), Western blot, radioimmunoassay (RIA) and immunohistochemistry (IHC) assay. Methods of performing such assays are well known in the art and are briefly described above.

In some embodiments, provided are polyclonal antibodies specific for a *Phlebovirus* or *Phlebovirus* polypeptide. In other embodiments, provided are monoclonal antibodies specific for a *Phlebovirus* or *Phlebovirus* polypeptide. In some examples, the polyclonal or monoclonal antibody (or antigen-binding fragment thereof) recognizes a Phlebovirus particle, such as a particle of one of the *Phlebovirus* isolates disclosed herein. In other examples, the polyclonal or monoclonal antibody (or antigen-binding fragment thereof) specifically binds a *Phlebovirus* polypeptide disclosed herein.

Methods of making polyclonal and monoclonal antibodies are well known, and are described below. Polyclonal antibodies, antibodies which consist essentially of pooled monoclonal antibodies with different epitopic specificities, as well as distinct monoclonal antibody preparations, are contemplated. The preparation of polyclonal antibodies is well known to those skilled in the art (see, for example, Green et al., "Production of Polyclonal Antisera," in: *Immunochemical Protocols*, pages 1-5, Manson, ed., Humana Press, 1992; Coligan et al., "Production of Polyclonal Antisera in Rabbits, Rats, Mice and Hamsters," in: *Current Protocols in Immunology*, section 2.4.1, 1992). For example, an antigen (such as a *Phlebovirus* polypeptide or fragment thereof) is administered to a host animal such as, but not limited to, a rabbit, mouse or rat, to induce the production of antisera containing polyclonal antibodies specific for the antigen. Various adjuvants can be used to increase the immunological response, depending on the host species. Exemplary adjuvants include Freund's (complete and incomplete) adjuvant, mineral gels such as aluminum hydroxide, surface active substances such as lysolecithin, pluronic polyols, polyanions, peptides, oil emulsions, keyhole limpet hemocyanins and dinitrophenol. Such adjuvants are well known in the art.

The preparation of monoclonal antibodies likewise is conventional (see, for example, Kohler & Milstein, *Nature* 256: 495, 1975; Coligan et al., sections 2.5.1-2.6.7; and Harlow et al. in: *Antibodies: a Laboratory Manual*, page 726, Cold Spring Harbor Pub., 1988). Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, e.g., Coligan et al., sections 2.7.1-2.7.12 and sections 2.9.1-2.9.3; Barnes et al., Purification of Immunoglobulin G (IgG), in: *Methods in Molecular Biology*, Vol. 10, pages 79-104, Humana Press, 1992).

Methods of in vitro and in vivo multiplication of monoclonal antibodies are well known to those skilled in the art. Multiplication in vitro may be carried out in suitable culture media such as Dulbecco's Modified Eagle Medium or RPMI 1640 medium, optionally supplemented by a mammalian serum such as fetal calf serum or trace elements and growth-sustaining supplements such as normal mouse peritoneal exudate cells, spleen cells, thymocytes or bone marrow macrophages. Production in vitro provides relatively pure antibody preparations and allows scale-up to yield large amounts of the desired antibodies. Large-scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, such as syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Antibodies can also be derived from a subhuman primate antibody. General techniques for raising therapeutically useful antibodies in baboons can be found, for example, in PCT Publication No. WO 91/11465; and Losman et al., *Int. J. Cancer* 46:310, 1990.

Alternatively, an antibody that specifically binds a *Phlebovirus* polypeptide can be derived from a humanized monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Natl. Acad. Sci. U.S.A.* 86:3833, 1989. Techniques for producing humanized monoclonal antibodies are described, for example, by Jones et al., *Nature* 321:522, 1986; Riechmann et al., Nature 332:323, 1988; Verhoeyen et al., *Science* 239:1534, 1988; Carter et al., *Proc. Natl. Acad. Sci. U.S.A.* 89:4285, 1992; Sandhu, *Crit. Rev. Biotech.* 12:437, 1992; and Singer et al., *J. Immunol.* 150:2844, 1993.

Antibodies can also be derived from human antibody fragments isolated from a combinatorial immunoglobulin library. See, for example, Barbas et al., in: *Methods: a Companion to Methods in Enzymology*, Vol. 2, page 119, 1991; Winter et al., *Ann. Rev. Immunol.* 12:433, 1994. Cloning and expression vectors that are useful for producing a human immunoglobulin phage library can be obtained, for example, from Stratagene Cloning Systems (La Jolla, Calif.).

In addition, antibodies can be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13, 1994; Lonberg et al., *Nature* 368:856, 1994; and Taylor et al., *Int. Immunol.* 6:579, 1994.

Antibodies include intact molecules as well as fragments thereof, such as Fab, $F(ab')_2$, and Fv which are capable of binding the epitopic determinant. These antibody fragments retain some ability to selectively bind with their antigen and are defined as follows:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody, defined as a genetically engineered molecule containing the variable region of the light chain, the variable region of the heavy chain, linked by a suitable polypeptide linker as a genetically fused single chain molecule.

Methods of making these fragments are known in the art (see for example, Harlow and Lane, *Antibodies: A Laboratory Manual*, Cold Spring Harbor Laboratory, New York, 1988). An epitope is any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647, and references contained therein; Nisonhoff et al., *Arch. Biochem. Biophys.* 89:230, 1960; Porter, *Biochem. J.* 73:119, 1959; Edelman et al., *Methods in Enzymology, Vol.* 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent (Inbar et al., *Proc. Natl. Acad. Sci. U.S.A.* 69:2659, 1972). Alternatively, the variable chains can be linked by an intermolecular disulfide bond or cross-linked by chemicals such as glutaraldehyde (see, for example, Sandhu, *Crit. Rev. Biotech.* 12:437, 1992). Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are known in the art (see Whitlow et al., *Methods: a Companion to Methods in Enzymology*, Vol. 2, page 97, 1991; Bird et al., Science 242:423, 1988; U.S. Pat. No. 4,946,778; Pack et al., Bio/Technology 11:1271, 1993; and Sandhu, *Crit. Rev. Biotech.* 12:437, 1992).

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (Larrick et al., *Methods: a Companion to Methods in Enzymology*, Vol. 2, page 106, 1991).

Antibodies can be prepared using an intact polypeptide or fragments containing small peptides of interest as the immunizing antigen. The polypeptide or a peptide used to immunize an animal can be derived from substantially purified polypeptide produced in host cells, in vitro translated cDNA, or chemical synthesis which can be conjugated to a carrier protein, if desired. Such commonly used carriers which are chemically coupled to the peptide include keyhole limpet hemocyanin, thyroglobulin, bovine serum albumin, and tetanus toxoid. The coupled peptide is then used to immunize the animal (e.g., a mouse, a rat, or a rabbit).

Monoclonal antibodies can also be prepared by well-known recombinant methods or using phage display. In some embodiments, monoclonal antibodies are generated using any phage display method known in the art. In phage display methods, functional antibody domains are displayed on the surface of phage particles which carry the polynucleotide sequences encoding them. In some cases, the phage displays antigen binding fragments, such as Fab and Fv or disulfide-bond stabilized Fv, expressed from a repertoire or combinatorial antibody library (e.g., human or murine). Phage expressing an antigen binding fragment is generally selected using labeled antigen or antigen bound or captured to a solid surface or bead. Phages used in these methods are typically filamentous phage, such as M13 phage. Generally, the antigen binding fragments are expressed as a recombinantly fused protein to either the phage gene III or gene VIII protein. Exemplary phage display methods are described in Brinkman et al. (*J Immunol Methods* 182:41-50, 1995), Ames et al. (*J Immunol Methods* 184:177-186, 1995), Kettleborough et al. (*Eur J Immunol* 24:952-958, 1994), Persic et al. (*Gene* 187: 9-18, 1997), Burton et al. (*Advances in Immunology*, 57:191-280, 1994), and in PCT Publication Nos. WO 90/02809; WO 91/10737; WO 92/01047; WO 92/18619; WO 93/11236; WO 95/15982; WO 95/20401; and in U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

After phage selection, the antibody coding regions from the phage are isolated and can be used to generate whole antibodies, including human antibodies, or any other desired fragments, and expressed in any desired host, including mammalian cells, insect cells, plant cells, yeast, and bacteria.

Polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (see, for example, Coligan et al., Unit 9, *Current Protocols in Immunology*, Wiley Interscience, 1991).

The following examples are provided to illustrate certain particular features and/or embodiments. These examples should not be construed to limit the disclosure to the particular features or embodiments described.

EXAMPLES

Example 1

Patient Reports and Methods

This example describes the patients from which a novel *Phlebovirus* was isolated and the methods used for isolation and identification of the virus.

Patient 1

Patient 1 is a healthy 57-year-old male who lives on a 70-acre farm in northwestern Missouri with horses and cats. In early June 2009, he noticed a small nymphal tick embedded on his abdomen, which his wife removed with tweezers. He had not applied tick repellant, nor did he know how long the tick had been embedded. There was no rash or localized itching. The following day, he noticed a fever and his symptoms subsequently progressed to severe fatigue, headache, anorexia, nausea, and non-bloody diarrhea. Four days later, he was admitted to hospital. He denied visual changes or symptoms of neuropathy, cough, shortness of breath, lymph node enlargement, vomiting or abdominal pain. His temperature was 37.9° C. and peaked at 38.2° C. The next day, his temperature reached 39.1° C. Initial laboratory results showed a low white blood cell count of 1900 cells/µL (normal 4500-11000 cells/µL), low platelet count of $115 \times 10^3$ cells/µL (normal $150\text{-}450 \times 10^3$ cells/µL), and low sodium 132 mEq/L (normal 136-146 mEq/L) (FIG. 4). Serum levels of liver transaminases were slightly elevated with an ALT of 57 U/L (normal 10-40 U/L) and AST of 44 (normal 10-30 U/L). A serum C reactive protein of 2.9 mg/dL (normal<0.9 mg/dL) was found.

The patient was hospitalized for 10 days. Moderate thrombocytopenia progressed to severe with a nadir of $37 \times 10^3$ cells/µL at day 5 and $40 \times 10^3$ cells/µL at days 6 and 7. Leukopenia continued throughout hospitalization with notable lymphopenia and mild neutropenia that progressed to moderate neutropenia at day 7 (FIG. 1A). Band forms were detected at day 2 and day 8. An erythrocyte sedimentation rate of 9 mm/hr (normal, 0-15 mm/hr), erythrocyte count, and hemoglobin were unremarkable and stable. Hematocrit was slightly low during hospitalization (FIG. 1D and FIG. 4). Prothrombin time and partial thromboplastin time were normal (FIG. 4).

Serum hepatic transaminases increased during hospitalization and peaked with an ALT of 315 U/L and AST of 431 U/L at day 8 (FIG. 1C). Alkaline phosphatase levels rose within normal limits and peaked at 101 U/L (normal 25-100 U/L) at day 9. Creatine and blood urea nitrogen levels remained normal. A urinalysis demonstrated trace protein, 1+ ketones and was otherwise normal. Serum albumin levels were low as well as mildly low serum sodium and calcium levels (FIG. 4).

Tests specific for influenza A and B and *Borrelia* were negative. EDTA treated blood was sent to CDC for testing on the second day of hospitalization and subsequently shown to be negative for *Ehrlichia chaffeensis, Ehrlihia ewingii*, and spotted fever group rickettsiae by PCR. Serology confirmed negative results for spotted fever group and typhus in an IgM and IgG assay.

On the second day of hospitalization, the patient was empirically placed on doxycycline (100 mg) by vein twice daily for a total of 14 days for suspected ehrlichiosis. Non-bloody diarrhea persisted through the fourth day of hospitalization. Stool specimens were negative for leukocytes, *Salmonella, Shigella*, and *Campylobacter* and *Clostridium difficile* toxins. A 2-D echocardiogram and chest x-ray were unremarkable.

Since hospital discharge, the patient has experienced fatigue and generalized headaches on an almost daily basis, which have persisted for over 2 years. Additionally, he had short-term memory difficulty, which slowly improved, and anorexia that resolved after the initial 4-6 weeks following discharge.

The *Phlebovirus* isolated from Patient 1 is referred to herein as *Phlebovirus* isolate #2 or "Mo7."

Patient 2

Patient 2 is a 67-year-old male with a 5 year history of type 2 diabetes, but otherwise healthy. He lives on an approximately 100-acre farm in northwestern Missouri with numerous horses, dogs, and cats. In the spring of 2009, he received an average of 15-20 tick bites daily for approximately 2 weeks while building a fence on his property. He had not used tick repellant. He removed the embedded ticks with his fingers and tweezers. The last tick bite occurred 1 week before hospitalization. Approximately 4-5 days before hospitalization he developed subjective fever, fatigue, and anorexia. Additional symptoms included myalgias, dry cough, and non-bloody diarrhea. No rash was noted before or during hospitalization.

On hospital entry in June 2009, his temperature was 37.1° C. and reached a maximum of 38.1° C. that day. The following day his temperature reached 39.1° C. Laboratory studies conducted on admission were notable for a low white blood count of 2100 cells/µL, a low platelet count of $78 \times 10^3$ cells/µL, and an elevated AST of 54 U/L (FIG. 1B-1D). The serum sodium was slightly low at 130 mEq/L and calcium low at 7.8 mEq/L. A urinalysis was unremarkable.

The patient was hospitalized for 12 days. After day 2, moderate thrombocytopenia progressed to severe with a nadir of $34 \times 10^3$ cells/µL at days 5 and 6. Platelet numbers began to increase at day 8 and reached normal by day 11 (FIG. 1D). He tested negative for anti-platelet antibodies. Leukopenia continued until day 10 with mild neutropenia progressing to moderate neutropenia at day 6 to day 8 (FIG. 1B). Band forms were present at days 2 to 7 and lymphocytes gradually increased into a normal range by day 8 (FIG. 1B). Erythrocyte counts and hemoglobin were within normal limits, and the hematocrit was slightly low throughout hospitalization (FIG. 4). Prothrombin time, partial thromboplastin time and fibrinogen concentration were normal, but serum D-dimer elevated at 4.08 mg/L (FIG. 4).

Blood was collected on day 2 of hospitalization and sent to CDC. PCR results were found to be negative for *Ehrlichia chaffeensis* and a wide range of *Ehrichia* and *Anaplasma* species.

Aspartate and alanine aminotransferase levels were elevated and increased to 355 U/L at day 8 and 302 U/L at day 10, respectfully (FIG. 1C). Alkaline phosphatase was temporally high at day 10, but then resumed normal levels (FIG. 4). Creatinine and blood urea nitrogen levels remained normal. Serum albumin and sodium remained low throughout hospitalization. Low serum calcium concentrations increased to normal by day 10.

A bone marrow aspiration and biopsy was performed on day 2 of hospitalization. The peripheral smear found red cells to be normochromic and normocytic with the presence of ovalocytes along with acanthocytes and dacrocytes. Platelets showed normal morphology with no clumping or satellitosis. The bone marrow aspirate contained few cells. Red cells were normoblastic with frequent dysplastic forms of abnormal nuclear lobation and dyssynchrony between nuclear and cytoplasmic maturation and intracytoplasmic nuclear fragments. Granulocytogenesis was progressive and showed complete maturation. Blastocytes were less than 1% of the bone marrow population. Megakarocytes were present with micromegakarocytes and hypolobated forms noted. Plasma cells were 3-4% of the bone marrow cellularity. The myeloid to erythroid ratio of 3:1 was normal. Ringed sideroblasts were not seen. Flow cytometry demonstrated a 3% monoclonal plasma cell population with lambda light chain restriction. An evolving myelodysplastic syndrome could not be excluded. No infiltrates of infectious or neoplastic nature were noted.

Tests specific for Lyme disease were negative as well as cultures for fungus and acid-fast bacilli were negative. A chest radiograph and abdominal ultrasound were unremarkable. He was initially treated empirically with intravenous piperacillin/tazobactam, switched to ceftriaxone on hospital day 2, and to oral doxycycline (100 mg) twice daily on day 3 for suspected ehrlichiosis. He completed a course of doxycycline 100 mg twice daily for a total of 14 days.

After hospital discharge, the patient noted fatigue, short-term memory difficulty and anorexia. All of these symptoms abated after 4-6 weeks and have not recurred in 2 years. Six months after discharge, CDC confirmed the patient was negative for *Ehrlichia chaffeensis* and *Anaplasma phagocytophilum* by IgG assay.

The *Phlebovirus* isolated from Patient 2 is referred to herein as *Phlebovirus* isolate #1 or "Mo4."

Virus Isolation

Leukocytes were separated from EDTA-treated blood in a Ficoll-histopaque gradient. The separated leukocytes were inoculated onto the canine monocyte cell line, DH82, cultivated in Eagle's MEM with 2 mM L-glutamine, 1 mM sodium pyruvate, 0.1 mM non-essential amino acids, 10 mM HEPES and 10% fetal bovine serum (Childs et al., *J Clin Microbiol* 37:2997-3000, 1999). Adherent and non-adherent cells were placed on glass slides by cytocentrifugation and examined using a modified rapid Wright-Giemsa stain (Diff-Quik). When cytologic changes were noted in the cells, media from the DH82 cell culture was collected, filtered to remove host cells, and inoculated onto VeroE6 cells grown in the same medium. When cytologic changes were noted in the recipient cells, infected VeroE6 cells were fixed in glutaraldehyde and processed into ultrathin sections and negative stained for transmission electron microscopy to visualize virus particles.

Metagenomic Analysis to Identify Virus

Total RNA was isolated from infected cell culture media by TriPure™ extraction and subsequent RNA purification using RNAeasy™ columns followed by DNaseI treatment on the column (Qiagen). RNA was denatured at 75° C. for 5 min and stored on ice. A random cDNA library was generated in a reverse transcription reaction using SuperScript III (Invitrogen) and random hexamer primers linked to an arbitrary 17-mer anchor sequence (GTTTCCCAGTAG-GTCTCNNNNNNNN; SEQ ID NO: 52) at 42° C. for 50 min and 70° C. for 15 min (McMullan et al., Virology 422:1-5, 2012). Residual RNA was removed by RNase H treatment at 37° C. for 20 min and subsequent inactivation at 95° C. for 5 min. The cDNA was randomly amplified by PCR using a primer specific for the 17-mer anchor sequence and the random hexamer primer with the anchor sequence and an extension of CGCC at the 5' end (CGCCGTTTCCCAGTAG-GTCTC; SEQ ID NO: 53) in a 9:1 ratio with 8 cycles annealing at 25° C. and 49 cycles annealing at 55° C. Products smaller than 70 nucleotides were removed using a MinElute™ column (Qiagen). Adapters for next generation sequencing were ligated without fragmentation and sequencing was performed on a 454 FLX Genome Sequencer (Roche). Sequence reads were trimmed of adapter and primer sequences and searched using the BLASTx algorithm (CLC Genomics, NCBI). Sequences showing significant similarity were parsed using MEGAN (Huson et al., *Genome Res* 17:377-386, 2007). Gaps in the virus genome were filled in using PCR and traditional Sanger sequencing. The 3' and 5' end of the virus were amplified in a 3' RACE reaction and sequenced. *Phlebovirus* sequences of each virus protein were aligned using MAFFT and phylogenic relationships inferred using the UPGMA method with 2,000 bootstrap replicates for statistical support (CLC Genomics, Geneious). Heartland virus (HRTLV) was proposed as the name for the newly discovered virus.

Analysis of Biopsy Specimens

Sections cut from formalin-fixed paraffin embedded bone marrow biopsy and clot specimens obtained from Patient 2 on day 2 of hospitalization were analyzed for the presence of Heartland virus by quantitative reverse transcription PCR (qRT-PCR) and immunohistochemistry. RNA was extracted from tissue sections and used as template in qRT-PCR assays, using primers and probes specific for the S, M, and L virus segments and human GAPDH, in a one-step reaction at 50° C. for 30 min, 94° C. 2 min, and 40 cycles of 94° C. and 60° C. 1 min (UltraSense, Invitrogen). The following probes and primers were used:

```
Sprobe:
                                         (SEQ ID NO: 15)
6-fam/TCCCTCTTC/zen/TTCCCAAATGCCACC/IABKFQ

S1:
                                         (SEQ ID NO: 16)
GATGCTTCCTTGGTTGCTG

S2:
                                         (SEQ ID NO: 17)
TGCCAAATTCAGAGACCCTC

Mprobe:
                                         (SEQ ID NO: 18)
6-fam/CAGGATGGC/zen/GCTGCATTAAAACACC/IABkFQ M1:
                                         (SEQ ID NO: 19)
ACACGATTGGATGGGTTCTC

M2:
                                         (SEQ ID NO: 20)
TGGGCAAACAGGATGGAC

Lprobe:
                                         (SEQ ID NO: 21)
6-fam/ACCCCTGGA/zen/ATTGATAACACCGCC/IABkFQ

L1:
                                         (SEQ ID NO: 22)
AACCCCTGCTTTCTGAGTG

L2:
                                         (SEQ ID NO: 23)
ATTGGACTCATGGGCTTGG
(6-fam = 6-carboxyfluorescein; zen = quencher;
IABkFQ = Iowa Black ™ FQ)
```

Ct values were related to known quantity of RNA standard generated from a T7 transcript of the S segment. The Heartland qRT-PCR assay for the S segment has a sensitivity of detection of approximately 2 molecules of in vitro transcribed RNA and an efficiency of 95.6% (slope −3.44).

An immunoalkaline phosphatase technique was performed using a 1:1000 dilution of hyperimmune rabbit serum reactive with Heartland virus nucleoprotein.

Example 2

Discovery of a New *Phlebovirus* Associated with Severe Febrile Illness Following Tick Bite in Two Patients in Missouri This example describes the isolation and identification of a novel *Phlebovirus* from patients reporting a recent tick bite.

Isolation of the Virus

Initially, cell cultures showed cytopathic effects similar to those seen in early cultures of *Ehrlichia chaffeensis*. However, cellular vacuoles did not contain the typical bacterial microcolonies, known as morulae. Passage of the culture supernatant onto fresh DH82 cells yielded similar cytopathic effects in 9-11 days. Cytopathic changes were less evident, but also noted in the inoculated VeroE6 cell culture 9 days post infection. Thin section electron microscopy revealed enveloped particles averaging 86 nm in size, typical of a virus in the family Bunyaviridae (FIG. 2).

Genetic Analysis of Heartland Virus

To identify the virus, RNA from infected cell culture media was nonspecifically amplified and the cDNA products were sequenced using 454 next generation sequencing (NGS). Next, the non-redundant protein database was searched against all NGS reads translated in all 6 reading frames using the BLASTx algorithm and sequences significantly similar to those of viruses in the family Bunyaviridae, genus *Phlebovirus* were found. Contiguous sequences were assembled from the NGS reads and additional Sanger sequencing performed to elucidate the complete genomic sequence for the virus isolates from both patients. The two virus genomes were closely related with 98%, 95%, and 99% identity for the S, M and L segment respectfully at the nucleic acid level. The high genetic identity indicates that both patients were infected with the Heartland virus, but the numerous differences imply that the two patients were infected independently.

There are over 70 members of the *Phlebovirus* family that share a similar genome organization with a negative-sense tripartite coding strategy (Nichol et al., Family Bunyaviradae. In: Fauquet et al. ed. Virus Taxomony: classification and nomenclature of viruses. San Diego, Calif.: Elsevier Academic Press; 2005:695-716). The L segment is 6,368 nucleotides in length and encodes a large RNA-dependent RNA polymerase with 3 regions and 6 motifs responsible for the process of transcription and replication; these regions are conserved among all *phleboviruses* and are present in Heartland virus. The M segment is 3427 nucleotides in length and encodes a polyprotein processed by host cell proteases into the virus glycoproteins Gn and Gc which are used for virion entry and assembly. There are 4 predicted N-linked glycosylation sites. The S segment is 1772 nucleotides and encodes the nucleoprotein that encapsidates the genomic RNA and a nonstructural NSs protein in an ambisense coding strategy. Each of the virus genome segments is potentially circularized by complementary base pairing of the genomic termini to form a panhandle structure.

Phylogenetic Analysis

Figures 3A, 3B:
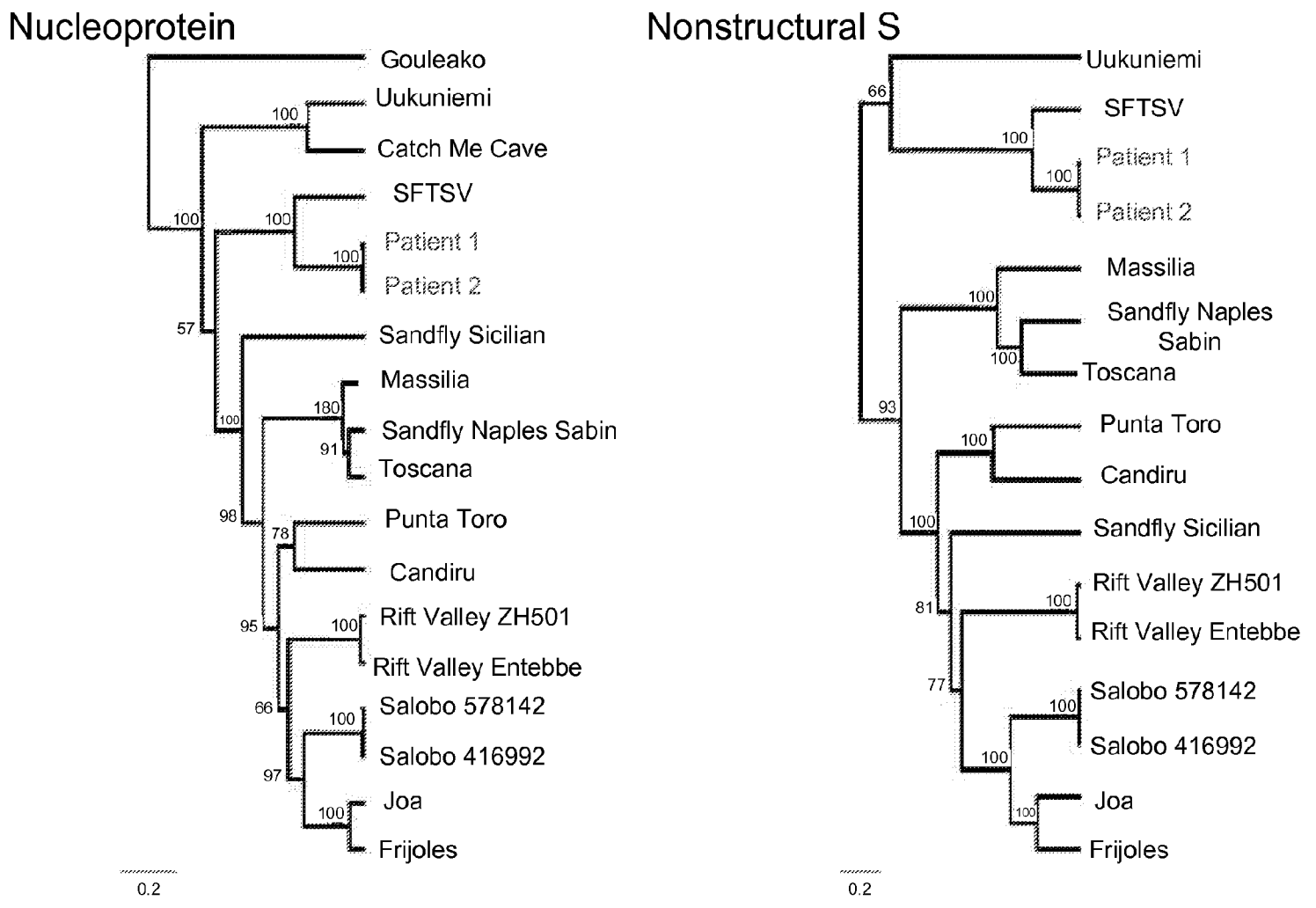

Phylogenetic analysis indicates Heartland virus is a distinct member of the genus *Phlebovirus*. Comparison of the aligned amino acid sequence of the polymerase, glycoproteins, nucleoprotein, and NSs protein all show Heartland virus to be distantly related to representative *phlebovirus* members of the Sicilian and Naples Sandfly, Joa, Salobo, Chandiru, Punta Toro, Rift Valley Fever, and Uukuniemi complexes (FIG. 3). The Heartland virus is most closely related to the Severe Fever with Thrombocytopenia Syndrome Virus (SFTSV), recently identified in central and northeastern China (Yu et al., *N Engl J Med* 364:1523-1532, 2011; Xu et al., *PLoS Pathog* 7:e1002369, 2011). This relationship is distant however, as pair-wise comparisons of the viral polymerase and nucleoprotein, the two most conserved virus proteins, show amino acid differences of 27% and 38.4%, respectively. The *phlebovirus* complexes are separated by at least 35% protein differences emphasizing the remote relationship between Heartland virus and SFTSV. An alignment of NP from several different *Phleboviruses* is shown in FIG. 5.

The genus *Phlebovirus* is divided into the sand fly- and mosquito-borne virus groups and the nonpathogenic tick-borne Uukuniemi (UUK) virus. Both Heartland virus and SFTSV exhibit a relatively close relationship with the tick-borne UUK for all virus proteins. Heartland virus was also distinct from an uncharacterized Bunyavirus isolated from a nymphal *Amblyomma americanum* tick embedded on a woodchuck in 1967 in western Kentucky, named the Lone Star virus (Kokernot et al., *Am J Trop Med Hyg* 18:789-795, 1969). Comparison of the polymerase amino acid sequence shows Lone Star virus to share only 34% identity with Heartland virus, while SFTSV and Heartland virus share 73% identity. Heartland virus is the only pathogenic *phlebovirus* isolated from humans in the Americas.

Detection of Virus RNA and Antigen in Patient Bone Marrow Specimen

Heartland virus RNA was detected in sections of bone marrow biopsy and clot. Quantifying the copies of the housekeeping beta-2 microglobulin mRNA indicate equivalent amounts of total RNA were compared. Immunohistochemical staining revealed the presence of virus nucleocapsid protein in hematopoietic cells of the bone marrow. In particular, megakarocytes were positive for virus antigen.

Discussion

Described herein is a new, potentially tick-borne, pathogenic virus in the United States. Heartland virus is a distinct member of the genus *Phlebovirus* and is most closely related to tick-borne *phleboviruses*, notably the recently isolated SFTSV. While clinical data based on two patients may not reflect the entire spectrum of illness associated with Heartland virus, both illnesses had a very similar clinical course. For instance, symptoms of infection for these two patients included fever, fatigue, anorexia, diarrhea, leukopenia, thrombocytopenia, and elevated hepatic transaminase levels. Both patients were viremic at day 2 of hospitalization, approximately 7 days after onset of symptoms. The temporal trends in white blood and platelet cell counts, and AST and ALT levels were strikingly similar in both patients. Both patients presented with neutropenia that continued to decline to levels below 700 at days 6 and 7 of hospitalization. Thrombocytopenia also continued until day 7 for both patients. Slightly elevated AST and ALT levels spiked at day 7 and day 8. After this time, there was an increase in circulating neutrophils, lymphocytes, monocytes, and platelets. Hepatic transaminase levels begin to decline. Clinical evidence did not suggest respiratory or kidney involvement in either patient.

Many of the clinical and laboratory facets of this illness are similar to those reported for SFTS. However, renal abnormalities are common for SFTS with 84% of patients having proteinuria and 59% with hematuria, in contrast to the patients in this report who showed normal creatine and blood urea nitrogen levels (Yu et al., *N Engl J Med* 364:1523-1532, 2011). Coagulation abnormalities were also not observed despite a marked low platelet count whereas a minority of SFTS cases had elongated partial thromboplastin time, thrombin time, elevated fibrinogen levels and symptoms of gingival bleeding and hemorrhage with fatalities of disseminated intravascular coagulation and cerebral hemorrhage (Gai et al., *Clin Infect Dis* 54:249-252, 2012; Zhang et al., *Clin Infect Dis* 54(4):527-533, 2011). There have been numerous reports of person-to-person transmission upon exposure to SFTSV infected blood and SFTSV has been detected in patient blood, throat swabs, urine and feces (Gai et al., *Clin Infect Dis* 54:249-252, 2012; Zhang et al., *Clin Infect Dis* 54(4):527-533, 2011; Bao et al., *Clin Infect Dis* 53:1208-1214, 2011; Liu Y et al., *Vector Borne Zoonotic Dis* 12(2): 156-160, 2011). It remains to be determined if Heartland virus can be transmitted person-to-person; no family members of either patient reported symptoms resembling Heartland virus infection. It will be important to determine how patients acquire Heartland virus infection in order to promote risk reduction practices.

It should be noted that the clinical signs and symptoms that were observed, as well as epidemiologic exposures (tick bites), are similar to those of ehrlichiosis (Childs et al., *J Clin Microbiol* 37:2997-3000, 1999). Heartland virus should be considered as a possible etiologic agent in these instances, particularly when a suspected ehrlichiosis does not improve within a few days with antibiotic treatment.

Although the virus has not been isolated from the tick as the tick specimens from the patients were not available, the presumed vector for Heartland virus is the lone star tick, *Amblyomma americanum*. Recent ecological studies of ticks captured in central and southern Missouri found 99.9% of the captured ticks to be *A. americanum* (Brown et al., *Clin Infect Dis* 33:1586-1594, 2001). In northwestern Missouri, *A. americanum* is abundant and multiple isolates of *Ehrlichia chaffeensis* have originated from the regional hospital (Roche et al., First culture isolations of *Ehrlichia chaffeensis* from a Missouri patient. In: 22nd Annual Meeting of the Society for Vector Ecology. Ft. Collins, Colo., 2008; Paddock et al., *Clin Infect Dis* 33:1586-1594, 2001). *A. americanum* is found throughout the southeastern and south central United States, extending up the Atlantic coast reaching all the way to Maine (Childs and Paddock, *Annu Rev Entomol* 48:307-337, 2003). Both the patients resided in fragmented deciduous forest and old fields, suitable habitats for *A. americanum*.

Heartland virus is the first pathogenic *phlebovirus* identified in the Americas. UUK virus, the prototypical tick-borne *phlebovirus* is considered nonpathogenic to humans. Members of the sand fly *phlebovirus* complex found in Asia, Africa, and around the Mediterranean Basin, commonly result in a self-limiting "3 day fever" with the exception of Toscana virus, which can causes aseptic meningitis (Depaquit et al., *Euro Surveill* 15:19507, 2010). The mosquito-borne Rift Valley fever virus can cause large-scale epizootics; human infection is a self-limiting febrile illness that may progress to hepatitis, encephalitis, or hemorrhagic fever (Bird et al., *J Am Vet Med Assoc* 234:883-893, 2009). The recent identification of the SFTSV from northeastern China, Catchme-Cave virus from the subantarctic island of Macquarie, and the Finnish Uukuniemi virus demonstrates the extensive geographic distribution of viruses in this genus.

Example 3

Plasmids for Reverse Genetics and Mini-Genome Reporters

This example describes plasmids that were generated for a reverse genetics system, such as for the production of recombinant *Phlebovirus*, and for the development of mini-genome reporters, which can be used to screen for antiviral compounds and/or drug resistant virus mutants.

Description of Plasmids

Plasmids for launching the reverse genetics system use the pSMART-LCKan backbone (Lucigen, Middleton, Wis.) altered to include (in the 5' to 3' direction) a T7 promoter, a single G nucleotide, a *Phlebovirus* S, M or L segment in the positive orientation (virus complementary sense or anti-genomic), hepatitis delta virus ribozyme and a T7 terminator. Plasmids for expression of viral proteins (NP, L, GnGc and the complete M ORF) use the pCAGGS vector. Table 1 below summarizes the plasmids that can be used for reverse genetics and mini-genome reporters.

TABLE 1

Description of Plasmids

| Plasmid Name | Description | SEQ ID NO: |
| --- | --- | --- |
| pcMo4GnGc | pCAGGS vector expressing GnGc | 40 |
| pcMo4L | pCAGGS vector expressing L protein | 41 |
| pcMo4NP | pCAGGS vector expressing NP | 42 |
| pcMo4Morf | pCAGGS vector expressing complete M ORF[1] | 43 |
| pLCK-Mo4Lvc | Mo4 L segment in the positive orientation | 44 |
| pLCK-Mo4Mvc | Mo4 M segment in the positive orientation | 45 |
| pLCK-Mo4Svc | Mo4 S segment in the positive orientation | 46 |
| pLCK-Mo4SvcDelNSs_GLuc | Mo4 S segment in the positive orientation with the NSs ORF replaced by Gaussia luciferase | 47 |
| pLCK-Mo4M_EGFPBlastNeg | Mo4 M segment UTRs flanking an EGFP-Blasticidin reporter | 48 |
| pLCK-Mo7Lvc | Mo7 L segment in the positive orientation | 49 |
| pLCK-Mo7Mvc | Mo7 M segment in the positive orientation | 50 |
| pLCK-Mo7Svc | Mo7 S segment in the positive orientation | 51 |

[1]Includes a putative NSm and glycoproteins expressed as a polyprotein

Reverse Genetics

Recombinant *Phleboviruses* can be generated using a reverse genetics system that parallels the reverse genetics system previously described for Rift Valley fever virus (see PCT Publication No. WO 2009/082647, which is herein incorporated by reference).

Rescue of recombinant *Phleboviruses* is accomplished by simultaneous transfection of S, M and L anti-genomic plasmids into cells stably expressing T7 polymerase (for example, BSR-T7/5 cells). The genome segments of each plasmid are flanked by a T7 promoter, which enables generation of the primary RNA transcript, and the hepatitis delta virus ribozyme, which removes extraneous nucleotides from the 3' end of the primary transcriptional products. The T7 RNA polymerase generated transcripts are identical copies of the *Phlebovirus*-encoding plasmids, with the exception of an extra G nucleotide on the 5' end derived from the T7 promoter.

In one example, a recombinant *Phlebovirus* can be generated by transfection of the pLCK-Mo4Lvc, pLCK-Mo4Mvc and pLCK-Mo4Svc plasmids into BSR-T7/5 cells (or any other cell type expressing T7 polymerase). In another example, a recombinant *Phlebovirus* can be generated by transfection of the pLCK-Mo7Lvc, pLCK-Mo7Mvc and pLCK-Mo7Svc plasmids. Alternatively, the Mo4 and Mo7 gene segment plasmids can be used in any combination so long as at least one S segment, at least one M segment and at least one L segment plasmid is transfected into the T7 polymerase expressing cells.

Recombinant *Phleboviruses* can also be generated using an S segment anti-genomic plasmid in which the NSs ORF is replaced by a reporter gene. Thus, in one example, the recombinant *Phlebovirus* is generated by transfection of the pLCK-Mo4Lvc, pLCK-Mo4Mvc and pLCK-Mo4SvcDelNSs_GLuc plasmids. In another example, the recombinant *Phlebovirus* is generated by transfection of the pLCK-Mo7Lvc, pLCK-Mo7Mvc and pLCK-Mo4SvcDelNSs_GLuc plasmid. Alternatively, a plasmid encoding the Mo7 S segment with the NSs ORF replaced by a reporter (such as Gaussia luciferase) can be generated and used to produce recombinant virus.

Furthermore, the S, M and L segment anti-genomic plasmids can be further altered to introduce any desired mutations (including deletions, additions and substitutions), such as to produce reporter viruses, produce attenuated virus and/or identify virulence factors.

Exemplary methods for producing recombinant virus using reverse genetics are described in PCT Publication No. WO 2009/082647. In one example, plasmids encoding *Phlebovirus* L, M and S segments are transfected in approximately 1 µg quantities with LT-1 (Mirus) at a ratio of 6:1 and transferred onto sub-confluent (approximately 60-70% confluent) monolayers of BSR-T7/5 cells stably expressing T7 polymerase (Buchholz et al., *J. Virol.* 73(1):251-259, 1999). Four to five days post transfection, the cell supernatant is clarified by low speed centrifugation and passaged twice on confluent monolayers of Vero E6 cells. After passage and prior to use in subsequent experiments, the complete genome sequence of each rescued recombinant virus can be confirmed by previously described techniques (Bird et al., *J. Virol.* 81:2805-2816, 2007).

Mini-Genome Reporters

Mini-genome reporter systems have been developed for several negative sense RNA viruses (see, for example, Jasenosky et al., *Antimicrob Agents Chemother* 54(7):3007-3010, 2010; Freiberg et al., *Virology* 370(1):33-44, 2008; Dumas et al., *J Virol Methods* 142(1-2):59-66, 2007; Hoenen et al., *Antiviral Res* 91(2):195-208, 2011). These systems allow for the development of cell lines that produce replicating virus. Such cell lines can be used, for example, to screen for compounds that inhibit viral replication, and to select for virus mutants that escape drug pressure.

To produce a *Phlebovirus* mini-genome system, a first plasmid contains a reporter gene that is flanked by viral UTRs from any of the three *Phlebovirus* gene segments. This plasmid is transfected into cells along with a plasmid or plasmids expressing the necessary replication factors, which for *Phlebovirus* are the NP and L proteins. As one example, the reporter gene can be an antibiotic resistance gene. Thus, after transfection of the reporter plasmid and plasmids expressing NP and L, cells that are undergoing viral replication can be selected based on antibiotic resistance. Cells can further be transfected with a plasmid encoding the *Phlebovirus* glycoproteins (GnGc) in order to package the replicating viral segments.

In some cases, the mini-genome reporter system includes a plasmid encoding an S segment (which encodes NP), a plasmid encoding an L segment (which encodes the L protein) and a reporter plasmid comprising an antibiotic resistance gene flanked by the M segment UTRs. As one example, the mini-genome reporter system uses the pLCK-Mo4Svc, pLCK-Mo4Lvc and pLCK-M_EGFPBlastNeg plasmids. Viral packaging can then be achieved by transfection of a plasmid encoding GnGc (such as the pcMo4GnGc plasmid) or a plasmid encoding the complete M ORF (such as the pcMo4Morf plasmid). In an alternative example, instead of using plasmids encoding the complete S and L segments, the mini-genome reporter system uses a plasmid expressing the L protein (such as pcMo4L) and a plasmid expressing NP (such as pcMo4NP). The selected combination of plasmids is transfected into cells expressing T7 polymerase. Packaged virus can then be isolated and used to infect cells such as VeroE6, A549 or HuH7 cells.

In another example, one can evaluate viral replication only (without packaging) using a plasmid encoding the viral L segment (such as pLCK-Mo4Lvc or pLCK-Mo7vc) and a plasmid encoding an S segment in which the NSs ORF is replaced by a reporter (such as the pLCK-Mo4SvcDelNSs_GLuc plasmid).

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A *Phlebovirus* polypeptide chemically coupled to a carrier, wherein the amino acid sequence of the polypeptide is at least 95% identical to SEQ ID NO: 4, 5, 6, 7, 11, 12, 13 or 14.

2. The *Phlebovirus* polypeptide of claim 1, wherein the amino acid sequence of the polypeptide comprises or consists of SEQ ID NO: 4, 5, 6, 7, 11, 12, 13 or 14.

3. An expression vector comprising a nucleic acid molecule, wherein the nucleotide sequence of the nucleic acid molecule is at least 95% identical to SEQ ID NO: 1, 2, 3, 8, 9, or 10.

4. An isolated host cell comprising the expression vector of claim 3.

5. An oligonucleotide 12 to 40 nucleotides in length, wherein the oligonucleotide specifically hybridizes under conditions of high stringency with a nucleic acid molecule comprising the nucleotide sequence of SEQ ID NO: 1, 2, 3, 8, 9 or 10, and wherein the oligonucleotide is attached to a detectable label.

6. The oligonucleotide of claim 5, wherein the nucleotide sequence of the oligonucleotide is at least 95% identical to SEQ ID NO: 15, 16, 17, 18, 19, 20, 21, 22 or 23.

7. The oligonucleotide of claim 6, wherein the nucleotide sequence of the oligonucleotide comprises or consists of SEQ ID NO: 15, 16, 17, 18, 19, 20, 21, 22 or 23.

8. The oligonucleotide of claim 5, wherein the oligonucleotide is 18 to 24 nucleotides in length.

9. The oligonucleotide of claim 5, wherein the detectable label comprises a fluorophore, a quencher or both.

10. An isolated antibody or antigen-binding fragment thereof that specifically binds to a *Phlebovirus* nucleoprotein (NP), glycoprotein (GP), NSs protein or L protein, wherein the antibody or antigen-binding fragment is conjugated to a detectable label or a magnetic bead, and wherein:
the NP comprises the amino acid sequence of SEQ ID NO: 4 or SEQ ID NO: 11;
the GP comprises the amino acid sequence of SEQ ID NO: 6 or SEQ ID NO: 13;
the NSs protein comprises the amino acid sequence of SEQ ID NO: 5 or SEQ ID NO: 12; or
the L protein comprises the amino acid sequence of SEQ ID NO: 7 or SEQ ID NO: 14.

11. A recombinant *Phlebovirus*, wherein the genome of the recombinant *Phlebovirus* comprises:
(i) an S segment having a nucleotide sequence at least 95% identical to SEQ ID NO: 1 or SEQ ID NO: 8;
(ii) an M segment having a nucleotide sequence at least 95% identical to SEQ ID NO: 2 or SEQ ID NO: 9; or
(iii) an L segment having a nucleotide sequence at least 95% identical to SEQ ID NO: 3 or SEQ ID NO: 10,
wherein the recombinant *Phlebovirus* comprises a heterologous gene.

12. The recombinant *Phlebovirus* of claim 11, wherein the S segment comprises a deletion of the NSs open reading frame (ORF), or the NSs ORF is replaced by the ORF of a reporter gene.

13. An immunogenic composition comprising the recombinant *Phlebovirus* of claim 11 and a pharmaceutically acceptable carrier.

14. A method of eliciting an immune response against *Phlebovirus* in a subject, comprising administering to the subject a therapeutically effective amount of the recombinant *Phlebovirus* of claim 11.

15. A *Phlebovirus* reverse genetics system, comprising a first plasmid comprising an anti-genomic *Phlebovirus* S segment, a second plasmid comprising an anti-genomic *Phlebovirus* M segment and a third plasmid comprising an anti-genomic *Phlebovirus* L segment, wherein each plasmid comprises a T7 promoter and a hepatitis delta virus ribozyme, and wherein:
(i) the first plasmid comprises a nucleotide sequence at least 95% identical to nucleotides 107-1878 of SEQ ID NO: 46, nucleotides 107-1536 of SEQ ID NO: 47, or nucleotides 107-1878 of SEQ ID NO: 51;
(ii) the second plasmid comprises a nucleotide sequence at least 95% identical to nucleotides 107-3533 of SEQ ID NO: 45 or nucleotides 107-3533 of SEQ ID NO: 50; and
(iii) the third plasmid comprises a nucleotide sequence at least 95% identical to nucleotides 107-6474 of SEQ ID NO: 44 or nucleotides 107-6474 of SEQ ID NO: 49.

16. A *Phlebovirus* mini-genome reporter system, comprising a first plasmid comprising a reporter gene flanked by UTR sequences of a *Phlebovirus* S, M or L segment, a second plasmid encoding a *Phlebovirus* NP, and a third plasmid encoding a *Phlebovirus* L protein, wherein:
(i) the second plasmid comprises a nucleotide sequence at least 95% identical to nucleotides 107-1878 of SEQ ID NO: 46 or nucleotides 107-1878 of SEQ ID NO: 51; and
(ii) the third plasmid comprises a nucleotide sequence at least 95% identical to nucleotides 107-6474 of SEQ ID NO: 44 or nucleotides 107-6474 of SEQ ID NO: 49.

17. The *Phlebovirus* mini-genome reporter system of claim 16, further comprising a fourth plasmid, wherein the fourth plasmid encodes *Phlebovirus* GnGc.

18. A method of producing *Phlebovirus* pseudo-virus, comprising transfecting cells expressing T7 polymerase with the first, second, third and fourth plasmids of the *Phlebovirus* mini-genome reporter system of claim 17.

19. The expression vector of claim 3, further comprising a selectable marker.

20. The expression vector of claim 3, further comprising a T7 promoter, a hepatitis delta virus ribozyme, or both.

21. The oligonucleotide of claim 5, wherein the detectable label comprises a radioactive isotope, an enzyme substrate, a co-factor, a ligand, a chemiluminescent agent, a fluorescent agent, a hapten or an enzyme.

22. The recombinant *Phlebovirus* of claim 11, wherein the heterologous gene comprises a reporter gene.

23. The recombinant *Phlebovirus* of claim 22, wherein the reporter gene encodes a fluorescent protein or an enzyme.

* * * * *

SEQUENCE LISTING

```
<160> NUMBER OF SEQ ID NOS: 53

<210> SEQ ID NO 1
<211> LENGTH: 1772
<212> TYPE: DNA
<213> ORGANISM: Heartland virus

<400> SEQUENCE: 1
acacaaagaa cccctttgaat tttcaaaaca tgtccttgtc taaagcctct cagcccagcg      60
tcaagagtgc ctgcgttagg cttcccatcg tggttcttga gcctaatctg gccgagctca     120
gcacctcata tgttggcctg gtctcatgta agtgctctgt tcttacatgc tccatgatga     180
ggaaaatgaa ggccttcacc aatactgtct ggcttttgg caatcccaac aatcctctac      240
atgctctaga gccagctgtt gagcaacttc ttgatgagta ctctggggac ctgggctctt     300
atagtcagca ggagaagagt gcattgaggt ggccgagtgg gaaaccgtca gtccatttcc     360
tgcaggctgc tcatttattc ttctccctca agaacacctg ggcagtcgag acaggtcagg     420
aaaattggag aggtttcttc cacaggataa catctgggaa aaaatacaaa ttcgagggg      480 acatggtcat tgactcttgc tacaaaattg atgagagacg taggcgaatg ggtctgcctg     540
atactttcat aacaggattg aacccaataa tggacgtggc tctcctccaa attgagtcac     600
ttttgcgtgt taggggtctc acactcaact accaccttt cacatcaccc ttccttgaca      660
agcctctcct tgactcctta tactttgcca tctggagaga caagaagaaa gatgatgggt     720
catattccca agatgagggg gcccgccagg atgaccctct caaccccttg gatgagctct     780
tgtacctgtc tggcttgccc aaaccactag cacattatct gaataaatgc cctctccata     840
atataatcat gcatgatgag gaggtcagag aggcctatct taatcccatc tggggaaagg     900
actggccagc actttccagc tcccctagg gggagctaat ttagatcgaa ttcatttgat      960
ttgaccaatt ggaatttggc gccaaattca aaatttatca gctgcttaca tgtttctgta    1020
agcagcagcc gcagccttca ctgagccgga tgcttccttg gttgctgtga gcaagccctt    1080
ggcctgcagc cagctgatcc tggtggcatt tgggaagaag agggaattga cagctgcatg    1140
cagagggtct ctgaatttgg catacacctc tgcctttgtc atcttccttt ggtccacatt    1200
gattgttcga gcaaatgtgt cttgccaaag ggaataggca tccatgaagt cctttatgac    1260
```

```
ttcaattgag acatctgcct gtggaatcag tgagccaaag gccatgcaca tcatttccag    1320
tggataacct tggattttgt tgtgcatgat tgctggccca acagggaggt actccttgat    1380
tgctgctgca gcagcacagg tccaggttgg caggcactgg gcaactctca ctggtgtcac    1440
agccattctg tcaacagcat tctccttcag ctcataaact ctagccagat tgtcatcct    1500 ctcagcgcct tcttagaca tcttgccaca tgctttcact atcttgttcc ctctggtgag    1560
agcaaataca atgatgtact tcacatcatt cctccagttc tcaccccctc tctcacgaag    1620
cagccccaag atcacagcag atccaggcc ctcataagct atttcctttg caaactcgac    1680
caaagctgga acatccagtg gctcgttgcc aatctcaaca gctattgcgg accagtcagt    1740
catgcttgat gattcaaagg ggttctctgt gt                                   1772

<210> SEQ ID NO 2
<211> LENGTH: 3427
<212> TYPE: DNA
<213> ORGANISM: Heartland virus

<400> SEQUENCE: 2
acacagagac ggctatacat taaggtagag gtaaaccgta atccactgag atgattgccc     60
cagttgtcct gttttcact ctctgtccgt cccaactcag cgcctggggc tctccaggag     120
accccattgt ttgtggtgtg aggaccgaaa caaacaaatc cattcagatt gagtggaagg     180
aggggagatc agagaaatta tgccagattg acagacttgg acatgtcaca agctggttaa     240
gaaatcactc atctttccag gggcttattg gtcaggtgaa ggggaggcca agtgtttcct     300
acttcccgga aggagcttct taccctaggt ggagcgggct attaagccca tgtgatgctg     360
aatggctggg actaatagca gtgagcaagg ctggggatac agacatgatt gtcccaggcc     420
caacttacaa aggcaaaatc tttgttgaga gaccaacgta caatggttat aaaggctggg     480
ggtgtgcaga tgggaagtca ctaagccact ctggcacata ttgtgaaact gacagctcag     540
taagttctgg gttaattcag ggtgataggg ttctctgggt tggggaagta gtctgtcaga     600
gagggacacc tgtgccagaa gatgtattta gtgaactgat tagcttgagt caaagtgagt     660
tcccagatgt gtgcaaggtt gatggggttg cactgaacca atgtgagcag agagcatcc     720 cccagccact ggacgttgca tggattgatg ttggaaggtc tcataaagtg ctgatgagag    780
aacacaaaac taaatgggtc caagagagct cagcaaagga ctttgtgtgc ttcaaggtgg    840
gtcaggggcc atgttcaaaa caagaggaag atgactgcat gagtaagggc aactgccatg    900
gggatgaggt tttctgcagg atggcaggat gctctgcccg tatgcaagat aatcaagaag    960
gctgtaggtg cgaactgctc caaaaacctg agaaatcat tgtgaattat ggaggcgtct   1020
ctgtaagacc aacttgttat ggattctcta gaatgatggc aacattggaa gttcacaagc   1080
ctgatagaga attaacaggg tgcacggtt gtcacctaga gtgcatagag ggagggggca    1140
aaattgtaac acttacaagc gagctgagaa gtgcaacagt ttgtgcttca catttttgtg   1200
catccgcaaa aggggctca agacaactg acatactctt ccacactggt gctctcgttg    1260
gacccaaatc cattagaatt acgggccagt tgttagatgg gagcaagttc tccttttgatg   1320 ggcactgcat attcccagat gggtgcatgg cacttgactg caccttctgt aaggagttcc   1380
tgagaaaccc acaatgttac ccagtaaaga atggctctt cttggtggta ttgtgatgt    1440 gctgctattg cgcactgatg ctgcttacta acatactgag agctataggt gttttgggaa   1500
catgggtttt tgctccaata aagttagttc tagcattagg attgaggctt gccaaactat   1560
```

-continued

```
caaagaaggg gttggttgct gtggttacaa ggggccaaat gatcgtgaat gatgagctgc      1620
accagattcg agtggagaga ggtgagcaaa atgagggaag actaggtcat ggcccaagag      1680
gtcccgtccg tcactggcta tactcacctg ccctcattct cattctgacc acttcaattt      1740
gctctggatg tgatgagctc gttcatgctg agagtaaatc tatcacatgc aagtctgcat      1800
ctgggaatga aaggagtgc tcagtgacag gcagagcttt actcccagct gttaatccag       1860
gacaggaggc ctgcttgcac ttcagtatgc cagggagccc agactctaag tgcctcaaga      1920
tcaaagtgaa atcaataaat ctcagatgca agcaagcctc ttcatattat gttcctgaag      1980
caaaggcaag atgtacatct gtaagaaggt gcaggtgggc aggtgactgt caatctgggt      2040
gtccaacata tttcagctca aactcattct cagatgactg ggcaaacagg atggacaggg      2100
ctgggctcgg gatgagtggg tgctcagatg ggtgtggtgg ggctgcatgt gggtgtttca      2160
atgcagcgcc atcctgcatc ttttggagaa agtgggtgga gaacccatcc aatcgtgtct      2220
ggaaggtgtc accttgtgca tcatgggtgc tagctgcaat cattgagttg actttgccat      2280
caggagaggt taagactcta gagcctgtca cagggcaagc aactcaaatg tttaaggggtg     2340
ttgcaatcac gtatctgggt tcatccattg agattgttgg catgaccagg ctatgcgaga      2400
tgaaagagat gggaactggg attatggcac tagcccctg caatgaccct gggcacgcca       2460
taatgggaaa tgtgggtgag atccaatgca gtagtataga aagcgcaaag cacatcagat      2520
ctgatgggtg catttggaat gctgacctag ttgggataga attaagggtt gatgatgctg      2580
tgtgtttctc aaaactcacc agtgttgagg cagtcgcaaa tttctcaaaa atcccggcaa      2640
taatttctgg ggtccgtttt gatcaaggga atcatggaga atcgcgaatc tatggtagcc      2700
cattagacat cacgaaggtt agtggggaat tctcagtgtc attcagggg atgaggctta       2760
aactgtctga gatatcagca agctgcacag gtgagataac aaacgtctct ggttgctact      2820
cctgcatgac tggggcctct gtcagcataa agctacatag cagtaagaac acaacaggtc      2880
atcttaaatg tgattcagat gagactgcat tcagtgtcat ggagggaaca cacacttata      2940
ggcctcacat gagctttgat aaagcagtgg tagatgagga gtgtgtgcta aactgtggtg      3000
gccattcatc aaagctgttg cttaaggga gccttgtctt catggacgtg ccaaggtttg       3060
ttgatgggag ttatgttcaa acataccata gcaaggtgcc tgctggggga agggtcccaa      3120
atccagtaga ttggctcaac gcgctgtttg gagatgcat aacacgatgg attcttggga      3180
ttataggagt tctgttggca tgtgtcttgc tatttgtggt ggtggtggcc atcactaggc      3240
gattgatcaa ggggctgact caaagggcga aggtggcatg attggcatta attaacaaat      3300
aagcaagcct cctgtttcaa acctctggtg ggccagaagc ctgacagagg tttgaaacag      3360
atgctctgac atctggggtg tgaatgataa tgggtgggtt ttcaatttgt atagccggtc      3420
tttgtgt                                                                3427
```

<210> SEQ ID NO 3
<211> LENGTH: 6368
<212> TYPE: DNA
<213> ORGANISM: Heartland virus

<400> SEQUENCE: 3

```
acacaaagac gtccagatga atttagaagc tctttgctct agagtgcttt cagagagagg       60
gctatcaact ggtgagcctg ggtatatga ccagattttt gaaaggcctg gcctcccaaa       120
ccttgaagtc acagtagact ccactggggt agttgtcgat gttggggcca ttcctgactc      180
agcatcacag ctagggtcct cgataaatgc aggtgtgctc accataccctc tctcagaagc    240
```

```
atataagata aatcatgact tcactttctc tggactgact aagacaacgg ataggaagtt    300
gtctgaagta ttcccttggg ttcatgatgg ctcagactca atgaccccg atgtgataca    360 cacaagacta gatggaacag tagttgtaat tgaattcaca acaaccagaa gcaccaacat    420
gggaggactt gaggctgcct atcggagcaa gcttgaaaaa taccgtgacc cactaaacag    480
aagatcagac ataatgcctg atgcatcaat ttactttgga atcattgttg ttagtgcatc    540
tggtgttctc acaaatatgc ctctgaccca agatgaagct gaagaattga tgttcaggtt    600
ctgtgtggca aacgagattt attctcaggc aagagcaatg gatgctgagg ttgaacttca    660
aaagtcagag gaggaatatg aggccatatc cagagcaaga gctttcttca cgcttttgta    720
ctatgacgat ggcaagctct ctgaggcatt ccctaactct gacattgaga tgctcagaag    780
atttctgagt cagcctgtag acacaagttt tgtgaccgca accctcaaag aaaagagca    840 agaggcttat aagagaatgt gtgaggagca ctatctaaaa agtggcatga gcacaaaaga    900
gaggcttgag gcaaatcgca atgatgcaat agacaaaact agagctctca tggaaagact    960
ccacaacatg agcagcaagg agctacactc gaataagagc acagtgaagt tgccccctg    1020 ggtagtgaag ccttctgata ggacgttaga tgtcaaaacg gacacgggat caggggagct    1080
actcaaccat ggcccatatg gggagttgtg gtcaagatgc ttcctggaga ttatccttgg    1140
gaatgtggaa ggggtcatca gcagccctga aaaggagctg gagatcgcca tcagtgatga    1200
ccctgaggct gacacccta aggctgcaaa gataaaatac cacaggttca ggcctgagct    1260
cagtttagag agcaagcatg aatttttcatt acaaggcatc gagggcaaaa gatggaagca    1320
ttcagctagg aatgtcctta agatgaaat gtcccataag acaatgagcc catttgttga    1380
tgtctcgaac attgaggagt ttctgataat gaacaacctg ttaaatgaca catcttttaa    1440
tcgggaaggg ctgcaagaaa caatcaacct gttgttggag aaggctactg aaatgcacca    1500
aaatggctta tcaacagctt tgaatgattc cttcaagaga aacttcaaca caaacgtagt    1560
gcagtggagc atgtgggtct catgcttagc tcaggaattg gcaagtgctt tgaagcaaca    1620
ttgcaagcct ggtgagttta tcatcaaaaa attaatgcac tggccaatat tcgcccataat    1680 taagcccact aagtcatcaa gtcacatatt ctacagcttg gcaataaaaa aaaccaacat    1740
taagaggagg ctgattggtg acgtattcac agacacaatt gatgcggggg agtgggagtt    1800
ttcagaattc aaaagcctca agacttgcaa gctgacaaat ctcattaacc tgccgtgcac    1860
catgctcaac tcaattgcgt tctggagaga aagatggga gtagcccct ggatttctag    1920 aaaggcctgc tcagagctca gggaacaagt ggcaatcact ttccttatga gtctggaaga    1980
caaatcaaca acagaagagc ttgttactct cacgaggtat tcacaaatgg agggatttgt    2040
gtctccaccc ctgctcccta aacccagaa gatggtggaa aagttagaag ttccttgcg    2100 aacaaagctt caagtgtttt tgtttaggag gcatcttgat gctattgtta gagttgctgc    2160
atctccattc cccattgtgg caagagatgg tcgagtggaa tggacaggga cattcaatgc    2220
aatcactggc cgaagcactg gctggaaaaa catggtaaac aactggtata tcggctatta    2280
taaaaacaaa gaagagtcga ccgagctaaa tgccttaggt gagatgtata aaagattgt    2340 tgagattgag gctgagaagc cagcatcttc tgagtactta gggtggggag acactagcag    2400
ccctaagagg catgagttca gtagaagctt cctcaagtca gcatgcatat ctcttgagaa    2460
ggagatagag atgaggcatg ggaagagctg gaagcaaagc ttggaggaga gagtccttaa    2520
agaactgggc tcaaagaact tgctggactt agcaacaatg aaggcaacaa gcaactttag    2580
```

```
caaggaatgg gaagctttct cagaagtcag aacaaaagaa tatcataggt ctaaactcct   2640
agaaaagatg gctgaactaa tagagcatgg gttaatgtgg tatgttgatg cagcaggtca   2700
tgcatggaag gctgtccttg atgacaaatg tatgagaata tgcttgttta agaaaaatca   2760
gcacggaggc ctgagggaaa tttatgtaac gaatgcaaat gcaaggcttg tccaatttgg   2820
agtagagaca atggcacggt gtgtgtgtga gctaagccca catgaaacaa tagctaaccc   2880
tagactcaag tcaagcatca tagagaatca tggtctcaag agtgctcgac aattggggca   2940
ggggaccatt aatgtcaact cttcaaatga cgcaaaaaaa tggagtcagg gtcattatac   3000
aaccaagttg gccatggtat tatgctggtt catgccagca aaattccata ggttcatatg   3060
ggcaggcatc tcaatgttta ggtgcaagaa gatgatgatg gatctcaggt ttttagaaaa   3120
actgagcaca aaggctaatc agaaaactga tgatgacttc aggaaagact tagctggggc   3180
cttccatggc aatgttgaag ttccatggat gactcaaggg gctacatatc tccagactga   3240
gacagggatg atgcaaggga tcctgcattt tacatcaagc ctactgcatt catgcgtcca   3300
aagttttttac aaggcatatt ttttgtctcg gcttaaagaa gggatcgcag gcaaaaccat   3360
caaggcagct atagatgttt tagaaggctc tgatgactca gctatcatga taagcttgaa   3420
gccagcctca gacaatgagg aagcaatggc tcggttttta acagccaact tgctatactc   3480
agtcagagtc ataaacccgc tctttggcat ttatagctct gagaagtcaa cagtaaatac   3540
cttattttgt gtggagtaca actcagagtt ccacttccac aagcatttag tcaggcctac   3600
aatcagatgg gttgcagcat cccaccaaat ctctgagtca gaagccctgg caagcaggca   3660
ggaagattat gcgaaccttc tcactcaatg tcttgaaggg ggttcatcat tctctctaac   3720
atatttgatc cagtgtgccc agctcgtcca tcattatatg ctgctcgggc tctgcttgca   3780
cccgctgttt ggaacatttg tagggatgct gattgaggat ccagatccag ccctaggctt   3840
cttcataatg gacaatccag cttttgcagg gggagctgga tttagattca acctttggag   3900
gtcttgcaag ttcacaaacc ttggcaaaaa gtatgcattc tttttcaatg agattcaagg   3960
aaaaaccaag ggggatgcag attacagagc actggatgca acaactggtg gaacattaag   4020
ccactctgtg atgatctact gggggacag gagaaagtac caacatctcc tagacaggat   4080
ggggcttccc aaggactggg ttgagaggat agatgaaaac ccaagcgtct tatacaggag   4140
gcctgagaac aagcaggaac ttatcttgag gctggcagaa aaagtgcatt ctccaggtgt   4200
cacttccagc ttcagcaagg ggcatgttgt acctagagtg gtggcagctg gagtctactt   4260
gctgtcaaga cattgcttca ggtacactgc atcaatccac ggtaggggag catctcagaa   4320
ggcgagtcta attaagctgc ttgtcatgtc ttcaacatca gctgagagga atcaaggaag   4380
gctaaatcca aatcaagaaa gaatgctctt tccccaagtc caagagtatg aaagagtact   4440
gaccttgtta gatgaggtca ctgcgctcac agggaagttt gttgtgagag aaaggaacat   4500
agtcaaaagc agagtagagc ttttccagga gcctgtggac ttaaggtgta aagctgaaaa   4560
cctcattgca gaaatgtggt ttggacttaa agaacaaag ttgggcccaa ggctgctaaa   4620
ggaagaatgg gacaaactcc gcgcctcctt ctcatggttg agcactgatc ataaagaaac   4680
actggatgtg ggaccatttc ttagtcatgt tcaattcagg aatttcattg cacatgtgga   4740
tgcgaagtct aggagtgttc gactcttggg ggcccctgtc aagaagtcag gaggagtgac   4800
tacagtgtcc caggtggtga aatctaaattt cttcccaggt ttcatttggg actccagtga   4860
gagcttagat gaccaagaga gggttgaggg ggtgtcaatc ttgaaacaca ttctatttat   4920
gaccttgaat ggcccttaca ctgatgagca aaagaaagct atggttctgg aggccttcca   4980
```

-continued

```
atattttgca ctgccacatg ctgctgaggt tgtgaagaga tcacggtcat taaccctatg    5040
tttgatgaag aattttattg agcagagagg agggtcaata cttgaccaaa ttgaaaaggc    5100
tcagtcaggt acagttggtg gattcagtaa gccccagaag ccttaccgca acaatctgg     5160
aggcattggc tacaagggga aaggtgtttg acaggcata atggaaaaca caatgtaca     5220
gatcctgata gatggtgatg gttcatcgaa ctggatagaa gaaattaggc tgagtagtga    5280
gtccaggcta tttgatgtca tagaatctgt caggaggctg tgtgatgaca ttaatgtcaa    5340
caatagggtt acatcaagct ttcggggtca ttgcatggtg aggctcagca attttaaggt    5400
caagccagct tcaagggtag aagggtgccc agtgcgactt atgccctcct cattccggat    5460
aaaggagctc caaacccag atgaggtctt cttaagggtg aggggagaca ttctaaacct     5520
gtccatcctc cttcaagagg accgagtcat gaatctgctt agctacagag ctcgtgacac    5580
tgacatctca gagtctgcag catcctacct atggatgaat agaactgact tctcatttgg    5640
aaagaaggag ccatcttgca gctggatgtg cttgaaaaca ttggactcat gggcttggaa    5700
tcaagcagca agagttcttg aaagaaacat caaaaccct ggaattgata cacccgccat     5760
ggggaacatt ttcaaggatt gcttagaaag ctcactcaga aagcaggggt tgcttagatc    5820
tagaattgct gagatggtgg aacgacatgt tattccacta acaagtcagg agctggtgga    5880
tatcctggag gaagatgtcg attttttcaga aatgatgcaa tctgatataa tggaagggga   5940
cctagacatt gatatcctga tggaagggtc accaatgctc tgggcagcag aagtggagga   6000
aatgggagaa gctatggtga tactcagtca gtcaggaaag tattatcatc taaaattaat    6060
ggatcaagca gcaacaaccc tttcaacaat ccttgggaaa gatggttgca ggctcctact    6120
gggagagcgt acatgtggat caaatctcag ggagcaggtg aagccctact tgacattatt    6180
gcaaataaga gagggagatg tcaactgggt ttctgagtac aaagacgaca cacgtggtct    6240
tgatgaagac tccgcagaaa tgtggggtta aaccaaccag gactgggct cgggttgagg    6300
tgaagtgact ctgctgtctc acttgagctt tcagtaccta aaggttgata tctggacggt    6360
ctttgtgt                                                             6368
```

<210> SEQ ID NO 4
<211> LENGTH: 245
<212> TYPE: PRT
<213> ORGANISM: Heartland virus

<400> SEQUENCE: 4

```
Met Thr Asp Trp Ser Ala Ile Ala Val Glu Ile Gly Asn Glu Pro Leu
1               5                   10                  15

Asp Val Pro Ala Leu Val Glu Phe Ala Lys Glu Ile Ala Tyr Glu Gly
                20                  25                  30

Leu Asp Pro Ala Val Ile Leu Gly Leu Leu Arg Glu Arg Gly Gly Glu
            35                  40                  45

Asn Trp Arg Asn Asp Val Lys Tyr Ile Ile Val Phe Ala Leu Thr Arg
        50                  55                  60

Gly Asn Lys Ile Val Lys Ala Cys Gly Lys Met Ser Lys Lys Gly Ala
65                  70                  75                  80

Glu Arg Met Thr Asn Leu Ala Arg Val Tyr Glu Leu Lys Glu Asn Ala
                85                  90                  95

Val Asp Arg Met Ala Val Thr Pro Val Arg Val Ala Gln Cys Leu Pro
            100                 105                 110

Thr Trp Thr Cys Ala Ala Ala Ala Ala Ile Lys Glu Tyr Leu Pro Val
```

```
            115                 120                 125
Gly Pro Ala Ile Met His Asn Lys Ile Gln Gly Tyr Pro Leu Glu Met
        130                 135                 140

Met Cys Met Ala Phe Gly Ser Leu Ile Pro Gln Ala Asp Val Ser Ile
145                 150                 155                 160

Glu Val Ile Lys Asp Phe Met Asp Ala Tyr Ser Leu Trp Gln Asp Thr
                165                 170                 175

Phe Ala Arg Thr Ile Asn Val Asp Gln Arg Lys Met Thr Lys Ala Glu
            180                 185                 190

Val Tyr Ala Lys Phe Arg Asp Pro Leu His Ala Ala Val Asn Ser Leu
        195                 200                 205

Phe Phe Pro Asn Ala Thr Arg Ile Ser Trp Leu Gln Ala Lys Gly Leu
    210                 215                 220

Leu Thr Ala Thr Lys Glu Ala Ser Gly Ser Val Lys Ala Ala Ala Ala
225                 230                 235                 240

Ala Tyr Arg Asn Met
                245

<210> SEQ ID NO 5
<211> LENGTH: 299
<212> TYPE: PRT
<213> ORGANISM: Heartland virus

<400> SEQUENCE: 5

Met Ser Leu Ser Lys Ala Ser Gln Pro Ser Lys Ser Ala Cys Val
1               5                   10                  15

Arg Leu Pro Ile Val Val Leu Glu Pro Asn Leu Ala Glu Leu Ser Thr
            20                  25                  30

Ser Tyr Val Gly Leu Val Ser Cys Lys Cys Ser Val Leu Thr Cys Ser
        35                  40                  45

Met Met Arg Lys Met Lys Ala Phe Thr Asn Thr Val Trp Leu Phe Gly
    50                  55                  60

Asn Pro Asn Asn Pro Leu His Ala Leu Glu Pro Ala Val Glu Gln Leu
65                  70                  75                  80

Leu Asp Glu Tyr Ser Gly Asp Leu Gly Ser Tyr Ser Gln Gln Glu Lys
                85                  90                  95

Ser Ala Leu Arg Trp Pro Ser Gly Lys Pro Ser Val His Phe Leu Gln
            100                 105                 110

Ala Ala His Leu Phe Phe Ser Leu Lys Asn Thr Trp Ala Val Glu Thr
        115                 120                 125

Gly Gln Glu Asn Trp Arg Gly Phe Phe His Arg Ile Thr Ser Gly Lys
    130                 135                 140

Lys Tyr Lys Phe Glu Gly Asp Met Val Ile Asp Ser Cys Tyr Lys Ile
145                 150                 155                 160

Asp Glu Arg Arg Arg Arg Met Gly Leu Pro Asp Thr Phe Ile Thr Gly
                165                 170                 175

Leu Asn Pro Ile Met Asp Val Ala Leu Leu Gln Ile Glu Ser Leu Leu
            180                 185                 190

Arg Val Arg Gly Leu Thr Leu Asn Tyr His Leu Phe Thr Ser Pro Phe
        195                 200                 205

Leu Asp Lys Pro Leu Leu Asp Ser Leu Tyr Phe Ala Ile Trp Arg Asp
    210                 215                 220

Lys Lys Lys Asp Asp Gly Ser Tyr Ser Gln Asp Glu Gly Ala Arg Gln
225                 230                 235                 240
```

```
Asp Asp Pro Leu Asn Pro Leu Asp Glu Leu Leu Tyr Leu Ser Gly Leu
                245                 250                 255

Pro Lys Pro Leu Ala His Tyr Leu Asn Lys Cys Pro Leu His Asn Ile
            260                 265                 270

Ile Met His Asp Glu Glu Val Arg Glu Ala Tyr Leu Asn Pro Ile Trp
        275                 280                 285

Gly Lys Asp Trp Pro Ala Leu Ser Ser Ser Pro
    290                 295

<210> SEQ ID NO 6
<211> LENGTH: 1076
<212> TYPE: PRT
<213> ORGANISM: Heartland virus

<400> SEQUENCE: 6

Met Ile Ala Pro Val Val Leu Phe Phe Thr Leu Cys Pro Ser Gln Leu
1               5                   10                  15

Ser Ala Trp Gly Ser Pro Gly Asp Pro Ile Val Cys Gly Val Arg Thr
            20                  25                  30

Glu Thr Asn Lys Ser Ile Gln Ile Glu Trp Lys Glu Gly Arg Ser Glu
        35                  40                  45

Lys Leu Cys Gln Ile Asp Arg Leu Gly His Val Thr Ser Trp Leu Arg
    50                  55                  60

Asn His Ser Ser Phe Gln Gly Leu Ile Gly Gln Val Lys Gly Arg Pro
65                  70                  75                  80

Ser Val Ser Tyr Phe Pro Glu Gly Ala Ser Tyr Pro Arg Trp Ser Gly
                85                  90                  95

Leu Leu Ser Pro Cys Asp Ala Glu Trp Leu Gly Leu Ile Ala Val Ser
            100                 105                 110

Lys Ala Gly Asp Thr Asp Met Ile Val Pro Gly Pro Thr Tyr Lys Gly
        115                 120                 125

Lys Ile Phe Val Glu Arg Pro Thr Tyr Asn Gly Tyr Lys Gly Trp Gly
    130                 135                 140

Cys Ala Asp Gly Lys Ser Leu Ser His Ser Gly Thr Tyr Cys Glu Thr
145                 150                 155                 160

Asp Ser Ser Val Ser Ser Gly Leu Ile Gln Gly Asp Arg Val Leu Trp
                165                 170                 175

Val Gly Glu Val Val Cys Gln Arg Gly Thr Pro Val Pro Glu Asp Val
            180                 185                 190

Phe Ser Glu Leu Ile Ser Leu Ser Gln Ser Glu Phe Pro Asp Val Cys
        195                 200                 205

Lys Val Asp Gly Val Ala Leu Asn Gln Cys Glu Gln Glu Ser Ile Pro
    210                 215                 220

Gln Pro Leu Asp Val Ala Trp Ile Asp Val Gly Arg Ser His Lys Val
225                 230                 235                 240

Leu Met Arg Glu His Lys Thr Lys Trp Val Gln Glu Ser Ser Ala Lys
                245                 250                 255

Asp Phe Val Cys Phe Lys Val Gly Gln Gly Pro Cys Ser Lys Gln Glu
            260                 265                 270

Glu Asp Asp Cys Met Ser Lys Gly Asn Cys His Gly Asp Glu Val Phe
        275                 280                 285

Cys Arg Met Ala Gly Cys Ser Ala Arg Met Gln Asp Asn Gln Glu Gly
    290                 295                 300

Cys Arg Cys Glu Leu Leu Gln Lys Pro Gly Glu Ile Ile Val Asn Tyr
305                 310                 315                 320
```

```
Gly Gly Val Ser Val Arg Pro Thr Cys Tyr Gly Phe Ser Arg Met Met
            325                 330                 335

Ala Thr Leu Glu Val His Lys Pro Asp Arg Glu Leu Thr Gly Cys Thr
            340                 345                 350

Gly Cys His Leu Glu Cys Ile Glu Gly Val Lys Ile Val Thr Leu
            355                 360             365

Thr Ser Glu Leu Arg Ser Ala Thr Val Cys Ala Ser His Phe Cys Ala
370                 375                 380

Ser Ala Lys Gly Gly Ser Lys Thr Thr Asp Ile Leu Phe His Thr Gly
385                 390                 395                 400

Ala Leu Val Gly Pro Lys Ser Ile Arg Ile Thr Gly Gln Leu Leu Asp
            405                 410                 415

Gly Ser Lys Phe Ser Phe Asp Gly His Cys Ile Phe Pro Asp Gly Cys
            420                 425                 430

Met Ala Leu Asp Cys Thr Phe Cys Lys Glu Phe Leu Arg Asn Pro Gln
            435                 440                 445

Cys Tyr Pro Val Lys Lys Trp Leu Phe Leu Val Val Val Met Cys
            450                 455             460

Cys Tyr Cys Ala Leu Met Leu Leu Thr Asn Ile Leu Arg Ala Ile Gly
465                 470                 475                 480

Val Trp Gly Thr Trp Val Phe Ala Pro Ile Lys Leu Val Leu Ala Leu
            485                 490                 495

Gly Leu Arg Leu Ala Lys Leu Ser Lys Lys Gly Leu Val Ala Val Val
            500                 505                 510

Thr Arg Gly Gln Met Ile Val Asn Asp Glu Leu His Gln Ile Arg Val
            515                 520                 525

Glu Arg Gly Glu Gln Asn Glu Gly Arg Leu Gly His Gly Pro Arg Gly
            530                 535                 540

Pro Val Arg His Trp Leu Tyr Ser Pro Ala Leu Ile Leu Ile Leu Thr
545                 550                 555                 560

Thr Ser Ile Cys Ser Gly Cys Asp Glu Leu Val His Ala Glu Ser Lys
            565                 570                 575

Ser Ile Thr Cys Lys Ser Ala Ser Gly Asn Glu Lys Glu Cys Ser Val
            580                 585                 590

Thr Gly Arg Ala Leu Leu Pro Ala Val Asn Pro Gly Gln Glu Ala Cys
            595                 600                 605

Leu His Phe Ser Met Pro Gly Ser Pro Asp Ser Lys Cys Leu Lys Ile
            610                 615                 620

Lys Val Lys Ser Ile Asn Leu Arg Cys Lys Gln Ala Ser Ser Tyr Tyr
625                 630                 635                 640

Val Pro Glu Ala Lys Ala Arg Cys Thr Ser Val Arg Arg Cys Arg Trp
            645                 650                 655

Ala Gly Asp Cys Gln Ser Gly Cys Pro Thr Tyr Phe Ser Ser Asn Ser
            660                 665                 670

Phe Ser Asp Asp Trp Ala Asn Arg Met Asp Arg Ala Gly Leu Gly Met
            675                 680                 685

Ser Gly Cys Ser Asp Gly Cys Gly Gly Ala Ala Cys Gly Cys Phe Asn
            690                 695             700

Ala Ala Pro Ser Cys Ile Phe Trp Arg Lys Trp Val Glu Asn Pro Ser
705                 710                 715                 720

Asn Arg Val Trp Lys Val Ser Pro Cys Ala Ser Trp Val Leu Ala Ala
            725                 730                 735
```

```
Ile Ile Glu Leu Thr Leu Pro Ser Gly Val Lys Thr Leu Glu Pro
            740                 745                 750

Val Thr Gly Gln Ala Thr Gln Met Phe Lys Gly Val Ala Ile Thr Tyr
            755                 760                 765

Leu Gly Ser Ser Ile Glu Ile Val Gly Met Thr Arg Leu Cys Glu Met
        770                 775                 780

Lys Glu Met Gly Thr Gly Ile Met Ala Leu Ala Pro Cys Asn Asp Pro
785                 790                 795                 800

Gly His Ala Ile Met Gly Asn Val Gly Glu Ile Gln Cys Ser Ser Ile
                805                 810                 815

Glu Ser Ala Lys His Ile Arg Ser Asp Gly Cys Ile Trp Asn Ala Asp
            820                 825                 830

Leu Val Gly Ile Glu Leu Arg Val Asp Asp Ala Val Cys Phe Ser Lys
        835                 840                 845

Leu Thr Ser Val Glu Ala Val Ala Asn Phe Ser Lys Ile Pro Ala Ile
850                 855                 860

Ile Ser Gly Val Arg Phe Asp Gln Gly Asn His Gly Glu Ser Arg Ile
865                 870                 875                 880

Tyr Gly Ser Pro Leu Asp Ile Thr Lys Val Ser Gly Glu Phe Ser Val
            885                 890                 895

Ser Phe Arg Gly Met Arg Leu Lys Leu Ser Glu Ile Ser Ala Ser Cys
        900                 905                 910

Thr Gly Glu Ile Thr Asn Val Ser Gly Cys Tyr Ser Cys Met Thr Gly
            915                 920                 925

Ala Ser Val Ser Ile Lys Leu His Ser Ser Lys Asn Thr Thr Gly His
        930                 935                 940

Leu Lys Cys Asp Ser Asp Glu Thr Ala Phe Ser Val Met Glu Gly Thr
945                 950                 955                 960

His Thr Tyr Arg Pro His Met Ser Phe Asp Lys Ala Val Val Asp Glu
            965                 970                 975

Glu Cys Val Leu Asn Cys Gly Gly His Ser Ser Lys Leu Leu Leu Lys
        980                 985                 990

Gly Ser Leu Val Phe Met Asp Val Pro Arg Phe Val Asp Gly Ser Tyr
        995                 1000                1005

Val Gln Thr Tyr His Ser Lys Val Pro Ala Gly Gly Arg Val Pro
        1010                1015                1020

Asn Pro Val Asp Trp Leu Asn Ala Leu Phe Gly Asp Gly Ile Thr
        1025                1030                1035

Arg Trp Ile Leu Gly Ile Ile Gly Val Leu Leu Ala Cys Val Leu
        1040                1045                1050

Leu Phe Val Val Val Val Ala Ile Thr Arg Arg Leu Ile Lys Gly
        1055                1060                1065

Leu Thr Gln Arg Ala Lys Val Ala
        1070                1075

<210> SEQ ID NO 7
<211> LENGTH: 2084
<212> TYPE: PRT
<213> ORGANISM: Heartland virus

<400> SEQUENCE: 7

Met Asn Leu Glu Ala Leu Cys Ser Arg Val Leu Ser Glu Arg Gly Leu
1               5                   10                  15

Ser Thr Gly Glu Pro Gly Val Tyr Asp Gln Ile Phe Glu Arg Pro Gly
            20                  25                  30
```

```
Leu Pro Asn Leu Glu Val Thr Val Asp Ser Thr Gly Val Val Asp
         35                  40                  45
Val Gly Ala Ile Pro Asp Ser Ala Ser Gln Leu Gly Ser Ser Ile Asn
     50                  55                  60
Ala Gly Val Leu Thr Ile Pro Leu Ser Glu Ala Tyr Lys Ile Asn His
 65                  70                  75                  80
Asp Phe Thr Phe Ser Gly Leu Thr Lys Thr Thr Asp Arg Lys Leu Ser
                 85                  90                  95
Glu Val Phe Pro Leu Val His Asp Gly Ser Asp Ser Met Thr Pro Asp
            100                 105                 110
Val Ile His Thr Arg Leu Asp Gly Thr Val Val Ile Glu Phe Thr
            115                 120                 125
Thr Thr Arg Ser Thr Asn Met Gly Gly Leu Glu Ala Ala Tyr Arg Ser
        130                 135                 140
Lys Leu Glu Lys Tyr Arg Asp Pro Leu Asn Arg Arg Ser Asp Ile Met
145                 150                 155                 160
Pro Asp Ala Ser Ile Tyr Phe Gly Ile Ile Val Val Ser Ala Ser Gly
                165                 170                 175
Val Leu Thr Asn Met Pro Leu Thr Gln Asp Glu Ala Glu Leu Met
            180                 185                 190
Phe Arg Phe Cys Val Ala Asn Glu Ile Tyr Ser Gln Ala Arg Ala Met
        195                 200                 205
Asp Ala Glu Val Glu Leu Gln Lys Ser Glu Glu Tyr Glu Ala Ile
    210                 215                 220
Ser Arg Ala Arg Ala Phe Phe Thr Leu Phe Asp Tyr Asp Asp Gly Lys
225                 230                 235                 240
Leu Ser Glu Ala Phe Pro Asn Ser Asp Ile Glu Met Leu Arg Arg Phe
                245                 250                 255
Leu Ser Gln Pro Val Asp Thr Ser Phe Val Thr Ala Thr Leu Lys Glu
            260                 265                 270
Lys Glu Gln Glu Ala Tyr Lys Arg Met Cys Glu Glu His Tyr Leu Lys
        275                 280                 285
Ser Gly Met Ser Thr Lys Glu Arg Leu Glu Ala Asn Arg Asn Asp Ala
290                 295                 300
Ile Asp Lys Thr Arg Ala Leu Met Glu Arg Leu His Asn Met Ser Ser
305                 310                 315                 320
Lys Glu Leu His Ser Asn Lys Ser Thr Val Lys Leu Pro Pro Trp Val
                325                 330                 335
Val Lys Pro Ser Asp Arg Thr Leu Asp Val Lys Thr Asp Thr Gly Ser
            340                 345                 350
Gly Glu Leu Leu Asn His Gly Pro Tyr Gly Glu Leu Trp Ser Arg Cys
        355                 360                 365
Phe Leu Glu Ile Ile Leu Gly Asn Val Glu Gly Val Ile Ser Ser Pro
    370                 375                 380
Glu Lys Glu Leu Glu Ile Ala Ile Ser Asp Asp Pro Glu Ala Asp Thr
385                 390                 395                 400
Pro Lys Ala Ala Lys Ile Lys Tyr His Arg Phe Arg Pro Glu Leu Ser
                405                 410                 415
Leu Glu Ser Lys His Glu Phe Ser Leu Gln Gly Ile Glu Gly Lys Arg
            420                 425                 430
Trp Lys His Ser Ala Arg Asn Val Leu Lys Asp Glu Met Ser His Lys
        435                 440                 445
```

```
Thr Met Ser Pro Phe Val Asp Val Ser Asn Ile Glu Glu Phe Leu Ile
    450                 455                 460

Met Asn Asn Leu Leu Asn Asp Thr Ser Phe Asn Arg Glu Gly Leu Gln
465                 470                 475                 480

Glu Thr Ile Asn Leu Leu Leu Glu Lys Ala Thr Glu Met His Gln Asn
                485                 490                 495

Gly Leu Ser Thr Ala Leu Asn Asp Ser Phe Lys Arg Asn Phe Asn Thr
                500                 505                 510

Asn Val Val Gln Trp Ser Met Trp Val Ser Cys Leu Ala Gln Glu Leu
            515                 520                 525

Ala Ser Ala Leu Lys Gln His Cys Lys Pro Gly Glu Phe Ile Ile Lys
530                 535                 540

Lys Leu Met His Trp Pro Ile Phe Ala Ile Ile Lys Pro Thr Lys Ser
545                 550                 555                 560

Ser Ser His Ile Phe Tyr Ser Leu Ala Ile Lys Lys Thr Asn Ile Lys
                565                 570                 575

Arg Arg Leu Ile Gly Asp Val Phe Thr Asp Thr Ile Asp Ala Gly Glu
                580                 585                 590

Trp Glu Phe Ser Glu Phe Lys Ser Leu Lys Thr Cys Lys Leu Thr Asn
            595                 600                 605

Leu Ile Asn Leu Pro Cys Thr Met Leu Asn Ser Ile Ala Phe Trp Arg
610                 615                 620

Glu Lys Met Gly Val Ala Pro Trp Ile Ser Arg Lys Ala Cys Ser Glu
625                 630                 635                 640

Leu Arg Glu Gln Val Ala Ile Thr Phe Leu Met Ser Leu Glu Asp Lys
                645                 650                 655

Ser Thr Thr Glu Glu Leu Val Thr Leu Thr Arg Tyr Ser Gln Met Glu
                660                 665                 670

Gly Phe Val Ser Pro Pro Leu Leu Pro Lys Pro Gln Lys Met Val Glu
            675                 680                 685

Lys Leu Glu Val Pro Leu Arg Thr Lys Leu Gln Val Phe Leu Phe Arg
690                 695                 700

Arg His Leu Asp Ala Ile Val Arg Val Ala Ala Ser Pro Phe Pro Ile
705                 710                 715                 720

Val Ala Arg Asp Gly Arg Val Glu Trp Thr Gly Thr Phe Asn Ala Ile
                725                 730                 735

Thr Gly Arg Ser Thr Gly Leu Glu Asn Met Val Asn Asn Trp Tyr Ile
                740                 745                 750

Gly Tyr Tyr Lys Asn Lys Glu Glu Ser Thr Glu Leu Asn Ala Leu Gly
            755                 760                 765

Glu Met Tyr Lys Lys Ile Val Glu Ile Glu Ala Glu Lys Pro Ala Ser
770                 775                 780

Ser Glu Tyr Leu Gly Trp Gly Asp Thr Ser Ser Pro Lys Arg His Glu
785                 790                 795                 800

Phe Ser Arg Ser Phe Leu Lys Ser Ala Cys Ile Ser Leu Glu Lys Glu
                805                 810                 815

Ile Glu Met Arg His Gly Lys Ser Trp Lys Gln Ser Leu Glu Glu Arg
                820                 825                 830

Val Leu Lys Glu Leu Gly Ser Lys Asn Leu Leu Asp Leu Ala Thr Met
            835                 840                 845

Lys Ala Thr Ser Asn Phe Ser Lys Glu Trp Glu Ala Phe Ser Glu Val
850                 855                 860

Arg Thr Lys Glu Tyr His Arg Ser Lys Leu Leu Glu Lys Met Ala Glu
```

```
            865                 870                 875                 880
Leu Ile Glu His Gly Leu Met Trp Tyr Val Asp Ala Ala Gly His Ala
                    885                 890                 895
Trp Lys Ala Val Leu Asp Asp Lys Cys Met Arg Ile Cys Leu Phe Lys
                900                 905                 910
Lys Asn Gln His Gly Gly Leu Arg Glu Ile Tyr Val Thr Asn Ala Asn
                915                 920                 925
Ala Arg Leu Val Gln Phe Gly Val Glu Thr Met Ala Arg Cys Val Cys
            930                 935                 940
Glu Leu Ser Pro His Glu Thr Ile Ala Asn Pro Arg Leu Lys Ser Ser
945                 950                 955                 960
Ile Ile Glu Asn His Gly Leu Lys Ser Ala Arg Gln Leu Gly Gln Gly
                965                 970                 975
Thr Ile Asn Val Asn Ser Ser Asn Asp Ala Lys Lys Trp Ser Gln Gly
                980                 985                 990
His Tyr Thr Thr Lys Leu Ala Met Val Leu Cys Trp Phe Met Pro Ala
                995                 1000                1005
Lys Phe His Arg Phe Ile Trp Ala Gly Ile Ser Met Phe Arg Cys
            1010                1015                1020
Lys Lys Met Met Met Asp Leu Arg Phe Leu Glu Lys Leu Ser Thr
            1025                1030                1035
Lys Ala Asn Gln Lys Thr Asp Asp Asp Phe Arg Lys Asp Leu Ala
            1040                1045                1050
Gly Ala Phe His Gly Asn Val Glu Val Pro Trp Met Thr Gln Gly
            1055                1060                1065
Ala Thr Tyr Leu Gln Thr Glu Thr Gly Met Met Gln Gly Ile Leu
            1070                1075                1080
His Phe Thr Ser Ser Leu Leu His Ser Cys Val Gln Ser Phe Tyr
            1085                1090                1095
Lys Ala Tyr Phe Leu Ser Arg Leu Lys Glu Gly Ile Ala Gly Lys
            1100                1105                1110
Thr Ile Lys Ala Ala Ile Asp Val Leu Glu Gly Ser Asp Asp Ser
            1115                1120                1125
Ala Ile Met Ile Ser Leu Lys Pro Ala Ser Asp Asn Glu Glu Ala
            1130                1135                1140
Met Ala Arg Phe Leu Thr Ala Asn Leu Leu Tyr Ser Val Arg Val
            1145                1150                1155
Ile Asn Pro Leu Phe Gly Ile Tyr Ser Ser Glu Lys Ser Thr Val
            1160                1165                1170
Asn Thr Leu Phe Cys Val Glu Tyr Asn Ser Glu Phe His Phe His
            1175                1180                1185
Lys His Leu Val Arg Pro Thr Ile Arg Trp Val Ala Ala Ser His
            1190                1195                1200
Gln Ile Ser Glu Ser Glu Ala Leu Ala Ser Arg Gln Glu Asp Tyr
            1205                1210                1215
Ala Asn Leu Leu Thr Gln Cys Leu Glu Gly Gly Ser Ser Phe Ser
            1220                1225                1230
Leu Thr Tyr Leu Ile Gln Cys Ala Gln Leu Val His His Tyr Met
            1235                1240                1245
Leu Leu Gly Leu Cys Leu His Pro Leu Phe Gly Thr Phe Val Gly
            1250                1255                1260
Met Leu Ile Glu Asp Pro Asp Pro Ala Leu Gly Phe Phe Ile Met
            1265                1270                1275
```

-continued

```
Asp Asn Pro Ala Phe Ala Gly Gly Ala Gly Phe Arg Phe Asn Leu
    1280            1285                1290

Trp Arg Ser Cys Lys Phe Thr Asn Leu Gly Lys Lys Tyr Ala Phe
    1295            1300                1305

Phe Phe Asn Glu Ile Gln Gly Lys Thr Lys Gly Asp Ala Asp Tyr
    1310            1315                1320

Arg Ala Leu Asp Ala Thr Thr Gly Gly Thr Leu Ser His Ser Val
    1325            1330                1335

Met Ile Tyr Trp Gly Asp Arg Arg Lys Tyr Gln His Leu Leu Asp
    1340            1345                1350

Arg Met Gly Leu Pro Lys Asp Trp Val Glu Arg Ile Asp Glu Asn
    1355            1360                1365

Pro Ser Val Leu Tyr Arg Arg Pro Glu Asn Lys Gln Glu Leu Ile
    1370            1375                1380

Leu Arg Leu Ala Glu Lys Val His Ser Pro Gly Val Thr Ser Ser
    1385            1390                1395

Phe Ser Lys Gly His Val Val Pro Arg Val Val Ala Ala Gly Val
    1400            1405                1410

Tyr Leu Leu Ser Arg His Cys Phe Arg Tyr Thr Ala Ser Ile His
    1415            1420                1425

Gly Arg Gly Ala Ser Gln Lys Ala Ser Leu Ile Lys Leu Leu Val
    1430            1435                1440

Met Ser Ser Thr Ser Ala Glu Arg Asn Gln Gly Arg Leu Asn Pro
    1445            1450                1455

Asn Gln Glu Arg Met Leu Phe Pro Gln Val Gln Glu Tyr Glu Arg
    1460            1465                1470

Val Leu Thr Leu Leu Asp Glu Val Thr Ala Leu Thr Gly Lys Phe
    1475            1480                1485

Val Val Arg Glu Arg Asn Ile Val Lys Ser Arg Val Glu Leu Phe
    1490            1495                1500

Gln Glu Pro Val Asp Leu Arg Cys Lys Ala Glu Asn Leu Ile Ala
    1505            1510                1515

Glu Met Trp Phe Gly Leu Lys Arg Thr Lys Leu Gly Pro Arg Leu
    1520            1525                1530

Leu Lys Glu Glu Trp Asp Lys Leu Arg Ala Ser Phe Ser Trp Leu
    1535            1540                1545

Ser Thr Asp His Lys Glu Thr Leu Asp Val Gly Pro Phe Leu Ser
    1550            1555                1560

His Val Gln Phe Arg Asn Phe Ile Ala His Val Asp Ala Lys Ser
    1565            1570                1575

Arg Ser Val Arg Leu Leu Gly Ala Pro Val Lys Lys Ser Gly Gly
    1580            1585                1590

Val Thr Thr Val Ser Gln Val Val Lys Ser Asn Phe Phe Pro Gly
    1595            1600                1605

Phe Ile Leu Asp Ser Ser Glu Ser Leu Asp Asp Gln Glu Arg Val
    1610            1615                1620

Glu Gly Val Ser Ile Leu Lys His Ile Leu Phe Met Thr Leu Asn
    1625            1630                1635

Gly Pro Tyr Thr Asp Glu Gln Lys Lys Ala Met Val Leu Glu Ala
    1640            1645                1650

Phe Gln Tyr Phe Ala Leu Pro His Ala Ala Glu Val Val Lys Arg
    1655            1660                1665
```

-continued

```
Ser Arg Ser Leu Thr Leu Cys Leu Met Lys Asn Phe Ile Glu Gln
    1670            1675                1680
Arg Gly Gly Ser Ile Leu Asp Gln Ile Glu Lys Ala Gln Ser Gly
    1685            1690                1695
Thr Val Gly Gly Phe Ser Lys Pro Gln Lys Pro Tyr Arg Lys Gln
    1700            1705                1710
Ser Gly Gly Ile Gly Tyr Lys Gly Lys Gly Val Trp Thr Gly Ile
    1715            1720                1725
Met Glu Asn Thr Asn Val Gln Ile Leu Ile Asp Gly Asp Gly Ser
    1730            1735                1740
Ser Asn Trp Ile Glu Glu Ile Arg Leu Ser Ser Glu Ser Arg Leu
    1745            1750                1755
Phe Asp Val Ile Glu Ser Val Arg Arg Leu Cys Asp Asp Ile Asn
    1760            1765                1770
Val Asn Asn Arg Val Thr Ser Ser Phe Arg Gly His Cys Met Val
    1775            1780                1785
Arg Leu Ser Asn Phe Lys Val Lys Pro Ala Ser Arg Val Glu Gly
    1790            1795                1800
Cys Pro Val Arg Leu Met Pro Ser Ser Phe Arg Ile Lys Glu Leu
    1805            1810                1815
Gln Asn Pro Asp Glu Val Phe Leu Arg Val Arg Gly Asp Ile Leu
    1820            1825                1830
Asn Leu Ser Ile Leu Leu Gln Glu Asp Arg Val Met Asn Leu Leu
    1835            1840                1845
Ser Tyr Arg Ala Arg Asp Thr Asp Ile Ser Glu Ser Ala Ala Ser
    1850            1855                1860
Tyr Leu Trp Met Asn Arg Thr Asp Phe Ser Phe Gly Lys Lys Glu
    1865            1870                1875
Pro Ser Cys Ser Trp Met Cys Leu Lys Thr Leu Asp Ser Trp Ala
    1880            1885                1890
Trp Asn Gln Ala Ala Arg Val Leu Glu Arg Asn Ile Lys Thr Pro
    1895            1900                1905
Gly Ile Asp Asn Thr Ala Met Gly Asn Ile Phe Lys Asp Cys Leu
    1910            1915                1920
Glu Ser Ser Leu Arg Lys Gln Gly Leu Leu Arg Ser Arg Ile Ala
    1925            1930                1935
Glu Met Val Glu Arg His Val Ile Pro Leu Thr Ser Gln Glu Leu
    1940            1945                1950
Val Asp Ile Leu Glu Glu Asp Val Asp Phe Ser Glu Met Met Gln
    1955            1960                1965
Ser Asp Ile Met Glu Gly Asp Leu Asp Ile Asp Ile Leu Met Glu
    1970            1975                1980
Gly Ser Pro Met Leu Trp Ala Ala Glu Val Glu Glu Met Gly Glu
    1985            1990                1995
Ala Met Val Ile Leu Ser Gln Ser Gly Lys Tyr Tyr His Leu Lys
    2000            2005                2010
Leu Met Asp Gln Ala Ala Thr Thr Leu Ser Thr Ile Leu Gly Lys
    2015            2020                2025
Asp Gly Cys Arg Leu Leu Leu Gly Glu Arg Thr Cys Gly Ser Asn
    2030            2035                2040
Leu Arg Glu Gln Val Lys Pro Tyr Leu Thr Leu Leu Gln Ile Arg
    2045            2050                2055
Glu Gly Asp Val Asn Trp Val Ser Glu Tyr Lys Asp Asp Thr Arg
```

```
                  2060              2065              2070
Gly Leu  Asp Glu  Asp Ser  Ala  Glu Met  Trp Gly
               2075              2080

<210> SEQ ID NO 8
<211> LENGTH: 1772
<212> TYPE: DNA
<213> ORGANISM: Heartland virus

<400> SEQUENCE: 8
acacaaagaa ccccttgaat tatcaaaaca tgtccttgtc taaagcctct cagcccagcg     60
tcaagagtgc ctgcgttagg cttcccatcg tggttcttga gcctaatctg gccgagctca    120
gcacctcata tgttggcctg gtctcatgta agtgctcagt tcttacatgc tccatgatga    180
ggaaaatgaa ggccttcacc aatactgtct ggctgtttgg caatcccaac aatcctctac    240
atgctctaga gccagctgtt gagcaacttc ttgatgagta ctctggggac ttaggctctt    300
atagccagca ggagaagagt gcattgaggt ggccgagtgg gaaaccgtca gtccatttct    360
tgcaggctgc tcatttattc ttctccctca gaacacctg gcagtcgag acaggtcagg    420
aaaattggag aggtttcttc cacaggataa catctgggaa aaaatacaaa ttcgaggggg    480
acatggtcat tgactcttgc tacaaaattg atgagagacg taggcgaatg ggtctgcctg    540
atactttcat aacaggactg aacccaataa tggatgtggc tctcctccaa attgagtcac    600
ttttgcgtgt tagggctctc acactcaact atcaccttt cacatcatcc ttccttgaca    660
agcctctcct tgattcctta tattttgcca tctggagaga caaaaagaaa gatgatgggt    720
catattccca agatgagggg gcccgccagg atgaccctct caaccccttg gatgagctct    780
tgtacctgtc tgacttgccc aaaccactag cacattatct aaataaatgc cctctccata    840
atataatcat gcatgatgag gaggtcagag aggcctatct aaatcccatc tggggaaagg    900
actggccagc acttttccagc tccccttagg gggagctaat ttagatcgaa ttcatttgat    960
ttgaccaatt ggaatttagc gccaaattca aaatttatca gctgcttaca tgtttctgta   1020
agcagcagct gcagccttca ctgagccgga tgcttccttg gttgctgtga gcaagccctt   1080
ggcctgcagc cagctgatcc tggtggcatt tgggaagaag agggaattga cagctgcatg   1140
cagagggtct ctgaatttgg catacacctc tgcctttgtc atcttccttt ggtccacatt   1200
gattgttcga gcaaatgtgt cttgccaaag ggagtaggca tccatgaagt cctttatgac   1260
ttcaattgag acatctgcct gtgggatcaa tgagccaaag gccatgcaca tcatttccag   1320
tggataacct tggatcttgt tgtgcatgat tgctggccca acaggaggt actccttgat   1380
tgctgctgca gcagcacagg tccaggttgg caggcactgg gcaactctca ctggtgtcac   1440
agccattctg tcaacagcat tctccttcag ctcatagact ctagccaggt ttgtcatcct   1500
ctcagcgcct tcttagaca tcttgccaca tgctttcact atcttgttcc ctctagtgag   1560
agcaaataca atgatgtact tcacatcatt cctccagttc tcaccccccc tctcacgaag   1620
cagcccaaag atcacagcag atccaggcc ctcataagct atctcctttg caaactcgac   1680
caaagctgga acatccagtg gctcgttgcc aatctcaaca gctattgcag accagtcagt   1740
catgcttgat gattcaaagg ggttctctgt gt                                 1772

<210> SEQ ID NO 9
<211> LENGTH: 3427
<212> TYPE: DNA
<213> ORGANISM: Heartland virus
```

```
<400> SEQUENCE: 9
acacagagac ggctatacat taaagtagag gtaaaccgta atccactgag atgattgtcc      60
cgattgtcct gtttctcacg ctctgtccgt ccgaactcag tgcctggggc tccccaggag     120
accctattgt ttgtggtgtg aggactgaaa caaacaaatc cattcagatt gagtggaagg     180
agggaagatc agagaagcta tgccagattg acaggcttgg gcatgtcaca agctggttaa     240
gaaaccactc atctttccag gggcttattg gtcaggtgaa ggggagacca agtgtttcct     300
acttcccgga agggcttct tacccaaggt ggagcggcct attaagccca tgtgatgctg      360
aatggctggg actgatagca gtgagcaagg ctggagacac agacatgatt gtcccaggcc     420
caacttacaa agggaaaatc tttgttgaga gaccaacata caacggttac aaaggctggg     480
gttgtgcaga tggaaagtca ctaagccact caggcacata ttgtgaaact gacagctcag     540
tgagttctgg tttaattcag ggagataggg ttctctgggt tggggaagta gtctgtcaga     600
gagggacccc tgtgccagaa gatgtattta gtgaactggt tagcttgagt caaagtgagt     660
tcccagatgt gtgcaagatt gatggtgttg cactgaacca gtgtgagcag agagcatcc      720 cccagccact ggacgttgca tggattgatg ttggaaggtc tcataaggta ctgatgagag     780
aacacaaaac taaatgggtc caagagagct cagcaaagga ctttgtgtgt ttcaaggtgg     840
gtcaggggcc atgttcgaaa caagaggaag atgactgcat gagtaagggc aactgccatg     900
gggatgaggt tttctgcagg atggcaggat gctctgcccg tatgcaagat aatcaagaag     960
gctgcaggtg cgaactgctt caaaaacctg gagaaatcat tgtgaattat ggaggcgtct    1020
ctgtgagacc aacctgttat ggattctcca gaatgatggc aacattggaa gttcacaaac    1080
ctgatagaga attaacaggg tgcacggggtt gtcacctaga gtgcatagag gaggagtta    1140 aaattgtaac gcttacaagc gagctgagaa gtgcaacagt ttgtgcttca cattttgtg     1200 catctgcaaa gggggggctca agacaactg acatactctt ccacactggt gctctcgttg    1260
gacccaattc cattagaata actggtcagt tgttagatgg gagcaagttc tcctttgatg    1320
ggcactgcat attcccagat gggtgcatgg ctcttgactg caccttctgt aaagagttcc    1380
tgagaaaccc gcaatgttac cctgtaaaga aatggctctt cctggtggta gttataatgt    1440
gctgctattg tgccctgatg ctgcttacta acatactgag agctataggt gtttggggga    1500
catgggtttt tgctccaata aagttggctc tagcattagg gttgaggctt gccaaactgt    1560
caaagaaggg gctggttgct gtggttacaa ggggccaaat gatcgtgaat gatgagctgc    1620
accaggttcg agtggagaga ggtgagcaaa atgagggaag acaaggttat ggcccaagag    1680
gccccatccg tcactggcta tactcacctg ccctcattct cattctcacc acttcaatt     1740 gctctgatg tgatgagctt gttcatgctg agagtaaatc catcacatgc aagtctgcat     1800
ctgggaatga aaggagtgc tcagtgacag gcagagcttt gctcccagct gtcaatccag      1860
ggcaggaggc ctgcttgcac tttagcgtgc caggaagccc agactccaag tgccttaaga    1920
tcaaagtgaa atcaataaat ctcagatgta agcaagcctc ttcatattat gttcctgaag    1980
caaaggcaag atgtacatct gtcagaaggt gcaggtgggc aggtgactgt caatctgggt    2040
gtccaacata tttcagctca aactcattct cagatgattg gcaaacagg atggacaggg     2100 ctgggctcgg gatgagtggg tgctcagatg ggtgtggtgg agctgcatgt gggtgtttta    2160
atgcagcgcc atcctgcatc tttttggaga aagtgggtgga gaacccatcc aatcgtgtct    2220
ggaaggtgtc accttgtgca tcatgggtgc tagctgcaac cattgagttg actttgccat    2280
caggagaggt taagactcta gagcctgtca cagggcaagc aactcagatg ttcaagggtg    2340
```

```
ttgcaatcac atatctggga tcatccattg agattgttgg catgaccagg ctatgtgaga    2400
tgaaagagat ggggactggg ataatggcac tggcccsctg caatgatcca gggcacgcca    2460
taatgggaaa tgtgggtgag atccaatgca gtagtataga aagcgcaaag cacatcaggt    2520
ctgatgggtg catttggaat gctgacctag ttggaataga attgagggtt gatgatgctg    2580
tgtgtttctc gaaactcact agtgttgagg cagttgcaaa ttttcaaaa atcccggcaa     2640 caatttctgg ggttcgcttt gatcaaggga atcatggaga atcacgtatc tatggtagcc    2700
cattagatat cacgagggtt agtggggaat tctcagtgtc attcagaggg atgaggctca    2760
aactatctga gatatcagca agctgcacag gtgagataac aaacgtctct ggttgttact    2820
cctgcatgac tggggcctca gtcagcataa aattacatag cagtaagaac acaacaggtc    2880
atcttaagtg tgattcagat gagactgcat tcagtgtcat ggagggaaca cacacatata    2940
ggcctcacat gagctttgat aaagcagtaa tagatgagga gtgtgtgcta aactgtggtg    3000
gccactcatc aaaactgttg cttaaaggga gccttgtttt tatggacgtg ccaaggtttg    3060
ttgatggaag ttatgtccaa acatatcaca gcaaggtgcc cgctggggga agggtcccaa    3120
atccggtaga ctggctcaac gcactgtttg gagatgcat aacacgatgg attcttggga     3180 ttatagggt tctgctggca tgtgtcatgc tatttgtggt ggtggttgcc atcactaggc     3240
gattgatcaa gggactgact caaagggcga aggtggcatg attggcgtta attgacaaat    3300
aagcaagcct cctgttttcaa acctctggtg ggccagaagc ctgacagagg tttgaaacaa    3360
atgctctgac atctgaggca tgaatgataa tgggtgggtt ttcaatttgt atagccggtc    3420
tttgtgt                                                              3427
```

<210> SEQ ID NO 10
<211> LENGTH: 6368
<212> TYPE: DNA
<213> ORGANISM: Heartland virus

<400> SEQUENCE: 10

```
acacaaagac gtccagatga atttagaagc tctttgctct agagtgcttt cagagagagg     60
gctatcaact ggtgagcctg gggtatatga ccagattttt gaaaggcctg gcctcccaaa    120
ccttgaagtc acagtggact ccactggggt agttgtcgat gttggggcca ttcctgactc    180
agcatcacag ctagggtcct cgataaatgc aggcgtgctc accatacctc tctcagaagc    240
atataagata aatcatgact tcactttctc tggactgact aagacaacag ataggaagtt    300
gtctgaagta ttccctttgg ttcatgatgg ctcagactca atgaccccg atgtgatcca     360 cacaagacta gatggaacag tagttgtaat tgaattcaca acaaccagaa gcacaaacat    420
gggaggactt gaggctgcct atcggagcaa gcttgaaaaa taccgtgacc cactaaacag    480
aagaacagac ataatgcctg atgcatcaat ttactttgga atcattgttg ttagtgcatc    540
tggtgttctc acaaatatgc ctctgaccca agatgaagct gaagaattga tgttcaggtt    600
ctgtgtggca aatgagattt attcccaggc aagagcaatg gatgctgagg ttgaacttca    660
aaagtcagag gaggaaatat gaggccatatc cagagcaaga gcttcttca cgcttttga    720 ctatgacgat ggtaagctct ctgaggcatt ccctaactct gacattgaga tgctcagaag    780
atttctgagt cagcctgtag acacaagttt tgtgaccaca accctcaaag aaaaagagca    840
agaggcttat aagagaatgt gtgaggagca ctatctaaag agtggcatga gcacaaaaga    900
gaggcttgag gcgaatcgca gtgatgcaat agacaaaact agagctctca tggagagact    960
```

```
ccacaacatg agcagcaagg agctacactc gaataagagc acagtgaagt tgcctccctg    1020
ggtagtgaag ccttctgata ggacgttaga tgtcaaaacg gacacgggat caggggagct    1080
actcaaccat ggcccatatg gggagttgtg gtcaagatgc ttcctggaga ttgtccttgg    1140
gaatgtggag gggtcatca gcagccctga aaaggagctg gagatcgcca tcagtgatga    1200
ccctgaggct gacaccccta aggctgcaaa gattaaatac cataggttcc ggcctgagct    1260
cagtttagag agcaagcatg aattttcatt acaaggcatc gagggcaaaa gatggaagca    1320
ttcagctagg aatgtcctta aagatgaaat gtcccacaag acaatgagcc catttgttga    1380
tgtctcgaac attgaggagt ttctgattat gaacaacctg ttaaatgaca catcttttaa    1440
tcgggaagga ctgcaagaaa caatcaacct gttgttggag aaggctactg aaatgcacca    1500
aaatggctta tcaacagctt tgaatgattc cttcaagaga aacttcaaca caaacgttgt    1560
gcagtggagc atgtgggtct catgcttagc tcaggaattg gcaagtgctt tgaagcaaca    1620
ttgcaagcct ggtgagttta tcatcaaaaa attaatgcac tggccaatat tcgtcataat    1680
taagcccact aagtcatcaa gtcacatatt ctacagcttg gcaataaaaa aagccaacat    1740
taagaggagg ctgattggtg atgtattcac agacacaatt gatgcggggg agtgggagtt    1800
ttcagaattc aaaagcctca agacgtgcaa gctgacaaat ctcattaacc tgccgtgcac    1860
catgctcaac tcaatagcgt tctggagaga gaagatggga gtagccccct ggatttctag    1920
aaaggcctgc tcagagctca gggaacaagt ggcaatcact ttccttatga gtctggaaga    1980
caaatcaaca acagaagagc ttgttactct cacgaggtat tcacaaatgg agggatttgt    2040
gtctccaccc ctgctcccta acccccagaa gatggtggaa aagttagaag ttcctttgcg    2100
aacaaagctt caagtgtttt tgtttaggag gcatcttgat gctattgtta gagttgctgc    2160
atccccattc cccattgtgg caagagatgg tcgagtggaa tggacaggga cattcaatgc    2220
aatcactggc cgaagcactg ggctggaaaa catggtaaac aactggtata ttggctacta    2280 taaaacaaa gaagagtcga ccgagctaaa tgccttgggc gagatgtaca agaagattgt    2340
tgagattgag gctgagaagc caacatcttc tgagtaccta ggatggggag acactagcag    2400
ccctaagagg catgagttca gtagaagctt cctcaagtca gcatgcatat ctcttgagaa    2460
ggagatagag atgaggcatg gaaagagctg gaagcaaagc ttggaggaga gagtccttaa    2520
agagctgggc tcaaagaact tgctggactt agcaacaatg aaggcaacaa gcaacttag    2580 caaggaatgg gaagctttct cagaagtcag aacaaaagaa taccataggt ccaaactcct    2640
agaaaagatg gctgaactaa tagagcatgg gttaatgtgg tatgttgatg ctgcaggtca    2700
tgcatggaag gctgtccttg atgacaagtg tatgagaata tgcttgttta agaaaaatca    2760
gcatggaggc ctgagggaaa tttatgtaac gaatgcaaat gcaaggcttg ttcaatttgg    2820
agtagagaca atggcacggt gtgtgtgtga gctaagccca catgaaacaa tagctaaccc    2880
tagactcaag tcaagcatca tagagaatca tggtctcaag agtgctcgac aattagggca    2940
ggggaccatt aatgtcaact cttcaaatga cgcaaaaaaa tggagtcagg gccattatac    3000
aaccaaattg gctatggtat tatgctggtt catgccagct aagttccata ggttcatatg    3060
ggcaggcatc tcaatgttta ggtgcaagaa gatgatgatg gacctcaggt ttttagaaaa    3120
attgagcaca aaggctaatc agaaaactga tgatgacttc aggaaagact agctggggc    3180 cttccatggc aatgttgagg ttccttggat gactcaagga gctacatatc tccagactga    3240
gacagggatg atgcaaggga tcctgcattt tacatcaagc ctactgcatt catgcgtcca    3300
aagtttttac aaggcatatt ttttatctcg gcttaaagaa gggatcgcag gcagaaccat    3360
```

```
caaggcagct atagatgttt tagaaggctc tgatgactca gctatcatga taagcttgaa    3420
gccagcctca gacaatgagg aagcgatggc tcggttttta acagccaact tgctatactc    3480
agtcagagtc ataaacccgc tctttggcat ttatagctct gagaagtcaa cagtaaatac    3540
cttattttgt gtggaataca actcagagtt ccacttccac aagcatttag tcaggcctac    3600
aatcagatgg gttgcagcat cccaccaaat ctctgagtca gaagccctgg caagcaggca    3660
ggaagattat gcgaaccttc tcactcaatg tcttgaaggg ggttcatcat tctctctaac    3720
atatttgatc cagtgtgccc agctcgtcca tcattatatg ctgctcgggc tctgcttgca    3780
cccgctgttt gggacatttg tagggatgct gattgaggat ccagatccag ccctaggctt    3840
cttcataatg acaatccag cttttgcagg gggagctgga tttagattca accttttggag   3900
atcttgcaag ttcacaaacc ttggcaaaaa gtatgcattc ttttcaatg agattcaagg     3960
aaaaaccaag ggggatgcag attacagagc actggatgca acaactggtg gaacattaag    4020
ccactctgta atgaccctact gggggacag gagaaagtac caacatctcc tagacaggat    4080
ggggcttccc aaggactggg ttgagaggat agatgaaaac ccaagcatct tatataggag    4140
gcctgagaac aagcaggaac ttatcttgag gctggcagaa aaagtgcatt ctccaggtgt    4200
cacttccagc ttcagcaaag ggcatgttgt acctagggtg gtggcagctg gagtctactt    4260
gctgtcaaga cattgcttca ggtacactgc atcaatccac ggtagggggg catctcagaa    4320
ggcgagtctg attaagctgc ttgtcatgtc ttcaacatca gctgagagga atcaaggaag    4380
gctgaaccca atcaagaaa gaatgctctt tcctcaagtc caagagtatg aaagagtatt     4440
gaccttgtta gatgaggtta ctgcgctcac agggaagttt gttgtgagag aaaggaacat    4500
agtcaaaagc agagtagagc ttttccagga gcctgtggac ttaaggtgca aagctgaaaa    4560
cctcattgca gaaatgtggt ttggacttaa aagaacaaag ttgggcccaa ggctgctaaa    4620
ggaagaatgg gacaaactcc gcgcctcctt ctcatggtta agcactgatc ataaagaaac    4680
actggatgtg ggtccatttc ttagtcatgt tcaattcagg aatttcattg cacatgtgga    4740
tgcgaagtct aggagtgttc gacttttggg ggcccctgtc aagaagtctg gaggagtgac    4800
tacagtgtcc caggtggtga aatctaattt cttttccaggt ttcattttgg actccagtga   4860
gagcttagat gaccaagaga gggttgaggg ggtgtcaatc ttaaaacaca ttctatttat    4920
gaccttgaat ggcccttaca ctgatgagca aagaaagcc atggttctgg agaccttcca     4980
atattttgca ctgccacatg ctgctgaagt tgtgaagaga tcacgatcac taaccctatg    5040
cttgatgaag aattttattg agcagagagg agggtcaata cttgaccaaa ttgaaaaggc    5100
tcagtcaggt acagtgggtg gattcagtaa gccccagaag ccttaccgca aacagtcagg    5160
aggcattggc tacaagggga aaggtgtttg gtcaggcata atgggaaaaca caaatgtaca   5220
gatcctgata gatggtgatg gttcatcaaa ctggatagaa gaaatcaggc tgagtagtga    5280
gtccaggcta tttgatgtca tagaatctgt caggaggctg tgtgatgaca ttaatgtcaa    5340
taatagagtt acatcaagct ttcggggtca ttgcatggtg aggcttagca actttaaggt    5400
caagccagct tcaagggtag aaggttgccc agtgcgactc atgcccctctt cattccggat   5460
aaaggagctc caaacccag atgaggtctt cttaaggggtg aggggagaca ttctaaacct    5520
gtccatcctc cttcaagagg accgagtcat gaatctgctt agctacagag ctcgtgacac    5580
tgacatctca gagtctgcag catcctacct atggatgaat agaacagact tctcatttgg    5640
aaagaaggag ccatcttgca gctggatgtg cttgaaaaca ttggactcat gggcttggaa    5700
```

-continued

```
tcaagcagca agagttcttg aaagaaacat caaaacccct ggaattgata acaccgccat    5760
ggggaacatt ttcaaggatt gcttagaaag ctcactcaga aagcaggggt tgcttagatc    5820
tagaattgct gagatggtgg aacgtcatgt tatcccacta acaagtcagg agctggtgga    5880
tatcctggag gaagatgtcg acttttcaga aatgatgcaa tctgatataa tggaagggga    5940
cctagacatt gatatcctga tggaagggtc accaatgctc tgggcagcag aagtggagga    6000
gatgggagaa gctatggtga tactcagtca gtcaggaaag tattatcatc taaaattaat    6060
ggatcaagca gcaacaaccc tttcaacaat ccttgggaaa gatggttgca ggcttctact    6120
ggggagacct actgggagat caaatctcag ggagcaggtg aagccctact tgacattatt    6180
gcaaataaga gagggagatg tcaactgggt ttctgagtac aaagatgaca cacgtggtct    6240
tgatgaagac tctgcagaaa tgtggggtta aaccaaccag gactgggggct cgggttgagg    6300 tgaagtgact ctgctgtctc acttgagcta tcagtaccta aaggttgata tctggacggt    6360
ctttgtgt                                                             6368
```

<210> SEQ ID NO 11
<211> LENGTH: 245
<212> TYPE: PRT
<213> ORGANISM: Heartland virus

<400> SEQUENCE: 11

```
Met Thr Asp Trp Ser Ala Ile Ala Val Glu Ile Gly Asn Glu Pro Leu
1               5                   10                  15

Asp Val Pro Ala Leu Val Glu Phe Ala Lys Glu Ile Ala Tyr Glu Gly
            20                  25                  30

Leu Asp Pro Ala Val Ile Phe Gly Leu Leu Arg Glu Arg Gly Gly Glu
        35                  40                  45

Asn Trp Arg Asn Asp Val Lys Tyr Ile Ile Val Phe Ala Leu Thr Arg
    50                  55                  60

Gly Asn Lys Ile Val Lys Ala Cys Gly Lys Met Ser Lys Lys Gly Ala
65                  70                  75                  80

Glu Arg Met Thr Asn Leu Ala Arg Val Tyr Glu Leu Lys Glu Asn Ala
                85                  90                  95

Val Asp Arg Met Ala Val Thr Pro Val Arg Val Ala Gln Cys Leu Pro
            100                 105                 110

Thr Trp Thr Cys Ala Ala Ala Ala Ile Lys Glu Tyr Leu Pro Val
        115                 120                 125

Gly Pro Ala Ile Met His Asn Lys Ile Gln Gly Tyr Pro Leu Glu Met
    130                 135                 140

Met Cys Met Ala Phe Gly Ser Leu Ile Pro Gln Ala Asp Val Ser Ile
145                 150                 155                 160

Glu Val Ile Lys Asp Phe Met Asp Ala Tyr Ser Leu Trp Gln Asp Thr
                165                 170                 175

Phe Ala Arg Thr Ile Asn Val Asp Gln Arg Lys Met Thr Lys Ala Glu
            180                 185                 190

Val Tyr Ala Lys Phe Arg Asp Pro Leu His Ala Ala Val Asn Ser Leu
        195                 200                 205

Phe Phe Pro Asn Ala Thr Arg Ile Ser Trp Leu Gln Ala Lys Gly Leu
    210                 215                 220

Leu Thr Ala Thr Lys Glu Ala Ser Gly Ser Val Lys Ala Ala Ala Ala
225                 230                 235                 240

Ala Tyr Arg Asn Met
                245
```

<210> SEQ ID NO 12
<211> LENGTH: 299
<212> TYPE: PRT
<213> ORGANISM: Heartland virus

<400> SEQUENCE: 12

Met Ser Leu Ser Lys Ala Ser Gln Pro Ser Lys Ser Ala Cys Val
1               5                   10                  15

Arg Leu Pro Ile Val Val Leu Glu Pro Asn Leu Ala Glu Leu Ser Thr
            20                  25                  30

Ser Tyr Val Gly Leu Val Ser Cys Lys Cys Ser Val Leu Thr Cys Ser
        35                  40                  45

Met Met Arg Lys Met Lys Ala Phe Thr Asn Thr Val Trp Leu Phe Gly
    50                  55                  60

Asn Pro Asn Asn Pro Leu His Ala Leu Glu Pro Ala Val Glu Gln Leu
65                  70                  75                  80

Leu Asp Glu Tyr Ser Gly Asp Leu Gly Ser Tyr Ser Gln Gln Glu Lys
                85                  90                  95

Ser Ala Leu Arg Trp Pro Ser Gly Lys Pro Ser Val His Phe Leu Gln
            100                 105                 110

Ala Ala His Leu Phe Phe Ser Leu Lys Asn Thr Trp Ala Val Glu Thr
        115                 120                 125

Gly Gln Glu Asn Trp Arg Gly Phe Phe His Arg Ile Thr Ser Gly Lys
    130                 135                 140

Lys Tyr Lys Phe Glu Gly Asp Met Val Ile Asp Ser Cys Tyr Lys Ile
145                 150                 155                 160

Asp Glu Arg Arg Arg Met Gly Leu Pro Asp Thr Phe Ile Thr Gly
                165                 170                 175

Leu Asn Pro Ile Met Asp Val Ala Leu Leu Gln Ile Glu Ser Leu Leu
            180                 185                 190

Arg Val Arg Gly Leu Thr Leu Asn Tyr His Leu Phe Thr Ser Ser Phe
        195                 200                 205

Leu Asp Lys Pro Leu Leu Asp Ser Leu Tyr Phe Ala Ile Trp Arg Asp
    210                 215                 220

Lys Lys Lys Asp Asp Gly Ser Tyr Ser Gln Asp Glu Gly Ala Arg Gln
225                 230                 235                 240

Asp Asp Pro Leu Asn Pro Leu Asp Glu Leu Leu Tyr Leu Ser Asp Leu
                245                 250                 255

Pro Lys Pro Leu Ala His Tyr Leu Asn Lys Cys Pro Leu His Asn Ile
            260                 265                 270

Ile Met His Asp Glu Glu Val Arg Glu Ala Tyr Leu Asn Pro Ile Trp
        275                 280                 285

Gly Lys Asp Trp Pro Ala Leu Ser Ser Ser Pro
    290                 295

<210> SEQ ID NO 13
<211> LENGTH: 1076
<212> TYPE: PRT
<213> ORGANISM: Heartland virus

<400> SEQUENCE: 13

Met Ile Val Pro Ile Val Leu Phe Leu Thr Leu Cys Pro Ser Glu Leu
1               5                   10                  15

Ser Ala Trp Gly Ser Pro Gly Asp Pro Ile Val Cys Gly Val Arg Thr
            20                  25                  30

Glu Thr Asn Lys Ser Ile Gln Ile Glu Trp Lys Glu Gly Arg Ser Glu
            35                  40                  45

Lys Leu Cys Gln Ile Asp Arg Leu Gly His Val Thr Ser Trp Leu Arg
 50                  55                  60

Asn His Ser Ser Phe Gln Gly Leu Ile Gly Gln Val Lys Gly Arg Pro
 65                  70                  75                  80

Ser Val Ser Tyr Phe Pro Glu Gly Ala Ser Tyr Pro Arg Trp Ser Gly
                 85                  90                  95

Leu Leu Ser Pro Cys Asp Ala Glu Trp Leu Gly Leu Ile Ala Val Ser
                100                 105                 110

Lys Ala Gly Asp Thr Asp Met Ile Val Pro Gly Pro Thr Tyr Lys Gly
            115                 120                 125

Lys Ile Phe Val Glu Arg Pro Thr Tyr Asn Gly Tyr Lys Gly Trp Gly
            130                 135                 140

Cys Ala Asp Gly Lys Ser Leu Ser His Ser Gly Thr Tyr Cys Glu Thr
145                 150                 155                 160

Asp Ser Ser Val Ser Ser Gly Leu Ile Gln Gly Asp Arg Val Leu Trp
                165                 170                 175

Val Gly Glu Val Val Cys Gln Arg Gly Thr Pro Val Pro Glu Asp Val
            180                 185                 190

Phe Ser Glu Leu Val Ser Leu Ser Gln Ser Glu Phe Pro Asp Val Cys
            195                 200                 205

Lys Ile Asp Gly Val Ala Leu Asn Gln Cys Glu Gln Glu Ser Ile Pro
            210                 215                 220

Gln Pro Leu Asp Val Ala Trp Ile Asp Val Gly Arg Ser His Lys Val
225                 230                 235                 240

Leu Met Arg Glu His Lys Thr Lys Trp Val Gln Glu Ser Ser Ala Lys
                245                 250                 255

Asp Phe Val Cys Phe Lys Val Gly Gln Gly Pro Cys Ser Lys Gln Glu
            260                 265                 270

Glu Asp Asp Cys Met Ser Lys Gly Asn Cys His Gly Asp Glu Val Phe
            275                 280                 285

Cys Arg Met Ala Gly Cys Ser Ala Arg Met Gln Asp Asn Gln Glu Gly
            290                 295                 300

Cys Arg Cys Glu Leu Leu Gln Lys Pro Gly Glu Ile Ile Val Asn Tyr
305                 310                 315                 320

Gly Gly Val Ser Val Arg Pro Thr Cys Tyr Gly Phe Ser Arg Met Met
                325                 330                 335

Ala Thr Leu Glu Val His Lys Pro Asp Arg Glu Leu Thr Gly Cys Thr
            340                 345                 350

Gly Cys His Leu Glu Cys Ile Glu Gly Gly Val Lys Ile Val Thr Leu
            355                 360                 365

Thr Ser Glu Leu Arg Ser Ala Thr Val Cys Ala Ser His Phe Cys Ala
            370                 375                 380

Ser Ala Lys Gly Gly Ser Lys Thr Thr Asp Ile Leu Phe His Thr Gly
385                 390                 395                 400

Ala Leu Val Gly Pro Asn Ser Ile Arg Ile Thr Gly Gln Leu Leu Asp
                405                 410                 415

Gly Ser Lys Phe Ser Phe Asp Gly His Cys Ile Phe Pro Asp Gly Cys
                420                 425                 430

Met Ala Leu Asp Cys Thr Phe Cys Lys Glu Phe Leu Arg Asn Pro Gln
            435                 440                 445

```
Cys Tyr Pro Val Lys Lys Trp Leu Phe Leu Val Val Ile Met Cys
    450                 455                 460

Cys Tyr Cys Ala Leu Met Leu Leu Thr Asn Ile Leu Arg Ala Ile Gly
465                 470                 475                 480

Val Trp Gly Thr Trp Val Phe Ala Pro Ile Lys Leu Ala Leu Ala Leu
                485                 490                 495

Gly Leu Arg Leu Ala Lys Leu Ser Lys Lys Gly Leu Val Ala Val Val
                500                 505                 510

Thr Arg Gly Gln Met Ile Val Asn Asp Glu Leu His Gln Val Arg Val
                515                 520                 525

Glu Arg Gly Glu Gln Asn Glu Gly Arg Gln Gly Tyr Gly Pro Arg Gly
530                 535                 540

Pro Ile Arg His Trp Leu Tyr Ser Pro Ala Leu Ile Leu Ile Leu Thr
545                 550                 555                 560

Thr Ser Ile Cys Ser Gly Cys Asp Glu Leu Val His Ala Glu Ser Lys
                565                 570                 575

Ser Ile Thr Cys Lys Ser Ala Ser Gly Asn Lys Glu Cys Ser Val
                580                 585                 590

Thr Gly Arg Ala Leu Leu Pro Ala Val Asn Pro Gly Gln Glu Ala Cys
                595                 600                 605

Leu His Phe Ser Val Pro Gly Ser Pro Asp Ser Lys Cys Leu Lys Ile
                610                 615                 620

Lys Val Lys Ser Ile Asn Leu Arg Cys Lys Gln Ala Ser Ser Tyr Tyr
625                 630                 635                 640

Val Pro Glu Ala Lys Ala Arg Cys Thr Ser Val Arg Arg Cys Arg Trp
                645                 650                 655

Ala Gly Asp Cys Gln Ser Gly Cys Pro Thr Tyr Phe Ser Ser Asn Ser
                660                 665                 670

Phe Ser Asp Asp Trp Ala Asn Arg Met Asp Arg Ala Gly Leu Gly Met
                675                 680                 685

Ser Gly Cys Ser Asp Gly Cys Gly Gly Ala Ala Cys Gly Cys Phe Asn
                690                 695                 700

Ala Ala Pro Ser Cys Ile Phe Trp Arg Lys Trp Val Glu Asn Pro Ser
705                 710                 715                 720

Asn Arg Val Trp Lys Val Ser Pro Cys Ala Ser Trp Val Leu Ala Ala
                725                 730                 735

Thr Ile Glu Leu Thr Leu Pro Ser Gly Glu Val Lys Thr Leu Glu Pro
                740                 745                 750

Val Thr Gly Gln Ala Thr Gln Met Phe Lys Gly Val Ala Ile Thr Tyr
                755                 760                 765

Leu Gly Ser Ser Ile Glu Ile Val Gly Met Thr Arg Leu Cys Glu Met
770                 775                 780

Lys Glu Met Gly Thr Gly Ile Met Ala Leu Ala Pro Cys Asn Asp Pro
785                 790                 795                 800

Gly His Ala Ile Met Gly Asn Val Gly Glu Ile Gln Cys Ser Ser Ile
                805                 810                 815

Glu Ser Ala Lys His Ile Arg Ser Asp Gly Cys Ile Trp Asn Ala Asp
                820                 825                 830

Leu Val Gly Ile Glu Leu Arg Val Asp Asp Ala Val Cys Phe Ser Lys
                835                 840                 845

Leu Thr Ser Val Glu Ala Val Ala Asn Phe Ser Lys Ile Pro Ala Thr
850                 855                 860

Ile Ser Gly Val Arg Phe Asp Gln Gly Asn His Gly Glu Ser Arg Ile
```

-continued

```
                865                 870                 875                 880
Tyr Gly Ser Pro Leu Asp Ile Thr Arg Val Ser Gly Glu Phe Ser Val
                    885                 890                 895

Ser Phe Arg Gly Met Arg Leu Lys Leu Ser Glu Ile Ser Ala Ser Cys
                900                 905                 910

Thr Gly Glu Ile Thr Asn Val Ser Gly Cys Tyr Ser Cys Met Thr Gly
                915                 920                 925

Ala Ser Val Ser Ile Lys Leu His Ser Ser Lys Asn Thr Thr Gly His
                930                 935                 940

Leu Lys Cys Asp Ser Asp Glu Thr Ala Phe Ser Val Met Glu Gly Thr
945                 950                 955                 960

His Thr Tyr Arg Pro His Met Ser Phe Asp Lys Ala Val Ile Asp Glu
                965                 970                 975

Glu Cys Val Leu Asn Cys Gly Gly His Ser Ser Lys Leu Leu Leu Lys
                980                 985                 990

Gly Ser Leu Val Phe Met Asp Val Pro Arg Phe Val Asp Gly Ser Tyr
                995                1000                1005

Val Gln Thr Tyr His Ser Lys Val Pro Ala Gly Gly Arg Val Pro
    1010                1015                1020

Asn Pro Val Asp Trp Leu Asn Ala Leu Phe Gly Asp Gly Ile Thr
    1025                1030                1035

Arg Trp Ile Leu Gly Ile Ile Gly Val Leu Leu Ala Cys Val Met
    1040                1045                1050

Leu Phe Val Val Val Val Ala Ile Thr Arg Arg Leu Ile Lys Gly
    1055                1060                1065

Leu Thr Gln Arg Ala Lys Val Ala
    1070                1075

<210> SEQ ID NO 14
<211> LENGTH: 2084
<212> TYPE: PRT
<213> ORGANISM: Heartland virus

<400> SEQUENCE: 14

Met Asn Leu Glu Ala Leu Cys Ser Arg Val Leu Ser Glu Arg Gly Leu
1               5                   10                  15

Ser Thr Gly Glu Pro Gly Val Tyr Asp Gln Ile Phe Glu Arg Pro Gly
                20                  25                  30

Leu Pro Asn Leu Glu Val Thr Val Asp Ser Thr Gly Val Val Val Asp
            35                  40                  45

Val Gly Ala Ile Pro Asp Ser Ala Ser Gln Leu Gly Ser Ser Ile Asn
        50                  55                  60

Ala Gly Val Leu Thr Ile Pro Leu Ser Glu Ala Tyr Lys Ile Asn His
65                  70                  75                  80

Asp Phe Thr Phe Ser Gly Leu Thr Lys Thr Thr Asp Arg Lys Leu Ser
                85                  90                  95

Glu Val Phe Pro Leu Val His Asp Gly Ser Asp Ser Met Thr Pro Asp
                100                 105                 110

Val Ile His Thr Arg Leu Asp Gly Thr Val Val Ile Glu Phe Thr
            115                 120                 125

Thr Thr Arg Ser Thr Asn Met Gly Gly Leu Glu Ala Ala Tyr Arg Ser
        130                 135                 140

Lys Leu Glu Lys Tyr Arg Asp Pro Leu Asn Arg Arg Thr Asp Ile Met
145                 150                 155                 160
```

```
Pro Asp Ala Ser Ile Tyr Phe Gly Ile Ile Val Ser Ala Ser Gly
            165                 170                 175

Val Leu Thr Asn Met Pro Leu Thr Gln Asp Glu Ala Glu Leu Met
            180                 185                 190

Phe Arg Phe Cys Val Ala Asn Glu Ile Tyr Ser Gln Ala Arg Ala Met
            195                 200                 205

Asp Ala Glu Val Glu Leu Gln Lys Ser Glu Glu Tyr Glu Ala Ile
            210                 215                 220

Ser Arg Ala Arg Ala Phe Phe Thr Leu Phe Asp Tyr Asp Gly Lys
225                 230                 235                 240

Leu Ser Glu Ala Phe Pro Asn Ser Asp Ile Glu Met Leu Arg Arg Phe
                245                 250                 255

Leu Ser Gln Pro Val Asp Thr Ser Phe Val Thr Thr Leu Lys Glu
            260                 265                 270

Lys Glu Gln Glu Ala Tyr Lys Arg Met Cys Glu Glu His Tyr Leu Lys
            275                 280                 285

Ser Gly Met Ser Thr Lys Glu Arg Leu Glu Ala Asn Arg Ser Asp Ala
            290                 295                 300

Ile Asp Lys Thr Arg Ala Leu Met Glu Arg Leu His Asn Met Ser Ser
305                 310                 315                 320

Lys Glu Leu His Ser Asn Lys Ser Thr Val Lys Leu Pro Pro Trp Val
                325                 330                 335

Val Lys Pro Ser Asp Arg Thr Leu Asp Val Lys Thr Asp Thr Gly Ser
                340                 345                 350

Gly Glu Leu Leu Asn His Gly Pro Tyr Gly Glu Leu Trp Ser Arg Cys
            355                 360                 365

Phe Leu Glu Ile Val Leu Gly Asn Val Glu Gly Val Ile Ser Ser Pro
370                 375                 380

Glu Lys Glu Leu Glu Ile Ala Ile Ser Asp Asp Pro Glu Ala Asp Thr
385                 390                 395                 400

Pro Lys Ala Ala Lys Ile Lys Tyr His Arg Phe Arg Pro Glu Leu Ser
                405                 410                 415

Leu Glu Ser Lys His Glu Phe Ser Leu Gln Gly Ile Glu Gly Lys Arg
            420                 425                 430

Trp Lys His Ser Ala Arg Asn Val Leu Lys Asp Glu Met Ser His Lys
            435                 440                 445

Thr Met Ser Pro Phe Val Asp Val Ser Asn Ile Glu Glu Phe Leu Ile
450                 455                 460

Met Asn Asn Leu Leu Asn Asp Thr Ser Phe Asn Arg Glu Gly Leu Gln
465                 470                 475                 480

Glu Thr Ile Asn Leu Leu Leu Glu Lys Ala Thr Glu Met His Gln Asn
                485                 490                 495

Gly Leu Ser Thr Ala Leu Asn Asp Ser Phe Lys Arg Asn Phe Asn Thr
            500                 505                 510

Asn Val Val Gln Trp Ser Met Trp Val Ser Cys Leu Ala Gln Glu Leu
            515                 520                 525

Ala Ser Ala Leu Lys Gln His Cys Lys Pro Gly Glu Phe Ile Ile Lys
530                 535                 540

Lys Leu Met His Trp Pro Ile Phe Val Ile Lys Pro Thr Lys Ser
545                 550                 555                 560

Ser Ser His Ile Phe Tyr Ser Leu Ala Ile Lys Lys Ala Asn Ile Lys
                565                 570                 575

Arg Arg Leu Ile Gly Asp Val Phe Thr Asp Thr Ile Asp Ala Gly Glu
```

```
                    580                 585                 590
Trp Glu Phe Ser Glu Phe Lys Ser Leu Lys Thr Cys Lys Leu Thr Asn
            595                 600                 605

Leu Ile Asn Leu Pro Cys Thr Met Leu Asn Ser Ile Ala Phe Trp Arg
    610                 615                 620

Glu Lys Met Gly Val Ala Pro Trp Ile Ser Arg Lys Ala Cys Ser Glu
625                 630                 635                 640

Leu Arg Glu Gln Val Ala Ile Thr Phe Leu Met Ser Leu Glu Asp Lys
                645                 650                 655

Ser Thr Thr Glu Glu Leu Val Thr Leu Thr Arg Tyr Ser Gln Met Glu
            660                 665                 670

Gly Phe Val Ser Pro Pro Leu Leu Pro Lys Pro Gln Lys Met Val Glu
    675                 680                 685

Lys Leu Glu Val Pro Leu Arg Thr Lys Leu Gln Val Phe Leu Phe Arg
690                 695                 700

Arg His Leu Asp Ala Ile Val Arg Val Ala Ala Ser Pro Phe Pro Ile
705                 710                 715                 720

Val Ala Arg Asp Gly Arg Val Glu Trp Thr Gly Thr Phe Asn Ala Ile
                725                 730                 735

Thr Gly Arg Ser Thr Gly Leu Glu Asn Met Val Asn Asn Trp Tyr Ile
            740                 745                 750

Gly Tyr Tyr Lys Asn Lys Glu Glu Ser Thr Glu Leu Asn Ala Leu Gly
    755                 760                 765

Glu Met Tyr Lys Lys Ile Val Glu Ile Glu Ala Glu Lys Pro Thr Ser
770                 775                 780

Ser Glu Tyr Leu Gly Trp Gly Asp Thr Ser Ser Pro Lys Arg His Glu
785                 790                 795                 800

Phe Ser Arg Ser Phe Leu Lys Ser Ala Cys Ile Ser Leu Glu Lys Glu
                805                 810                 815

Ile Glu Met Arg His Gly Lys Ser Trp Lys Gln Ser Leu Glu Glu Arg
            820                 825                 830

Val Leu Lys Glu Leu Gly Ser Lys Asn Leu Leu Asp Leu Ala Thr Met
    835                 840                 845

Lys Ala Thr Ser Asn Phe Ser Lys Glu Trp Glu Ala Phe Ser Glu Val
850                 855                 860

Arg Thr Lys Glu Tyr His Arg Ser Lys Leu Leu Glu Lys Met Ala Glu
865                 870                 875                 880

Leu Ile Glu His Gly Leu Met Trp Tyr Val Asp Ala Ala Gly His Ala
                885                 890                 895

Trp Lys Ala Val Leu Asp Asp Lys Cys Met Arg Ile Cys Leu Phe Lys
            900                 905                 910

Lys Asn Gln His Gly Gly Leu Arg Glu Ile Tyr Val Thr Asn Ala Asn
    915                 920                 925

Ala Arg Leu Val Gln Phe Gly Val Glu Thr Met Ala Arg Cys Val Cys
930                 935                 940

Glu Leu Ser Pro His Glu Thr Ile Ala Asn Pro Arg Leu Lys Ser Ser
945                 950                 955                 960

Ile Ile Glu Asn His Gly Leu Lys Ser Ala Arg Gln Leu Gly Gln Gly
                965                 970                 975

Thr Ile Asn Val Asn Ser Ser Asn Asp Ala Lys Lys Trp Ser Gln Gly
            980                 985                 990

His Tyr Thr Thr Lys Leu Ala Met  Val Leu Cys Trp Phe Met Pro Ala
    995                  1000                1005
```

```
Lys Phe His Arg Phe Ile Trp Ala Gly Ile Ser Met Phe Arg Cys
    1010                1015                1020

Lys Lys Met Met Met Asp Leu Arg Phe Leu Glu Lys Leu Ser Thr
    1025                1030                1035

Lys Ala Asn Gln Lys Thr Asp Asp Asp Phe Arg Lys Asp Leu Ala
    1040                1045                1050

Gly Ala Phe His Gly Asn Val Glu Val Pro Trp Met Thr Gln Gly
    1055                1060                1065

Ala Thr Tyr Leu Gln Thr Glu Thr Gly Met Met Gln Gly Ile Leu
    1070                1075                1080

His Phe Thr Ser Ser Leu Leu His Ser Cys Val Gln Ser Phe Tyr
    1085                1090                1095

Lys Ala Tyr Phe Leu Ser Arg Leu Lys Glu Gly Ile Ala Gly Arg
    1100                1105                1110

Thr Ile Lys Ala Ala Ile Asp Val Leu Glu Gly Ser Asp Asp Ser
    1115                1120                1125

Ala Ile Met Ile Ser Leu Lys Pro Ala Ser Asp Asn Glu Glu Ala
    1130                1135                1140

Met Ala Arg Phe Leu Thr Ala Asn Leu Leu Tyr Ser Val Arg Val
    1145                1150                1155

Ile Asn Pro Leu Phe Gly Ile Tyr Ser Ser Glu Lys Ser Thr Val
    1160                1165                1170

Asn Thr Leu Phe Cys Val Glu Tyr Asn Ser Glu Phe His Phe His
    1175                1180                1185

Lys His Leu Val Arg Pro Thr Ile Arg Trp Val Ala Ala Ser His
    1190                1195                1200

Gln Ile Ser Glu Ser Glu Ala Leu Ala Ser Arg Gln Glu Asp Tyr
    1205                1210                1215

Ala Asn Leu Leu Thr Gln Cys Leu Glu Gly Gly Ser Ser Phe Ser
    1220                1225                1230

Leu Thr Tyr Leu Ile Gln Cys Ala Gln Leu Val His His Tyr Met
    1235                1240                1245

Leu Leu Gly Leu Cys Leu His Pro Leu Phe Gly Thr Phe Val Gly
    1250                1255                1260

Met Leu Ile Glu Asp Pro Pro Ala Leu Gly Phe Phe Ile Met
    1265                1270                1275

Asp Asn Pro Ala Phe Ala Gly Gly Ala Gly Phe Arg Phe Asn Leu
    1280                1285                1290

Trp Arg Ser Cys Lys Phe Thr Asn Leu Gly Lys Lys Tyr Ala Phe
    1295                1300                1305

Phe Phe Asn Glu Ile Gln Gly Lys Thr Lys Gly Asp Ala Asp Tyr
    1310                1315                1320

Arg Ala Leu Asp Ala Thr Thr Gly Gly Thr Leu Ser His Ser Val
    1325                1330                1335

Met Thr Tyr Trp Gly Asp Arg Arg Lys Tyr Gln His Leu Leu Asp
    1340                1345                1350

Arg Met Gly Leu Pro Lys Asp Trp Val Glu Arg Ile Asp Glu Asn
    1355                1360                1365

Pro Ser Ile Leu Tyr Arg Arg Pro Glu Asn Lys Gln Glu Leu Ile
    1370                1375                1380

Leu Arg Leu Ala Glu Lys Val His Ser Pro Gly Val Thr Ser Ser
    1385                1390                1395
```

```
Phe Ser Lys Gly His Val Val Pro Arg Val Val Ala Ala Gly Val
1400                1405                1410

Tyr Leu Leu Ser Arg His Cys Phe Arg Tyr Thr Ala Ser Ile His
1415                1420                1425

Gly Arg Gly Ala Ser Gln Lys Ala Ser Leu Ile Lys Leu Leu Val
1430                1435                1440

Met Ser Ser Thr Ser Ala Glu Arg Asn Gln Gly Arg Leu Asn Pro
1445                1450                1455

Asn Gln Glu Arg Met Leu Phe Pro Gln Val Gln Glu Tyr Glu Arg
1460                1465                1470

Val Leu Thr Leu Leu Asp Glu Val Thr Ala Leu Thr Gly Lys Phe
1475                1480                1485

Val Val Arg Glu Arg Asn Ile Val Lys Ser Arg Val Glu Leu Phe
1490                1495                1500

Gln Glu Pro Val Asp Leu Arg Cys Lys Ala Glu Asn Leu Ile Ala
1505                1510                1515

Glu Met Trp Phe Gly Leu Lys Arg Thr Lys Leu Gly Pro Arg Leu
1520                1525                1530

Leu Lys Glu Glu Trp Asp Lys Leu Arg Ala Ser Phe Ser Trp Leu
1535                1540                1545

Ser Thr Asp His Lys Glu Thr Leu Asp Val Gly Pro Phe Leu Ser
1550                1555                1560

His Val Gln Phe Arg Asn Phe Ile Ala His Val Asp Ala Lys Ser
1565                1570                1575

Arg Ser Val Arg Leu Leu Gly Ala Pro Val Lys Lys Ser Gly Gly
1580                1585                1590

Val Thr Thr Val Ser Gln Val Lys Ser Asn Phe Phe Pro Gly
1595                1600                1605

Phe Ile Leu Asp Ser Ser Glu Ser Leu Asp Asp Gln Glu Arg Val
1610                1615                1620

Glu Gly Val Ser Ile Leu Lys His Ile Leu Phe Met Thr Leu Asn
1625                1630                1635

Gly Pro Tyr Thr Asp Glu Gln Lys Lys Ala Met Val Leu Glu Thr
1640                1645                1650

Phe Gln Tyr Phe Ala Leu Pro His Ala Ala Glu Val Val Lys Arg
1655                1660                1665

Ser Arg Ser Leu Thr Leu Cys Leu Met Lys Asn Phe Ile Glu Gln
1670                1675                1680

Arg Gly Gly Ser Ile Leu Asp Gln Ile Glu Lys Ala Gln Ser Gly
1685                1690                1695

Thr Val Gly Gly Phe Ser Lys Pro Gln Lys Pro Tyr Arg Lys Gln
1700                1705                1710

Ser Gly Gly Ile Gly Tyr Lys Gly Lys Gly Val Trp Ser Gly Ile
1715                1720                1725

Met Glu Asn Thr Asn Val Gln Ile Leu Ile Asp Gly Asp Gly Ser
1730                1735                1740

Ser Asn Trp Ile Glu Glu Ile Arg Leu Ser Ser Glu Ser Arg Leu
1745                1750                1755

Phe Asp Val Ile Glu Ser Val Arg Arg Leu Cys Asp Asp Ile Asn
1760                1765                1770

Val Asn Asn Arg Val Thr Ser Ser Phe Arg Gly His Cys Met Val
1775                1780                1785

Arg Leu Ser Asn Phe Lys Val Lys Pro Ala Ser Arg Val Glu Gly
```

Cys Pro Val Arg Leu Met Pro Ser Ser Phe Arg Ile Lys Glu Leu
    1805                1810                1815

Gln Asn Pro Asp Glu Val Phe Leu Arg Val Arg Gly Asp Ile Leu
    1820                1825                1830

Asn Leu Ser Ile Leu Leu Gln Glu Asp Arg Val Met Asn Leu Leu
    1835                1840                1845

Ser Tyr Arg Ala Arg Asp Thr Asp Ile Ser Glu Ser Ala Ala Ser
    1850                1855                1860

Tyr Leu Trp Met Asn Arg Thr Asp Phe Ser Phe Gly Lys Lys Glu
    1865                1870                1875

Pro Ser Cys Ser Trp Met Cys Leu Lys Thr Leu Asp Ser Trp Ala
    1880                1885                1890

Trp Asn Gln Ala Ala Arg Val Leu Glu Arg Asn Ile Lys Thr Pro
    1895                1900                1905

Gly Ile Asp Asn Thr Ala Met Gly Asn Ile Phe Lys Asp Cys Leu
    1910                1915                1920

Glu Ser Ser Leu Arg Lys Gln Gly Leu Leu Arg Ser Arg Ile Ala
    1925                1930                1935

Glu Met Val Glu Arg His Val Ile Pro Leu Thr Ser Gln Glu Leu
    1940                1945                1950

Val Asp Ile Leu Glu Glu Asp Val Asp Phe Ser Glu Met Met Gln
    1955                1960                1965

Ser Asp Ile Met Glu Gly Asp Leu Asp Ile Asp Ile Leu Met Glu
    1970                1975                1980

Gly Ser Pro Met Leu Trp Ala Ala Glu Val Glu Glu Met Gly Glu
    1985                1990                1995

Ala Met Val Ile Leu Ser Gln Ser Gly Lys Tyr Tyr His Leu Lys
    2000                2005                2010

Leu Met Asp Gln Ala Ala Thr Thr Leu Ser Thr Ile Leu Gly Lys
    2015                2020                2025

Asp Gly Cys Arg Leu Leu Leu Gly Arg Pro Thr Gly Arg Ser Asn
    2030                2035                2040

Leu Arg Glu Gln Val Lys Pro Tyr Leu Thr Leu Leu Gln Ile Arg
    2045                2050                2055

Glu Gly Asp Val Asn Trp Val Ser Glu Tyr Lys Asp Asp Thr Arg
    2060                2065                2070

Gly Leu Asp Glu Asp Ser Ala Glu Met Trp Gly
    2075                2080

<210> SEQ ID NO 15
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 15
tccctcttct tcccaaatgc cacc                                            24

<210> SEQ ID NO 16
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 16
gatgcttcct tggttgctg                                                        19

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
tgccaaattc agagaccctc                                                       20

<210> SEQ ID NO 18
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 18
caggatggcg ctgcattaaa acacc                                                 25

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
acacgattgg atgggttctc                                                       20

<210> SEQ ID NO 20
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 20
tgggcaaaca ggatggac                                                         18

<210> SEQ ID NO 21
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 21
acccctggaa ttgataacac cgcc                                                  24

<210> SEQ ID NO 22
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 22
aacccctgct ttctgagtg                                                        19

<210> SEQ ID NO 23
<211> LENGTH: 19

```
<212> TYPE: DNA
<213> ORGANISM: Artificial Sequence
<220> FEATURE:
<223> OTHER INFORMATION: Synthetic oligonucleotide

<400> SEQUENCE: 23
attggactca tgggcttgg                                                    19

<210> SEQ ID NO 24
<211> LENGTH: 246
<212> TYPE: PRT
<213> ORGANISM: Sandfly fever Sicilian virus

<400> SEQUENCE: 24
```

Met Asp Glu Tyr Gln Lys Ile Ala Val Glu Phe Gly Glu Gln Ala Ile
1               5                   10                  15

Asp Glu Thr Val Ile Gln Asp Trp Leu Gln Ala Phe Ala Tyr Gln Gly
                20                  25                  30

Phe Asp Ala Arg Thr Ile Ile His Asn Leu Val Gln Leu Gly Gly Lys
            35                  40                  45

Ser Trp Glu Glu Asp Ala Lys Lys Met Ile Ile Leu Ser Leu Thr Arg
    50                  55                  60

Gly Asn Lys Pro Lys Lys Met Val Glu Arg Met Ser Pro Glu Gly Ala
65                  70                  75                  80

Arg Glu Val Lys Ser Leu Val Ala Lys Tyr Lys Ile Val Glu Gly Arg
                85                  90                  95

Pro Gly Arg Asn Gly Ile Thr Leu Ser Arg Val Leu Gln Pro Trp Leu
            100                 105                 110

Gly Gly Gln Ser Lys Leu Trp Lys Trp Leu Lys Thr Ser Tyr Gln Ser
        115                 120                 125

Gln Gly Ala Gln Trp Thr Ala Leu Cys Gly Gln Thr Tyr Pro Arg Gln
    130                 135                 140

Met Met His Pro Ser Phe Ala Gly Leu Ile Asp Pro Ser Leu Asp Gln
145                 150                 155                 160

Glu Asp Phe Asn Ala Val Leu Asp Ala His Lys Leu Phe Leu Phe Met
                165                 170                 175

Phe Ser Lys Thr Ile Asn Val Ser Leu Arg Gly Ala Gln Lys Arg Asp
            180                 185                 190

Ile Glu Glu Ser Phe Ser Gln Pro Met Leu Ala Ala Ile Asn Ser Ser
        195                 200                 205

Phe Ile Asp Asn Thr Gln Arg Arg Ala Phe Leu Thr Lys Phe Gly Ile
    210                 215                 220

Leu Thr Ser Gly Ala Arg Ala Thr Ala Val Val Lys Lys Ile Ala Glu
225                 230                 235                 240

Val Tyr Arg Lys Leu Glu
                245

```
<210> SEQ ID NO 25
<211> LENGTH: 245
<212> TYPE: PRT
<213> ORGANISM: Rift Valley fever virus

<400> SEQUENCE: 25
```

Met Asp Asn Tyr Gln Glu Leu Ala Ile Gln Phe Ala Ala Gln Ala Val
1               5                   10                  15

Asp Arg Asn Glu Ile Glu Gln Trp Val Arg Glu Phe Ala Tyr Gln Gly
                20                  25                  30

-continued

```
Phe Asp Ala Arg Arg Val Ile Glu Leu Leu Lys Gln Tyr Gly Gly Ala
             35                  40                  45

Asp Trp Glu Lys Asp Ala Lys Lys Met Ile Val Leu Ala Leu Thr Arg
 50                  55                  60

Gly Asn Lys Pro Arg Arg Met Met Met Lys Met Ser Lys Glu Gly Lys
 65                  70                  75                  80

Ala Thr Val Glu Ala Leu Ile Asn Lys Tyr Lys Leu Lys Glu Gly Asn
                 85                  90                  95

Pro Ser Arg Asp Glu Leu Thr Leu Ser Arg Val Ala Ala Leu Ala
                100                 105                 110

Gly Trp Thr Cys Gln Ala Leu Val Val Leu Ser Glu Trp Leu Pro Val
                115                 120                 125

Thr Gly Thr Thr Met Asp Gly Leu Ser Pro Ala Tyr Pro Arg His Met
            130                 135                 140

Met His Pro Ser Phe Ala Gly Met Val Asp Pro Ser Leu Pro Gly Asp
145                 150                 155                 160

Tyr Leu Arg Ala Ile Leu Asp Ala His Ser Leu Tyr Leu Leu Gln Phe
                165                 170                 175

Ser Arg Val Ile Asn Pro Asn Leu Arg Gly Arg Thr Lys Glu Glu Val
                180                 185                 190

Ala Ala Thr Phe Thr Gln Pro Met Asn Ala Ala Val Asn Ser Asn Phe
            195                 200                 205

Ile Ser His Glu Lys Arg Arg Glu Phe Leu Lys Ala Phe Gly Leu Val
        210                 215                 220

Asp Ser Asn Gly Lys Pro Ser Ala Ala Val Met Ala Ala Ala Gln Ala
225                 230                 235                 240

Tyr Lys Thr Ala Ala
                245

<210> SEQ ID NO 26
<211> LENGTH: 245
<212> TYPE: PRT
<213> ORGANISM: Phlebovirus sp. Be An 578142

<400> SEQUENCE: 26

Met Ala Asp Tyr Ala Arg Ile Ala Val Glu Phe Ser Gly Glu Ala Ile
 1               5                  10                  15

Asn Leu Ala Glu Ile Gln Gly Trp Val Thr Asp Phe Ala Tyr Gln Gly
                 20                  25                  30

Phe Asp Ala Arg Arg Ile Val Glu Leu Val Gln Gln Lys Gly Gly Ala
             35                  40                  45

Gly Trp Lys Asp Asp Val Lys Met Met Ile Val Leu Cys Leu Thr Arg
 50                  55                  60

Gly Asn Lys Pro Thr Lys Met Val Glu Lys Met Ser Pro Glu Gly Lys
 65                  70                  75                  80

Val Lys Val Asn Arg Leu Ile Ser Thr Tyr Gly Leu Lys Ser Gly Asn
                 85                  90                  95

Pro Gly Arg Asp Asp Ile Thr Leu Ser Arg Val Ala Ala Ala Phe Ala
                100                 105                 110

Gly Trp Thr Cys Gln Ala Leu Asn Val Leu His Pro Tyr Leu Pro Val
                115                 120                 125

Ser Gly Thr Thr Met Asp Ala Ile Ser Pro Asn Tyr Pro Arg Ala Met
            130                 135                 140

Met His Pro Cys Phe Ala Gly Leu Val Asp Gln Thr Ile Pro Thr Glu
145                 150                 155                 160
```

```
Tyr Cys Gln Thr Ile Val Asp Ala Met Ser Val Phe Leu Ile Gln Phe
            165                 170                 175

Ser Arg Thr Ile Asn Lys Asn Leu Arg Gly Gln Pro Lys Glu Val Val
            180                 185                 190

Ile Glu Ser Phe Ile Gln Pro Met Gln Ala Ala Met Ser Ser Ser Phe
            195                 200                 205

Ile Ala Pro Ala Glu Arg Arg Lys Leu Met Ile Ala Leu Gly Ile Val
            210                 215                 220

Asp Ala Asn Gly Lys Pro Ser Ala Asn Val Ala Ala Ala Ala Val
225                 230                 235                 240

Phe Pro Arg Leu Leu
            245

<210> SEQ ID NO 27
<211> LENGTH: 245
<212> TYPE: PRT
<213> ORGANISM: Phlebovirus sp. Be An 416992

<400> SEQUENCE: 27

Met Ala Asp Tyr Ala Arg Ile Ala Val Glu Phe Ser Gly Glu Ala Ile
1

<213> ORGANISM: Phlebovirus sp. Be Ar 371637

<400> SEQUENCE: 28

```
Met Thr Asp Tyr Ala Glu Ile Ala Val Ala Phe Ala Gly Glu Pro Val
1               5                   10                  15

Asn Asn Ala Glu Val Met Gly Trp Val Asn Glu Phe Ala Tyr Glu Gly
            20                  25                  30

Phe Ser Ala Gln Arg Ile Ile Gln Leu Val Gln Glu Arg Gly Pro Gln
        35                  40                  45

Thr Trp Gln Thr Asp Val Lys Met Met Ile Val Leu Ala Leu Thr Arg
50                  55                  60

Gly Asn Lys Pro Ala Lys Met Ile Glu Lys Met Ser Ala Glu Gly Lys
65                  70                  75                  80

Lys Lys Ala Thr Arg Leu Ile Thr Met Tyr Asn Leu Lys Ser Gly Asn
                85                  90                  95

Pro Gly Arg Asp Asp Leu Thr Leu Ser Arg Val Ala Ser Ala Phe Ala
            100                 105                 110

Gly Trp Thr Cys Gln Ala Leu Ala Val Leu His Pro Tyr Leu Pro Val
        115                 120                 125

Thr Gly Ala Ser Met Asp Ser Ile Ser Pro Gly Tyr Pro Arg Ala Met
130                 135                 140

Met His Pro Ser Phe Ala Gly Leu Ile Asp Asn Ser Ile Pro Glu Ala
145                 150                 155                 160

Phe Leu Gln Thr Val Val Asp Ala His Ala Leu Tyr Leu Leu Gln Phe
                165                 170                 175

Ser Arg Val Ile Asn Lys Asn Met Arg Gly Gln Pro Lys Ser Val Val
            180                 185                 190

Val Ser Ser Phe Leu Gln Pro Met Asn Ala Ala Ile Val Ser Gly Phe
        195                 200                 205

Ile Ser His Asp Lys Arg Arg Lys Met Leu Met Ala Phe Gly Ile Val
210                 215                 220

Asp Gln Asn Gly Lys Pro Thr Gln Ala Val Glu Thr Ala Ala Lys Ala
225                 230                 235                 240

Phe Met Thr Ile Asn
                245
```

<210> SEQ ID NO 29
<211> LENGTH: 245
<212> TYPE: PRT
<213> ORGANISM: Phlebovirus sp. VP161A

<400> SEQUENCE: 29

```
Met Thr Asp Tyr Ala Asp Ile Ala Ile Ala Phe Ala Gly Glu Pro Ile
1               5                   10                  15

Asn Asn Ala Glu Val Met Gly Trp Val Asn Glu Phe Ala Tyr Glu Gly
            20                  25                  30

Phe Asn Ala Gln Arg Ile Ile Gln Leu Val Gln Glu Lys Gly Pro Gln
        35                  40                  45

Thr Trp Gln Thr Asp Val Lys Met Met Ile Val Leu Ala Leu Thr Arg
50                  55                  60

Gly Asn Lys Pro Ser Lys Met Ile Glu Lys Met Ser Ala Glu Gly Lys
65                  70                  75                  80

Lys Lys Ala Ser Arg Leu Ile Thr Ile Tyr Gly Leu Lys Ser Gly Asn
                85                  90                  95

Pro Gly Arg Asp Asp Leu Thr Leu Ser Arg Ile Ala Ala Ala Phe Ala
```

```
            100                 105                 110
Gly Trp Thr Cys Gln Ala Leu Ala Thr Leu His Pro Tyr Leu Pro Val
            115                 120                 125

Thr Gly Ala Ala Met Asp Ala Ile Ser Pro Gly Tyr Pro Arg Ala Met
130                 135                 140

Met His Pro Ser Phe Ala Gly Leu Ile Asp Asn Ser Ile Pro Glu Ala
145                 150                 155                 160

Tyr Leu Gln Val Val Asp Ala His Ala Leu Tyr Leu Leu Gln Phe
                165                 170                 175

Ser Arg Val Ile Asn Arg Asn Met Arg Gly Gln Pro Lys Ser Val Val
            180                 185                 190

Val Ser Ser Phe Leu Gln Pro Met Asn Ala Ala Ile Val Ser Gly Phe
        195                 200                 205

Ile Ser Asn Asp Arg Arg Lys Met Leu Met Ala Phe Gly Ile Val
        210                 215                 220

Asp Gln Asn Gly Lys Pro Thr Ala Ala Val Glu Ser Ala Ala Lys Ala
225                 230                 235                 240

Phe Met Thr Ala Val
                245

<210> SEQ ID NO 30
<211> LENGTH: 253
<212> TYPE: PRT
<213> ORGANISM: Sandfly fever Naples virus

<400> SEQUENCE: 30

Met Ser Glu Glu Asn Tyr Arg Glu Ile Ala Leu Ala Phe Leu Asp Glu
1               5                   10                  15

Ala Ala Asp Ser Gly Thr Ile Thr Ala Trp Val Asn Glu Phe Ala Tyr
                20                  25                  30

Gln Gly Phe Asp Pro Lys Arg Ile Val Gln Leu Val Lys Glu Arg Gly
            35                  40                  45

Thr Ala Lys Gly Arg Asp Trp Lys Lys Asp Val Lys Met Met Ile Val
        50                  55                  60

Leu Asn Leu Val Arg Gly Asn Lys Pro Glu Ala Met Met Lys Lys Met
65                  70                  75                  80

Ser Glu Lys Gly Ala Gly Ile Val Ala Gln Leu Ile Ser Val Tyr Gln
                85                  90                  95

Leu Lys Glu Gly Asn Pro Gly Arg Asp Thr Ile Thr Leu Ser Arg Val
            100                 105                 110

Ser Ala Ala Phe Val Pro Trp Thr Ile Gln Ala Leu Arg Val Leu Ser
        115                 120                 125

Asp Ser Leu Pro Val Thr Gly Thr Thr Met Asp Ala Ile Ala Gly Val
130                 135                 140

Thr Tyr Pro Arg Ala Met Met His Pro Ser Phe Ala Gly Ile Ile Asp
145                 150                 155                 160

Leu Asp Leu Pro Asn Arg Ala Gly Glu Ala Ile Ala Asp Ala His Gly
                165                 170                 175

Leu Phe Met Leu Glu Phe Ser Lys Thr Ile Asn Pro Ser Leu Arg Thr
            180                 185                 190

Lys Gln Pro Asn Glu Ile Ala Ala Thr Phe Glu Lys Pro Asn Met Ala
        195                 200                 205

Ala Met Ser Gly Arg Phe Phe Thr Arg Glu Asp Lys Lys Lys Leu Leu
    210                 215                 220
```

```
Met Ala Val Gly Ile Leu Asn Glu Asp Leu Val Leu Thr Pro Ala Ile
225                 230                 235                 240

Val Lys Cys Ala Glu Lys Tyr Cys Ser Lys Val Gly Lys
                245                 250
```

<210> SEQ ID NO 31
<211> LENGTH: 254
<212> TYPE: PRT
<213> ORGANISM: Massilia virus

<400> SEQUENCE: 31

```
Met Ser Glu Asp Asn Tyr Arg Thr Ile Ala Leu Ala Phe Leu Asp Glu
1               5                   10                  15

Ser Ala Asp Ser Thr Thr Ile Asn Ala Trp Val Asn Glu Phe Ala Tyr
                20                  25                  30

Gln Gly Phe Asp Pro Lys Arg Ile Val Gln Leu Val Lys Glu Arg Gly
            35                  40                  45

Thr Ala Lys Gly Arg Asp Trp Lys Lys Asp Val Lys Met Met Ile Val
50                  55                  60

Leu Asn Leu Val Arg Gly Asn Lys Pro Glu Ser Met Met Lys Lys Met
65                  70                  75                  80

Ser Glu Lys Gly Ala Ala Ile Val Thr Gln Leu Ile Ser Thr Tyr Gln
                85                  90                  95

Leu Lys Glu Gly Asn Pro Gly Arg Asp Thr Ile Thr Leu Ser Arg Val
            100                 105                 110

Ser Ala Ala Phe Val Pro Trp Thr Val Gln Ala Leu Lys Thr Leu Ser
        115                 120                 125

Glu Ser Leu Pro Val Thr Gly Thr Thr Met Asp Ser Ile Ala Gly Thr
130                 135                 140

Thr Tyr Pro Arg Cys Met Met His Pro Ser Phe Ala Gly Ile Ile Asp
145                 150                 155                 160

Leu Glu Leu Pro Asn Asn Thr Gly Ala Met Leu Ala Asp Ala His Gly
                165                 170                 175

Leu Phe Met Leu Glu Phe Ser Lys Thr Ile Asn Pro Ser Leu Arg Thr
            180                 185                 190

Lys Gln Pro Asn Glu Ile Ala Ala Thr Phe Glu Lys Pro Asn Met Ala
        195                 200                 205

Ala Met Thr Gly Arg Phe Phe Thr Arg Asp Asp Lys Lys Lys Leu Leu
210                 215                 220

Ile Ala Ile Gly Val Leu Asp Glu Asp Leu Val Pro Asn Pro Ala Ile
225                 230                 235                 240

Glu Lys Cys Ala Glu Lys Tyr Lys Ala Lys Val Gly Lys Val
                245                 250
```

<210> SEQ ID NO 32
<211> LENGTH: 253
<212> TYPE: PRT
<213> ORGANISM: Toscana virus

<400> SEQUENCE: 32

```
Met Ser Asp Glu Asn Tyr Arg Asp Ile Ala Leu Ala Phe Leu Asp Glu
1               5                   10                  15

Ser Ala Asp Ser Gly Thr Ile Asn Ala Trp Val Asn Glu Phe Ala Ty

```
Thr Ala Lys Gly Arg Asp Trp Lys Lys Asp Val Lys Met Met Ile Val
 50                  55                  60

Leu Asn Leu Val Arg Gly Asn Lys Pro Glu Ala Met Met Lys Lys Met
 65                  70                  75                  80

Ser Glu Lys Gly Ala Ser Ile Val Ala Asn Leu Ile Ser Val Tyr Gln
                 85                  90                  95

Leu Lys Glu Gly Asn Pro Gly Arg Asp Thr Ile Thr Leu Ser Arg Val
            100                 105                 110

Ser Ala Ala Phe Val Pro Trp Thr Val Gln Ala Leu Arg Val Leu Ser
            115                 120                 125

Glu Ser Leu Pro Val Ser Gly Thr Thr Met Asp Ala Ile Ala Gly Val
130                 135                 140

Thr Tyr Pro Arg Ala Met Met His Pro Ser Phe Ala Gly Ile Ile Asp
145                 150                 155                 160

Leu Asp Leu Pro Asn Gly Ala Gly Ala Thr Ile Ala Asp Ala His Gly
                165                 170                 175

Leu Phe Met Ile Glu Phe Ser Lys Thr Ile Asn Pro Ser Leu Arg Thr
            180                 185                 190

Lys Gln Ala Asn Glu Val Ala Ala Thr Phe Glu Lys Pro Asn Met Ala
            195                 200                 205

Ala Met Ser Gly Arg Phe Phe Thr Arg Glu Asp Lys Lys Lys Leu Leu
210                 215                 220

Ile Ala Val Gly Ile Ile Asp Glu Asp Leu Val Leu Ala Ser Ala Val
225                 230                 235                 240

Val Arg Ser Ala Glu Lys Tyr Arg Ala Lys Val Gly Lys
                245                 250

<210> SEQ ID NO 33
<211> LENGTH: 254
<212> TYPE: PRT
<213> ORGANISM: Uukuniemi virus

<400> SEQUENCE: 33

Met Ala Met Pro Glu Asn Trp Val Arg Phe Ala Ile Glu Ile Ser Asp
1               5                   10                  15

Ala Gln Trp Glu Glu Glu Ile Arg Glu Phe Ile Asn Leu Phe Gln
                20                  25                  30

Tyr Gln Gly Phe Asp Ala Ala Val Val Leu Ser Arg Ile Phe Glu Leu
            35                  40                  45

Ala Lys Lys Ala Asp Leu Ser Arg Asp Gln Met Leu Arg Asp Ile Arg
 50                  55                  60

Ala Leu Ile Thr Leu His Leu Thr Arg Gly Asn Lys Leu Ser Ser Ile
 65                  70                  75                  80

Glu Lys Arg Leu Ser Glu Gly Lys Lys Glu Phe Ala Leu Leu Lys
                 85                  90                  95

Ala Arg Tyr Gln Leu Val Asp Lys Ala Lys Glu Ala Ala Asp Leu Thr
            100                 105                 110

Leu Ser Arg Ile Ala Ile Ala Asn Ala Gly Leu Thr Cys Arg Ile Leu
            115                 120                 125

Pro Gln Val Val Ala His Thr Ala Val Thr Arg Ser Arg Met Glu Ser
130                 135                 140

Leu Ser Ala Asp Tyr Pro Val Cys Met Met His Asn Ala Phe Ala Gly
145                 150                 155                 160

Leu Ile Asp Glu Thr Leu Pro Glu Asp Ser Ile Lys Ala Leu Val Asp
                165                 170                 175
```

```
Ala His Arg Leu Tyr Leu Leu Glu Phe Ser Arg Thr Ile Asn Val Lys
            180                 185                 190

His Arg Gly Met Glu Ala Lys Glu Ile Leu Asp Ala Asn Asp Ser Ala
        195                 200                 205

Leu Gln Ala Gly Leu Ala Ser Ser Phe Leu Thr Pro Ser Gln Lys Arg
210                 215                 220

Ala Tyr Leu Leu Ser Phe Lys Leu Val Asp Gly Asn Gly Lys Val Asn
225                 230                 235                 240

Lys Ala Val Gln Gln Ala Ala Thr Val Leu Arg Ser Leu Ile
                245                 250
```

<210> SEQ ID NO 34
<211> LENGTH: 245
<212> TYPE: PRT
<213> ORGANISM: Phlebovirus HB29/China/2010 (SFTSV)

<400> SEQUENCE: 34

```
Met Ser Glu Trp Ser Arg Ile Ala Val Glu Phe Gly Glu Gln Gln Leu
1               5                   10                  15

Asn Leu Thr Glu Leu Glu Asp Phe Ala Arg Glu Leu Ala Tyr Glu Gly
            20                  25                  30

Leu Asp Pro Ala Leu Ile Ile Lys Lys Leu Lys Glu Thr Gly Gly Asp
        35                  40                  45

Asp Trp Val Lys Asp Thr Lys Phe Ile Ile Val Phe Ala Leu Thr Arg
    50                  55                  60

Gly Asn Lys Ile Val Lys Ala Ser Gly Lys Met Ser Asn Ser Gly Ser
65                  70                  75                  80

Lys Arg Leu Met Ala Leu Gln Glu Lys Tyr Gly Leu Val Glu Arg Ala
                85                  90                  95

Glu Thr Arg Leu Ser Ile Thr Pro Val Arg Val Ala Gln Ser Leu Pro
            100                 105                 110

Thr Trp Thr Cys Ala Ala Ala Ala Leu Lys Glu Tyr Leu Pro Val
        115                 120                 125

Gly Pro Ala Val Met Asn Leu Lys Val Glu Asn Tyr Pro Pro Glu Met
    130                 135                 140

Met Cys Met Ala Phe Gly Ser Leu Ile Pro Thr Ala Gly Val Ser Glu
145                 150                 155                 160

Ala Thr Thr Lys Thr Leu Met Glu Ala Tyr Ser Leu Trp Gln Asp Ala
                165                 170                 175

Phe Thr Lys Thr Ile Asn Val Lys Met Arg Gly Ala Ser Lys Thr Glu
            180                 185                 190

Val Tyr Asn Ser Phe Arg Asp Pro Leu His Ala Ala Val Asn Ser Val
        195                 200                 205

Phe Phe Pro Asn Asp Val Arg Val Lys Trp Leu Lys Ala Lys Gly Ile
    210                 215                 220

Leu Gly Pro Asp Gly Val Pro Ser Arg Ala Ala Glu Val Ala Ala Ala
225                 230                 235                 240

Ala Tyr Arg Asn Leu
                245
```

<210> SEQ ID NO 35
<211> LENGTH: 104
<212> TYPE: PRT
<213> ORGANISM: Gabek Forest virus

<400> SEQUENCE: 35

```
Phe Asp Pro Arg Ile Val Val Lys Leu Val Ser Glu Val Glu Gly Trp
1               5                   10                  15

Gln Thr Asp Val Lys Lys Met Ile Ile Leu Ala Leu Thr Arg Gly Asn
            20                  25                  30

Lys Pro Glu Lys Met Val Thr Lys Met Ser Ala Lys Gly Arg Glu Glu
        35                  40                  45

Val Ala Lys Leu Val Lys Lys Tyr Lys Leu Lys Ser Gly Asn Pro Gly
    50                  55                  60

Arg Asn Asp Leu Thr Leu Ser Arg Val Ala Ala Ala Phe Ala Ser Trp
65                  70                  75                  80

Thr Cys Asn Ala Ile Tyr His Val Gln Tyr Tyr Leu Pro Val Thr Gly
                85                  90                  95

Asn His Met Asp Ala Ile Ser Lys
            100

<210> SEQ ID NO 36
<211> LENGTH: 243
<212> TYPE: PRT
<213> ORGANISM: Punta Toro virus

<400> SEQUENCE: 36

Met Ser Tyr Glu Glu Ile Ala Val Gln Phe Ala Ser Glu Ser Ile Asp
1               5                   10                  15

Glu Gln Ala Val Ala Gly Trp Val Thr Asp Phe Ala Tyr Gln Gly Phe
            20                  25                  30

Asp Ala Lys Arg Val Ile Ala Leu Val Lys Glu Arg Gly Gly Glu Asp
        35                  40                  45

Trp Lys Gln Asp Val Lys Lys Met Ile Val Leu Ser Leu Thr Arg Gly
    50                  55                  60

Asn Lys Pro Asn Lys Met Val Leu Lys Met Ser Asp Lys Gly Lys Ala
65                  70                  75                  80

Met Val Asn Glu Leu Val Leu Lys Tyr Lys Leu Lys Ser Gly Asn Pro
                85                  90                  95

Ser Arg Asp Asp Leu Thr Leu Ser Arg Ile Thr Ala Ala Phe Ala Gly
            100                 105                 110

Trp Thr Cys Gln Ala Ala Asp Tyr Val Gln Glu Tyr Leu Pro Val Thr
        115                 120                 125

Gly Arg Ala Met Asp Thr Ile Ser Ser Gly Tyr Pro Arg Ala Met Met
    130                 135                 140

His Pro Ser Phe Ala Gly Leu Ile Asp Gln Glu Leu Pro Ala Asp Val
145                 150                 155                 160

Leu Ser Glu Ile Thr Gln Ala His Cys Leu Phe Met Ile Gln Phe Ser
                165                 170                 175

Lys Thr Ile Asn Pro Ser Leu Arg Gly Leu Ser Lys Asp Glu Ile Val
            180                 185                 190

Ser Ser Phe Glu Arg Pro Met Gln Ala Ala Ile Ser Ser Thr Phe Leu
        195                 200                 205

Thr Ser Ala Asn Arg Arg Ala Met Leu Lys Thr Leu Gly Ile Ile Asn
    210                 215                 220

Asp Asn Leu Lys Pro Ser Ser Ser Thr Val Ser Ala Ala Lys Val Phe
225                 230                 235                 240

Arg Ser Leu

<210> SEQ ID NO 37
```

-continued

```
<211> LENGTH: 245
<212> TYPE: PRT
<213> ORGANISM: Rift Valley fever virus

<400> SEQUENCE: 37

Met Asp Asn Tyr Gln Glu Leu Ala Ile Gln Phe Ala Ala Gln Ala Val
1               5                   10                  15

Asp Arg Asn Glu Ile Glu Gln Trp Val Arg Glu Phe Ala Tyr Gln Gly
            20                  25                  30

Phe Asp Ala Arg Arg Val Ile Glu Leu Leu Lys Gln Tyr Gly Gly Ala
        35                  40                  45

Asp Trp Glu Lys Asp Ala Lys Lys Met Ile Val Leu Ala Leu Thr Arg
    50                  55                  60

Gly Asn Lys Pro Arg Arg Met Met Met Lys Met Ser Lys Glu Gly Lys
65                  70                  75                  80

Ala Thr Val Glu Ala Leu Ile Asn Lys Tyr Lys Leu Lys Glu Gly Asn
                85                  90                  95

Pro Ser Arg Asp Glu Leu Thr Leu Ser Arg Val Ala Ala Ala Leu Ala
            100                 105                 110

Gly Trp Thr Cys Gln Ala Leu Val Val Leu Ser Glu Trp Leu Pro Val
        115                 120                 125

Thr Gly Thr Thr Met Asp Gly Leu Ser Pro Ala Tyr Pro Arg His Met
    130                 135                 140

Met His Pro Ser Phe Ala Gly Met Val Asp Pro Ser Leu Pro Glu Asp
145                 150                 155                 160

Tyr Leu Arg Ala Ile Leu Asp Ala His Ser Leu Tyr Leu Leu Gln Phe
                165                 170                 175

Ser Arg Val Ile Asn Pro Asn Leu Arg Gly Lys Thr Lys Glu Glu Val
            180                 185                 190

Ala Ala Thr Phe Thr Gln Pro Met Asn Ala Ala Val Asn Ser Ser Phe
        195                 200                 205

Ile Ser His Glu Lys Arg Arg Glu Phe Leu Arg Ala Phe Gly Leu Val
    210                 215                 220

Asp Ser Asn Gly Lys Pro Ser Ala Ala Val Met Ala Ala Gln Ala
225                 230                 235                 240

Tyr Lys Thr Ala Ala
                245

<210> SEQ ID NO 38
<211> LENGTH: 244
<212> TYPE: PRT
<213> ORGANISM: Chandiru virus

<400> SEQUENCE: 38

Met Ser Tyr Glu Lys Leu Ala Val Asp Ile Ala Gly His Glu Ile Asp
1               5                   10                  15

Ala Asp Thr Ile Lys Ala Trp Val Gln Ala Phe Ala Tyr Gln Gly Phe
            20                  25                  30

Asp Ala Lys Arg Val Met Glu Leu Leu Val Glu Arg Gly Gly Asp Asp
        35                  40                  45

Trp Val Glu Asp Ala Lys Gln Met Ile Ile Leu Cys Leu Thr Arg Gly
    50                  55                  60

Asn Lys Pro Ser Lys Met Met Val Lys Met Ser Glu Lys Gly Lys Lys
65                  70                  75                  80

Ile Val Gln Ala Leu Val Lys Arg Tyr Ser Leu Lys Glu Gly Asn Pro
                85                  90                  95
```

```
Ser Arg Asp Asp Leu Thr Leu Ser Arg Val Thr Ala Ala Leu Ala Gly
            100                 105                 110

Tyr Thr Cys Gln Ala Thr Glu Tyr Val Glu Glu Phe Leu Pro Val Thr
        115                 120                 125

Gly Lys Asn Met Asp Asp Leu Ser Lys Asn Tyr Pro Arg Ala Met Met
    130                 135                 140

His Pro Ser Phe Ala Gly Leu Ile Asp Pro Lys Leu Pro Pro Asp Val
145                 150                 155                 160

Leu Ser Thr Ile Cys Asp Ala Phe Ser Leu Phe Met Val Gln Phe Ser
                165                 170                 175

Arg Thr Ile Asn Pro Arg Asn Arg Gly Leu Ser Val Ser Glu Val Ala
                180                 185                 190

Ser Thr Phe Asp Arg Pro Ile Asn Ala Ala Met Asn Ser Ser Phe Ile
            195                 200                 205

Ser Gly Glu Gln Arg Lys Ser Phe Leu Arg Asn Leu Gly Ile Leu Asp
        210                 215                 220

Glu Asn Met Gln Pro Ser Asn Pro Val Lys Ala Ala Lys Val Phe
225                 230                 235                 240

Arg Gly Leu Lys

<210> SEQ ID NO 39
<211> LENGTH: 104
<212> TYPE: PRT
<213> ORGANISM: Rio Grande virus

<400> SEQUENCE: 39

Ala Tyr Gln Gly Phe Asp Ala Asn Arg Val Val Glu Leu Val Gln Glu
1               5                   10                  15

Arg Ala Lys Gly Arg Lys Trp Gln Glu Asp Val Lys Arg Met Ile Ile
            20                  25                  30

Leu Ala Leu Thr Arg Gly Asn Lys Pro Asp Lys Met Arg Lys Lys Met
        35                  40                  45

Ser Pro Glu Gly Ile Ala Val Leu Asp Asp Leu Val Lys Thr Tyr Gln
    50                  55                  60

Leu Lys Ser Ser Ser Pro Gly Arg Asp Asp Leu Thr Leu Ala Arg Ile
65                  70                  75                  80

Ala Ala Ala Phe Ala Pro Trp Thr Cys Gln Thr Glu Ala Val Glu
                85                  90                  95

Asn Tyr Met Pro Val Asn Gly Ala
            100

<210> SEQ ID NO 40
<211> LENGTH: 7666
<212> TYPE: DNA
<213> ORGANISM: Artificial Sequence
<220> FEATURE:
<223> OTHER INFORMATION: Synthetic construct (pcMo4GnGc vector)

<400> SEQUENCE: 40
gtcgacattg attattgact agttattaat agtaatcaat tacggggtca ttagttcata      60
gcccatatat ggagttccgc gttacataac ttacggtaaa tggcccgcct ggctgaccgc     120
ccaacgaccc ccgcccattg acgtcaataa tgacgtatgt tcccatagta acgccaatag     180
ggactttcca ttgacgtcaa tgggtggact atttacggta aactgcccac ttggcagtac     240
atcaagtgta tcatatgcca agtacgcccc ctattgacgt caatgacggt aaatggcccg     300
```

```
cctggcatta tgcccagtac atgaccttat gggactttcc tacttggcag tacatctacg    360
tattagtcat cgctattacc atgggtcgag gtgagcccca cgttctgctt cactctcccc    420
atctccccct cctcccacc cccaattttg tatttattta ttttttaatt attttgtgca    480
gcgatggggg cggggggggg gggggcgcgc gccaggcggg gcgggcggg gcgaggggcg    540 gggcggggcg aggcggagag gtgcggcggc agccaatcag agcggcgcgc tccgaaagtt    600
tccttttatg gcgaggcggc ggcggcgcg gccctataaa aagcgaagcg cgcggcgggc    660
gggagtcgct gcgttgcctt cgccccgtgc cccgctccgc gccgcctcgc gccgccgcc    720 ccggctctga ctgaccgcgt tactcccaca ggtgagcggg cgggacgcc cttctcctcc    780 gggctgtaat tagcgcttgg tttaatgacg gctcgtttct tttctgtggc tgcgtgaaag    840
ccttaaaggg ctccgggagg gccctttgtg cgggggggag cggctcgggg ggtgcgtgcg    900
tgtgtgtgtg cgtggggagc gccgcgtgcg gcccgcgctg cccggcggct gtgagcgctg    960
cgggcgcggc gcgggctttt gtgcgctccg cgtgtgcgcg aggggagcgc ggccgggggc   1020
ggtgccccgc ggtgcggggg ggctgcgagg ggaacaaagg ctgcgtgcgg ggtgtgtgcg   1080 tggggggtg agcaggggt gtgggcgcgg cggtcgggct gtaacccccc cctgcacccc   1140
cctccccgag ttgctgagca cggccccggct tcggtgcgg ggctccgtgc ggggcgtggc   1200
gcggggctcg ccgtgccggg cggggggtgg cggcaggtgg gggtgccggg cggggcgggg   1260
ccgcctcggg ccggggaggg ctcggggag gggcgcggcg gccccggagc gccggcggct   1320
gtcgaggcgc ggcgagccgc agccattgcc ttttatggta atcgtgcgag agggcgcagg   1380
gacttccttt gtcccaaatc tggcggagcc gaaatctggg aggcgccgcc gcaccccctc   1440
tagcgggcgc gggcgaagcg gtgcggcgcc ggcaggaagg aaatgggcgg ggagggcctt   1500
cgtgcgtcgc cgcgccgccg tcccttctc catctccagc ctcggggctg ccgcaggggg   1560
acggctgcct tcgggggga cggggcaggg cggggttcgg cttctggcgt gtgaccggcg   1620
gctctagagc ctctgctaac catgttcatg ccttcttctt tttcctacag ctcctgggca   1680
acgtgctggt tgttgtgctg tctcatcatt ttggcaaaga attcatgatt gtcccaggcc   1740
caacttacaa aggcaaaatc tttgttgaga gaccaacgta caatggttat aaaggctggg   1800
ggtgtgcaga tgggaagtca ctaagccact ctggcacata ttgtgaaact gacagctcag   1860
taagttctgg gttaattcag ggtgataggg ttctctgggt tggggaagta gtctgtcaga   1920
gagggacacc tgtgccagaa gatgtatttta gtgaactgat tagcttgagt caaagtgagt   1980
tcccagatgt gtgcaaggtt gatggggttg cactgaacca atgtgagcag gagagcatcc   2040
cccagccact ggacgttgca tggattgatg ttggaaggtc tcataaagtg ctgatgagag   2100
aacacaaaac taaatgggtc caagagagct cagcaaagga ctttgtgtgc ttcaaggtgg   2160
gtcaggggcc atgttcaaaa caagaggaag atgactgcat gagtaagggc aactgccatg   2220
gggatgaggt tttctgcagg atggcaggat gctctgcccg tatgcaagat aatcaagaag   2280
gctgtaggtg cgaactgctc caaaaacctg agaaatcat tgtgaattat ggaggcgtct   2340
ctgtaagacc aacttgttat ggattctcta gaatgatggc aacattggaa gttcacaagc   2400
ctgatagaga attaacaggg tgcacggggtt gtcacctaga gtgcatagag ggagggtca   2460 aaattgtaac acttacaagc gagctgagaa gtgcaacagt ttgtgcttca cattttgtg   2520 catccgcaaa agggggctca agacaactg acatactctt ccacactggt gctctcgttg   2580
gacccaaatc cattagaatt acgggccagt tgttagatgg gagcaagttc tcctttgatg   2640
ggcactgcat attcccagat gggtgcatgg cacttgactg caccttctgt aaggagttcc   2700
```

```
tgagaaaccc acaatgttac ccagtaaaga aatggctctt cttggtggta gttgtgatgt   2760
gctgctattg cgcactgatg ctgcttacta acatactgag agctataggt gtttggggaa   2820
catgggtttt tgctccaata aagttagttc tagcattagg attgaggctt gccaaactat   2880
caaagaaggg gttggttgct gtggttacaa ggggccaaat gatcgtgaat gatgagctgc   2940
accagattcg agtggagaga ggtgagcaaa atgaggaag actaggtcat ggcccaagag    3000
gtcccgtccg tcactggcta tactcacctg ccctcattct cattctgacc acttcaattt   3060
gctctggatg tgatgagctc gttcatgctg agagtaaatc tatcacatgc aagtctgcat   3120
ctgggaatga aaggagtgc tcagtgacag gcagagcttt actcccagct gttaatccag     3180
gacaggaggc ctgcttgcac ttcagtatgc cagggagccc agactctaag tgcctcaaga   3240
tcaaagtgaa atcaataaat ctcagatgca agcaagcctc ttcatattat gttcctgaag   3300
caaaggcaag atgtacatct gtaagaaggt gcaggtgggc aggtgactgt caatctgggt   3360
gtccaacata tttcagctca aactcattct cagatgactg ggcaaacagg atggacaggg   3420
ctgggctcgg gatgagtggg tgctcagatg ggtgtggtgg ggctgcatgt gggtgtttca   3480
atgcagcgcc atcctgcatc ttttggagaa agtgggtgga gaacccatcc aatcgtgtct   3540
ggaaggtgtc accttgtgca tcatgggtgc tagctgcaat cattgagttg actttgccat   3600
caggagaggt taagactcta gagcctgtca cagggcaagc aactcaaatg tttaagggtg   3660
ttgcaatcac gtatctgggt tcatccattg agattgttgg catgaccagg ctatgcgaga   3720
tgaaagagat gggaactggg attatggcac tagcccctg caatgaccct gggcacgcca    3780
taatgggaaa tgtgggtgag atccaatgca gtagtataga aagcgcaaag cacatcagat   3840
ctgatgggtg catttggaat gctgacctag ttgggataga attaagggtt gatgatgctg   3900
tgtgtttctc aaaactcacc agtgttgagg cagtcgcaaa tttctcaaaa atcccggcaa   3960
taatttctgg ggtccgtttt gatcaaggga atcatggaga atcgcgaatc tatggtagcc   4020
cattagacat cacgaaggtt agtggggaat tctcagtgtc attcagggg atgaggctta    4080 aactgtctga gatatcagca agctgcacag gtgagataac aaacgtctct ggttgctact   4140
cctgcatgac tggggcctct gtcagcataa agctacatag cagtaagaac acaacaggtc   4200
atcttaaatg tgattcagat gagactgcat tcagtgtcat ggagggaaca cacacttata   4260
ggcctcacat gagctttgat aaagcagtgg tagatgagga gtgtgtgcta aactgtggtg   4320
gccattcatc aaagctgttg cttaagggga gccttgtctt catggacgtg ccaaggtttg   4380
ttgatgggag ttatgttcaa acataccata gcaaggtgcc tgctggggga agggtcccaa   4440
atccagtaga ttggctcaac gcgctgtttg gagatggcat aacacgatgg attcttggga   4500
ttataggagt tctgttggca tgtgtcttgc tatttgtggt ggtggtggcc atcactaggc   4560
gattgatcaa ggggctgact caaagggcga aggtggcatg ctcgaggaat tcactcctca   4620
ggtgcaggct gcctatcaga aggtggtggc tggtgtggcc aatgccctgg ctcacaaata   4680
ccactgagat cttttccct ctgccaaaaa ttatggggac atcatgaagc cccttgagca    4740
tctgacttct ggctaataaa ggaaatttat tttcattgca atagtgtgtt ggaatttttt   4800
gtgtctctca ctcggaagga catatgggag ggcaaatcat ttaaaacatc agaatgagta   4860
tttggtttag agtttggcaa catatgccat atgctggctg ccatgaacaa aggtggctat   4920
aaagaggtca tcagtatatg aaacagcccc ctgctgtcca ttccttattc catagaaaag   4980
ccttgacttg aggttagatt ttttttatat tttgtttgt gttattttt tctttaacat      5040
```

```
ccctaaaatt ttccttacat gttttactag ccagattttt cctcctctcc tgactactcc    5100
cagtcatagc tgtccctctt ctcttatgaa gatccctcga cctgcagccc aagcttggcg    5160
taatcatggt catagctgtt tcctgtgtga aattgttatc cgctcacaat tccacacaac    5220
atacgagccg gaagcataaa gtgtaaagcc tggggtgcct aatgagtgag ctaactcaca    5280
ttaattgcgt tgcgctcact gcccgctttc cagtcgggaa acctgtcgtg ccagcggatc    5340
cgcatctcaa ttagtcagca accatagtcc cgcccctaac tccgcccatc ccgcccctaa    5400
ctccgcccag ttccgcccat tctccgcccc atggctgact aattttttt atttatgcag    5460
aggccgaggc cgcctcggcc tctgagctat tccagaagta gtgaggaggc ttttttggag    5520
gcctaggctt ttgcaaaaag ctaacttgtt tattgcagct tataatggtt acaaataaag    5580
caatagcatc acaaatttca caaataaagc attttttca ctgcattcta gttgtggttt    5640
gtccaaactc atcaatgtat cttatcatgt ctggatccgc tgcattaatg aatcggccaa    5700
cgcgcgggga gaggcggttt gcgtattggg cgctcttccg cttcctcgct cactgactcg    5760
ctgcgctcgg tcgttcggct gcggcgagcg gtatcagctc actcaaaggc ggtaatacgg    5820
ttatccacag aatcagggga taacgcagga aagaacatgt gagcaaaagg ccagcaaaag    5880
gccaggaacc gtaaaaaggc cgcgttgctg gcgtttttcc ataggctccg cccccctgac    5940
gagcatcaca aaaatcgacg ctcaagtcag aggtggcgaa acccgacagg actataaaga    6000
taccaggcgt ttccccctgg aagctccctc gtgcgctctc ctgttccgac cctgccgctt    6060
accggatacc tgtccgcctt tctcccttcg ggaagcgtgg cgctttctca atgctcacgc    6120
tgtaggtatc tcagttcggt gtaggtcgtt cgctccaagc tgggctgtgt gcacgaaccc    6180
cccgttcagc ccgaccgctg cgccttatcc ggtaactatc gtcttgagtc caacccggta    6240
agacacgact tatcgccact ggcagcagcc actggtaaca ggattagcag agcgaggtat    6300
gtaggcggtg ctacagagtt cttgaagtgg tggcctaact acggctacac tagaaggaca    6360
gtatttggta tctgcgctct gctgaagcca gttaccttcg gaaaaagagt tggtagctct    6420
tgatccggca aacaaaccac cgctggtagc ggtggttttt ttgtttgcaa gcagcagatt    6480
acgcgcagaa aaaaggatc tcaagaagat cctttgatct tttctacggg gtctgacgct    6540
cagtggaacg aaaactcacg ttaagggatt ttggtcatga gattatcaaa aaggatcttc    6600
acctagatcc ttttaaatta aaaatgaagt tttaaatcaa tctaaagtat atatgagtaa    6660
acttggtctg acagttacca atgcttaatc agtgaggcac ctatctcagc gatctgtcta    6720
tttcgttcat ccatagttgc ctgactcccc gtcgtgtaga taactacgat acgggagggc    6780
ttaccatctg gccccagtgc tgcaatgata ccgcgagacc cacgctcacc ggctccagat    6840
ttatcagcaa taaaccagcc agccggaagg gccgagcgca gaagtggtcc tgcaacttta    6900
tccgcctcca tccagtctat taattgttgc cgggaagcta gagtaagtag ttcgccagtt    6960
aatagtttgc gcaacgttgt tgccattgct acaggcatcg tggtgtcacg ctcgtcgttt    7020
ggtatggctt cattcagctc cggttcccaa cgatcaaggc gagttacatg atcccccatg    7080
ttgtgcaaaa aagcggttag ctccttcggt cctccgatcg ttgtcagaag taagttggcc    7140
gcagtgttat cactcatggt tatggcagca ctgcataatt ctcttactgt catgccatcc    7200
gtaagatgct tttctgtgac tggtgagtac tcaaccaagt cattctgaga atagtgtatg    7260
cggcgaccga gttgctcttg cccggcgtca atacgggata ataccgcgcc acatagcaga    7320
actttaaaag tgctcatcat tggaaaacgt tcttcggggc gaaaactctc aaggatctta    7380
ccgctgttga gatccagttc gatgtaaccc actcgtgcac ccaactgatc ttcagcatct    7440
```

-continued

| | |
|---|---|
| tttactttca ccagcgtttc tgggtgagca aaaacaggaa ggcaaaatgc cgcaaaaaag | 7500 |
| ggaataaggg cgacacggaa atgttgaata ctcatactct tcctttttca atattattga | 7560 |
| agcatttatc agggttattg tctcatgagc ggatacatat ttgaatgtat ttagaaaaat | 7620 |
| aaacaaatag gggttccgcg cacatttccc cgaaaagtgc cacctg | 7666 |

<210> SEQ ID NO 41
<211> LENGTH: 11042
<212> TYPE: DNA
<213> ORGANISM: Artificial Sequence
<220> FEATURE:
<223> OTHER INFORMATION: Synthetic construct (pcMo4L vector)

<400> SEQUENCE: 41

| | |
|---|---|
| gtcgacattg attattgact agttattaat agtaatcaat tacggggtca ttagttcata | 60 |
| gcccatatat ggagttccgc gttacataac ttacggtaaa tggcccgcct ggctgaccgc | 120 |
| ccaacgaccc ccgcccattg acgtcaataa tgacgtatgt tcccatagta acgccaatag | 180 |
| ggactttcca ttgacgtcaa tgggtggact atttacggta aactgcccac ttggcagtac | 240 |
| atcaagtgta tcatatgcca agtacgcccc ctattgacgt caatgacggt aaatggcccg | 300 |
| cctggcatta tgcccagtac atgaccttat gggactttcc tacttggcag tacatctacg | 360 |
| tattagtcat cgctattacc atgggtcgag gtgagcccca cgttctgctt cactctcccc | 420 |
| atctcccccc cctccccacc cccaattttg tatttattta ttttttaatt attttgtgca | 480 |
| gcgatggggg cggggggggg ggggcgcgc gccaggcggg gcgggcggg gcgaggggcg | 540 |
| gggcggggcg aggcggagag gtgcggcggc agccaatcag agcggcgcgc tccgaaagtt | 600 |
| tccttttatg gcgaggcggc ggcggcgcg gccctataaa aagcgaagcg cgcggcgggc | 660 |
| gggagtcgct gcgttgcctt cgccccgtgc cccgctccgc gccgcctcgc gccgcccgcc | 720 |
| ccggctctga ctgaccgcgt tactcccaca ggtgagcggg cgggacggcc cttctcctcc | 780 |
| gggctgtaat tagcgcttgg tttaatgacg gctcgtttct tttctgtggc tgcgtgaaag | 840 |
| ccttaaaggg ctccgggagg gccctttgtg cggggggag cggctcgggg ggtgcgtgcg | 900 |
| tgtgtgtgtg cgtggggagc gccgcgtgcg gcccgcgctg cccggcggct gtgagcgctg | 960 |
| cgggcgcggc gcgggcttt gtgcgctccg cgtgtgcgcg aggggagcgc ggccgggggc | 1020 |
| ggtgccccgc ggtgcggggg ggctgcgagg ggaacaaagg ctgcgtgcgg ggtgtgtgcg | 1080 |
| tgggggggtg agcagggggt gtgggcgcgg cggtcgggct gtaaccccc cctgcacccc | 1140 |
| cctccccgag ttgctgagca cggcccggct tcggtgcgg ggctccgtgc ggggcgtggc | 1200 |
| gcggggctcg ccgtgccggg cggggggtgg cggcaggtgg gggtgccggg cggggcgggg | 1260 |
| ccgcctcggg ccggggaggg ctcggggag gggcgcggcg gccccggagc gccggcggct | 1320 |
| gtcgaggcgc ggcgagccgc agccattgcc ttttatggta atcgtgcgag agggcgcagg | 1380 |
| gacttccttt gtcccaaatc tggcggagcc gaaatctggg aggcgccgcc gcaccccctc | 1440 |
| tagcgggcgc gggcgaagcg gtgcggcgcc ggcaggaagg aaatgggcgg gagggccctt | 1500 |
| cgtgcgtcgc cgcgccgccg tcccctctc catctccagc ctcggggctg ccgcaggggg | 1560 |
| acggctgcct tcgggggga cggggcaggg cggggttcgg cttctggcgt gtgaccggcg | 1620 |
| gctctagagc ctctgctaac catgttcatg ccttcttctt tttcctacag ctcctgggca | 1680 |
| acgtgctggt tgttgtgctg tctcatcatt ttggcaaaga attcatgaat ttagaagctc | 1740 |
| tttgctctag agtgctttca gagagagggc tatcaactgg tgagcctggg gtatatgacc | 1800 |

```
agattttga aaggcctggc ctcccaaacc ttgaagtcac agtagactcc actggggtag      1860
ttgtcgatgt tggggccatt cctgactcag catcacagct agggtcctcg ataaatgcag      1920
gtgtgctcac catacctctc tcagaagcat ataagataaa tcatgacttc actttctctg      1980
gactgactaa gacaacggat aggaagttgt ctgaagtatt cccttttggtt catgatggct     2040 cagactcaat gaccccgat gtgatacaca caagactaga tggaacagta gttgtaattg       2100
aattcacaac aaccgaaagc accaacatgg gaggacttga ggctgcctat cggagcaagc      2160
ttgaaaaata ccgtgaccca ctaaacagaa gatcagacat aatgcctgat gcatcaattt      2220
actttggaat cattgttgtt agtgcatctg gtgttctcac aaatatgcct ctgacccaag      2280
atgaagctga agaattgatg ttcaggttct gtgtggcaaa cgagatttat tctcaggcaa      2340
gagcaatgga tgctgaggtt gaacttcaaa agtcagagga ggaatatgag gccatatcca      2400
gagcaagagc tttcttcacg cttttttgact atgacgatgg caagctctct gaggcattcc     2460
ctaactctga cattgagatg ctcagaagat ttctgagtca gcctgtagac acaagttttg      2520
tgaccgcaac cctcaaagaa aaagagcaag aggcttataa gagaatgtgt gaggagcact     2580
atctaaaaag tggcatgagc acaaaagaga ggcttgaggc aaatcgcaat gatgcaatag      2640
acaaaactag agctctcatg gaaagactcc acaacatgag cagcaaggag ctacactcga     2700
ataagagcac agtgaagttg ccccccctggg tagtgaagcc ttctgatagg acgttagatg     2760
tcaaaacgga cacgggatca ggggagctac tcaaccatgg cccatatggg gagttgtggt      2820
caagatgctt cctggagatt atccttggga atgtggaagg ggtcatcagc agccctgaaa      2880
aggagctgga gatcgccatc agtgatgacc ctgaggctga cacccctaag gctgcaaaga     2940
taaaatacca caggttcagg cctgagctca gtttagagag caagcatgaa ttttcattac      3000
aaggcatcga gggcaaaaga tggaagcatt cagctaggaa tgtccttaaa gatgaaatgt     3060
cccataagac aatgagccca tttgttgatg tctcgaacat tgaggagttt ctgataatga     3120
acaacctgtt aaatgacaca tcttttaatc gggaagggct gcaagaaaca atcaacctgt     3180
tgttggagaa ggctactgaa atgcaccaaa atggcttatc aacagctttg aatgattcct      3240
tcaagagaaa cttcaacaca aacgtagtgc agtggagcat gtgggtctca tgcttagctc      3300
aggaattggc aagtgctttg aagcaacatt gcaagcctgg tgagtttatc atcaaaaaat     3360
taatgcactg gccaatattc gccataatta agcccactaa gtcatcaagt cacatattct      3420
acagcttggc aataaaaaaa accaacatta agaggaggct gattggtgac gtattcacag     3480
acacaattga tgcggggggag tgggagttttt cagaattcaa aagcctcaag acttgcaagc    3540
tgacaaatct cattaacctg ccgtgcacca tgctcaactc aattgcgttc tggagagaga     3600
agatgggagt agcccctgg atttctagaa aggcctgctc agagctcagg gaacaagtgg       3660
caatcacttt ccttatgagt ctggaagaca aatcaacaac agaagagctt gttactctca      3720
cgaggtattc acaaatggag ggatttgtgt ctccacccct gctccctaaa cccagaagg       3780 tggtggaaaa gttagaagtt cccttgcgaa caaagcttca agtgttttg tttaggaggc       3840 atcttgatgc tattgttaga gttgctgcat ctccattccc cattgtggca agagatggtc     3900
gagtggaatg gacagggaca ttcaatgcaa tcactggccg aagcactggg ctggaaaaca     3960
tggtaaacaa ctggtatatc ggctattata aaaacaaaga gagtcgacc gagctaaatg      4020 ccttaggtga gatgtataaa aagattgttg agattgaggc tgagaagcca gcatcttctg     4080
agtacttagg gtggggagac actagcagcc ctaagaggca tgagttcagt agaagcttcc     4140
tcaagtcagc atgcatatct cttgagaagg agatagagat gaggcatggg aagagctgga     4200
```

```
agcaaagctt ggaggagaga gtccttaaag aactgggctc aaagaacttg ctggacttag    4260
caacaatgaa ggcaacaagc aactttagca aggaatggga agcttctca gaagtcagaa     4320 caaaagaata tcataggtct aaactcctag aaaagatggc tgaactaata gagcatgggt    4380
taatgtggta tgttgatgca gcaggtcatg catggaaggc tgtccttgat gacaaatgta    4440
tgagaatatg cttgtttaag aaaaatcagc acggaggcct gagggaaatt tatgtaacga    4500
atgcaaatgc aaggcttgtc caatttggag tagagacaat ggcacggtgt gtgtgtgagc    4560
taagcccaca tgaaacaata gctaacccta gactcaagtc aagcatcata gagaatcatg    4620
gtctcaagag tgctcgacaa ttggggcagg ggaccattaa tgtcaactct tcaaatgacg    4680
caaaaaaatg gagtcagggt cattatacaa ccaagttggc catggtatta tgctggttca    4740
tgccagcaaa attccatagg ttcatatggg caggcatctc aatgtttagg tgcaagaaga    4800
tgatgatgga tctcaggttt ttagaaaaac tgagcacaaa ggctaatcag aaaactgatg    4860
atgacttcag gaaagactta gctggggcct tccatggcaa tgttgaagtt ccatggatga    4920
ctcaaggggc tacatatctc cagactgaga cagggatgat gcaagggatc ctgcatttta    4980
catcaagcct actgcattca tgcgtccaaa gttttacaa ggcatatttt ttgtctcggc     5040
ttaaagaagg gatcgcaggc aaaaccatca aggcagctat agatgtttta aaggctctg    5100 atgactcagc tatcatgata agcttgaagc cagcctcaga caatgaggaa gcaatggctc    5160 ggttttaac agccaacttg ctatactcag tcagagtcat aaacccgctc tttggcattt    5220
atagctctga gaagtcaaca gtaaatacct tattttgtgt ggagtacaac tcagagttcc    5280
acttccacaa gcatttagtc aggcctacaa tcagatgggt tgcagcatcc caccaaatct    5340
ctgagtcaga agccctggca agcaggcagg aagattatgc gaaccttctc actcaatgtc    5400
ttgaaggggg ttcatcattc tctctaacat atttgatcca gtgtgcccag ctcgtccatc    5460
attatatgct gctcgggctc tgcttgcacc cgctgtttgg aacatttgta gggatgctga    5520
ttgaggatcc agatccagcc ctaggcttct tcataatgga caatccagct tttgcagggg    5580
gagctggatt tagattcaac cttttggaggt cttgcaagtt cacaaacctt ggcaaaaagt    5640
atgcattctt tttcaatgag attcaaggaa aaaccaaggg ggatgcagat tacagagcac    5700
tggatgcaac aactggtgga acattaagcc actctgtgat gatctactgg ggggacagga    5760
gaaagtacca acatctccta gacaggatgg ggcttcccaa ggactgggtt gagaggatag    5820
atgaaaaccc aagcgtctta tacaggaggc ctgagaacaa gcaggaactt atcttgaggc    5880
tggcagaaaa agtgcattct ccaggtgtca cttccagctt cagcaagggg catgttgtac    5940
ctagagtggt ggcagctgga gtctacttgc tgtcaagaca ttgcttcagg tacactgcat    6000
caatccacgg tagggagca tctcagaagg cgagtctaat taagctgctt gtcatgtctt     6060
caacatcagc tgagaggaat caaggaaggc taaatccaaa tcaagaaaga atgctctttc    6120
cccaagtcca agagtatgaa agagtactga cctgttagga tgaggtcact gcgctcacag    6180
ggaagtttgt tgtgagagaa aggaacatag tcaaaagcag agtagagctt ttccaggagc    6240
ctgtggactt aaggtgtaaa gctgaaaacc tcattgcaga aatgtggttt ggacttaaaa    6300
gaacaaagtt gggcccaagg ctgctaaagg aagaatggga caaactccgc gcctccttct    6360
catggttgag cactgatcat aaagaaacac tggatgtggg accatttctt agtcatgttc    6420
aattcaggaa tttcattgca catgtggatg cgaagtctag gagtgttcga ctcttggggg    6480
cccctgtcaa gaagtcagga ggagtgacta cagtgtccca ggtggtgaaa tctaatttct    6540
```

```
ttccaggttt catttggac tccagtgaga gcttagatga ccaagagagg gttgagggg      6600
tgtcaatctt gaaacacatt ctatttatga ccttgaatgg cccttacact gatgagcaaa      6660
agaaagctat ggttctggag gccttccaat attttgcact gccacatgct gctgaggttg      6720
tgaagagatc acggtcatta accctatgtt tgatgaagaa ttttattgag cagagaggag      6780
ggtcaatact tgaccaaatt gaaaaggctc agtcaggtac agttggtgga ttcagtaagc      6840
cccagaagcc ttaccgcaaa caatctggag gcattggcta caaggggaaa ggtgtttgga      6900
caggcataat ggaaaacaca aatgtacaga tcctgataga tggtgatggt tcatcgaact      6960
ggatagaaga aattaggctg agtagtgagt ccaggctatt tgatgtcata gaatctgtca      7020
ggaggctgtg tgatgacatt aatgtcaaca atagggttac atcaagcttt cggggtcatt      7080
gcatggtgag gctcagcaat tttaaggtca agccagcttc aagggtagaa gggtgcccag      7140
tgcgacttat gccctcctca ttccggataa aggagctcca aaacccagat gaggtcttct      7200
taagggtgag gggagacatt ctaaacctgt ccatcctcct tcaagaggac cgagtcatga      7260
atctgcttag ctacagagct cgtgacactg acatctcaga gtctgcagca tcctacctat      7320
ggatgaatag aactgacttc tcatttggaa agaaggagcc atcttgcagc tggatgtgct      7380
tgaaaacatt ggactcatgg gcttggaatc aagcagcaag agttcttgaa agaaacatca      7440
aaaccctgg aattgataac accgccatgg ggaacatttt caaggattgc ttagaaagct      7500
cactcagaaa gcaggggttg cttagatcta gaattgctga gatggtggaa cgacatgtta      7560
ttccactaac aagtcaggag ctggtggata tcctggagga agatgtcgat ttttcagaaa      7620
tgatgcaatc tgatataatg gaaggggacc tagacattga tatcctgatg gaagggtcac      7680
caatgctctg ggcagcagaa gtggaggaaa tgggagaagc tatggtgata ctcagtcagt      7740
caggaaagta ttatcatcta aaattaatgg atcaagcagc aacaaccctt tcaacaatcc      7800
ttgggaaaga tggttgcagg ctcctactgg gagagcgtac atgtggatca aatctcaggg      7860
agcaggtgaa gccctacttg acattattgc aaataagaga gggagatgtc aactgggttt      7920
ctgagtacaa agacgacaca cgtggtcttg atgaagactc cgcagaaatg tggggtctcg      7980
aggaattcac tcctcaggtg caggctgcct atcagaaggt ggtggctggt gtggccaatg      8040
ccctggctca caaataccac tgagatcttt ttccctctgc caaaaattat ggggacatca      8100
tgaagcccct tgagcatctg acttctggct aataaaggaa attatttttc attgcaatag      8160
tgtgttggaa ttttttgtgt ctctcactcg gaaggacata tgggagggca aatcatttaa      8220
aacatcagaa tgagtatttg gtttagagtt tggcaacata tgccatatgc tggctgccat      8280
gaacaaaggt ggctataaag aggtcatcag tatatgaaac agcccctgc tgtccattcc      8340
ttattccata gaaaagcctt gacttgaggt tagattttt ttatattttg ttttgtgtta      8400
ttttttttctt taacatccct aaaatttttcc ttacatgttt tactagccag atttttcctc      8460
ctctcctgac tactcccagt catagctgtc cctcttctct tatgaagatc cctcgacctg      8520
cagcccaagc ttggcgtaat catggtcata gctgtttcct gtgtgaaatt gttatccgct      8580
cacaattcca cacaacatac gagccggaag cataaagtgt aaagcctggg gtgcctaatg      8640
agtgagctaa ctcacattaa ttgcgttgcg ctcactgccc gctttccagt cgggaaacct      8700
gtcgtgccag cggatccgca tctcaattag tcagcaacca tagtcccgcc cctaactccg      8760
cccatcccgc ccctaactcc gcccagttcc gcccattctc cgccccatgg ctgactaatt      8820
tttttttattt atgcagaggc cgaggccgcc tcggcctctg agctattcca gaagtagtga      8880
ggaggctttt ttggaggcct aggcttttgc aaaaagctaa cttgtttatt gcagcttata      8940
```

```
atggttacaa ataaagcaat agcatcacaa atttcacaaa taaagcattt ttttcactgc    9000
attctagttg tggtttgtcc aaactcatca atgtatctta tcatgtctgg atccgctgca    9060
ttaatgaatc ggccaacgcg cggggagagg cggtttgcgt attgggcgct cttccgcttc    9120
ctcgctcact gactcgctgc gctcggtcgt tcggctgcgg cgagcggtat cagctcactc    9180
aaaggcggta atacggttat ccacagaatc aggggataac gcaggaaaga acatgtgagc    9240
aaaaggccag caaaaggcca ggaaccgtaa aaaggccgcg ttgctggcgt ttttccatag    9300
gctccgcccc cctgacgagc atcacaaaaa tcgacgctca agtcagaggt ggcgaaaccc    9360
gacaggacta taaagatacc aggcgtttcc ccctggaagc tccctcgtgc gctctcctgt    9420
tccgaccctg ccgcttaccg gatacctgtc cgcctttctc ccttcgggaa gcgtggcgct    9480
ttctcaatgc tcacgctgta ggtatctcag ttcggtgtag tcgttcgct ccaagctggg    9540
ctgtgtgcac gaaccccccg ttcagcccga ccgctgcgcc ttatccggta actatcgtct    9600
tgagtccaac ccggtaagac acgacttatc gccactggca gcagccactg gtaacaggat    9660
tagcagagcg aggtatgtag gcggtgctac agagttcttg aagtggtggc ctaactacgg    9720
ctacactaga aggacagtat ttggtatctg cgctctgctg aagccagtta ccttcggaaa    9780
aagagttggt agctcttgat ccggcaaaca aaccaccgct ggtagcggtg gtttttttgt    9840
ttgcaagcag cagattacgc gcagaaaaaa aggatctcaa gaagatcctt tgatcttttc    9900
tacgggtct gacgctcagt ggaacgaaaa ctcacgttaa gggattttgg tcatgagatt    9960
atcaaaaagg atcttcacct agatcctttt aaattaaaaa tgaagtttta aatcaatcta   10020
aagtatatat gagtaaactt ggtctgacag ttaccaatgc ttaatcagtg aggcacctat   10080
ctcagcgatc tgtctatttc gttcatccat agttgcctga ctccccgtcg tgtagataac   10140
tacgatacgg gagggcttac catctggccc cagtgctgca atgataccgc gagacccacg   10200
ctcaccggct ccagatttat cagcaataaa ccagccagcc ggaagggccg agcgcagaag   10260
tggtcctgca actttatccg cctccatcca gtctattaat tgttgccggg aagctagagt   10320
aagtagttcg ccagttaata gtttgcgcaa cgttgttgcc attgctacag gcatcgtggt   10380
gtcacgctcg tcgtttggta tggcttcatt cagctccggt tcccaacgat caaggcgagt   10440
tacatgatcc cccatgttgt gcaaaaaagc ggttagctcc ttcggtcctc cgatcgttgt   10500
cagaagtaag ttggccgcag tgttatcact catggttatg gcagcactgc ataattctct   10560
tactgtcatg ccatccgtaa gatgcttttc tgtgactggt gagtactcaa ccaagtcatt   10620
ctgagaatag tgtatgcggc gaccgagttg ctcttgcccg gcgtcaatac gggataatac   10680
cgcgccacat agcagaactt taaaagtgct catcattgga aaacgttctt cggggcgaaa   10740
actctcaagg atcttaccgc tgttgagatc cagttcgatg taacccactc gtgcacccaa   10800
ctgatcttca gcatctttta ctttcaccag cgtttctggg tgagcaaaaa caggaaggca   10860
aaatgccgca aaaaagggaa taagggcgac acggaaatgt tgaatactca tactcttcct   10920
ttttcaatat tattgaagca tttatcaggg ttattgtctc atgagcggat acatatttga   10980
atgtatttag aaaataaaca aataggggt tccgcgcaca tttccccgaa aagtgccacc   11040
tg                                                                  11042
```

<210> SEQ ID NO 42
<211> LENGTH: 5528
<212> TYPE: DNA
<213> ORGANISM: Artificial Sequence
<220> FEATURE:

<223> OTHER INFORMATION: Synthetic construct (pcMo4NP vector)

<400> SEQUENCE: 42

```
gtcgacattg attattgact agttattaat agtaatcaat tacggggtca ttagttcata      60
gcccatatat ggagttccgc gttacataac ttacggtaaa tggcccgcct ggctgaccgc     120
ccaacgaccc ccgcccattg acgtcaataa tgacgtatgt tcccatagta acgccaatag     180
ggactttcca ttgacgtcaa tgggtggact atttacggta aactgcccac ttggcagtac     240
atcaagtgta tcatatgcca agtacgcccc ctattgacgt caatgacggt aaatggcccg     300
cctggcatta tgcccagtac atgaccttat gggactttcc tacttggcag tacatctacg     360
tattagtcat cgctattacc atgggtcgag gtgagcccca cgttctgctt cactctcccc     420
atctccccc cctccccacc cccaattttg tatttattta ttttttaatt attttgtgca     480
gcgatggggg cggggggggg gggggcgcgc gccaggcggg gcgggcggg gcgaggggcg     540
gggcggggcg aggcggagag gtgcggcggc agccaatcag agcggcgcgc tccgaaagtt     600
tccttttatg gcgaggcggc ggcggcggcg gccctataaa aagcgaagcg cgcggcgggc     660
gggagtcgct gcgttgcctt cgccccgtgc cccgctccgc gccgcctcgc gccgcccgcc     720
ccggctctga ctgaccgcgt tactcccaca ggtgagcggg cgggacgcc cttctcctcc     780
gggctgtaat tagcgcttgg tttaatgacg gctcgtttct tttctgtggc tgcgtgaaag     840
ccttaaaggg ctccgggagg gccctttgtg cggggggag cggctcgggg ggtgcgtgcg     900
tgtgtgtgtg cgtggggagc gccgcgtgcg gcccgcgctg cccggcggct gtgagcgctg     960
cgggcgcggc gcggggcttt gtgcgctccg cgtgtgcgcg aggggagcgc ggccgggggc    1020
ggtgccccgc ggtgcggggg ggctgcgagg ggaacaaagg ctgcgtgcgg ggtgtgtgcg    1080
tggggggtg agcaggggt gtgggcgcgg cggtcgggct gtaaccccc cctgcacccc    1140
cctccccgag ttgctgagca cggcccggct tcgggtgcgg ggctccgtgc ggggcgtggc    1200
gcggggctcg ccgtgccggg cggggggtgg cggcaggtgg gggtgccggg cggggcgggg    1260
ccgcctcggg ccggggaggg ctcggggag gggcgcggcg gccccggagc gccggcggct    1320
gtcgaggcgc ggcgagccgc agccattgcc ttttatggta atcgtgcgag agggcgcagg    1380
gacttccttt gtcccaaatc tggcggagcc gaaatctggg aggcgccgcc gcacccctc    1440
tagcgggcgc gggcgaagcg gtgcggcgcc ggcaggaagg aaatgggcgg gagggcctt    1500
cgtgcgtcgc cgcgccgccg tccccttctc catctccagc ctcggggctg ccgcaggggg    1560
acggctgcct tcgggggga cggggcaggg cggggttcgg cttctggcgt gtgaccggcg    1620
gctctagagc ctctgctaac catgttcatg ccttcttctt tttcctacag ctcctgggca    1680
acgtgctggt tgttgtgctg tctcatcatt ttggcaaaga attcatgact gactggtccg    1740
caatagctgt tgagattggc aacgagccac tggatgttcc agctttggtc gagtttgcaa    1800
aggaaatagc ttatgagggc ctggatcctg ctgtgatctt gggctgctt cgtgagagag    1860
ggggtgagaa ctggaggaat gatgtgaagt acatcattg atttgctctc accagaggga    1920
acaagatagt gaaagcatgt ggcaagatgt ctaagaaagg cgctgagagg atgacaaatc    1980
tggctagagt ttatgagctg aaggagaatg ctgttgacag aatggctgtg acaccagtga    2040
gagttgccca gtgcctgcca acctggacct gtgctgctgc agcagcaatc aaggagtacc    2100
tccctgttgg gccagcaatc atgcacaaca aaatccaagg ttatccactg gaaatgatgt    2160
gcatggcctt tggctcactg attccacagg cagatgtctc aattgaagtc ataaggact    2220
tcatggatgc ctattccctt tggcaagaca catttgctcg aacaatcaat gtggaccaaa    2280
```

```
ggaagatgac aaaggcagag gtgtatgcca aattcagaga ccctctgcat gcagctgtca   2340
attccctctt cttcccaaat gccaccagga tcagctggct gcaggccaag gcttgctca    2400 cagcaaccaa ggaagcatcc ggctcagtga aggctgcggc tgctgcttac agaaacatgt   2460
aactcgagga attcactcct caggtgcagg ctgcctatca aaggtggtg gctggtgtgg    2520 ccaatgccct ggctcacaaa taccactgag atcttttttcc ctctgccaaa aattatgggg  2580
acatcatgaa gccccttgag catctgactt ctggctaata aggaaattt attttcattg    2640 caatagtgtg ttggaatttt ttgtgtctct cactcggaag acatatggg agggcaaatc    2700 atttaaaaca tcagaatgag tatttggttt agagtttggc aacatatgcc atatgctggc   2760
tgccatgaac aaaggtggct ataaagaggt catcagtata tgaaacagcc cctgctgtc    2820 cattccttat tccatagaaa agccttgact tgaggttaga ttttttttat attttgtttt   2880
gtgttatttt tttctttaac atccctaaaa ttttccttac atgttttact agccagattt   2940
ttcctcctct cctgactact cccagtcata gctgtccctc ttctcttatg aagatccctc   3000
gacctgcagc ccaagcttgg cgtaatcatg gtcatagctg tttcctgtgt gaaattgtta   3060
tccgctcaca attccacaca acatacgagc cggaagcata aagtgtaaag cctggggtgc   3120
ctaatgagtg agctaactca cattaattgc gttgcgctca ctgcccgctt tccagtcggg   3180
aaacctgtcg tgccagcgga tccgcatctc aattagtcag caaccatagt cccgccccta   3240
actccgccca tcccgcccct aactccgccc agttccgccc attctccgcc ccatggctga   3300
ctaatttttt ttatttatgc agaggccgag gccgcctcgg cctctgagct attccagaag   3360
tagtgaggag gcttttttgg aggcctaggc ttttgcaaaa agctaacttg tttattgcag   3420
cttataatgg ttacaaataa agcaatagca tcacaaattt cacaaataaa gcattttttt   3480
cactgcattc tagttgtggt ttgtccaaac tcatcaatgt atcttatcat gtctggatcc   3540
gctgcattaa tgaatcggcc aacgcgcggg gagaggcggt ttgcgtattg ggcgctcttc   3600
cgcttcctcg ctcactgact cgctgcgctc ggtcgttcgg ctgcggcgag cggtatcagc   3660
tcactcaaag gcggtaatac ggttatccac agaatcaggg gataacgcag gaaagaacat   3720
gtgagcaaaa ggccagcaaa aggccaggaa ccgtaaaaag gccgcgttgc tggcgttttt   3780
ccataggctc cgcccccctg acgagcatca caaaaatcga cgctcaagtc agaggtggcg   3840
aaacccgaca ggactataaa gataccaggc gtttccccct ggaagctccc tcgtgcgctc   3900
tcctgttccg accctgccgc ttaccggata cctgtccgcc tttctccctt cgggaagcgt   3960
ggcgctttct caatgctcac gctgtaggta tctcagttcg gtgtaggtcg ttcgctccaa   4020
gctgggctgt gtgcacgaac cccccgttca gcccgaccgc tgcgccttat ccggtaacta   4080
tcgtcttgag tccaacccgg taagacacga cttatcgcca ctggcagcag ccactggtaa   4140
caggattagc agagcgaggt atgtaggcgg tgctacagag ttcttgaagt ggtggcctaa   4200
ctacggctac actagaagga cagtatttgg tatctgcgct ctgctgaagc cagttacctt   4260
cggaaaaaga gttggtagct cttgatccgg caaacaaacc accgctggta gcggtggttt   4320
ttttgtttgc aagcagcaga ttacgcgcag aaaaaaagga tctcaagaag atcctttgat   4380
cttttctacg gggtctgacg ctcagtggaa cgaaaactca cgttaaggga ttttggtcat   4440
gagattatca aaaaggatct tcacctagat ccttttaaat taaaaatgaa gttttaaatc   4500
aatctaaagt atatatgagt aaacttggtc tgacagttac caatgcttaa tcagtgaggc   4560
acctatctca gcgatctgtc tatttcgttc atccatagtt gcctgactcc ccgtcgtgta   4620
```

```
gataactacg atacgggagg gcttaccatc tggccccagt gctgcaatga taccgcgaga    4680
cccacgctca ccggctccag atttatcagc aataaaccag ccagccggaa gggccgagcg    4740
cagaagtggt cctgcaactt tatccgcctc catccagtct attaattgtt gccgggaagc    4800
tagagtaagt agttcgccag ttaatagttt gcgcaacgtt gttgccattg ctacaggcat    4860
cgtggtgtca cgctcgtcgt ttggtatggc ttcattcagc tccggttccc aacgatcaag    4920
gcgagttaca tgatccccca tgttgtgcaa aaaagcggtt agctccttcg gtcctccgat    4980
cgttgtcaga gtaagttgg ccgcagtgtt atcactcatg gttatggcag cactgcataa    5040
ttctcttact gtcatgccat ccgtaagatg cttttctgtg actggtgagt actcaaccaa    5100
gtcattctga gaatagtgta tgcggcgacc gagttgctct tgcccggcgt caatacggga    5160
taataccgcg ccacatagca gaactttaaa agtgctcatc attggaaaac gttcttcggg    5220
gcgaaaactc tcaaggatct taccgctgtt gagatccagt tcgatgtaac ccactcgtgc    5280
acccaactga tcttcagcat cttttacttt caccagcgtt tctgggtgag caaaaacagg    5340
aaggcaaaat gccgcaaaaa agggaataag ggcgacacgg aaatgttgaa tactcatact    5400 cttcctttt caatattatt gaagcattta tcagggttat tgtctcatga gcggatacat    5460
atttgaatgt atttagaaaa ataaacaaat aggggttccg cgcacatttc cccgaaaagt    5520
gccacctg                                                             5528

<210> SEQ ID NO 43
<211> LENGTH: 8018
<212> TYPE: DNA
<213> ORGANISM: Artificial Sequence
<220> FEATURE:
<223> OTHER INFORMATION: Synthetic construct (pcMo4Morf vector)

<400> SEQUENCE: 43
gtcgacattg attattgact agttattaat agtaatcaat tacgggtca ttagttcata      60 gcccatatat ggagttccgc gttacataac ttacggtaaa tggcccgcct ggctgaccgc     120
ccaacgaccc ccgcccattg acgtcaataa tgacgtatgt tcccatagta acgccaatag     180
ggactttcca ttgacgtcaa tgggtggact atttacggta aactgcccac ttggcagtac     240
atcaagtgta tcatatgcca gtacgcccc ctattgacgt caatgacggt aaatggcccg     300
cctggcatta tgcccagtac atgaccttat gggactttcc tacttggcag tacatctacg     360
tattagtcat cgctattacc atgggtcgag gtgagcccca cgttctgctt cactctcccc     420 atctccccc cctccccacc cccaattttg tatttattta ttttttaatt attttgtgca     480
gcgatggggg cggggggggg ggggcgcgc gccaggcggg gcggggcggg gcgaggggcg     540
gggcggggcg aggcggagag gtgcggcggc agccaatcag agcggcgcgc tccgaaagtt     600
tccttttatg gcgaggcggc ggcggcggcg gccctataaa aagcgaagcg cgcggcgggc     660
gggagtcgct gcgttgcctt cgccccgtgc cccgctccgc gccgcctcgc gccgcccgcc     720
ccggctctga ctgaccgcgt tactcccaca ggtgagcggg cggacggcc cttctcctcc     780 gggctgtaat agcgcttgg tttaatgacg gctcgtttct tttctgtggc tgcgtgaaag     840
ccttaaaggg ctccgggagg gccctttgtg cggggggag cggctcgggg ggtgcgtgcg     900
tgtgtgtgtg cgtggggagc gccgcgtgcg gcccgcgctg cccggcggct gtgagcgctg    960
cgggcgcggc gcggggcttt gtgcgctccg cgtgtgcgcg aggggagcgc ggccggggc    1020 ggtgccccgc ggtgcggggg ggctgcgagg ggaacaaagg ctgcgtgcgg ggtgtgtgcg    1080 tggggggtg agcagggggt gtgggcgcgg cggtcgggct gtaaccccc cctgcacccc    1140
```

```
cctccccgag ttgctgagca cggcccggct tcgggtgcgg ggctccgtgc ggggcgtggc    1200
gcggggctcg ccgtgccggg cgggggtgg cggcaggtgg gggtgccggg cggggcgggg    1260
ccgcctcggg ccggggaggg ctcggggag gggcgcggcg ccccggagc gccggcggct    1320 gtcgaggcgc ggcgagccgc agccattgcc ttttatggta atcgtgcgag agggcgcagg    1380
gacttccttt gtcccaaatc tggcggagcc gaaatctggg aggcgccgcc gcacccctc    1440 tagcgggcg gggcgaagcg gtgcggcgcc ggcaggaagg aaatgggcgg ggagggcctt    1500
cgtgcgtcgc cgcgccgccg tccccttctc catctccagc ctcggggctg ccgcaggggg    1560
acggctgcct tcgggggga cggggcaggg cggggttcgg cttctggcgt gtgaccggcg    1620
gctctagagc ctctgctaac catgttcatg ccttcttctt tttcctacag ctcctgggca    1680
acgtgctggt tgttgtgctg tctcatcatt ttggcaaaga attcatgatt gcccccagttg    1740 tcctgttttt cactctctgt ccgtcccaac tcagcgcctg gggctctcca ggagacccca    1800
ttgtttgtgg tgtgaggacc gaaacaaaca aatccattca gattgagtgg aaggaggga    1860 gatcagagaa attatgccag attgacagac ttggacatgt cacaagctgg ttaagaaatc    1920 actcatctt ccagggctt attggtcagg tgaaggggag gccaagtgtt tcctacttcc    1980
cggaaggagc ttcttaccct aggtggagcg ggctattaag cccatgtgat gctgaatggc    2040
tgggactaat agcagtgagc aaggctgggg atacagacat gattgtccca ggcccaactt    2100
acaaaggcaa aatctttgtt gagagaccaa cgtacaatgg ttataaaggc tggggtgtg    2160 cagatgggaa gtcactaagc cactctggca catattgtga aactgacagc tcagtaagtt    2220
ctgggttaat tcagggtgat agggttctct gggttgggga agtagtctgt cagagaggga    2280
cacctgtgcc agaagatgta tttagtgaac tgattagctt gagtcaaagt gagttcccag    2340
atgtgtgcaa ggttgatggg gttgcactga accaatgtga gcaggagagc atccccccagc    2400 cactggacgt tgcatggatt gatgttggaa ggtctcataa agtgctgatg agaaacaca    2460 aaactaaatg ggtccaagag agctcagcaa aggactttgt gtgcttcaag gtgggtcagg    2520
ggccatgttc aaaacaagag gaagatgact gcatgagtaa gggcaactgc catgggatg    2580 aggttttctg caggatggca ggatgctctg cccgtatgca agataatcaa gaaggctgta    2640
ggtgcgaact gctccaaaa cctggagaaa tcattgtgaa ttatggaggc gtctctgtaa    2700
gaccaacttg ttatggattc tctagaatga tggcaacatt ggaagttcac aagcctgata    2760
gagaattaac agggtgcacg ggttgtcacc tagagtgcat agagggaggg gtcaaaattg    2820
taacacttac aagcgagctg agaagtgcaa cagtttgtgc ttcacatttt tgtgcatccg    2880
caaaaggggg ctcaaagaca actgacatac tcttccacac tggtgctctc gttggaccca    2940
aatccattag aattacgggc cagttgttag atgggagcaa gttctccttt gatgggcact    3000
gcatattccc agatgggtgc atggcacttg actgcacctt ctgtaaggag ttcctgagaa    3060
acccacaatg ttacccagta aagaaatggc tcttcttggt ggtagttgtg atgtgctgct    3120
attgcgcact gatgctgctt actaacatac tgagagctat aggtgtttgg ggaacatggg    3180
tttttgctcc aataaagtta gttctagcat taggattgag gcttgccaaa ctatcaaaga    3240
aggggttggt tgctgtggtt acaaggggcc aaatgatcgt gaatgatgag ctgcaccaga    3300
ttcgagtgga gagaggtgag caaaatgagg gaagactagg tcatggccca agaggtcccg    3360
tccgtcactg gctatactca cctgccctca ttctcattct gaccacttca atttgctctg    3420
gatgtgatga gctcgttcat gctgagagta aatctatcac atgcaagtct gcatctggga    3480
```

```
atgagaagga gtgctcagtg acaggcagag ctttactccc agctgttaat ccaggacagg    3540
aggcctgctt gcacttcagt atgccaggga gcccagactc taagtgcctc aagatcaaag    3600
tgaaatcaat aaatctcaga tgcaagcaag cctcttcata ttatgttcct gaagcaaagg    3660
caagatgtac atctgtaaga aggtgcaggt gggcaggtga ctgtcaatct gggtgtccaa    3720
catatttcag ctcaaactca ttctcagatg actgggcaaa caggatggac agggctgggc    3780
tcgggatgag tgggtgctca gatgggtgtg gtggggctgc atgtgggtgt ttcaatgcag    3840
cgccatcctg catcttttgg agaaagtggg tggagaaccc atccaatcgt gtctggaagg    3900
tgtcaccttg tgcatcatgg gtgctagctg caatcattga gttgactttg ccatcaggag    3960
aggttaagac tctagagcct gtcacagggc aagcaactca aatgtttaag ggtgttgcaa    4020
tcacgtatct gggttcatcc attgagattg ttggcatgac caggctatgc gagatgaaag    4080
agatgggaac tgggattatg gcactagccc cctgcaatga ccctgggcac gccataatgg    4140
gaaatgtggg tgagatccaa tgcagtagta tagaaagcgc aaagcacatc agatctgatg    4200
ggtgcatttg gaatgctgac ctagttggga tagaattaag ggttgatgat gctgtgtgtt    4260
tctcaaaact caccagtgtt gaggcagtcg caaatttctc aaaaatcccg gcaataattt    4320
ctggggtccg ttttgatcaa gggaatcatg agaatcgcg aatctatggt agcccattag    4380
acatcacgaa ggttagtggg gaattctcag tgtcattcag ggggatgagg cttaaactgt    4440
ctgagatatc agcaagctgc acaggtgaga taacaaacgt ctctggttgc tactcctgca    4500
tgactggggc ctctgtcagc ataaagctac atagcagtaa gaacacaaca ggtcatctta    4560
aatgtgattc agatgagact gcattcagtg tcatggaggg aacacacact tataggcctc    4620
acatgagctt tgataaagca gtggtagatg aggagtgtgt gctaaactgt ggtggccatt    4680
catcaaagct gttgcttaag gggagccttg tcttcatgga cgtgccaagg tttgttgatg    4740
ggagttatgt tcaaacatac catagcaagg tgcctgctgg gggaagggtc ccaaatccag    4800
tagattggct caacgcgctg tttggagatg cataacacg atggattctt gggattatag    4860
gagttctgtt ggcatgtgtc ttgctatttg tggtggtggt ggccatcact aggcgattga    4920
tcaagggggct gactcaaagg gcgaaggtgg cactcgagga attcactcct caggtgcagg    4980
ctgcctatca gaaggtggtg gctggtgtgg ccaatgccct ggctcacaaa taccactgag    5040
atctttttcc ctctgccaaa aattatgggg acatcatgaa gcccttgag catctgactt    5100
ctggctaata aaggaaattt attttcattg caatagtgtg ttggaatttt ttgtgtctct    5160
cactcggaag gacatatggg agggcaaatc atttaaaaca tcagaatgag tatttggttt    5220
agagtttggc aacatatgcc atatgctggc tgccatgaac aaaggtggct ataaagaggt    5280
catcagtata tgaaacagcc ccctgctgtc cattccttat tccatagaaa agccttgact    5340
tgaggttaga tttttttat attttgtttt gtgttatttt tttctttaac atccctaaaa    5400
ttttccttac atgttttact agccagattt ttcctcctct cctgactact cccagtcata    5460
gctgtccctc ttctcttatg aagatccctc gacctgcagc ccaagcttgg cgtaatcatg    5520
gtcatagctg tttcctgtgt gaaattgtta tccgctcaca attccacaca acatacgagc    5580
cggaagcata aagtgtaaag cctggggtgc ctaatgagtg agctaactca cattaattgc    5640
gttgcgctca ctgcccgctt tccagtcggg aaacctgtcg tgccagcgga tccgcatctc    5700
aattagtcag caaccatagt cccgccccta actccgccca tcccgcccct aactccgccc    5760
agttccgccc attctccgcc ccatggctga ctaattttt ttatttatgc agaggccgag    5820
gccgcctcgg cctctgagct attccagaag tagtgaggag gcttttttgg aggcctaggc    5880
```

```
ttttgcaaaa agctaacttg tttattgcag cttataatgg ttacaaataa agcaatagca    5940
tcacaaattt cacaaataaa gcatttttt cactgcattc tagttgtggt ttgtccaaac     6000
tcatcaatgt atcttatcat gtctggatcc gctgcattaa tgaatcggcc aacgcgcggg    6060
gagaggcggt ttgcgtattg ggcgctcttc cgcttcctcg ctcactgact cgctgcgctc    6120
ggtcgttcgg ctgcggcgag cggtatcagc tcactcaaag gcggtaatac ggttatccac    6180
agaatcaggg gataacgcag gaaagaacat gtgagcaaaa ggccagcaaa aggccaggaa    6240
ccgtaaaaag gccgcgttgc tggcgttttt ccataggctc cgcccccctg acgagcatca    6300
caaaatcga cgctcaagtc agaggtggcg aaacccgaca ggactataaa gataccaggc     6360
gtttccccct ggaagctccc tcgtgcgctc tcctgttccg accctgccgc ttaccggata    6420
cctgtccgcc tttctccctt cgggaagcgt ggcgctttct caatgctcac gctgtaggta    6480
tctcagttcg gtgtaggtcg ttcgctccaa gctgggctgt gtgcacgaac cccccgttca    6540
gcccgaccgc tgcgccttat ccggtaacta tcgtcttgag tccaacccgg taagacacga    6600
cttatcgcca ctggcagcag ccactggtaa caggattagc agagcgaggt atgtaggcgg    6660
tgctacagag ttcttgaagt ggtggcctaa ctacggctac actagaagga cagtatttgg    6720
tatctgcgct ctgctgaagc cagttacctt cggaaaaaga gttggtagct cttgatccgg    6780
caaacaaacc accgctggta gcggtggttt tttgtttgc aagcagcaga ttacgcgcag     6840
aaaaaaagga tctcaagaag atcctttgat cttttctacg gggtctgacg ctcagtggaa    6900
cgaaaactca cgttaaggga ttttggtcat gagattatca aaaaggatct tcacctagat    6960
cctttaaat taaaatgaa gttttaaatc aatctaaagt atatatgagt aaacttggtc       7020
tgacagttac caatgcttaa tcagtgaggc acctatctca gcgatctgtc tatttcgttc    7080
atccatagtt gcctgactcc ccgtcgtgta gataactacg atacgggagg gcttaccatc    7140
tggccccagt gctgcaatga taccgcgaga cccacgctca ccggctccag atttatcagc    7200
aataaaccag ccagccggaa gggccgagcg cagaagtggt cctgcaactt tatccgcctc    7260
catccagtct attaattgtt gccgggaagc tagagtaagt agttcgccag ttaatagttt    7320
gcgcaacgtt gttgccattg ctacaggcat cgtggtgtca cgctcgtcgt ttggtatggc    7380
ttcattcagc tccggttccc aacgatcaag gcgagttaca tgatccccca tgttgtgcaa    7440
aaaagcggtt agctccttcg gtcctccgat cgttgtcaga agtaagttgg ccgcagtgtt    7500
atcactcatg gttatggcag cactgcataa ttctcttact gtcatgccat ccgtaagatg    7560
cttttctgtg actggtgagt actcaaccaa gtcattctga atagtgta tgcggcgacc       7620
gagttgctct tgcccggcgt caatacggga taataccgcg ccacatagca gaactttaaa    7680
agtgctcatc attggaaaac gttcttcggg gcgaaaactc tcaaggatct taccgctgtt    7740
gagatccagt tcgatgtaac ccactcgtgc acccaactga tcttcagcat cttttacttt    7800
caccagcgtt tctgggtgag caaaaacagg aaggcaaaat gccgcaaaaa agggaataag    7860
ggcgacacgg aaatgttgaa tactcatact cttccttttt caatattatt gaagcattta    7920
tcagggttat tgtctcatga gcggatacat atttgaatgt atttagaaaa ataaacaaat    7980
agggggtccg cgcacatttc cccgaaaagt gccacctg                             8018

<210> SEQ ID NO 44
<211> LENGTH: 8673
<212> TYPE: DNA
<213> ORGANISM: Artificial Sequence
<220> FEATURE:
```

<223> OTHER INFORMATION: Synthetic construct (pLCK-Mo4Lvc)

<400> SEQUENCE: 44

```
ggaagcggaa gagcgcccaa tacgcaaacc gcctctcccc gcgcgttggc cgattcatta        60
atgcagggg  atctcgatcc cgcgaaatta atacgactca ctatagacac aaagacgtcc       120
agatgaattt agaagctctt tgctctagag tgctttcaga gagagggcta tcaactggtg       180
agcctggggt atatgaccag atttttgaaa ggcctggcct cccaaacctt gaagtcacag       240
tagactccac tggggtagtt gtcgatgttg gggccattcc tgactcagca tcacagctag       300
ggtcctcgat aaatgcaggt gtgctcacca tacctctctc agaagcatat aagataaatc       360
atgacttcac tttctctgga ctgactaaga caacggatag gaagttgtct gaagtattcc       420
ctttggttca tgatggctca gactcaatga cccccgatgt gatacacaca agactagatg       480
gaacagtagt tgtaattgaa ttcacaacaa ccagaagcac caacatggga ggacttgagg       540
ctgcctatcg gagcaagctt gaaaaatacc gtgacccact aaacagaaga tcagacataa       600
tgcctgatgc atcaatttac tttggaatca ttgttgttag tgcatctggt gttctcacaa       660
atatgcctct gacccaagat gaagctgaag aattgatgtt caggttctgt gtggcaaacg       720
agatttattc tcaggcaaga gcaatggatg ctgaggttga acttcaaaag tcagaggagg       780
aatatgaggc catatccaga gcaagagctt tcttcacgct ttttgactat gacgatggca       840
agctctctga ggcattccct aactctgaca ttgagatgtg cagaagattt ctgagtcagc       900
ctgtagacac aagttttgtg accgcaaccc tcaaagaaaa agagcaagag cttataaga       960
gaatgtgtga ggagcactat ctaaaaagtg gcatgagcac aaaagagagg cttgaggcaa      1020
atcgcaatga tgcaatagac aaaactagag ctctcatgga aagactccac aacatgagca      1080
gcaaggagct acactcgaat aagagcacag tgaagttgcc cccctgggta gtgaagcctt      1140
ctgataggac gttagatgtc aaaacggaca cgggatcagg ggagctactc aaccatggcc      1200
catatgggga gttgtggtca agatgcttcc tggagattat ccttgggaat gtggaagggg      1260
tcatcagcag ccctgaaaag gagctggaga tcgccatcag tgatgaccct gaggctgaca      1320
cccctaaggc tgcaaagata aaataccaca ggttcaggcc tgagctcagt ttagagagca      1380
agcatgaatt ttcattacaa ggcatcgagg gcaaagatg gaagcattca gctaggaatg      1440
tccttaaaga tgaaatgtcc cataagacaa tgagcccatt tgttgatgtc tcgaacattg      1500
aggagtttct gataatgaac aacctgttaa atgacacatc ttttaatcgg gaagggctgc      1560
aagaaacaat caacctgttg ttggagaagg ctactgaaat gcaccaaaat ggcttatcaa      1620
cagctttgaa tgattccttc aagagaaact tcaacacaaa cgtagtgcag tggagcatgt      1680
gggtctcatg cttagctcag gaattggcaa gtgctttgaa gcaacattgc aagcctggtg      1740
agtttatcat caaaaaatta atgcactggc aatattcgc cataattaag cccactaagt      1800
catcaagtca catattctac agcttggcaa taaaaaaaac caacattaag aggaggctga      1860
ttggtgacgt attcacagac acaattgatg cgggggagtg ggagttttca gaattcaaaa      1920
gcctcaagac ttgcaagctg acaaatctca ttaacctgcc gtgcaccatg ctcaactcaa      1980
ttgcgttctg gagagagaag atgggagtag cccccctggat ttctagaaag gcctgctcag      2040
agctcaggga acaagtggca atcactttcc ttatgagtct ggaagacaaa tcaacaacag      2100
aagagcttgt tactctcacg aggtattcac aaatggaggg atttgtgtct ccacccctgc      2160
tccctaaacc ccagaagatg gtggaaaagt tagaagttcc cttgcaaaca aagcttcaag      2220
tgtttttgtt taggaggcat cttgatgcta ttgttagagt tgctgcatct ccattcccca      2280
```

```
ttgtggcaag agatggtcga gtggaatgga cagggacatt caatgcaatc actggccgaa    2340
gcactgggct ggaaaacatg gtaaacaact ggtatatcgg ctattataaa aacaaagaag    2400
agtcgaccga gctaaatgcc ttaggtgaga tgtataaaaa gattgttgag attgaggctg    2460
agaagccagc atcttctgag tacttagggt ggggagacac tagcagccct aagaggcatg    2520
agttcagtag aagcttcctc aagtcagcat gcatatctct tgagaaggag atagagatga    2580
ggcatgggaa gagctggaag caaagcttgg aggagagagt ccttaaagaa ctgggctcaa    2640
agaacttgct ggacttagca acaatgaagg caacaagcaa ctttagcaag gaatgggaag    2700
ctttctcaga agtcagaaca aaagaatatc ataggtctaa actcctagaa aagatggctg    2760
aactaataga gcatgggtta atgtggtatg ttgatgcagc aggtcatgca tggaaggctg    2820
tccttgatga caaatgtatg agaatatgct tgtttaagaa aaatcagcac ggaggcctga    2880
gggaaattta tgtaacgaat gcaaatgcaa ggcttgtcca atttggagta gagacaatgg    2940
cacggtgtgt gtgtgagcta agcccacatg aaacaatagc taaccctaga ctcaagtcaa    3000
gcatcataga gaatcatggt ctcaagagtg ctcgacaatt ggggcagggg accattaatg    3060
tcaactcttc aaatgacgca aaaaaatgga gtcaggtcta ttatacaacc aagttggcca    3120
tggtattatg ctggttcatg ccagcaaaat tccataggtt catatgggca ggcatctcaa    3180
tgtttaggtg caagaagatg atgatggatc tcaggttttt agaaaaactg agcacaaagg    3240
ctaatcagaa aactgatgat gacttcagga aagacttagc tggggccttc catggcaatg    3300
ttgaagttcc atggatgact caaggggcta catatctcca gactgagaca gggatgatgc    3360
aagggatcct gcattttaca tcaagcctac tgcattcatg cgtccaaagt ttttacaagg    3420 catattttt gtctcggctt aaagaaggga tcgcaggcaa aaccatcaag gcagctatag    3480
atgttttaga aggctctgat gactcagcta tcatgataag cttgaagcca gcctcagaca    3540
atgaggaagc aatggctcgg ttttttaacag ccaacttgct atactcagtc agagtcataa    3600
acccgctctt tggcatttat agctctgaga agtcaacagt aaataccttta ttttgtgtgg    3660 agtacaactc agagttccac ttccacaagc atttagtcag gcctacaatc agatgggttg    3720
cagcatccca ccaaatctct gagtcagaag ccctggcaag caggcaggaa gattatgcga    3780
accttctcac tcaatgtctt gaaggggtt catcattctc tctaacatat ttgatccagt    3840
gtgcccagct cgtccatcat tatatgctgc tcgggctctg cttgcacccg ctgtttggaa    3900
catttgtagg gatgctgatt gaggatccag atccagccct aggcttcttc ataatggaca    3960
atccagcttt tgcaggggga gctggattta gattcaacct ttggaggtct tgcaagttca    4020
caaaccttgg caaaaagtat gcattctttt tcaatgagat tcaaggaaaa accaaggggg    4080
atgcagatta cagagcactg gatgcaacaa ctggtggaac attaagccac tctgtgatga    4140
tctactgggg ggacaggaga aagtaccaac atctcctaga caggatgggg cttcccaagg    4200
actgggttga gaggatagat gaaaacccaa gcgtcttata caggaggcct gagaacaagc    4260
aggaacttat cttgaggctg gcagaaaaag tgcattctcc aggtgtcact tccagcttca    4320
gcaaggggca tgttgtacct agagtggtgg cagctggagt ctacttgctg tcaagacatt    4380
gcttcaggta cactgcatca atccacggta ggggagcatc tcagaaggcg agtctaatta    4440
agctgcttgt catgtcttca acatcagctg agaggaatca aggaaggcta aatccaaatc    4500
aagaaagaat gctctttccc caagtccaag agtatgaaag agtactgacc ttgttagatg    4560
aggtcactgc gctcacaggg aagtttgttg tgagagaaag gaacatagtc aaaagcagag    4620
```

```
tagagctttt ccaggagcct gtggacttaa ggtgtaaagc tgaaaacctc attgcagaaa    4680
tgtggtttgg acttaaaaga acaaagttgg gcccaaggct gctaaaggaa gaatgggaca    4740
aactccgcgc ctccttctca tggttgagca ctgatcataa agaaacactg gatgtgggac    4800
catttcttag tcatgttcaa ttcaggaatt tcattgcaca tgtggatgcg aagtctagga    4860
gtgttcgact cttgggggcc cctgtcaaga agtcaggagg agtgactaca gtgtcccagg    4920
tggtgaaatc taatttcttt ccaggtttca ttttggactc cagtgagagc ttagatgacc    4980
aagagagggt tgagggggtg tcaatcttga aacacattct atttatgacc ttgaatggcc    5040
cttacactga tgagcaaaag aaagctatgg ttctggaggc cttccaatat tttgcactgc    5100
cacatgctgc tgaggttgtg aagagatcac ggtcattaac cctatgtttg atgaagaatt    5160
ttattgagca gagaggaggg tcaatacttg accaaattga aaaggctcag tcaggtacag    5220
ttggtggatt cagtaagccc cagaagcctt accgcaaaca atctggaggc attggctaca    5280
aggggaaagg tgtttggaca ggcataatgg aaaacacaaa tgtacagatc ctgatagatg    5340
gtgatggttc atcgaactgg atagaagaaa ttaggctgag tagtgagtcc aggctatttg    5400
atgtcataga atctgtcagg aggctgtgtg atgacattaa tgtcaacaat agggttacat    5460
caagctttcg gggtcattgc atggtgaggc tcagcaattt taaggtcaag ccagcttcaa    5520
gggtagaagg gtgcccagtg cgacttatgc cctcctcatt ccggataaag gagctccaaa    5580
acccagatga ggtcttctta agggtgaggg gagacattct aaacctgtcc atcctccttc    5640
aagaggaccg agtcatgaat ctgcttagct acagagctcg tgacactgac atctcagagt    5700
ctgcagcatc ctacctatgg atgaatagaa ctgacttctc atttgaaaag aaggagccat    5760
cttgcagctg gatgtgcttg aaaacattgg actcatgggc ttggaatcaa gcagcaagag    5820
ttcttgaaag aaacatcaaa acccctggaa ttgataacac cgccatgggg aacatttca    5880 aggattgctt agaaagctca ctcagaaagc aggggttgct tagatctaga attgctgaga    5940
tggtggaacg acatgttatt ccactaacaa gtcaggagct ggtggatatc ctggaggaag    6000
atgtcgattt ttcagaaatg atgcaatctg atataatgga aggggaccta gacattgata    6060
tcctgatgga agggtcacca atgctctggg cagcagaagt ggaggaaatg ggagaagcta    6120
tggtgatact cagtcagtca ggaaagtatt atcatctaaa attaatggat caagcagcaa    6180
caaccctttc aacaatcctt gggaaagatg gttgcaggct cctactggga gagcgtacat    6240
gtggatcaaa tctcagggag caggtgaagc cctacttgac attattgcaa ataagagagg    6300
gagatgtcaa ctgggtttct gagtacaaag acgacacacg tggtcttgat gaagactccg    6360
cagaaatgtg gggttaaacc aaccaggact ggggctcggg ttgaggtgaa gtgactctgc    6420
tgtctcactt gagctttcag tacctaaagg ttgatatctg gacggtcttt gtgtgggtcg    6480
gcatggcatc tccacctcct cgcggtccga cctgggcatc cgaaggagga cgtcgtccac    6540
tcggatggct aagggagagc tcggatccgg ctgctaacaa agcccgaaag gaagctgagt    6600
tggctgctgc caccgctgag caataactag cataacccct tggggcctct aaacgggtct    6660
tgaggggttt tttgctgaaa ggaggaacta tatgacgaat tctctagata tcgctcaata    6720
ctgaccattt aaatcatacc tgacctccat agcagaaagt caaaagcctc cgaccggagg    6780
cttttgactt gatcggcacg taagaggttc caactttcac cataatgaaa taagatcact    6840
accgggcgta tttttgagt tatcgagatt tcaggagct aaggaagcta aaatgagcca    6900
tattcaacgg gaaacgtctt gctcgaggcc gcgattaaat tccaacatgg atgctgattt    6960
atatgggtat aaatgggctc gcgataatgt cgggcaatca ggtgcgacaa tctatcgatt    7020
```

-continued

```
gtatgggaag cccgatgcgc cagagttgtt tctgaaacat ggcaaaggta gcgttgccaa      7080
tgatgttaca gatgagatgg tcaggctaaa ctggctgacg gaatttatgc ctcttccgac      7140
catcaagcat tttatccgta ctcctgatga tgcatggtta ctcaccactg cgatcccagg      7200
gaaaacagca ttccaggtat tagaagaata tcctgattca ggtgaaaata ttgttgatgc      7260
gctggcagtg ttcctgcgcc ggttgcattc gattcctgtt tgtaattgtc cttttaacgg      7320
cgatcgcgta tttcgtctcg ctcaggcgca atcacgaatg aataacggtt tggttggtgc      7380
gagtgatttt gatgacgagc gtaatggctg gcctgttgaa caagtctgga agaaatgca      7440 taagcttttg ccattctcac cggattcagt cgtcactcat ggtgatttct cacttgataa      7500
ccttattttt gacgagggga attaataggt tgtattgat gttggacgag tcggaatcgc      7560
agaccgatac caggatcttg ccatcctatg gaactgcctc ggtgagtttt ctccttcatt      7620
acagaaacgg cttttcaaa aatatggtat tgataatcct gatatgaata aattgcagtt      7680
tcacttgatg ctcgatgagt ttttctaaat gaccaaacag gaaaaaaccg cccttaacat      7740
ggcccgcttt atcagaagcc agacattaac gcttctggag aaactcaacg agctggacgc      7800
ggatgaacag gcagacatct gtgaatcgct tcacgaccac gctgatgagc tttaccgcag      7860
ctgcctcgcg cgtttcggtg atgacggtga aaacctctga tgagggccca aatgtaatca      7920
cctggctcac cttcgggtgg gccttctgc gttgctggcg ttttccata ggctccgccc      7980 ccctgacgag catcacaaaa atcgatgctc aagtcagagg tggcgaaacc cgacaggact      8040
ataaagatac caggcgtttc cccctggaag ctccctcgtg cgctctcctg ttccgaccct      8100
gccgcttacc ggatacctgt ccgcctttct cccttcggga agcgtggcgc tttctcatag      8160
ctcacgctgt aggtatctca gttcggtgta ggtcgttcgc tccaagctgg gctgtgtgca      8220 cgaaccccc gttcagcccg accgctgcgc cttatccggt aactatcgtc ttgagtccaa      8280
cccggtaaga cacgacttat cgccactggc agcagccact ggtaacagga ttagcagagc      8340
gaggtatgta ggcggtgcta cagagttctt gaagtggtgg cctaactacg gctacactag      8400
aagaacagta tttggtatct gcgctctgct gaagccagtt acctcggaaa aagagttggt      8460
agctcttgat ccggcaaaca aaccaccgct ggtagcggtg gtttttttgt ttgcaagcag      8520
cagattacgc gcagaaaaaa aggatctcaa gaagatcctt tgatttcta ccgaagaaag      8580 gcccaccgt gaaggtgagc cagtgagttg attgcagtcc agttacgctg gagtctgagg      8640
ctcgtcctga atgatatcaa gcttgaattc gtt                                  8673
```

<210> SEQ ID NO 45
<211> LENGTH: 5732
<212> TYPE: DNA
<213> ORGANISM: Artificial Sequence
<220> FEATURE:
<223> OTHER INFORMATION: Synthetic construct (pLCK-Mo4Mvc vector)

<400> SEQUENCE: 45

```
ggaagcggaa gagcgcccaa tacgcaaacc gcctctcccc gcgcgttggc cgattcatta       60
atgcaggggg atctcgatcc cgcgaaatta atacgactca ctatagacac agagacggct      120
atacattaag gtagaggtaa accgtaatcc actgagatga ttgccccagt tgtcctgttt      180
ttcactctct gtccgtccca actcagcgcc tggggctctc caggagaccc cattgtttgt      240
ggtgtgagga ccgaaacaaa caaatccatt cagattgagt ggaaggaggg gagatcagag      300
aaattatgcc agattgacag acttggacat gtcacaagct ggttaagaaa tcactcatct      360
```

```
ttccagggge ttattggtca ggtgaagggg aggccaagtg tttcctactt cccggaagga    420
gcttcttacc ctaggtggag cgggctatta agcccatgtg atgctgaatg gctgggacta    480
atagcagtga gcaaggctgg ggatacagac atgattgtcc caggcccaac ttacaaaggc    540
aaaatctttg ttgagagacc aacgtacaat ggttataaag gctgggggtg tgcagatggg    600
aagtcactaa gccactctgg cacatattgt gaaactgaca gctcagtaag ttctgggtta    660
attcagggtg atagggttct ctgggttggg gaagtagtct gtcagagagg gacacctgtg    720
ccagaagatg tatttagtga actgattagc ttgagtcaaa gtgagttccc agatgtgtgc    780
aaggttgatg gggttgcact gaaccaatgt gagcaggaga gcatccccca gccactggac    840
gttgcatgga ttgatgttgg aaggtctcat aaagtgctga tgagagaaca caaaactaaa    900
tgggtccaag agagctcagc aaaggacttt gtgtgcttca aggtgggtca ggggccatgt    960
tcaaaacaag aggaagatga ctgcatgagt aagggcaact gccatgggga tgaggttttc   1020
tgcaggatgg caggatgctc tgcccgtatg caagataatc aagaaggctg taggtgcgaa   1080
ctgctccaaa aacctggaga aatcattgtg aattatggag gcgtctctgt aagaccaact   1140
tgttatggat tctctagaat gatggcaaca ttggaagttc acaagcctga tagagaatta   1200
acagggtgca cgggttgtca cctagagtgc atagagggag gggtcaaaat tgtaacactt   1260
acaagcgagc tgagaagtgc aacagtttgt gcttcacatt tttgtgcatc cgcaaaaggg   1320
ggctcaaaga caactgacat actcttccac actggtgctc tcgttggacc caaatccatt   1380
agaattacgg gccagttgtt agatgggagc aagttctcct ttgatgggca ctgcatattc   1440
ccagatgggt gcatggcact tgactgcacc ttctgtaagg agttcctgag aaacccacaa   1500
tgttacccag taaagaaatg gctcttcttg gtggtagttg tgatgtgctg ctattgcgca   1560
ctgatgctgc ttactaacat actgagagct ataggtgttt ggggaacatg gttttttgct   1620
ccaataaagt tagttctagc attaggattg aggcttgcca aactatcaaa gaaggggttg   1680
gttgctgtgg ttacaagggg ccaaatgatc gtgaatgatg agctgcacca gattcgagtg   1740
gagagaggtg agcaaaatga gggaagacta ggtcatggcc caagaggtcc cgtccgtcac   1800
tggctatact cacctgccct cattctcatt ctgaccactt caatttgctc tggatgtgat   1860
gagctcgttc atgctgagag taaatctatc acatgcaagt ctgcatctgg gaatgagaag   1920
gagtgctcag tgacaggcag agctttactc ccagctgtta atccaggaca ggaggcctgc   1980
ttgcacttca gtatgccagg gagcccagac tctaagtgcc tcaagatcaa agtgaaatca   2040
ataaatctca gatgcaagca agcctcttca tattatgttc ctgaagcaaa ggcaagatgt   2100
acatctgtaa gaaggtgcag gtgggcaggt gactgtcaat ctgggtgtcc aacatatttc   2160
agctcaaact cattctcaga tgactgggca aacaggatgg acagggctgg gctcgggatg   2220
agtgggtgct cagatgggtg tggtggggct gcatgtgggt gtttcaatgc agcgccatcc   2280
tgcatctttt ggagaaagtg ggtggagaac ccatccaatc gtgtctggaa ggtgtcacct   2340
tgtgcatcat gggtgctagc tgcaatcatt gagttgactt tgccatcagg agaggttaag   2400
actctagagc ctgtcacagg gcaagcaact caaatgttta agggtgttgc aatcacgtat   2460
ctgggttcat ccattgagat tgttggcatg accaggctat gcgagatgaa agagatggga   2520
actgggatta tggcactagc cccctgcaat gaccctgggc acgccataat gggaaatgtg   2580
ggtgagatcc aatgcagtag tatagaaagc gcaaagcaca tcagatctga tgggtgcatt   2640
tggaatgctg acctagttgg gatagaatta agggttgatg atgctgtgtg tttctcaaaa   2700
ctcaccagtg ttgaggcagt cgcaaatttc tcaaaaatcc cggcaataat ttctggggtc   2760
```

```
cgttttgatc aagggaatca tggagaatcg cgaatctatg gtagcccatt agacatcacg    2820
aaggttagtg gggaattctc agtgtcattc aggggggatga ggcttaaact gtctgagata   2880
tcagcaagct gcacaggtga gataacaaac gtctctggtt gctactcctg catgactggg   2940
gcctctgtca gcataaagct acatagcagt aagaacacaa caggtcatct taaatgtgat   3000
tcagatgaga ctgcattcag tgtcatggag ggaacacaca cttataggcc tcacatgagc   3060
tttgataaag cagtggtaga tgaggagtgt gtgctaaact gtggtggcca ttcatcaaag   3120
ctgttgctta aggggagcct tgtcttcatg gacgtgccaa ggtttgttga tgggagttat   3180
gttcaaacat accatagcaa ggtgcctgct gggggaaggg tcccaaatcc agtagattgg   3240
ctcaacgcgc tgtttggaga tggcataaca cgatggattc ttgggattat aggagttctg   3300
ttggcatgtg tcttgctatt tgtggtggtg gtggccatca ctaggcgatt gatcaagggg   3360
ctgactcaaa gggcgaaggt ggcatgattg gcattaatta acaaataagc aagcctcctg   3420
tttcaaacct ctggtgggcc agaagcctga cagaggtttg aaacagatgc tctgacatct   3480
ggggtgtgaa tgataatggg tgggttttca atttgtatag ccggtctttg tgtgggtcgg   3540
catggcatct ccacctcctc gcggtccgac ctgggcatcc gaaggaggac gtcgtccact   3600
cggatggcta agggagagct cggatccggc tgctaacaaa gcccgaaagg aagctgagtt   3660
ggctgctgcc accgctgagc aataactagc ataaccccctt ggggcctcta acgggtctt   3720 gagggggtttt ttgctgaaag gaggaactat atgacgaatt ctctagatat cgctcaatac   3780
tgaccattta aatcatacct gacctccata gcagaaagtc aaaagcctcc gaccggaggc   3840
ttttgacttg atcggcacgt aagaggttcc aactttcacc ataatgaaat aagatcacta   3900
ccgggcgtat ttttttgagtt atcgagattt tcaggagcta aggaagctaa atgagccat   3960 attcaacggg aaacgtcttg ctcgaggccg cgattaaatt ccaacatgga tgctgattta   4020
tatgggtata aatgggctcg cgataatgtc gggcaatcag gtgcgacaat ctatcgattg   4080
tatgggaagc ccgatgcgcc agagttgttt ctgaaacatg gcaaaggtag cgttgccaat   4140
gatgttacag atgagatggt caggctaaac tggctgacgg aatttatgcc tcttccgacc   4200
atcaagcatt ttatccgtac tcctgatgat gcatggttac tcaccactgc gatcccaggg   4260
aaaacagcat tccaggtatt agaagaatat cctgattcag gtgaaaatat tgttgatgcg   4320
ctggcagtgt tcctgcgccg gttgcattcg attcctgttt gtaattgtcc ttttaacggc   4380
gatcgcgtat ttcgtctcgc tcaggcgcaa tcacgaatga ataacggttt ggttggtgcg   4440
agtgattttg atgacgagcg taatggctgg cctgttgaac aagtctggaa agaaatgcat   4500
aagcttttgc cattctcacc ggattcagtc gtcactcatg gtgatttctc acttgataac   4560 cttattttg acgaggggaa attaataggt tgtattgatg ttggacgagt cggaatcgca   4620
gaccgatacc aggatcttgc catcctatgg aactgcctcg gtgagtttc tccttcatta   4680 cagaaacggc ttttttcaaaa atatggtatt gataatcctg atatgaataa attgcagttt   4740
cacttgatgc tcgatgagtt tttctaaatg accaaacagg aaaaaaccgc ccttaacatg   4800
gcccgcttta tcagaagcca gacattaacg cttctggaga aactcaacga gctgacgcg   4860 gatgaacagg cagacatctg tgaatcgctt cacgaccacg ctgatgagct ttaccgcagc   4920
tgcctcgcgc gtttcggtga tgacggtgaa aacctctgat gagggcccaa atgtaatcac   4980
ctggctcacc ttcgggtggg cctttctgcg ttgctggcgt ttttccatag gctccgcccc   5040
cctgacgagc atcacaaaaa tcgatgctca agtcagaggt ggcgaaaccc gacaggacta   5100
```

| | |
|---|---:|
| taaagatacc aggcgtttcc ccctggaagc tccctcgtgc gctctcctgt tccgaccctg | 5160 |
| ccgcttaccg gatacctgtc cgcctttctc ccttcgggaa gcgtggcgct ttctcatagc | 5220 |
| tcacgctgta ggtatctcag ttcggtgtag gtcgttcgct ccaagctggg ctgtgtgcac | 5280 |
| gaaccccccg ttcagcccga ccgctgcgcc ttatccggta actatcgtct tgagtccaac | 5340 |
| ccggtaagac acgacttatc gccactggca gcagccactg gtaacaggat tagcagagcg | 5400 |
| aggtatgtag gcggtgctac agagttcttg aagtggtggc ctaactacgg ctacactaga | 5460 |
| agaacagtat ttggtatctg cgctctgctg aagccagtta cctcggaaaa agagttggta | 5520 |
| gctcttgatc cggcaaacaa accaccgctg gtagcggtgg ttttttttgtt tgcaagcagc | 5580 |
| agattacgcg cagaaaaaaa ggatctcaag aagatccttt gatttttctac cgaagaaagg | 5640 |
| cccacccgtg aaggtgagcc agtgagttga ttgcagtcca gttacgctgg agtctgaggc | 5700 |
| tcgtcctgaa tgatatcaag cttgaattcg tt | 5732 |

<210> SEQ ID NO 46
<211> LENGTH: 4077
<212> TYPE: DNA
<213> ORGANISM: Artificial Sequence
<220> FEATURE:
<223> OTHER INFORMATION: Synthetic construct (pLCK-Mo4Svc vector)

<400> SEQUENCE: 46

| | |
|---|---:|
| ggaagcggaa gagcgcccaa tacgcaaacc gcctctcccc gcgcgttggc cgattcatta | 60 |
| atgcaggggg atctcgatcc cgcgaaatta atacgactca ctatagacac agagaacccc | 120 |
| tttgaatcat caagcatgac tgactggtcc gcaatagctg ttgagattgg caacgagcca | 180 |
| ctggatgttc cagctttggt cgagtttgca aggaaatag cttatgaggg cctggatcct | 240 |
| gctgtgatct tggggctgct tcgtgagaga ggggtgaga actggaggaa tgatgtgaag | 300 |
| tacatcattg tatttgctct caccagaggg aacaagatag tgaaagcatg tggcaagatg | 360 |
| tctaagaaag gcgctgagag gatgacaaat ctggctagag tttatgagct gaaggagaat | 420 |
| gctgttgaca gaatggctgt gacaccagtg agagttgccc agtgcctgcc aacctggacc | 480 |
| tgtgctgctg cagcagcaat caaggagtac ctccctgttg gccagcaat catgcacaac | 540 |
| aaaatccaag gttatccact ggaaatgatg tgcatggcct ttggctcact gattccacag | 600 |
| gcagatgtct caattgaagt cataaaggac ttcatggatg cctattccct ttggcaagac | 660 |
| acatttgctc gaacaatcaa tgtggaccaa aggaagatga caaaggcaga ggtgtatgcc | 720 |
| aaattcagag accctctgca tgcagctgtc aattccctct tcttcccaaa tgccaccagg | 780 |
| atcagctggc tgcaggccaa gggcttgctc acagcaacca aggaagcatc cggctcagtg | 840 |
| aaggctgcgg ctgctgctta cagaaacatg taagcagctg ataaattttg aatttggcgc | 900 |
| caaattccaa ttggtcaaat caaatgaatt cgatctaaat tagctccccc taggggagc | 960 |
| tggaaagtgc tggccagtcc tttccccaga tgggattaag ataggcctct ctgacctcct | 1020 |
| catcatgcat gattatatta tggagagggc atttattcag ataatgtgct agtggtttgg | 1080 |
| gcaagccaga caggtacaag agctcatcca aggggttgag agggtcatcc tggcgggccc | 1140 |
| cctcatcttg gaatatgac ccatcatctt tcttcttgtc tctccagatg gcaaagtata | 1200 |
| aggagtcaag gagaggcttg tcaaggaagg gtgatgtgaa aaggtggtag ttgagtgtga | 1260 |
| gaccctaac acgcaaaagt gactcaattt ggaggagagc cacgtccatt attgggttca | 1320 |
| atcctgttat gaaagtatca ggcagaccca ttcgcctacg tctctcatca attttgtagc | 1380 |
| aagagtcaat gaccatgtcc cctcgaattt tgtatttttt cccagatgtt atcctgtgga | 1440 |

```
agaaacctct ccaattttcc tgacctgtct cgactgccca ggtgttcttg agggagaaga   1500
ataaatgagc agcctgcagg aaatggactg acggtttccc actcggccac ctcaatgcac   1560
tcttctcctg ctgactataa gagcccaggt ccccagagta ctcatcaaga agttgctcaa   1620
cagctggctc tagagcatgt agaggattgt tgggattgcc aaaaagccag acagtattgg   1680
tgaaggcctt cattttcctc atcatggagc atgtaagaac agagcactta catgagacca   1740
ggccaacata tgaggtgctg agctcggcca gattaggctc aagaaccacg atgggaagcc   1800
taacgcaggc actcttgacg ctgggctgag aggctttaga caaggacatg ttttgaaaat   1860
tcaagggggtt ctttgtgtgg gtcggcatgg catctccacc tcctcgcggt ccgacctggg   1920
catccgaagg aggacgtcgt ccactcggat ggctaaggga gagctcggat ccggctgcta   1980
acaaagcccg aaaggaagct gagttggctg ctgccaccgc tgagcaataa ctagcataac   2040
cccttggggc ctctaaacgg gtcttgaggg gttttttgct gaaaggagga actatatgac   2100
gaattctcta gatatcgctc aatactgacc atttaaatca tacctgacct ccatagcaga   2160
aagtcaaaag cctccgaccg gaggcttttg acttgatcgg cacgtaagag gttccaactt   2220
tcaccataat gaaataagat cactaccggg cgtattttt gagttatcga gattttcagg   2280
agctaaggaa gctaaaatga gccatattca acgggaaacg tcttgctcga ggccgcgatt   2340
aaattccaac atggatgctg atttatatgg gtataaatgg gctcgcgata atgtcgggca   2400
atcaggtgcg acaatctatc gattgtatgg gaagcccgat gcgccagagt tgtttctgaa   2460
acatggcaaa ggtagcgttg ccaatgatgt tacagatgag atggtcaggc taaactggct   2520
gacggaattt atgcctcttc cgaccatcaa gcatttatc cgtactcctg atgatgcatg   2580
gttactcacc actgcgatcc cagggaaaac agcattccag gtattagaag aatatcctga   2640
ttcaggtgaa aatattgttg atgcgctggc agtgttcctg cgccggttgc attcgattcc   2700
tgtttgtaat tgtccttta acggcgatcg cgtatttcgt ctcgctcagg cgcaatcacg   2760
aatgaataac ggtttggttg gtgcgagtga ttttgatgac gagcgtaatg gctggcctgt   2820
tgaacaagtc tggaaagaaa tgcataagct tttgccattc tcaccggatt cagtcgtcac   2880
tcatggtgat ttctcacttg ataaccttat ttttgacgag gggaaattaa taggttgtat   2940
tgatgttgga cgagtcggaa tcgcagaccg ataccaggat cttgccatcc tatggaactg   3000
cctcggtgag ttttctcctt cattacagaa acggcttttt caaaaatatg gtattgataa   3060
tcctgatatg aataaattgc agtttcactt gatgctcgat gagttttct aaatgaccaa   3120
acaggaaaaa accgcccttα acatggcccg ctttatcaga agccagacat taacgcttct   3180
ggagaaactc aacgagctgg acgcggatga acaggcagac atctgtgaat cgcttcacga   3240
ccacgctgat gagctttacc gcagctgcct cgcgcgtttc ggtgatgacg gtgaaaacct   3300
ctgatgaggg cccaaatgta atcacctggc tcaccttcgg gtgggccttt ctgcgttgct   3360
ggcgttttc cataggctcc gccccctga cgagcatcac aaaaatcgat gctcaagtca   3420
gaggtggcga aacccgacag gactataaag ataccaggcg tttccccctg gaagctccct   3480
cgtgcgctct cctgttccga ccctgccgct taccggatac ctgtccgcct ttctcccttc   3540
gggaagcgtg gcgctttctc atagctcacg ctgtaggtat ctcagttcgg tgtaggtcgt   3600
tcgctccaag ctgggctgtg tgcacgaacc ccccgttcag cccgaccgct gcgccttatc   3660
cggtaactat cgtcttgagt ccaacccggt aagacacgac ttatcgccac tggcagcagc   3720
cactggtaac aggattagca gagcgaggta tgtaggcggt gctacagagt tcttgaagtg   3780
```

```
gtggcctaac tacggctaca ctagaagaac agtatttggt atctgcgctc tgctgaagcc    3840
agttacctcg gaaaaagagt tggtagctct tgatccggca acaaaccac cgctggtagc     3900 ggtggttttt ttgtttgcaa gcagcagatt acgcgcagaa aaaaggatc tcaagaagat     3960 cctttgattt tctaccgaag aaaggcccac ccgtgaaggt gagccagtga gttgattgca    4020
gtccagttac gctggagtct gaggctcgtc ctgaatgata tcaagcttga attcgtt       4077
```

<210> SEQ ID NO 47
<211> LENGTH: 3735
<212> TYPE: DNA
<213> ORGANISM: Artificial Sequence
<220> FEATURE:
<223> OTHER INFORMATION: Synthetic construct (pLCK-Mo4SvcDelNSs_GLuc
      vector)

<400> SEQUENCE: 47

```
ggaagcggaa gagcgcccaa tacgcaaacc gcctctcccc gcgcgttggc cgattcatta      60
atgcaggggg atctcgatcc cgcgaaatta atacgactca ctatagacac agagaacccc    120
tttgaatcat caagcatgac tgactggtcc gcaatagctg ttgagattgg caacgagcca    180
ctggatgttc cagctttggt cgagtttgca aggaaatag cttatgaggg cctggatcct     240
gctgtgatct tggggctgct tcgtgagaga ggggtgaga actggaggaa tgatgtgaag     300
tacatcattg tatttgctct caccagaggg aacaagatga tgaaagcatg tggcaagatg    360
tctaagaaag gcgctgagag gatgacaaat ctggctagag tttatgagct gaaggagaat    420
gctgttgaca gaatggctgt gacaccagtg agagttgccc agtgcctgcc aacctggacc    480
tgtgctgctg cagcagcaat caaggagtac ctccctgttg ggccagcaat catgcacaac    540
aaaatccaag ttatccact ggaaatgatg tgcatggcct ttggctcact gattccacag     600
gcagatgtct caattgaagt cataaaggac ttcatggatg cctattccct ttggcaagac    660
acatttgctc gaacaatcaa tgtgaccaa aggaagatga caaaggcaga ggtgtatgcc     720
aaattcagag accctctgca tgcagctgtc aattccctct tcttcccaaa tgccaccagg    780
atcagctggc tgcaggccaa gggcttgctc acagcaacca aggaagcatc cggctcagtg    840
aaggctgcgg ctgctgctta cagaaacatg taagcagctg ataaatttttg aatttggcgc    900 caaattccaa ttggtcaaat caatgaatt cgatctaaat tagctcccct tagtcaccac     960 cggcccccttt gatcttgtcc acctggccct ggatcttgct ggcaaaggtc gcacagcgtt   1020
gcggcagcca cttcttgagc aggtcagaac actgcacgtt ggcaagccct tgaggcagc    1080 cagttgtgca gtccacacac agatcgacct gtgcgatgaa ctgctccatg gctccaagt    1140 ccttgaaccc aggaatctca ggaatgtcga cgatcgcctc gcctatgccg ccctgtgcgg    1200
actctttgtc gccttcgtag gtgtggcagc gtcctgggat gaacttcttc atctgggcg    1260 tgcacttgat gtgggacagg cagatcagac agccctggt gcagccagct tccgggcat    1320 tggcttccat ctctttgagc acctccacgc gcagcttctt gccgggcaac ttcccgcggt   1380
cagcatcgag atccgtggtc gcgaagttgc tggccacggc cacgatgttg aagtcttcgt    1440
tgttctcggt gggcttggcc tcggccacag cgatgcagat cagggcaaac agaactttga   1500
ctcccatgtt ttgaaaattc aagggggttct ttgtgtgggg cggcatggca tctccacctc    1560
ctcgcggtcc gacctgggca tccgaaggag gacgtcgtcc actcgatgg ctaagggaga    1620 gctcggatcc ggctgctaac aaagcccgaa aggaagctga gttggctgct gccaccgctg    1680
agcaataact agcataaccc cttggggcct ctaaacgggt cttgagggt ttttttgctga    1740
```

| | | | | |
|---|---|---|---|---|
| aaggaggaac | tatatgacga | attctctaga | tatcgctcaa | tactgaccat ttaaatcata | 1800 |
| cctgacctcc | atagcagaaa | gtcaaaagcc | tccgaccgga | ggcttttgac ttgatcggca | 1860 |
| cgtaagaggt | tccaactttc | accataatga | aataagatca | ctaccgggcg tattttttga | 1920 |
| gttatcgaga | ttttcaggag | ctaaggaagc | taaaatgagc | catattcaac gggaaacgtc | 1980 |
| ttgctcgagg | ccgcgattaa | attccaacat | ggatgctgat | ttatatgggt ataaatgggc | 2040 |
| tcgcgataat | gtcgggcaat | caggtgcgac | aatctatcga | ttgtatggga agcccgatgc | 2100 |
| gccagagttg | tttctgaaac | atggcaaagg | tagcgttgcc | aatgatgtta cagatgagat | 2160 |
| ggtcaggcta | aactggctga | cggaatttat | gcctcttccg | accatcaagc attttatccg | 2220 |
| tactcctgat | gatgcatggt | tactcaccac | tgcgatccca | gggaaaacag cattccaggt | 2280 |
| attagaagaa | tatcctgatt | caggtgaaaa | tattgttgat | gcgctggcag tgttcctgcg | 2340 |
| ccggttgcat | tcgattcctg | tttgtaattg | tccttttaac | ggcgatcgcg tatttcgtct | 2400 |
| cgctcaggcg | caatcacgaa | tgaataacg | tttggttggt | gcgagtgatt ttgatgacga | 2460 |
| gcgtaatggc | tggcctgttg | aacaagtctg | gaaagaaatg | cataagcttt tgccattctc | 2520 |
| accggattca | gtcgtcactc | atggtgattt | ctcacttgat | aaccttattt ttgacgaggg | 2580 |
| gaaattaata | ggttgtattg | atgttggacg | agtcggaatc | gcagaccgat accaggatct | 2640 |
| tgccatccta | tggaactgcc | tcggtgagtt | ttctccttca | ttacagaaac ggcttttca | 2700 |
| aaaatatggt | attgataatc | ctgatatgaa | taaattgcag | tttcacttga tgctcgatga | 2760 |
| gtttttctaa | atgaccaaac | aggaaaaaac | cgcccttaac | atggcccgct ttatcagaag | 2820 |
| ccagacatta | acgcttctgg | agaaactcaa | cgagctggac | gcggatgaac aggcagacat | 2880 |
| ctgtgaatcg | cttcacgacc | acgctgatga | gctttaccgc | agctgcctcg cgcgtttcgg | 2940 |
| tgatgacggt | gaaaacctct | gatgagggcc | caaatgtaat | cacctggctc accttcgggt | 3000 |
| gggcctttct | gcgttgctgg | cgttttccca | taggctccgc | cccctgacg agcatcacaa | 3060 |
| aaatcgatgc | tcaagtcaga | ggtggcgaaa | cccgacagga | ctataaagat accaggcgtt | 3120 |
| tccccctgga | agctccctcg | tgcgctctcc | tgttccgacc | ctgccgctta ccggatacct | 3180 |
| gtccgccttt | ctcccttcgg | gaagcgtggc | gctttctcat | agctcacgct gtaggtatct | 3240 |
| cagttcggtg | taggtcgttc | gctccaagct | gggctgtgtg | cacgaacccc ccgttcagcc | 3300 |
| cgaccgctgc | gccttatccg | gtaactatcg | tcttgagtcc | aacccggtaa gacacgactt | 3360 |
| atcgccactg | gcagcagcca | ctggtaacag | gattagcaga | gcgaggtatg taggcggtgc | 3420 |
| tacagagttc | ttgaagtggt | ggcctaacta | cggctacact | agaagaacag tatttggtat | 3480 |
| ctgcgctctg | ctgaagccag | ttaccttcgga | aaaagagttg | gtagctcttg atccggcaaa | 3540 |
| caaaccaccg | ctggtagcgg | tggtttttt | gtttgcaagc | agcagattac gcgcagaaaa | 3600 |
| aaaggatctc | aagaagatcc | tttgattttc | taccgaagaa | aggcccaccc gtgaaggtga | 3660 |
| gccagtgagt | tgattgcagt | ccagttacgc | tggagtctga | ggctcgtcct gaatgatatc | 3720 |
| aagcttgaat | tcgtt | | | | 3735 |

<210> SEQ ID NO 48
<211> LENGTH: 3620
<212> TYPE: DNA
<213> ORGANISM: Artificial Sequence
<220> FEATURE:
<223> OTHER INFORMATION: Synthetic construct (pLCK-Mo4M_EGFPBlastNeg
      vector)

<400> SEQUENCE: 48

-continued

| | | | | | |
|---|---|---|---|---|---|
| ggaagcggaa | gagcgcccaa | tacgcaaacc | gcctctcccc | gcgcgttggc | cgattcatta | 60 |
| atgcagggg | atctcgatcc | cgcgaaatta | atacgactca | ctatagacac | agagacggct | 120 |
| atacattaag | gtagaggtaa | accgtaatcc | actgagttag | ccctcccaca | cataaccaga | 180 |
| gggcagcaat | tcacgaatcc | caactgccgt | cggctgtcca | tcactgtcct | tcactatggc | 240 |
| tttgatccca | ggatgcagat | cgagaagcac | ctgtcggcac | cgtccgcagg | ggctcaagat | 300 |
| gcccctgttc | tcatttccga | tcgcgacgat | acaagtcagg | ttgccagctg | ccgcagcagc | 360 |
| agcagtgccc | agcaccacga | gttctgcaca | aggtcccca | gtaaaatgat | atacattgac | 420 |
| accagtgaag | atgcggccgt | cgctagagag | agctgcgctg | gcgacgctgt | agtcttcaga | 480 |
| gatggggatg | ctgttgattg | tagccgttgc | tctttcaatg | agggtggatt | cttcttgaga | 540 |
| caaaggcttg | gccatcttgt | acagctcgtc | catgccgaga | gtgatcccgg | cggcggtcac | 600 |
| gaactccagc | aggaccatgt | gatcgcgctt | ctcgttgggg | tctttgctca | gggcggactg | 660 |
| ggtgctcagg | tagtggttgt | cgggcagcag | cacggggccg | tcgccgatgg | gggtgttctg | 720 |
| ctggtagtgg | tcggcgagct | gcacgctgcc | gtcctcgatg | ttgtggcgga | tcttgaagtt | 780 |
| caccttgatg | ccgttcttct | gcttgtcggc | catgatatag | acgttgtggc | tgttgtagtt | 840 |
| gtactccagc | ttgtgcccca | ggatgttgcc | gtcctccttg | aagtcgatgc | ccttcagctc | 900 |
| gatgcggttc | accagggtgt | cgccctcgaa | cttcacctcg | gcgcgggtct | tgtagttgcc | 960 |
| gtcgtccttg | aagaagatgg | tgcgctcctg | gacgtagcct | tcgggcatgg | cggacttgaa | 1020 |
| gaagtcgtgc | tgcttcatgt | ggtcggggta | gcggctgaag | cactgcacgc | cgtaggtcag | 1080 |
| ggtggtcacg | agggtgggcc | agggcacggg | cagcttgccg | gtggtgcaga | tgaacttcag | 1140 |
| ggtcagcttg | ccgtaggtgg | catcgccctc | gccctcgccg | gacacgctga | acttgtggcc | 1200 |
| gtttacgtcg | ccgtccagct | cgaccaggat | gggcaccacc | ccggtgaaca | gctcctcgcc | 1260 |
| cttgctcacc | attgattggc | attaattaac | aaataagcaa | gcctcctgtt | tcaaacctct | 1320 |
| ggtgggccag | aagcctgaca | gaggtttgaa | acagatgctc | tgacatctgg | ggtgtgaatg | 1380 |
| ataatgggtg | ggttttcaat | ttgtatagcc | ggtctttgtg | tgggtcggca | tggcatctcc | 1440 |
| acctcctcgc | ggtccgacct | gggcatccga | aggaggacgt | cgtccactcg | gatggctaag | 1500 |
| ggagagctcg | gatccggctg | ctaacaaagc | ccgaaaggaa | gctgagttgg | ctgctgccac | 1560 |
| cgctgagcaa | taactagcat | aaccccttgg | ggcctctaaa | cgggtcttga | ggggtttttt | 1620 |
| gctgaaagga | ggaactatat | gacgaattct | ctagatatcg | ctcaatactg | accatttaaa | 1680 |
| tcatacctga | cctccatagc | agaaagtcaa | aagcctccga | ccggaggctt | ttgacttgat | 1740 |
| cggcacgtaa | gaggttccaa | cttttcaccat | aatgaaataa | gatcactacc | gggcgtattt | 1800 |
| tttgagttat | cgagattttc | aggagctaag | gaagctaaaa | tgagccatat | tcaacgggaa | 1860 |
| acgtcttgct | cgaggccgcg | attaaattcc | aacatggatg | ctgatttata | tgggtataaa | 1920 |
| tgggctcgcg | ataatgtcgg | gcaatcaggt | gcgacaatct | atcgattgta | tgggaagccc | 1980 |
| gatgcgccag | agttgtttct | gaaacatggc | aaaggtagcg | ttgccaatga | tgttacagat | 2040 |
| gagatggtca | ggctaaactg | gctgacggaa | tttatgcctc | ttccgaccat | caagcatttt | 2100 |
| atccgtactc | ctgatgatgc | atggttactc | accactgcga | tcccagggaa | aacagcattc | 2160 |
| caggtattag | aagaatatcc | tgattcaggt | gaaaatattg | ttgatgcgct | ggcagtgttc | 2220 |
| ctgcgccggt | tgcattcgat | tcctgttttgt | aattgtcctt | ttaacggcga | tcgcgtattt | 2280 |
| cgtctcgctc | aggcgcaatc | acgaatgaat | aacggtttgg | ttggtgcgag | tgattttgat | 2340 |
| gacgagcgta | atggctggcc | tgttgaacaa | gtctggaaag | aaatgcataa | gcttttgcca | 2400 |

-continued

```
ttctcaccgg attcagtcgt cactcatggt gatttctcac ttgataacct tattttttgac    2460
gaggggaaat taataggttg tattgatgtt ggacgagtcg gaatcgcaga ccgataccag    2520
gatcttgcca tcctatggaa ctgcctcggt gagttttctc cttcattaca gaaacggctt    2580
tttcaaaaat atggtattga taatcctgat atgaataaat tgcagtttca cttgatgctc    2640
gatgagtttt tctaaatgac caaacaggaa aaaaccgccc ttaacatggc ccgctttatc    2700
agaagccaga cattaacgct tctggagaaa ctcaacgagc tggacgcgga tgaacaggca    2760
gacatctgtg aatcgcttca cgaccacgct gatgagcttt accgcagctg cctcgcgcgt    2820
ttcggtgatg acggtgaaaa cctctgatga gggcccaaat gtaatcacct ggctcacctt    2880
cgggtgggcc tttctgcgtt gctggcgttt tccataggc tccgcccccc tgacgagcat    2940
cacaaaaatc gatgctcaag tcagaggtgg cgaaacccga caggactata agataccag    3000
gcgtttcccc ctggaagctc cctcgtgcgc tctcctgttc cgaccctgcc gcttaccgga    3060
tacctgtccg cctttctccc ttcgggaagc gtggcgcttt ctcatagctc acgctgtagg    3120
tatctcagtt cggtgtaggt cgttcgctcc aagctgggct gtgtgcacga accccccgtt    3180
cagcccgacc gctgcgcctt atccggtaac tatcgtcttg agtccaaccc ggtaagacac    3240
gacttatcgc cactggcagc agccactggt aacaggatta gcagagcgag gtatgtaggc    3300
ggtgctacag agttcttgaa gtggtggcct aactacggct acactagaag aacagtattt    3360
ggtatctgcg ctctgctgaa gccagttacc tcggaaaaag agttggtagc tcttgatccg    3420
gcaaacaaac caccgctggt agcggtggtt tttttgtttg caagcagcag attacgcgca    3480
gaaaaaaagg atctcaagaa gatcctttga ttttctaccg aagaaggcc cacccgtgaa    3540
ggtgagccag tgagttgatt gcagtccagt tacgctggag tctgaggctc gtcctgaatg    3600
atatcaagct tgaattcgtt                                                3620
```

<210> SEQ ID NO 49
<211> LENGTH: 8673
<212> TYPE: DNA
<213> ORGANISM: Artificial Sequence
<220> FEATURE:
<223> OTHER INFORMATION: Synthetic construct (pLCK-Mo7Lvc vector)

<400> SEQUENCE: 49

```
ggaagcggaa gagcgcccaa tacgcaaacc gcctctcccc gcgcgttggc cgattcatta     60
atgcaggggg atctcgatcc cgcgaaatta atacgactca ctatagacac aaagacgtcc    120
agatgaattt agaagctctt tgctctagag tgctttcaga gagagggcta tcaactggtg    180
agcctggggt atatgaccag atttttgaaa ggcctggcct cccaaacctt gaagtcacag    240
tggactccac tggggtagtt gtcgatgttg ggccattcc tgactcagca tcacagctag    300
ggtcctcgat aaatgcaggc gtgctcacca tacctctctc agaagcatat aagataaatc    360
atgacttcac tttctctgga ctgactaaga caacagatag gaagttgtct gaagtattcc    420
ctttggttca tgatggctca gactcaatga ccccccgatgt gatccacaca agactagatg    480
gaacagtagt tgtaattgaa ttcacaacaa ccagaagcac aaacatggga ggacttgagg    540
ctgcctatcg gagcaagctt gaaaaatacc gtgacccact aaacagaaga acagacataa    600
tgcctgatgc atcaatttac tttggaatca ttgttgttag tgcatctggt gttctcacaa    660
atatgcctct gacccaagat gaagctgaag aattgatgtt caggtctgt gtggcaaatg    720
agatttattc ccaggcaaga gcaatggatg ctgaggttga acttcaaaag tcagaggagg    780
```

```
aatatgaggc catatccaga gcaagagctt tcttcacgct ttttgactat gacgatggta   840
agctctctga ggcattccct aactctgaca ttgagatgct cagaagattt ctgagtcagc   900
ctgtagacac aagttttgtg accacaaccc tcaaagaaaa agagcaagag cttataaga    960
gaatgtgtga ggagcactat ctaaagagtg gcatgagcac aaaagagagg cttgaggcga  1020
atcgcagtga tgcaatagac aaaactagag ctctcatgga gagactccac aacatgagca  1080
gcaaggagct acactcgaat aagagcacag tgaagttgcc tccctgggta gtgaagcctt  1140
ctgataggac gttagatgtc aaaacggaca cgggatcagg ggagctactc aaccatggcc  1200
catatgggga gttgtggtca agatgcttcc tggagattgt ccttgggaat gtggagggg   1260
tcatcagcag ccctgaaaag gagctggaga tcgccatcag tgatgaccct gaggctgaca  1320
cccctaaggc tgcaaagatt aaataccata ggttccggcc tgagctcagt ttagagagca  1380
agcatgaatt ttcattacaa ggcatcgagg gcaaaagatg gaagcattca gctaggaatg  1440
tccttaaaga tgaaatgtcc cacaagacaa tgagcccatt tgttgatgtc tcgaacattg  1500
aggagtttct gattatgaac aacctgttaa atgcacacatc ttttaatcgg gaaggactgc  1560
aagaaacaat caacctgttg ttggagaagg ctactgaaat gcaccaaaat ggcttatcaa  1620
cagctttgaa tgattccttc aagagaaact tcaacacaaa cgttgtgcag tggagcatgt  1680
gggtctcatg cttagctcag gaattggcaa gtgctttgaa gcaacattgc aagcctggtg  1740
agtttatcat caaaaaatta atgcactggc caatattcgt cataattaag cccactaagt  1800
catcaagtca catattctac agcttggcaa taaaaaaagc caacattaag aggaggctga  1860
ttggtgatgt attcacagac acaattgatg cgggggagtg ggagttttca gaattcaaaa  1920
gcctcaagac gtgcaagctg acaaatctca ttaacctgcc gtgcaccatg ctcaactcaa  1980
tagcgttctg gagagagaag atgggagtag cccccctggat ttctagaaag gcctgctcag  2040
agctcaggga acaagtggca atcactttcc ttatgagtct ggaagacaaa tcaacaacag  2100
aagagcttgt tactctcacg aggtattcac aaatggaggg atttgtgtct ccaccctgc   2160
tccctaaacc ccagaagatg gtggaaaagt tagaagttcc tttgcgaaca aagcttcaag  2220
tgttttttgtt taggaggcat cttgatgcta ttgttagagt tgctgcatcc ccattcccca  2280
ttgtggcaag agatggtcga gtggaatgga cagggacatt caatgcaatc actggccgaa  2340
gcactgggct ggaaaacatg gtaaacaact ggtatattgg ctactataaa aacaaagaag  2400
agtcgaccga gctaaatgcc ttgggcgaga tgtacaagaa gattgttgag attgaggctg  2460
agaagccaac atcttctgag tacctaggat ggggagacac tagcagccct aagaggcatg  2520
agttcagtag aagcttcctc aagtcagcat gcatatctct tgagaaggag atagagatga  2580
ggcatggaaa gagctggaag caaagcttgg aggagagagt ccttaaagag ctgggctcaa  2640
agaacttgct ggacttagca acaatgaagg caacaagcaa ctttagcaag gaatgggaag  2700
ctttctcaga agtcagaaca aaagaatacc ataggtccaa actcctagaa aagatggctg  2760
aactaataga gcatgggtta atgtggtatg ttgatgctgc aggtcatgca tggaaggctg  2820
tccttgatga caagtgtatg agaatatgct tgtttaagaa aaatcagcat ggaggcctga  2880
gggaaattta tgtaacgaat gcaaatgcaa ggcttgttca atttggagta gagacaatgg  2940
cacggtgtgt gtgtgagcta agcccacatg aaacaatagc taaccctaga ctcaagtcaa  3000
gcatcataga gaatcatggt ctcaagagtg ctcgacaatt agggcagggg accattaatg  3060
tcaactcttc aaatgacgca aaaaaatgga gtcaggccca ttatacaacc aaattggcta  3120
tggtattatg ctggttcatg ccagctaagt tccataggtt catatgggca ggcatctcaa  3180
```

```
tgtttaggtg caagaagatg atgatggacc tcaggttttt agaaaaattg agcacaaagg   3240
ctaatcagaa aactgatgat gacttcagga aagacttagc tggggccttc catggcaatg   3300
ttgaggttcc ttggatgact caaggagcta catatctcca gactgagaca gggatgatgc   3360
aagggatcct gcattttaca tcaagcctac tgcattcatg cgtccaaagt ttttacaagg   3420
catatttttt atctcggctt aaagaaggga tcgcaggcag aaccatcaag gcagctatag   3480
atgttttaga aggctctgat gactcagcta tcatgataag cttgaagcca gcctcagaca   3540
atgaggaagc gatggctcgg tttttaacag ccaacttgct atactcagtc agagtcataa   3600
acccgctctt tggcatttat agctctgaga agtcaacagt aaataccta ttttgtgtgg    3660 aatacaactc agagttccac ttccacaagc atttagtcag gcctacaatc agatgggttg   3720
cagcatccca ccaaatctct gagtcagaag ccctggcaag caggcaggaa gattatgcga   3780
accttctcac tcaatgtctt gaagggggtt catcattctc tctaacatat ttgatccagt   3840
gtgcccagct cgtccatcat tatatgctgc tcgggctctg cttgcacccg ctgtttggga   3900
catttgtagg gatgctgatt gaggatccag atccagccct aggcttcttc ataatggaca   3960
atccagcttt tgcaggggga gctggattta gattcaacct ttggagatct tgcaagttca   4020
caaaccttgg caaaaagtat gcattctttt tcaatgagat tcaaggaaaa accaaggggg   4080
atgcagatta cagagcactg gatgcaacaa ctggtggaac attaagccac tctgtaatga   4140
cctactgggg ggacaggaga agtaccaac atctcctaga caggatgggg cttcccaagg    4200
actgggttga gaggatagat gaaaacccaa gcatcttata taggaggcct gagaacaagc   4260
aggaacttat cttgaggctg gcagaaaaag tgcattctcc aggtgtcact tccagcttca   4320
gcaaagggca tgttgtacct agggtggtgg cagctggagt ctacttgctg tcaagacatt   4380
gcttcaggta cactgcatca atccacggta gggggcatc tcagaaggcg agtctgatta    4440
agctgcttgt catgtcttca acatcagctg agaggaatca aggaaggctg aacccaaatc   4500
aagaaagaat gctcttttcct caagtccaag agtatgaaag agtattgacc ttgttagatg   4560
aggttactgc gctcacaggg aagtttgttg tgagagaaag gaacatagtc aaaagcagag   4620
tagagctttt ccaggagcct gtggacttaa ggtgcaaagc tgaaaacctc attgcagaaa   4680
tgtggtttgg acttaaaaga acaaagttgg gcccaaggct gctaaaggaa gaatgggaca   4740
aactccgcgc ctccttctca tggttaagca ctgatcataa agaaacactg gatgtgggtc   4800
catttcttag tcatgttcaa ttcaggaatt tcattgcaca tgtggatgcg aagtctagga   4860
gtgttcgact tttgggggcc cctgtcaaga agtctggagg agtgactaca gtgtcccagg   4920
tggtgaaatc taatttcttt ccaggtttca ttttggactc cagtgagagc ttagatgacc   4980
aagagagggt tgaggggtg tcaatcttaa aacacattct atttatgacc ttgaatggcc    5040
cttacactga tgagcaaaag aaagccatgg ttctggagac cttccaatat tttgcactgc   5100
cacatgctgc tgaagttgtg aagagatcac gatcactaac cctatgcttg atgaagaatt   5160
ttattgagca gagaggaggg tcaatacttg accaaattga aaaggctcag tcaggtacag   5220
tgggtggatt cagtaagccc cagaagcctt accgcaaaca gtcaggaggc attggctaca   5280 agggaaagg tgtttggtca ggcataatgg aaaacacaaa tgtacagatc ctgatagatg    5340
gtgatggttc atcaaactgg atagaagaaa tcaggctgag tagtgagtcc aggctatttg   5400
atgtcataga atctgtcagg aggctgtgtg atgacattaa tgtcaataat agagttacat   5460
caagctttcg gggtcattgc atggtgaggc ttagcaactt taaggtcaag ccagcttcaa   5520
```

```
gggtagaagg ttgcccagtg cgactcatgc cctcttcatt ccggataaag gagctccaaa    5580
acccagatga ggtcttctta agggtgaggg gagacattct aaacctgtcc atcctccttc    5640
aagaggaccg agtcatgaat ctgcttagct acagagctcg tgacactgac atctcagagt    5700
ctgcagcatc ctacctatgg atgaatagaa cagacttctc atttggaaag aaggagccat    5760
cttgcagctg gatgtgcttg aaaacattgg actcatgggc ttggaatcaa gcagcaagag    5820
ttcttgaaag aaacatcaaa accoctggaa ttgataacac cgccatgggg aacattttca    5880
aggattgctt agaaagctca ctcagaaagc aggggttgct tagatctaga attgctgaga    5940
tggtggaacg tcatgttatc ccactaacaa gtcaggagct ggtggatatc ctggaggaag    6000
atgtcgactt ttcagaaatg atgcaatctg atataatgga aggggaccta gacattgata    6060
tcctgatgga agggtcacca atgctctggg cagcagaagt ggaggagatg ggagaagcta    6120
tggtgatact cagtcagtca ggaaagtatt atcatctaaa attaatggat caagcagcaa    6180
caacccttc aacaatcctt gggaaagatg gttgcaggct tctactgggg agacctactg    6240
ggagatcaaa tctcagggag caggtgaagc cctacttgac attattgcaa ataagagagg    6300
gagatgtcaa ctgggtttct gagtacaaag atgacacacg tggtcttgat gaagactctg    6360
cagaaatgtg gggttaaacc aaccaggact ggggctcggg ttgaggtgaa gtgactctgc    6420
tgtctcactt gagctatcag tacctaaagg ttgatatctg gacggtcttt gtgtgggtcg    6480
gcatggcatc tccacctcct cgcggtccga cctgggcatc cgaaggagga cgtcgtccac    6540
tcggatggct aagggagagc tcggatccgg ctgctaacaa agcccgaaag gaagctgagt    6600
tggctgctgc caccgctgag caataactag cataacccct tggggcctct aaacgggtct    6660
tgagggttt tttgctgaaa ggaggaacta tatgacgaat tctctagata tcgctcaata    6720
ctgaccattt aaatcatacc tgacctccat agcagaaagt caaaagcctc cgaccggagg    6780
cttttgactt gatcggcacg taagaggttc caactttcac cataatgaaa taagatcact    6840
accgggcgta ttttttgagt tatcgagatt ttcaggagct aaggaagcta aaatgagcca    6900
tattcaacgg gaaacgtctt gctcgaggcc gcgattaaat tccaacatgg atgctgattt    6960
atatgggtat aaatgggctc gcgataatgt cgggcaatca ggtgcgacaa tctatcgatt    7020
gtatgggaag cccgatgcgc cagagttgtt tctgaaacat ggcaaaggta gcgttgccaa    7080
tgatgttaca gatgagatgg tcaggctaaa ctggctgacg gaatttatgc ctcttccgac    7140
catcaagcat tttatccgta ctcctgatga tgcatggtta ctcaccactg cgatcccagg    7200
gaaaacagca ttccaggtat tagaagaata tcctgattca ggtgaaaata ttgttgatgc    7260
gctggcagtg ttcctgcgcc ggttgcattc gattcctgtt tgtaattgtc cttttaacgg    7320
cgatcgcgta tttcgtctcg ctcaggcgca atcacgaatg aataacggtt tggttggtgc    7380
gagtgatttt gatgacgagc gtaatggctg gcctgttgaa caagtctgga agaaatgca    7440
taagctttg ccattctcac cggattcagt cgtcactcat ggtgatttct cacttgataa    7500
ccttattttt gacgagggga aattaatagg ttgtattgat gttggacgag tcggaatcgc    7560
agaccgatac caggatcttg ccatcctatg aactgcctc ggtgagtttt ctccttcatt    7620
acagaaacgg cttttcaaa aatatggtat tgataatcct gatatgaata aattgcagtt    7680
tcacttgatg ctcgatgagt ttttctaaat gaccaaacag gaaaaaccg cccttaacat    7740
ggcccgcttt atcagaagcc agacattaac gcttctggag aaactcaacg agctggacgc    7800
ggatgaacag gcagacatct gtgaatcgct tcacgaccac gctgatgagc tttaccgcag    7860
ctgcctcgcg cgtttcggtg atgacggtga aaacctctga tgagggccca aatgtaatca    7920
```

```
cctggctcac cttcgggtgg gcctttctgc gttgctggcg ttttccata ggctccgccc      7980 ccctgacgag catcacaaaa atcgatgctc aagtcagagg tggcgaaacc cgacaggact      8040
ataaagatac caggcgtttc ccctggaag ctccctcgtg cgctctcctg ttccgaccct       8100
gccgcttacc ggatacctgt ccgcctttct cccttcggga agcgtggcgc tttctcatag      8160
ctcacgctgt aggtatctca gttcggtgta ggtcgttcgc tccaagctgg gctgtgtgca      8220 cgaaccccc gttcagcccg accgctgcgc cttatccggt aactatcgtc ttgagtccaa       8280
cccggtaaga cacgacttat cgccactggc agcagccact ggtaacagga ttagcagagc     8340
gaggtatgta ggcggtgcta cagagttctt gaagtggtgg cctaactacg gctacactag     8400
aagaacagta tttggtatct gcgctctgct gaagccagtt acctcggaaa aagagttggt      8460
agctcttgat ccggcaaaca aaccaccgct ggtagcggtg gtttttttgt ttgcaagcag     8520
cagattacgc gcagaaaaaa aggatctcaa gaagatcctt tgatttcta ccgaagaaag     8580 gcccacccgt gaaggtgagc cagtgagttg attgcagtcc agttacgctg gagtctgagg      8640
ctcgtcctga atgatatcaa gcttgaattc gtt                                  8673
```

<210> SEQ ID NO 50
<211> LENGTH: 5732
<212> TYPE: DNA
<213> ORGANISM: Artificial Sequence
<220> FEATURE:
<223> OTHER INFORMATION: Synthetic construct (pLCK-Mo7Mvc vector)

<400> SEQUENCE: 50

```
ggaagcggaa gagcgcccaa tacgcaaacc gcctctcccc gcgcgttggc cgattcatta      60
atgcaggggg atctcgatcc cgcgaaatta atacgactca ctatagacac agagacggct     120
atacattaaa gtagaggtaa accgtaatcc actgagatga ttgtcccgat tgtcctgttt     180
ctcacgctct gtccgtccga actcagtgcc tggggctccc caggagaccc tattgtttgt     240
ggtgtgagga ctgaaacaaa caaatccatt cagattgagt ggaaggaggg aagatcagag     300
aagctatgcc agattgacag gcttgggcat gtcacaagct ggttaagaaa ccactcatct     360
ttccaggggc ttattggtca ggtgaagggg agaccaagtg tttcctactt cccggaaggg     420
gcttcttacc caaggtggag cggcctatta agcccatgtg atgctgaatg gctgggactg     480
atagcagtga gcaaggctgg agacacagac atgattgtcc caggcccaac ttacaaaggg     540
aaaatctttg ttgagagacc aacatacaac ggttacaaag gctggggttg tgcagatgga      600
aagtcactaa gccactcagg cacatattgt gaaactgaca gctcagtgag ttctggttta     660
attcagggag atagggttct ctgggttggg gaagtagtct gtcagagagg gacccctgtg     720
ccagaagatg tatttagtga actggttagc ttgagtcaaa gtgagttccc agatgtgtgc     780
aagattgatg gtgttgcact gaaccagtgt gagcaggaga gcatcccca gccactggac      840 gttgcatgga ttgatgttgg aaggtctcat aaggtactga tgagagaaca caaaactaaa     900
tgggtccaag agagctcagc aaaggacttt gtgtgtttca aggtgggtca ggggccatgt      960
tcgaaacaag aggaagatga ctgcatgagt aagggcaact gccatgggga tgaggttttc     1020
tgcaggatgg caggatgctc tgcccgtatg caagataatc aagaaggctg caggtgcgaa     1080
ctgcttcaaa aacctggaga aatcattgtg aattatggag gcgtctctgt gagaccaacc     1140
tgttatggat tctccagaat gatggcaaca ttggaagttc acaaacctga tagaattga     1200 acagggtgca cgggttgtca cctagagtgc atagagggag gagttaaaat tgtaacgctt     1260
```

-continued

```
acaagcgagc tgagaagtgc aacagtttgt gcttcacatt tttgtgcatc tgcaaagggg    1320
ggctcaaaga caactgacat actcttccac actggtgctc tcgttggacc caattccatt    1380
agaataactg gtcagttgtt agatgggagc aagttctcct ttgatgggca ctgcatattc    1440
ccagatgggt gcatggctct tgactgcacc ttctgtaaag agttcctgag aaacccgcaa    1500
tgttaccctg taaagaaatg gctcttcctg gtggtagtta atgtgctg ctattgtgcc     1560
ctgatgctgc ttactaacat actgagagct ataggtgttt gggggacatg gttttttgct    1620
ccaataaagt tggctctagc attagggttg aggcttgcca aactgtcaaa gaaggggctg    1680
gttgctgtgg ttacaagggg ccaaatgatc gtgaatgatg agctgcacca ggttcgagtg    1740
gagagaggtg agcaaaatga gggaagacaa ggttatggcc caagaggccc catccgtcac    1800
tggctatact cacctgccct cattctcatt ctcaccactt caatttgctc tggatgtgat    1860
gagcttgttc atgctgagag taaatccatc acatgcaagt ctgcatctgg gaatgagaag    1920
gagtgctcag tgacaggcag agctttgctc ccagctgtca atccagggca ggaggcctgc    1980
ttgcacttta gcgtgccagg aagcccagac tccaagtgcc ttaagatcaa agtgaaatca    2040
ataaatctca gatgtaagca agcctcttca tattatgttc ctgaagcaaa ggcaagatgt    2100
acatctgtca gaaggtgcag gtgggcaggt gactgtcaat ctgggtgtcc aacatatttc    2160
agctcaaact cattctcaga tgattgggca acaggatgg acagggctgg gctcgggatg     2220
agtgggtgct cagatgggtg tggtggagct gcatgtgggt gttttaatgc agcgccatcc    2280
tgcatctttt ggagaaagtg ggtggagaac ccatccaatc gtgtctggaa ggtgtcacct    2340
tgtgcatcat gggtgctagc tgcaaccatt gagttgactt tgccatcagg agaggttaag    2400
actctagagc ctgtcacagg gcaagcaact cagatgttca agggtgttgc aatcacatat    2460
ctgggatcat ccattgagat tgttggcatg accaggctat gtgagatgaa agagatgggg    2520
actgggataa tggcactggc ccctgcaat gatccagggc acgccataat gggaaatgtg      2580
ggtgagatcc aatgcagtag tatagaaagc gcaaagcaca tcaggtctga tgggtgcatt    2640
tggaatgctg acctagttgg aatagaattg agggttgatg atgctgtgtg tttctcgaaa    2700
ctcactagtg ttgaggcagt tgcaaatttt tcaaaaatcc cggcaacaat ttctggggtt    2760
cgctttgatc aagggaatca tggagaatca cgtatctatg gtagcccatt agatatcacg    2820
agggttagtg gggaattctc agtgtcattc agagggatga ggctcaaact atctgagata    2880
tcagcaagct gcacaggtga gataacaaac gtctctggtt gttactcctg catgactggg    2940
gcctcagtca gcataaaatt acatagcagt aagaacacaa caggtcatct taagtgtgat    3000
tcagatgaga ctgcattcag tgtcatggag ggaacacaca catataggcc tcacatgagc    3060
tttgataaag cagtaataga tgaggagtgt gtgctaaact gtggtggcca ctcatcaaaa    3120
ctgttgctta aagggagcct tgtttttatg gacgtgccaa ggtttgttga tggaagttat    3180
gtccaaacat atcacagcaa ggtgcccgct gggggaaggg tcccaaatcc ggtagactgg    3240
ctcaacgcac tgtttggaga tggcataaca cgatggattc ttgggattat aggggttctg    3300
ctggcatgtg tcatgctatt tgtggtggtg gttgccatca ctaggcgatt gatcaaggga    3360
ctgactcaaa gggcgaaggt ggcatgattg gcgttaattg acaaataagc aagcctcctg    3420
tttcaaacct ctggtgggcc agaagcctga cagaggtttg aaacaaatgc tctgacatct    3480
gaggcatgaa tgataatggg tgggttttca atttgtatag ccggtctttg tgtgggtcgg    3540
catggcatct ccacctcctc gcggtccgac ctgggcatcc gaaggaggac gtcgtccact    3600
cggatggcta agggagagct cggatccggc tgctaacaaa gcccgaaagg aagctgagtt    3660
```

```
ggctgctgcc accgctgagc ataactagc ataacccctt ggggcctcta acgggtctt      3720
gagggtttt ttgctgaaag gaggaactat atgacgaatt ctctagatat cgctcaatac      3780
tgaccattta aatcataacct gacctccata gcagaaagtc aaaagcctcc gaccggaggc    3840
ttttgacttg atcggcacgt aagaggttcc aactttcacc ataatgaaat aagatcacta    3900
ccgggcgtat tttttgagtt atcgagattt tcaggagcta aggaagctaa atgagccat    3960
attcaacggg aaacgtcttg ctcgaggccg cgattaaatt ccaacatgga tgctgattta    4020
tatgggtata atgggctcg cgataatgtc gggcaatcag gtgcgacaat ctatcgattg    4080
tatgggaagc ccgatgcgcc agagttgttt ctgaaacatg gcaaaggtag cgttgccaat    4140
gatgttacag atgagatggt caggctaaac tggctgacgg aatttatgcc tcttccgacc    4200
atcaagcatt ttatccgtac tcctgatgat gcatggttac tcaccactgc gatcccaggg    4260
aaaacagcat tccaggtatt agaagaatat cctgattcag gtgaaaatat tgttgatgcg    4320
ctggcagtgt tcctgcgccg gttgcattcg attcctgttt gtaattgtcc ttttaacggc    4380
gatcgcgtat ttcgtctcgc tcaggcgcaa tcacgaatga ataacggttt ggttggtgcg    4440
agtgattttg atgacgagcg taatggctgg cctgttgaac aagtctggaa agaaatgcat    4500
aagctttgc cattctcacc ggattcagtc gtcactcatg gtgatttctc acttgataac    4560
cttattttg acgagggaa attaataggt tgtattgatg ttggacgagt cggaatcgca    4620
gaccgatacc aggatcttgc catcctatgg aactgcctcg gtgagttttc tccttcatta    4680
cagaaacggc ttttttcaaaa atatggtatt gataatcctg atatgaataa attgcagttt    4740
cacttgatgc tcgatgagtt tttctaaatg accaaacagg aaaaaaccgc ccttaacatg    4800
gcccgcttta tcagaagcca gacattaacg cttctggaga aactcaacga gctggacgcg    4860
gatgaacagg cagacatctg tgaatcgctt cacgaccacg ctgatgagct ttaccgcagc    4920
tgcctcgcgc gtttcggtga tgacggtgaa aacctctgat gagggcccaa atgtaatcac    4980
ctggctcacc ttcgggtggg cctttctgcg ttgctggcgt ttttccatag gctccgcccc    5040
cctgacgagc atcacaaaaa tcgatgctca agtcagaggt ggcgaaaccc gacaggacta    5100
taaagatacc aggcgtttcc ccctggaagc tccctcgtgc gctctcctgt tccgaccctg    5160
ccgcttaccg gatacctgtc cgcctttctc ccttcgggaa gcgtggcgct ttctcatagc    5220
tcacgctgta ggtatctcag ttcggtgtag gtcgttcgct ccaagctggg ctgtgtgcac    5280
gaaccccccg ttcagcccga ccgctgcgcc ttatccggta actatcgtct tgagtccaac    5340
ccggtaagac acgacttatc gccactggca gcagccactg gtaacaggat tagcagagcg    5400
aggtatgtag gcggtgctac agagttcttg aagtggtggc ctaactacgg ctacactaga    5460
agaacagtat ttggtatctg cgctctgctg aagccagtta cctcggaaaa agagttggta    5520
gctcttgatc cggcaaacaa accaccgctg gtagcggtgg ttttttttgtt tgcaagcagc    5580
agattacgcg cagaaaaaaa ggatctcaag aagatccttt gatttctac cgaagaaagg    5640
cccacccgtg aaggtgagcc agtgagttga ttgcagtcca gttacgctgg agtctgaggc    5700
tcgtcctgaa tgatatcaag cttgaattcg tt                                   5732
```

<210> SEQ ID NO 51
<211> LENGTH: 4077
<212> TYPE: DNA
<213> ORGANISM: Artificial Sequence
<220> FEATURE:
<223> OTHER INFORMATION: Synthetic construct (pLCK-Mo7Svc vector)

<400> SEQUENCE: 51

```
ggaagcggaa gagcgcccaa tacgcaaacc gcctctcccc gcgcgttggc cgattcatta      60
atgcaggggg atctcgatcc cgcgaaatta atacgactca ctatagacac agagaacccc     120
tttgaatcat caagcatgac tgactggtct gcaatagctg ttgagattgg caacgagcca     180
ctggatgttc cagctttggt cgagtttgca aaggagatag cttatgaggg cctggatcct     240
gctgtgatct ttgggctgct tcgtgagagg ggggtgaga actggaggaa tgatgtgaag      300
tacatcattg tatttgctct cactagaggg aacaagatag tgaaagcatg tggcaagatg     360
tctaagaaag cgctgagag gatgacaaac ctggctagag tctatgagct gaaggagaat      420
gctgttgaca gaatggctgt gacaccagtg agagttgccc agtgcctgcc aacctggacc     480
tgtgctgctg cagcagcaat caaggagtac ctccctgttg ggccagcaat catgcacaac     540
aagatccaag gttatccact ggaaatgatg tgcatggcct ttggctcatt gatcccacag     600
gcagatgtct caattgaagt cataaaggac ttcatggatg cctactccct ttggcaagac     660
acatttgctc gaacaatcaa tgtggaccaa aggaagatga caaaggcaga ggtgtatgcc     720
aaattcagag accctctgca tgcagctgtc aattccctct tcttcccaaa tgccaccagg     780
atcagctggc tgcaggccaa gggcttgctc acagcaacca aggaagcatc cggctcagtg     840
aaggctgcag ctgctgctta cagaaacatg taagcagctg ataaattttg aatttggcgc     900
taaattccaa ttggtcaaat caaatgaatt cgatctaaat tagctccccc taaggggagc     960
tggaaagtgc tggccagtcc tttccccaga tgggatttag ataggcctct ctgacctcct    1020
catcatgcat gattatatta tggagagggc atttatttag ataatgtgct agtggtttgg    1080
gcaagtcaga caggtacaag agctcatcca aggggttgag agggtcatcc tggcgggccc    1140
cctcatcttg gaatatgac ccatcatctt tcttttttgtc tctccagatg gcaaaatata    1200
aggaatcaag agagggcttg tcaaggaagg atgatgtgaa aaggtgatag ttgagtgtga    1260
gaccccctaac acgcaaaagt gactcaattt ggaggagagc cacatccatt attgggttca    1320
gtcctgttat gaaagtatca ggcagaccca ttcgcctacg tctctcatca attttgtagc    1380
aagagtcaat gaccatgtcc ccctcgaatt tgtattttttt cccagatgtt atcctgtgga    1440
agaaacctct ccaattttcc tgacctgtct cgactgccca ggtgttcttg agggagaaga    1500
ataaatgagc agcctgcaag aaatggactg acggtttccc actcggccac ctcaatgcac    1560
tcttctcctg ctggctataa gagcctaagt ccccagagta ctcatcaaga agttgctcaa    1620
cagctggctc tagagcatgt agaggattgt tgggattgcc aaacagccag acagtattgg    1680
tgaaggcctt catttttcctc atcatggagc atgtaagaac tgagcactta catgagacca    1740
ggccaacata tgaggtgctg agctcggcca gattaggctc aagaaccacg atgggaagcc    1800
taacgcaggc actcttgacg ctgggctgag aggctttaga caaggacatg ttttgataat    1860
tcaagggggtt ctttgtgtgg gtcggcatgg catctccacc tcctcgcggt ccgacctggg    1920
catccgaagg aggacgtcgt ccactcggat ggctaaggga gagctcggat ccggctgcta    1980
acaaagcccg aaaggaagct gagttggctg ctgccaccgc tgagcaataa ctagcataac    2040
cccttggggc ctctaaacgg gtcttgaggg gttttttgct gaaaggagga actatatgac    2100
gaattctcta gatatcgctc aatactgacc atttaaatca tacctgacct ccatagcaga    2160
aagtcaaaag cctccgaccg gaggcttttg acttgatcgg cacgtaagag gttccaactt    2220
tcaccataat gaaataagat cactaccggg cgtatttttt gagttatcga gattttcagg    2280
agctaaggaa gctaaaatga gccatattca acgggaaacg tcttgctcga ggccgcgatt    2340
```

```
aaattccaac atggatgctg atttatatgg gtataaatgg gctcgcgata atgtcgggca    2400
atcaggtgcg acaatctatc gattgtatgg gaagcccgat gcgccagagt tgtttctgaa    2460
acatggcaaa ggtagcgttg ccaatgatgt tacagatgag atggtcaggc taaactggct    2520
gacggaattt atgcctcttc cgaccatcaa gcatttatc cgtactcctg atgatgcatg     2580
gttactcacc actgcgatcc cagggaaaac agcattccag gtattagaag aatatcctga    2640
ttcaggtgaa aatattgttg atgcgctggc agtgttcctg cgccggttgc attcgattcc    2700
tgtttgtaat tgtccttta acggcgatcg cgtatttcgt ctcgctcagg cgcaatcacg     2760
aatgaataac ggtttggttg gtgcgagtga ttttgatgac gagcgtaatg gctggcctgt    2820
tgaacaagtc tggaaagaaa tgcataagct tttgccattc tcaccggatt cagtcgtcac    2880
tcatggtgat ttctcacttg ataaccttat ttttgacgg gggaaattaa taggttgtat     2940
tgatgttgga cgagtcggaa tcgcagaccg ataccaggat cttgccatcc tatggaactg    3000
cctcggtgag ttttctcctt cattacagaa acggcttttt caaaaatatg gtattgataa    3060
tcctgatatg aataaattgc agtttcactt gatgctcgat gagttttct aaatgaccaa     3120 acaggaaaaa accgcccttta acatggcccg ctttatcaga agccagacat taacgcttct    3180
ggagaaactc aacgagctgg acgcggatga acaggcagac atctgtgaat cgcttcacga    3240
ccacgctgat gagctttacc gcagctgcct cgcgcgtttc ggtgatgacg gtgaaaacct    3300
ctgatgaggg cccaaatgta atcacctggc tcaccttcgg gtgggccttt ctgcgttgct    3360 ggcgttttc cataggctcc gccccctga cgagcatcac aaaaatcgat gctcaagtca     3420
gaggtggcga aacccgacag gactataaag ataccaggcg ttttcccctg gaagctccct    3480
cgtgcgctct cctgttccga ccctgccgct taccggatac ctgtccgcct ttctcccttc    3540
gggaagcgtg gcgctttctc atagctcacg ctgtaggtat ctcagttcgg tgtaggtcgt    3600
tcgctccaag ctgggctgtg tgcacgaacc cccgttcag cccgaccgct gcgccttatc     3660
cggtaactat cgtcttgagt ccaacccggt aagacacgac ttatcgccac tggcagcagc    3720
cactggtaac aggattagca gagcgaggta tgtaggcggt gctacagagt tcttgaagtg    3780
gtggcctaac tacggctaca ctagaagaac agtatttggt atctgcgctc tgctgaagcc    3840
agttacctcg gaaaagagt tggtagctct tgatccggca acaaaccac cgctggtagc     3900 ggtggttttt ttgtttgcaa gcagcagatt acgcgcagaa aaaaggatc tcaagaagat    3960 cctttgattt tctaccgaag aaaggcccac ccgtgaaggt gagccagtga gttgattgca    4020
gtccagttac gctggagtct gaggctcgtc ctgaatgata tcaagcttga attcgtt       4077
```

<210> SEQ ID NO 52
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (18)..(25)
<223> OTHER INFORMATION: n is a, c, g, or t

<400> SEQUENCE: 52
gtttcccagt aggtctcnnn nnnnn                                            25

<210> SEQ ID NO 53
<211> LENGTH: 21
<212> TYPE: DNA

```
<213> ORGANISM: Artificial Sequence
<220> FEATURE:
<223> OTHER INFORMATION: Synthetic oligonucleotide

<400> SEQUENCE: 53
cgccgtttcc cagtaggtct c                                            21
```